US011566028B2

(12) United States Patent
Shvartsbart et al.

(10) Patent No.: US 11,566,028 B2
(45) Date of Patent: Jan. 31, 2023

(54) BICYCLIC HETEROCYCLES AS FGFR INHIBITORS

(71) Applicant: Incyte Corporation, Wilmington, DE (US)

(72) Inventors: Artem Shvartsbart, Kennett Square, PA (US); Jeremy Roach, Philadelphia, PA (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 126 days.

(21) Appl. No.: 17/071,675

(22) Filed: Oct. 15, 2020

(65) Prior Publication Data

US 2021/0115053 A1 Apr. 22, 2021

Related U.S. Application Data

(60) Provisional application No. 62/915,750, filed on Oct. 16, 2019.

(51) Int. Cl.

*C07D 487/04* (2006.01)
*A61P 35/00* (2006.01)
*C07D 519/00* (2006.01)

(52) U.S. Cl.

CPC ............ *C07D 487/04* (2013.01); *A61P 35/00* (2018.01); *C07D 519/00* (2013.01)

(58) Field of Classification Search

CPC ..... C07D 487/04; C07D 519/00; A61P 19/00; A61P 35/00

See application file for complete search history.

(56) References Cited

U.S. PATENT DOCUMENTS

| | | | |
|---|---|---|---|
| 850,370 | A | 4/1907 | Hynes |
| 3,894,021 | A | 7/1975 | Denzel et al. |
| 4,271,074 | A | 6/1981 | Lohmann et al. |
| 4,339,267 | A | 7/1982 | Levitt |
| 4,347,348 | A | 8/1982 | Chemikhov et al. |
| 4,402,878 | A | 9/1983 | D'Alelio et al. |
| 4,405,519 | A | 9/1983 | D'Alelio et al. |
| 4,405,520 | A | 9/1983 | D'Alelio et al. |
| 4,405,786 | A | 9/1983 | D'Alelio et al. |
| 4,460,773 | A | 7/1984 | Suzuki et al. |
| 4,874,803 | A | 10/1989 | Baron et al. |
| 4,940,705 | A | 7/1990 | Boshagen et al. |
| 5,159,054 | A | 10/1992 | Keller |
| 5,240,941 | A | 8/1993 | Bruneau |
| 5,480,887 | A | 1/1996 | Hornback et al. |
| 5,521,184 | A | 5/1996 | Zimmermann et al. |
| 5,536,725 | A | 7/1996 | Cullen et al. |
| 5,541,324 | A | 7/1996 | TenBrink et al. |
| 5,760,068 | A | 6/1998 | Talley et al. |
| 5,783,577 | A | 7/1998 | Houghten et al. |
| 5,845,025 | A | 12/1998 | Garito et al. |
| 5,994,364 | A | 11/1999 | Njoroge et al. |
| 6,465,484 | B1 | 10/2002 | Bilodeau et al. |
| 6,998,408 | B2 | 2/2006 | Pinto |
| 7,074,801 | B1 | 7/2006 | Yoshida et al. |
| 7,125,880 | B1 | 10/2006 | Chen |
| 7,488,802 | B2 | 2/2009 | Collins et al. |
| 7,618,975 | B2 | 11/2009 | Cai et al. |
| 7,642,255 | B2 | 1/2010 | Sim |
| 7,648,973 | B2 | 1/2010 | DeLuca et al. |
| 7,943,743 | B2 | 5/2011 | Korman et al. |
| 8,008,449 | B2 | 8/2011 | Korman et al. |
| 8,168,757 | B2 | 5/2012 | Finnefrock et al. |
| 8,217,149 | B2 | 7/2012 | Irving et al. |
| 8,759,398 | B2 | 1/2014 | Nelson |
| 8,754,114 | B2 | 6/2014 | Yao et al. |
| 8,889,711 | B2 | 11/2014 | Bedjeguelal |
| 9,266,892 | B2 | 2/2016 | Zhuo et al. |
| 9,388,185 | B2 | 7/2016 | Lu et al. |

(Continued)

FOREIGN PATENT DOCUMENTS

| | | |
|---|---|---|
| CL | 2014003355 | 6/2015 |
| CL | 2015002628 | 8/2016 |

(Continued)

OTHER PUBLICATIONS

Balek, L., "ARQ 087 inhibits FGFR signaling and rescues aberrant cell proliferation and differentiation in experimental models of craniosynostoses and chondrodysplasias caused by activating mutations in FGFR1, FGFR2 and FGFR3." Bone 105 (2017): 57-66.*

Porta, R., "FGFR a promising druggable target in cancer: Molecular biology and new drugs." Critical reviews in oncology/hematology 113 (2017): 256-267.*

"Sabiosciences.com" [online]. "FGF Pathway," 2000-2012, [retrieved on Jun. 23, 2015]. Retrieved from the Internet: URL <http://www.sabiosciences.com/pathway.php?sn=FGF_Signaling>, 3 pages.

(Continued)

*Primary Examiner* — John M Mauro

(74) *Attorney, Agent, or Firm* — Fish & Richardson P.C.

(57) ABSTRACT

The present invention relates to bicyclic heterocycles, and pharmaceutical compositions of the same, that are inhibitors of the FGFR enzyme and are useful in the treatment of FGFR-associated diseases such as cancer.

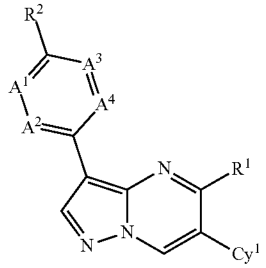

69 Claims, No Drawings

Specification includes a Sequence Listing.

(56) References Cited

U.S. PATENT DOCUMENTS

| | | | |
|---|---|---|---|
| 9,533,954 | B2 | 1/2017 | Yao et al. |
| 9,533,984 | B2 | 1/2017 | Sun et al. |
| 9,580,423 | B2 | 2/2017 | Lu et al. |
| 9,611,267 | B2 | 4/2017 | Wu et al. |
| 9,708,318 | B2 | 7/2017 | Lu et al. |
| 9,745,311 | B2 | 8/2017 | Lu et al. |
| 9,801,889 | B2 | 10/2017 | Lu et al. |
| 9,890,156 | B2 | 2/2018 | Lu et al. |
| 10,016,348 | B2 | 7/2018 | Lu et al. |
| 10,040,790 | B2 | 8/2018 | Sun et al. |
| 10,131,667 | B2 | 11/2018 | Wu et al. |
| 10,208,024 | B2 | 2/2019 | Andrews et al. |
| 10,213,427 | B2 | 2/2019 | Yao et al. |
| 10,214,528 | B2 | 2/2019 | Lu et al. |
| 10,251,892 | B2 | 4/2019 | Sokolsky et al. |
| 10,308,644 | B2 | 6/2019 | Wu et al. |
| 10,350,240 | B2 | 6/2019 | Gore et al. |
| 10,357,431 | B2 | 7/2019 | Staric et al. |
| 10,450,313 | B2 | 10/2019 | Lu et al. |
| 10,611,762 | B2 | 4/2020 | Jia et al. |
| 10,632,126 | B2 | 4/2020 | Lu et al. |
| 10,738,048 | B2 | 8/2020 | Lu et al. |
| 10,813,930 | B2 | 10/2020 | Yao et al. |
| 10,851,105 | B2 | 12/2020 | Wu et al. |
| 10,947,230 | B2 | 3/2021 | Sun et al. |
| 11,014,923 | B2 | 5/2021 | Lu et al. |
| 11,053,246 | B2 | 7/2021 | Wu et al. |
| 11,173,162 | B2 | 11/2021 | Sokolsky et al. |
| 11,174,257 | B2 | 11/2021 | Jia et al. |
| 2003/0078255 | A1 | 4/2003 | Pinto |
| 2003/0078277 | A1 | 4/2003 | Hibi et al. |
| 2003/0181622 | A1 | 9/2003 | Chiu et al. |
| 2004/0044012 | A1 | 3/2004 | Dobrusin et al. |
| 2004/0067948 | A1 | 4/2004 | Hallett |
| 2004/0097493 | A1 | 5/2004 | Chen et al. |
| 2004/0122029 | A1 | 6/2004 | Liu et al. |
| 2004/0127538 | A1 | 7/2004 | Oinuma et al. |
| 2004/0204427 | A1 | 10/2004 | Chen et al. |
| 2005/0009876 | A1 | 1/2005 | Bhagwat et al. |
| 2005/0070542 | A1 | 3/2005 | Hodgetts et al. |
| 2005/0148603 | A1 | 7/2005 | Jimenez et al. |
| 2005/0197340 | A1 | 9/2005 | Arora et al. |
| 2005/0222171 | A1 | 10/2005 | Bold et al. |
| 2006/0222637 | A1 | 10/2006 | Bamdad |
| 2006/0270849 | A1 | 11/2006 | Nishino et al. |
| 2007/0116984 | A1 | 5/2007 | Park et al. |
| 2007/0197510 | A1 | 8/2007 | Ohmoto et al. |
| 2007/0225286 | A1 | 9/2007 | Ren et al. |
| 2007/0280943 | A1 | 12/2007 | Friedman et al. |
| 2008/0249301 | A1 | 10/2008 | Hornberger et al. |
| 2009/0098086 | A1 | 4/2009 | Zask et al. |
| 2009/0099165 | A1 | 4/2009 | Hurley et al. |
| 2009/0099190 | A1 | 4/2009 | Flynn et al. |
| 2009/0105233 | A1 | 4/2009 | Chua et al. |
| 2009/0131467 | A1 | 5/2009 | Kanazawa et al. |
| 2009/0163545 | A1 | 6/2009 | Goldfarb |
| 2009/0246198 | A1 | 10/2009 | Dong et al. |
| 2010/0032626 | A1 | 2/2010 | Akino |
| 2010/0099684 | A1 | 4/2010 | Cook, II et al. |
| 2010/0105661 | A1 | 4/2010 | Shirakami et al. |
| 2010/0143547 | A1 | 6/2010 | Kriegel et al. |
| 2010/0204235 | A1 | 8/2010 | Lizos |
| 2010/0210636 | A1 | 8/2010 | Ishikawa et al. |
| 2010/0216798 | A1 | 8/2010 | Nakai et al. |
| 2010/0239496 | A1 | 9/2010 | Gangadharmath et al. |
| 2011/0045511 | A1 | 2/2011 | Graus Porta et al. |
| 2011/0159604 | A1 | 6/2011 | Fan et al. |
| 2011/0160203 | A1 | 6/2011 | Liu et al. |
| 2011/0195968 | A1 | 8/2011 | Greul et al. |
| 2011/0212077 | A1 | 9/2011 | Noronha et al. |
| 2011/0224155 | A1 | 9/2011 | Tachdjian et al. |
| 2011/0262525 | A1 | 10/2011 | Wang et al. |
| 2011/0313003 | A1 | 12/2011 | Shi et al. |
| 2012/0035153 | A1 | 2/2012 | Saxty et al. |
| 2012/0135997 | A1 | 5/2012 | Kato et al. |
| 2012/0165305 | A1 | 6/2012 | Yao et al. |
| 2012/0295881 | A1 | 11/2012 | Lange et al. |
| 2012/0319095 | A1 | 12/2012 | Tada et al. |
| 2013/0078731 | A1 | 3/2013 | George et al. |
| 2013/0200356 | A1 | 8/2013 | Jung et al. |
| 2013/0210825 | A1 | 8/2013 | Rehwinkel et al. |
| 2013/0338134 | A1 | 12/2013 | Wu et al. |
| 2014/0045814 | A1 | 2/2014 | Lu et al. |
| 2014/0054564 | A1 | 2/2014 | Kim et al. |
| 2014/0080892 | A1 | 3/2014 | Bhanot et al. |
| 2014/0088100 | A1 | 3/2014 | Bifulco, Jr. et al. |
| 2014/0103325 | A1 | 4/2014 | Shin et al. |
| 2014/0117318 | A1 | 5/2014 | Choi et al. |
| 2014/0148548 | A1 | 5/2014 | Yamanaka et al. |
| 2014/0171405 | A1 | 6/2014 | Zhuo et al. |
| 2014/0187559 | A1 | 7/2014 | Miduturu |
| 2014/0194430 | A1 | 7/2014 | Eis et al. |
| 2014/0228370 | A1 | 8/2014 | Eis et al. |
| 2014/0243308 | A1 | 8/2014 | Yao et al. |
| 2014/0288069 | A1 | 9/2014 | Eis et al. |
| 2014/0296233 | A1 | 10/2014 | D'Agostino et al. |
| 2014/0315902 | A1 | 10/2014 | Sun et al. |
| 2014/0374722 | A1 | 12/2014 | Kim et al. |
| 2014/0378468 | A1 | 12/2014 | Aichholz et al. |
| 2014/0378481 | A1 | 12/2014 | Bifulco, Jr. et al. |
| 2014/0378483 | A1 | 12/2014 | Benazet et al. |
| 2015/0011548 | A1 | 1/2015 | Linnanen et al. |
| 2015/0011560 | A1 | 1/2015 | Legeai-Mallet |
| 2015/0011579 | A1 | 1/2015 | Clary-Ceccato et al. |
| 2015/0038485 | A1 | 2/2015 | Eis et al. |
| 2015/0197519 | A1 | 7/2015 | Bifulco |
| 2016/0115164 | A1 | 4/2016 | Wu et al. |
| 2016/0244448 | A1 | 8/2016 | Lu et al. |
| 2016/0244449 | A1 | 8/2016 | Lu et al. |
| 2016/0244450 | A1 | 8/2016 | Lu et al. |
| 2016/0280713 | A1 | 9/2016 | Lu et al. |
| 2017/0107216 | A1 | 4/2017 | Wu et al. |
| 2017/0119782 | A1 | 5/2017 | Lu et al. |
| 2017/0137424 | A1 | 5/2017 | Wu et al. |
| 2017/0145025 | A1 | 5/2017 | Li et al. |
| 2017/0165263 | A1 | 6/2017 | Yao et al. |
| 2017/0166564 | A1 | 6/2017 | Sun et al. |
| 2017/0174671 | A1 | 6/2017 | Wu et al. |
| 2017/0174679 | A1 | 6/2017 | Lajkiewicz et al. |
| 2017/0260168 | A1 | 9/2017 | Andrews et al. |
| 2017/0290839 | A1 | 10/2017 | Lu et al. |
| 2017/0320875 | A1 | 11/2017 | Li et al. |
| 2017/0320877 | A1 | 11/2017 | Wu et al. |
| 2017/0342060 | A1 | 11/2017 | Lu et al. |
| 2017/0362253 | A1 | 12/2017 | Xiao et al. |
| 2018/0008610 | A1 | 1/2018 | Lu et al. |
| 2018/0016260 | A1 | 1/2018 | Yu et al. |
| 2018/0057486 | A1 | 3/2018 | Wu et al. |
| 2018/0072718 | A1 | 3/2018 | Liu et al. |
| 2018/0177784 | A1 | 6/2018 | Wu et al. |
| 2018/0177870 | A1 | 6/2018 | Liu et al. |
| 2018/0179179 | A1 | 6/2018 | Wu et al. |
| 2018/0179197 | A1 | 6/2018 | Wu et al. |
| 2018/0179201 | A1 | 6/2018 | Wu et al. |
| 2018/0179202 | A1 | 6/2018 | Wu et al. |
| 2018/0244672 | A1 | 8/2018 | Lu et al. |
| 2018/0273519 | A1 | 9/2018 | Wu et al. |
| 2019/0040082 | A1 | 2/2019 | Xiao et al. |
| 2019/0055237 | A1 | 2/2019 | Pan et al. |
| 2019/0062327 | A1 | 2/2019 | Sun et al. |
| 2019/0062345 | A1 | 2/2019 | Xiao et al. |
| 2019/0071439 | A1 | 3/2019 | Li et al. |
| 2019/0092767 | A1 | 3/2019 | Li et al. |
| 2019/0127376 | A1 | 5/2019 | Wu et al. |
| 2019/0127467 | A1 | 5/2019 | Shah et al. |
| 2019/0144439 | A1 | 5/2019 | Wu et al. |
| 2019/0202824 | A1 | 7/2019 | Wu et al. |
| 2019/0225601 | A1 | 7/2019 | Wu et al. |
| 2019/0240220 | A1 | 8/2019 | Yao et al. |
| 2019/0241560 | A1 | 8/2019 | Lu et al. |
| 2019/0269693 | A1 | 9/2019 | Lu et al. |
| 2019/0284187 | A1 | 9/2019 | Wu et al. |
| 2019/0300524 | A1 | 10/2019 | Wu et al. |
| 2019/0337948 | A1 | 11/2019 | Frietze et al. |

(56) References Cited

U.S. PATENT DOCUMENTS

| | | | |
|---|---|---|---|
| 2019/0345170 | A1 | 11/2019 | Wu et al. |
| 2020/0002338 | A1 | 1/2020 | Jia et al. |
| 2020/0055853 | A1 | 2/2020 | Ellies et al. |
| 2020/0095244 | A1 | 3/2020 | Sun et al. |
| 2020/0255424 | A1 | 8/2020 | Wu et al. |
| 2020/0270245 | A1 | 8/2020 | Pan et al. |
| 2020/0277309 | A1 | 9/2020 | Wu et al. |
| 2020/0306256 | A1 | 10/2020 | Lu et al. |
| 2020/0377504 | A1 | 12/2020 | Wu et al. |
| 2020/0399267 | A1 | 12/2020 | Lu et al. |
| 2021/0009582 | A1 | 1/2021 | Vechorkin et al. |
| 2021/0094935 | A1 | 4/2021 | Vechorkin |
| 2021/0106588 | A1 | 4/2021 | Vechorkin et al. |
| 2021/0171522 | A1 | 6/2021 | Tao et al. |
| 2021/0171535 | A1 | 6/2021 | McCammant et al. |
| 2021/0214366 | A1 | 7/2021 | Roach et al. |
| 2021/0380587 | A1 | 12/2021 | Wu et al. |
| 2021/0395246 | A1 | 12/2021 | Sun et al. |
| 2022/0009921 | A1 | 1/2022 | Lu et al. |
| 2022/0153740 | A1 | 5/2022 | Jia et al. |

FOREIGN PATENT DOCUMENTS

| | | |
|---|---|---|
| CL | 2017000654 | 12/2017 |
| CL | 2017001984 | 3/2018 |
| CL | 2018000089 | 5/2018 |
| CL | 2018000124 | 5/2018 |
| CL | 2017002117 | 6/2018 |
| CL | 2018000036 | 6/2018 |
| CL | 2018000128 | 6/2018 |
| CL | 2018003322 | 1/2019 |
| CN | 1863774 | 11/2006 |
| CN | 101007778 | 8/2007 |
| CN | 101679408 | 3/2010 |
| CN | 101715451 | 5/2010 |
| CN | 102399220 | 4/2012 |
| CN | 102399233 | 4/2012 |
| CN | 102666536 | 9/2012 |
| CN | 103571502 | 2/2014 |
| CN | 103588771 | 2/2014 |
| CN | 104262330 | 1/2015 |
| DE | 2156720 | 5/1973 |
| DE | 2934578 | 3/1981 |
| DE | 3432983 | 4/1985 |
| DE | 280853 | 7/1990 |
| DE | 3937633 | 5/1991 |
| DE | 4119767 | 12/1992 |
| DE | 19912638 | 9/2000 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| EP | 3184521 | 6/2017 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S 6310630 | 1/1988 |
| JP | 02009895 | 1/1990 |
| JP | H 0348656 | 3/1991 |
| JP | H 03275669 | 12/1991 |
| JP | 04179576 | 6/1992 |
| JP | H 04158084 | 6/1992 |
| JP | H 04328121 | 11/1992 |
| JP | H 05320173 | 12/1993 |
| JP | H 05320515 | 12/1993 |
| JP | H 09188812 | 7/1997 |
| JP | H 1060426 | 3/1998 |
| JP | H 11171865 | 6/1999 |
| JP | 2000123973 | 4/2000 |
| JP | 2001035664 | 2/2001 |
| JP | 2001265031 | 9/2001 |
| JP | 2002516327 | 6/2002 |
| JP | 2002296731 | 10/2002 |
| JP | 2003335788 | 11/2003 |
| JP | 2004203749 | 7/2004 |
| JP | 2004346145 | 12/2004 |
| JP | 2005015395 | 1/2005 |
| JP | 2005320288 | 11/2005 |
| JP | 2006028027 | 2/2006 |
| JP | 2006514624 | 5/2006 |
| JP | 2006284843 | 10/2006 |
| JP | 2006522756 | 10/2006 |
| JP | 2006316054 | 11/2006 |
| JP | 2007500725 | 1/2007 |
| JP | 2008198769 | 8/2008 |
| JP | 2009537520 | 10/2009 |
| JP | 2010180147 | 8/2010 |
| JP | 2010248429 | 11/2010 |
| JP | 2010267847 | 11/2010 |
| JP | 2010270245 | 12/2010 |
| JP | 2010272618 | 12/2010 |
| JP | 2010272727 | 12/2010 |
| JP | 2010278114 | 12/2010 |
| JP | 2011009348 | 1/2011 |
| JP | 2011044637 | 3/2011 |
| JP | 2011116840 | 6/2011 |
| JP | 2011222650 | 11/2011 |
| JP | 2012116825 | 6/2012 |
| JP | 2012136476 | 7/2012 |
| JP | 5120580 | 1/2013 |
| JP | 2013049251 | 3/2013 |
| JP | 2013179181 | 9/2013 |
| JP | 2015517376 | 6/2015 |
| JP | 20155017376 | 6/2015 |
| JP | 2018507214 | 3/2018 |
| JP | 2018511573 | 4/2018 |
| JP | 6336665 | 6/2018 |
| KR | 20010043829 | 5/2001 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 20140099105 | 8/2014 |
| WO | WO 1988/03025 | 5/1988 |
| WO | WO 1991/09835 | 7/1991 |
| WO | WO 1991/10172 | 7/1991 |
| WO | WO 1992/06078 | 4/1992 |
| WO | WO 1992/22552 | 12/1992 |
| WO | WO 1993/24488 | 12/1993 |
| WO | WO 1994/13669 | 6/1994 |
| WO | WO 1994/15995 | 7/1994 |
| WO | WO 1994/25438 | 11/1994 |
| WO | WO 1995/20965 | 8/1995 |
| WO | WO 1996/15128 | 5/1996 |
| WO | WO 1996/40707 | 12/1996 |
| WO | WO 1997/47601 | 12/1997 |
| WO | WO 1998/05661 | 2/1998 |
| WO | WO 1998/06703 | 2/1998 |
| WO | WO 1998/11438 | 3/1998 |
| WO | WO 1998/18781 | 5/1998 |
| WO | WO 1998/28281 | 7/1998 |
| WO | WO 1998/33798 | 8/1998 |
| WO | WO 1998/46609 | 10/1998 |
| WO | WO 1998/54156 | 12/1998 |
| WO | WO 1999/06422 | 2/1999 |
| WO | WO 1999/07732 | 2/1999 |
| WO | WO 1999/09030 | 2/1999 |
| WO | WO 1999/42442 | 8/1999 |
| WO | WO 1999/59975 | 11/1999 |
| WO | WO 1999/61444 | 12/1999 |
| WO | WO 1999/64400 | 12/1999 |
| WO | WO 2000/09495 | 2/2000 |
| WO | WO 2002/000196 | 2/2000 |
| WO | WO 2000/24744 | 5/2000 |
| WO | WO 2000/053595 | 9/2000 |

(56) References Cited

FOREIGN PATENT DOCUMENTS

| | | |
|---|---|---|
| WO | WO 2000/68186 | 11/2000 |
| WO | WO 2001/02369 | 1/2001 |
| WO | WO 2001/014402 | 3/2001 |
| WO | WO 2001/22938 | 4/2001 |
| WO | WO 2001/23386 | 4/2001 |
| WO | WO 2001/29041 | 4/2001 |
| WO | WO 2001/29042 | 4/2001 |
| WO | WO 2001/42247 | 6/2001 |
| WO | WO 2001/47892 | 7/2001 |
| WO | WO 2001/53273 | 7/2001 |
| WO | WO 2001/55148 | 8/2001 |
| WO | WO 2001/57037 | 8/2001 |
| WO | WO 2001/57038 | 8/2001 |
| WO | WO 2001/58899 | 8/2001 |
| WO | WO 2001/64655 | 9/2001 |
| WO | WO 2001/66099 | 9/2001 |
| WO | WO 2001/68647 | 9/2001 |
| WO | WO 2001/83472 | 11/2001 |
| WO | WO 2001/85722 | 11/2001 |
| WO | WO 2002/00655 | 1/2002 |
| WO | WO 2002/12442 | 2/2002 |
| WO | WO 2002/14315 | 2/2002 |
| WO | WO 2002/20011 | 3/2002 |
| WO | WO 2002/051831 | 7/2002 |
| WO | WO 2002/055082 | 7/2002 |
| WO | WO 2002/066481 | 8/2002 |
| WO | WO 2002/74754 | 9/2002 |
| WO | WO 2002/076953 | 10/2002 |
| WO | WO 2002/083648 | 10/2002 |
| WO | WO 2002/088095 | 11/2002 |
| WO | WO 2002/094825 | 11/2002 |
| WO | WO 2002/096873 | 12/2002 |
| WO | WO 2002/102793 | 12/2002 |
| WO | WO 2003/000187 | 1/2003 |
| WO | WO 2003/000688 | 1/2003 |
| WO | WO 2003/000690 | 1/2003 |
| WO | WO 2003/009852 | 2/2003 |
| WO | WO 2003/014083 | 2/2003 |
| WO | WO 2003/024967 | 3/2003 |
| WO | WO 2003/037347 | 5/2003 |
| WO | WO 2003/037891 | 5/2003 |
| WO | WO 2003/040131 | 5/2003 |
| WO | WO 2003/042402 | 5/2003 |
| WO | WO 2003/049542 | 6/2003 |
| WO | WO 2003/062236 | 7/2003 |
| WO | WO 2003/075836 | 9/2003 |
| WO | WO 2003/082871 | 10/2003 |
| WO | WO 2003/097609 | 11/2003 |
| WO | WO 2003/099771 | 12/2003 |
| WO | WO 2003/099818 | 12/2003 |
| WO | WO 2003/101985 | 12/2003 |
| WO | WO 2004/002986 | 1/2004 |
| WO | WO 2004/005281 | 1/2004 |
| WO | WO 2004/011465 | 2/2004 |
| WO | WO 2004/014382 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/046120 | 6/2004 |
| WO | WO 2004/046152 | 6/2004 |
| WO | WO 2004/048343 | 6/2004 |
| WO | WO 2004/052291 | 6/2004 |
| WO | WO 2004/052862 | 6/2004 |
| WO | WO 2004/056786 | 7/2004 |
| WO | WO 2004/056822 | 7/2004 |
| WO | WO 2004/056830 | 7/2004 |
| WO | WO 2004/065378 | 8/2004 |
| WO | WO 2004/080980 | 9/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/112793 | 12/2004 |
| WO | WO 2004/113307 | 12/2004 |
| WO | WO 2005/007653 | 1/2005 |
| WO | WO 2005/011597 | 2/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/028444 | 5/2005 |
| WO | WO 2005/040119 | 5/2005 |
| WO | WO 2005/047289 | 5/2005 |
| WO | WO 2005/056524 | 6/2005 |
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/105097 | 11/2005 |
| WO | WO 2005/113536 | 12/2005 |
| WO | WO 2005/116035 | 12/2005 |
| WO | WO 2005/121130 | 12/2005 |
| WO | WO 2005/121142 | 12/2005 |
| WO | WO 2006/000420 | 1/2006 |
| WO | WO 2006/024486 | 3/2006 |
| WO | WO 2006/024487 | 3/2006 |
| WO | WO 2006/024834 | 3/2006 |
| WO | WO 2006/028289 | 3/2006 |
| WO | WO 2006/030031 | 3/2006 |
| WO | WO 2006/038112 | 4/2006 |
| WO | WO 2006/050076 | 5/2006 |
| WO | WO 2006/050162 | 5/2006 |
| WO | WO 2006/052712 | 5/2006 |
| WO | WO 2006/055752 | 5/2006 |
| WO | WO 2006/024524 | 6/2006 |
| WO | WO 2006/056399 | 6/2006 |
| WO | WO 2006/058120 | 6/2006 |
| WO | WO 2006/062465 | 6/2006 |
| WO | WO 2006/065703 | 6/2006 |
| WO | WO 2006/074293 | 7/2006 |
| WO | WO 2006/087230 | 8/2006 |
| WO | WO 2006/092691 | 9/2006 |
| WO | WO 2006/102588 | 9/2006 |
| WO | WO 2006/102610 | 9/2006 |
| WO | WO 2006/105448 | 10/2006 |
| WO | WO 2006/107644 | 10/2006 |
| WO | WO 2006/112666 | 10/2006 |
| WO | WO 2006/119504 | 11/2006 |
| WO | WO 2006/124462 | 11/2006 |
| WO | WO 2006/124731 | 11/2006 |
| WO | WO 2006/135821 | 12/2006 |
| WO | WO 2006/136442 | 12/2006 |
| WO | WO 2007/013964 | 2/2007 |
| WO | WO 2007/017096 | 2/2007 |
| WO | WO 2007/021795 | 2/2007 |
| WO | WO 2007/022268 | 2/2007 |
| WO | WO 2007/023105 | 3/2007 |
| WO | WO 2007/025949 | 3/2007 |
| WO | WO 2007/030366 | 3/2007 |
| WO | WO 2007/032466 | 3/2007 |
| WO | WO 2007/033780 | 3/2007 |
| WO | WO 2007/038209 | 4/2007 |
| WO | WO 2007/044698 | 4/2007 |
| WO | WO 2007/044729 | 4/2007 |
| WO | WO 2007/048802 | 5/2007 |
| WO | WO 2007/053135 | 5/2007 |
| WO | WO 2007/053452 | 5/2007 |
| WO | WO 2007/053498 | 5/2007 |

(56) References Cited

FOREIGN PATENT DOCUMENTS

WO WO 2007/055418 5/2007
WO WO 2007/056023 5/2007
WO WO 2007/056075 5/2007
WO WO 2007/056170 5/2007
WO WO 2007/058392 5/2007
WO WO 2007/058626 5/2007
WO WO 2007/059108 5/2007
WO WO 2007/061554 5/2007
WO WO 2007/064883 6/2007
WO WO 2007/064931 6/2007
WO WO 2007/066189 6/2007
WO WO 2007/067444 6/2007
WO WO 2007/071752 6/2007
WO WO 2007/084314 7/2007
WO WO 2007/088999 8/2007
WO WO 2007/092879 8/2007
WO WO 2007/093901 8/2007
WO WO 2007/109334 9/2007
WO WO 2007/110868 10/2007
WO WO 2007/112347 10/2007
WO WO 2007/120097 10/2007
WO WO 2007/120339 10/2007
WO WO 2007/125351 11/2007
WO WO 2007/125405 11/2007
WO WO 2007/126841 11/2007
WO WO 2007/134259 11/2007
WO WO 2007/136465 11/2007
WO WO 2007/140957 12/2007
WO WO 2007/143600 12/2007
WO WO 2007/147217 12/2007
WO WO 2008/001070 1/2008
WO WO 2008/003766 1/2008
WO WO 2008/005877 1/2008
WO WO 2008/008234 1/2008
WO WO 2008/008747 1/2008
WO WO 2008/012635 1/2008
WO WO 2008/021389 2/2008
WO WO 2008/021851 2/2008
WO WO 2008/025556 3/2008
WO WO 2008/033858 3/2008
WO WO 2008/033999 3/2008
WO WO 2008/034859 3/2008
WO WO 2008/034860 3/2008
WO WO 2008/037459 4/2008
WO WO 2008/042639 4/2008
WO WO 2008/052898 5/2008
WO WO 2008/052934 5/2008
WO WO 2008/060907 5/2008
WO WO 2008/063583 5/2008
WO WO 2008/063609 5/2008
WO WO 2008/071455 6/2008
WO WO 2008/074068 6/2008
WO WO 2008/075068 6/2008
WO WO 2008/076278 6/2008
WO WO 2008/078091 7/2008
WO WO 2008/078100 7/2008
WO WO 2008/079460 7/2008
WO WO 2008/079933 7/2008
WO WO 2008/085942 7/2008
WO WO 2008/089105 7/2008
WO WO 2008/099075 8/2008
WO WO 2008/107436 9/2008
WO WO 2008/107544 9/2008
WO WO 2008/109181 9/2008
WO WO 2008/109943 9/2008
WO WO 2008/115974 9/2008
WO WO 2008/117269 10/2008
WO WO 2008/118454 10/2008
WO WO 2008/123755 10/2008
WO WO 2008/128141 10/2008
WO WO 2008/130584 10/2008
WO WO 2008/131972 11/2008
WO WO 2008/141065 11/2008
WO WO 2008/142720 11/2008
WO WO 2008/144253 11/2008
WO WO 2008/151184 12/2008
WO WO 2008/153207 12/2008
WO WO 2008/153852 12/2008
WO WO 2008/154221 12/2008
WO WO 2008/156712 12/2008
WO WO 2009/013335 1/2009
WO WO 2009/013354 1/2009
WO WO 2009/097446 1/2009
WO WO 2009/016253 2/2009
WO WO 2009/019518 2/2009
WO WO 2009/021083 2/2009
WO WO 2009/029473 3/2009
WO WO 2009/029625 3/2009
WO WO 2009/030871 3/2009
WO WO 2009/032861 3/2009
WO WO 2009/036012 3/2009
WO WO 2009/044788 4/2009
WO WO 2009/046606 4/2009
WO WO 2009/047255 4/2009
WO WO 2009/047506 4/2009
WO WO 2009/047522 4/2009
WO WO 2009/047993 4/2009
WO WO 2009/049018 4/2009
WO WO 2009/050183 4/2009
WO WO 2009/053737 4/2009
WO WO 2009/055828 4/2009
WO WO 2009/056886 5/2009
WO WO 2009/071535 6/2009
WO WO 2009/073153 6/2009
WO WO 2009/085185 7/2009
WO WO 2009/086130 7/2009
WO WO 2009/086509 7/2009
WO WO 2009/087238 7/2009
WO WO 2009/092764 7/2009
WO WO 2009/093209 7/2009
WO WO 2009/093210 7/2009
WO WO 2009/094528 7/2009
WO WO 2009/099982 8/2009
WO WO 2009/103652 8/2009
WO WO 2009/105717 8/2009
WO WO 2009/108332 9/2009
WO WO 2009/108827 9/2009
WO WO 2009/112826 9/2009
WO WO 2009/114870 9/2009
WO WO 2009/114874 9/2009
WO WO 2009/122180 10/2009
WO WO 2009/123967 10/2009
WO WO 2009/124755 10/2009
WO WO 2009/125808 10/2009
WO WO 2009/125809 10/2009
WO WO 2009/126584 10/2009
WO WO 2009/128520 10/2009
WO WO 2009/131687 10/2009
WO WO 2009/131926 10/2009
WO WO 2009/132980 11/2009
WO WO 2009/133127 11/2009
WO WO 2009/141386 11/2009
WO WO 2009/144205 12/2009
WO WO 2009/144302 12/2009
WO WO 2009/146034 12/2009
WO WO 2009/148916 12/2009
WO WO 2009/150150 12/2009
WO WO 2009/150240 12/2009
WO WO 2009/151997 12/2009
WO WO 2009/153592 12/2009
WO WO 2009/157423 12/2009
WO WO 2010/006947 1/2010
WO WO 2010/007099 1/2010
WO WO 2010/007116 1/2010
WO WO 2010/009155 1/2010
WO WO 2010/009195 1/2010
WO WO 2010/009207 1/2010
WO WO 2010/009735 1/2010
WO WO 2010/015643 2/2010
WO WO 2010/017047 2/2010
WO WO 2010/019210 2/2010
WO WO 2010/019899 2/2010
WO WO 2010/030027 3/2010
WO WO 2010/036959 4/2010

(56) References Cited

FOREIGN PATENT DOCUMENTS

| | | |
|---|---|---|
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/062571 | 6/2010 |
| WO | WO 2010/064621 | 6/2010 |
| WO | WO 2010/064875 | 6/2010 |
| WO | WO 2010/067886 | 6/2010 |
| WO | WO 2010/067888 | 6/2010 |
| WO | WO 2010/075074 | 7/2010 |
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/089411 | 8/2010 |
| WO | WO 2010/092181 | 8/2010 |
| WO | WO 2010/099938 | 9/2010 |
| WO | WO 2010/103306 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/053518 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/066342 | 6/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082400 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101409 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |
| WO | WO 2011/112995 | 9/2011 |
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |
| WO | WO 2011/147198 | 12/2011 |
| WO | WO 2011/147199 | 12/2011 |
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2011/159877 | 12/2011 |
| WO | WO 2011/161699 | 12/2011 |
| WO | WO 2011/163330 | 12/2011 |
| WO | WO 2012/000103 | 1/2012 |
| WO | WO 2012/003544 | 1/2012 |
| WO | WO 2012/004217 | 1/2012 |
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |
| WO | WO 2012/031004 | 3/2012 |
| WO | WO 2012/032031 | 3/2012 |
| WO | WO 2012/032065 | 3/2012 |
| WO | WO 2012/032067 | 3/2012 |

(56) References Cited

FOREIGN PATENT DOCUMENTS

| | | |
|---|---|---|
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061156 | 5/2012 |
| WO | WO 2012/061337 | 5/2012 |
| WO | WO 2012/062462 | 5/2012 |
| WO | WO 2012/063207 | 5/2012 |
| WO | WO 2012/064715 | 5/2012 |
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/078777 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |
| WO | WO 2012/083954 | 6/2012 |
| WO | WO 2012/084704 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/129344 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |
| WO | WO 2013/033981 | 3/2013 |
| WO | WO 2013/039854 | 3/2013 |
| WO | WO 2013/041634 | 3/2013 |
| WO | WO 2013/049352 | 4/2013 |
| WO | WO 2013/053051 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/170063 | 10/2014 |
| WO | WO 2014/171755 | 10/2014 |
| WO | WO 2014/172644 | 10/2014 |
| WO | WO 2014/174307 | 10/2014 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/057938 | 4/2015 |
| WO | WO 2015/057963 | 4/2015 |
| WO | WO 2015/059668 | 4/2015 |
| WO | WO 2015/061572 | 4/2015 |
| WO | WO 2015/066452 | 5/2015 |
| WO | WO 2015/108992 | 7/2015 |
| WO | WO 2016/064960 | 4/2016 |
| WO | WO 2016/134314 | 8/2016 |
| WO | WO 2016/192680 | 12/2016 |
| WO | WO 2017/023972 | 2/2017 |
| WO | WO 2017/023988 | 2/2017 |
| WO | WO 2017/023989 | 2/2017 |
| WO | WO 2017/024003 | 2/2017 |
| WO | WO 2017/024004 | 2/2017 |
| WO | WO 2017/024015 | 2/2017 |
| WO | WO 2017/024025 | 2/2017 |
| WO | WO 2017/028314 | 2/2017 |
| WO | WO 2017/223414 | 12/2017 |
| WO | WO 2018/041091 | 3/2018 |
| WO | WO 2018/049214 | 3/2018 |
| WO | WO 2018/067512 | 4/2018 |
| WO | WO 2018/093029 | 5/2018 |
| WO | WO 2018/093215 | 5/2018 |
| WO | WO 2018/105972 | 6/2018 |
| WO | WO 2018/105973 | 6/2018 |
| WO | WO 2018/234354 | 12/2018 |
| WO | WO 2019/037640 | 2/2019 |
| WO | WO 2019/079369 | 4/2019 |
| WO | WO 2019/105886 | 6/2019 |
| WO | WO 2019/213506 | 11/2019 |
| WO | WO 2020/049017 | 3/2020 |
| WO | WO 2020/131627 | 6/2020 |
| WO | WO 2020/131674 | 6/2020 |

OTHER PUBLICATIONS

"Substance Record for SID 240993001," Feb. 13, 2015, pp. 1-8.

Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.

Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.

Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.

Antonios-McCrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.

Anonymous, "American Society for Clinical Pharmacology and Therapeutics," Clin Pharma and Thera., Feb. 13, 2019, 105(S1):S5-S121.

Anonymous, "In Vitro Metabolism- and Transporter-Mediated Drug-Drug Interaction Studies Guidance for Industry", Clinical Pharmacology, Oct. 2017, 47 pages.

(56) References Cited

OTHER PUBLICATIONS

Arai et al., "Characterization of the cell or origin and propagation potential of the fibroblast growth factor 9-induced mouse model of lung adenocarcinoma," J. Pathol., Mar. 2015, 235(4): 593-605.
Arai et al., "Fibroblast growth factor receptor 2 tyrosine kinase fusions define a unique molecular subtype of cholangiocarcinoma," Hepatology, 2014, 59(4):1427-1434.
Argentina Office Action in Argentina Application No. 20130102068, dated Jul. 17, 2020, 10 pages.
Argentina Office Action in Argentina Application No. 20140101651, dated Nov. 21, 2019, 5 pages.
Argentina Office Action in Argentina Application No. 20140101651, dated Jul. 29, 2021, 9 pages.
Ash and Ash, "Handbook of Pharmaceutical Additives," Gower Publishing Company, 2007, 3rd ed, *********too voluminous to provide*******.
Atzrodt et al., "The Renaissance of H/D Exchange," Angew Chem Int Ed., 2007, 7744-7765.
Australian Office Action in Australian Application No. 2013287176, dated Sep. 12, 2017, 4 pages.
Australian Office Action in Australian Application No. 2014253798, dated Jul. 31, 2017, 4 pages.
Australian Office Action in Australian Application No. 2016219816, dated Aug. 26, 2019, 3 pages.
Australian Office Action in Australian Application No. 2016219822, dated Jul. 8, 2019, 4 pages.
Australian Office Action in Australian Application No. 2018208772, dated Jul. 1, 2018, 5 pages.
Australian Office Action in Australian Application No. 2019200066, dated Aug. 27, 2019, 6 pages.
Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.
Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.
Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.
Bavin, "Polymorphism in Process Development," Chemistry & Industry, Society of Chemical Industry, Aug. 1989, 527-529.
Bazyl et al., "The selective ortho-methoxylation of pentafluorobenzoic acid—a new way to tetrafluorosalicylic acid and its derivatives," J Flour Chem., Feb. 11, 1999, 94(1):11-13.
Beekman et al., "New Molecular Targets and Novel Agents in the Treatment of Advanced Urothelial Cancer," Semin Oncol, 2007, 34: 154-164.
Bello et al., "E-3810 is a potent dual inhibitor of VEGFR and FGFR that exerts antitumor activity in multiple preclinical models," Cancer Res, 2011.
Bello et al., "E-3810 is a potent dual inhibitor of VEGFR and FGFR that exerts antitumor activity in multiple preclinical models," Cancer Res, 2011, Supplemental figures, 4 pages.
Bello et al., "E-3810 is a potent dual inhibitor of VEGFR and FGFR that exerts antitumor activity in multiple preclinical models," Cancer Res, 2011, Supplemental table, 3 pages.
Bello et al., "E-3810 is a potent dual inhibitor of VEGFR and FGFR that exerts antitumor activity in multiple preclinical models," Cancer Res, 2011, Supplementary data, 4 pages.
Benet-Pages et al., "An FGF23 missense mutation causes familial tumoral calcinosis with hyperphosphatemia," Human Molecular Genetics, 2005, 14(3):385-390.
Berge et al., "Pharmaceutical Salts", Journal of Pharmaceutical Science, 1977, 66(2):1-19.
Bergwitz and Juppner, "Regulation of Phosphate Homeostasis by PTH, Vitamin D, and FGF23," Annu. Rev. Med., 2010, 61:91-104.
Bhide et al., "Discovery and Preclinical Studies of (R )-1-(4-(4-Fluoro-2-methyl-1H-indol-5-yloxy)-5-methylpyrrolo[2,1-*f*][1,2,4]triazin-6-yloxy)propan-2-ol (BMS-540215), an In Vivo Active Potent VEGFR-2 Inhibitor," Journal of Medicinal Chemistry, 2006, 49(7): 2143-2146.
Billerey et al., "Frequent FGFR3 Mutations in Papillary Non-Invasive Bladder (pTa) Tumors," American Journal of Pathology, Jun. 2001, 158(6): 1955-1959.
Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.
BioCentury, Week of Nov. 10, 2014, 52 pages.
Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.
Black et al., "Targeted therapies in bladder cancer—an update," Urologic Oncology: Seminars and Original Investigations, 2007, 433-438.
Blom et al., "Optimizing Preparative LC-MS Configurations and Methods for Parallel Synthesis Purification", J Combi Chem., 2003, 5:670.
Blom et al., Preparative LC-MS Purification: Improved Compound Specific Method Optimization, J Combi Chem. 2004, 6(6):874-883.
Blom, K., "Two-Pump At Column Dilution Configuration for Preparative LC-MS", J Combi Chem., 2002, 4:295.
Bonaventure et al., "Common Mutations in the Fibroblast Growth Factor Receptor 3 (FRFR3) Gene Account for Achondroplasia, Hypochondroplasia and Thanatophoric Dwarfism," Clin Pediatr Endocrinol, 1997, 105-113.
Bono et al., "Inhibition of Tumor Angiogenesis and Growth by a Small-Molecule Multi-FGF Receptor Blocker with Allosteric Properties," Cancer Cell, Apr. 2013, 477-488.
Borad et al., "Fibroblast growth factor receptor 2 fusions as a target for treating cholangiocarcinoma," Currrent opinion in Gastroenterology, May 2015, 31(3):264-268.
Brooks et al., "Fibroblast growth factor signaling: a new therapeutic opportunity in cancer," Clinical Cancer Research, 2012, 1-23.
Caira, "Crystalline Polymorphism of Organic Compounds," Topics in Current Chemistry, Jan. 1, 1998, 198:163-208.
Cancer [online], [retrieved on Jul. 6, 2007] Retrieved from the Internet, URL: http://www.nlm.nih.gov/medlineplus/cancer.html.
Capelletti et al., "Identification of Recurrent FGFR3-TACC3 Fusion Oncogenes from Lung Adenocarcinoma," AACR Journals, 2014, 6551-6558.
Cappellen et al., "Frequent activating mutations of FGFR3 in human bladder and cervix carcinomas," Nature Genetics, Sep. 1999, 23: 18-20.
Carmichael et al., "Familial Tumoral Calcinosis: A Forty-Year Follow-up on One Family," The Journal of Bone & Joint Surgery, 2009, 664-671.
Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.
Chandrani et al., "Drug-sensitive FGFR3 mutations in lung adenocarcinoma," Annals of Oncology, 2017, 28: 597-603.
Chase et al., "Activity of TKI258 against primary cells and cell lines with FGFR1 fusion genes associated with the 8p11 myeloproliferative syndryome," Blood, 2007, 110:3729-3734.
Chefetz and Sprecher, "Familial tumoral calcinosis and the role of O-glycosylation in the maintenance of phosphate homeostasis," Biochimica et Biophysica Acta, 2009, 847-852.
Chefetz et al., "A novel homozygous missense mutation in FGF23 causes Familial Tumoral Calcinosis associated with disseminated visceral calcification," Hum Genet, 2005, 118:261-266.
Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.

(56) References Cited

OTHER PUBLICATIONS

Chen et al., "Acenaphtho[1,2-b]pyrrole-Based Selective Fibroblast Growth Factor Receptors 1 (FRGR1) Inhibitors: Design, Synthesis, and Biological Activity," Jounal of Medicinal Chemistry, 2011, 54: 3732-3745.
Chen et al., "FGFR3 as a therapeutic target of the small molecule inhibitor PKC412 in hematopoietic malignancies," Oncogene, 2005, 24: 8259-8267.
Chen et al., "Genome-Wide Loss of Heterozygosity and DNA Copy Number Aberration in HPV-Negative Oral Squamous Cell Carcinoma and Their Associations with Disease-Specific Survival," PLOS One, Aug. 2015, 23 pages.
Cherukupalli et al., "An insight on synthetic and medicinal aspects of pyrazolo[1,5-a]pyrimidine scaffold," European Journal of Medicinal Chemistry, Nov. 10, 2016, 126:298-352.
Chesi et al., "Activated fibroblast growth factor receptor 3 is an oncogene that contributes to tumor progression in multiple myeloma," Blood, 2001, 97:729-736.
Chesi et al., "Frequent translocation t(4;14)(p16.3;q32.3) in multiple myeloma is associated with increased expression and activating mutations of fibroblast growth factor receptor 3," Nature Genetics, 1997, 260-264.
Chilean Office Action in Chilean Application No. 1984-2017, dated Sep. 12, 2019, 9 pages.
Chilean Office Action in Chilean Application No. 2015-003089, dated Apr. 24, 2017, 13 pages (English Summary).
Chilean Office Action in Chilean Application No. 2015-003089, dated Jan. 23, 2018, 8 pages.
Chilean Office Action in Chilean Application No. 2122-2017, dated Apr. 22, 2019, 25 pages.
Chilean Office Action in Chilean Application No. 2122-2017, dated Nov. 15, 2019, 15 pages.
Chilean Office Action in Chilean Application No. 3355-2014, dated Jan. 18, 2017, 17 pages (with English translation).
Chilean Office Action in Chilean Application No. 3439-2019, dated Feb. 10, 2021, 26 pages.
Chilean Opposition in Chilean Application No. 3355-2014, 3 pages (English translation only).
Chinese Office Action in Chinese Application No. 10874686.0, dated Oct. 8, 2019, 10 pages.
Chinese Office Action in Chinese Application No. 201380041027.9, dated Feb. 13, 2017, 10 pages (with English translation).
Chinese Office Action in Chinese Application No. 201380041027.9, dated Jul. 12, 2016, 11 pages (with English translation).
Chinese Office Action in Chinese Application No. 201380041027.9, dated Oct. 28, 2015, 17 pages (with English translation).
Chinese Office Action in Chinese Application No. 201480028858.7, dated Apr. 4, 2018, 10 pages (English Translation).
Chinese Office Action in Chinese Application No. 201480028858.7, dated Aug. 19, 2016, 18 pages (English Translation).
Chinese Office Action in Chinese Application No. 201480028858.7, dated Jul. 12, 2017, 10 pages (English Translation).
Chinese Office Action in Chinese Application No. 201680011332.7, dated Aug. 5, 2019, 14 pages.
Chinese Office Action in Chinese Application No. 201680011348.8, dated Aug. 2, 2019, 14 pages.
Chinese Office Action in Chinese Application No. 201710395346.X, dated Jan. 22, 2019, 17 pages.
Chinese Office Action in Chinese Application No. 201710395346.X, dated Sep. 9, 2019, 10 pages.
Chinese Office Action in Chinese Application No. 201710874686.0, dated Feb. 25, 2019, 17 pages.
Chinese Office Action in Chinese Application No. 201910023729.3, dated Mar. 3, 2021, 15 pages.
Chng et al., "Translocation t(4;14) retains prognostic significance even in the setting of high-risk molecular signature," Leukemia, 2008, 2: 459-461.
Chuaqui et al., "Interaction Profiles of Protein Kinase—Inhibitor Complexes and Their Application to Virtual Screening," J. Med. Chem., 2005, 48: 121-133.

Ciappetti and Geithlen "Molecular Variations Based on Isosteric Replacements," The Practice of Medicinal Chemistry, 2008, Chapter 15, pp. 290-341.
ClinicalTrials.gov, "A Study to Evaluate the Efficacy and Safety of Pemigatinib Versus Cherrotherapy in Unresectable or Metastatic Chol (FIGHT-302)," NCT03656536, Mar. 6, 2019, retrieved from URL <https://www.clinicaltrials.gov/ct2/history/NCT03656536?V_5=View#StudyPageTop,>, 4 pages.
Cole et al., "Inhibition of FGFR2 and FGFR1 increases cisplatin sensitivity in ovarian cancer," Cancer Biol. Therapy, Sep. 1, 2010, 10(5):495-504.
Coleman, "Positive and negative regulation of cellular sensitivity to anti-cancer drugs by FGF-2," Drug Resistance Updates, 2003, 85-94.
Colombian Office Action in Colombian Application No. 14-275934-6, dated May 31, 2016, 3 pages (English translation only).
Colombian Office Action in Colombian Application No. 14-275934-6, dated Nov. 17, 2015, 12 pages (English translation only).
Colombian Office Action in Colombian Application No. 16100866, dated Aug. 10, 2017, 9 pages.
Colombian Office Action in Colombian Application No. NC2017/0008795, dated Nov. 29, 2018, 8 pages.
Colombian Office Action in Colombian Application No. NC2017/0008795, dated Aug. 16, 2019, 6 pages.
Colombian Office Action in Colombian Application No. NC2017/0008795, dated Aug. 29, 2017, 2 pages.
Colombian Office Action in Colombian Application No. NC2017/0008824, dated Aug. 31, 2017, 3 pages.
Colombian Office Action in Colombian Application No. NC2017/0008824, dated Nov. 29, 2018, 8 pages.
Colombian Office Action in Colombian Application No. NC2019/0009690, dated Jan. 22, 2020, 20 pages.
Colombian Opposition in Colombian Application No. NC 2021/0004568, dated Apr. 15, 2021, 21 pages.
Cordovilla et al., "The Stille Reaction, 38 Years Later," ACS Catal., Apr. 17, 2015, 5(5):3040-3053.
Corre et al., "Synthesis and biological evaluation of a triazole-based library of pyrido[2,3-d]pyrimidines as FGFR3 tyrosine kinase inhibitors," Organic & Biomolecular Chemistry, 2010, 8:2164-2173.
Costa Rican Office Action in Costa Rican Application No. 2014-0577, dated Apr. 15, 2020, 18 pages.
Costa Rican Office Action in Costa Rican Application No. 2014-0577, dated Jun. 13, 2019, 17 pages.
Costa Rican Office Action in Costa Rican Application No. 2015-0578, dated Jun. 11, 2020, 15 pages.
Costa Rican Opposition in Costa Rican Application No. PCT/US2013/045309, dated Jun. 29, 2015, 14 pages (English Translation).
Covic et al., "Vascular calcification in chronic kidney disease," Clinical Science, 2010, 119: 111-121.
Crose et al., "FGFR4 Blockade Exerts Distinct Antitumorigenic Effects in Human Embryonal versus Alveolar Rhabdomyosarcoma," Clin Cancer Res., 2012, 18:3780-3790.
Dailey et al., "Mechanisms underlying differential responses to FGF signaling," Cytokine & Growth Factor Reviews, 2005, 233-247.
Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.
Desnoyers et al., "Targeting FGF19 inhibits tumor growth in colon cancer xenograft and FGF19 transgenic hepatocellular carcinoma models," Oncogene, 2008, 27:85-97.
Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.
Dieci et al., "Fibroblast Growth Factor Receptor Inhibitors as a Cancer Treatment: From a Biologic Rationale to Medical Perspectives," Cancer Discovery, 2013, 1-16.
Dienstmann et al., "Genomic aberrations in the FGFR pathway: opportunities for targeted therapies in solid tumors," Annals of Oncology, 2013, 1-12.
Diller and Li, "Kinases, Homology Models, and High Throughput Docking," J. Med. Chem., 2003, 46:4638-4647.

(56) References Cited

OTHER PUBLICATIONS

Dimopoulos et al., "Lenalidomide plus Dexamethasone for Relapsed or Refractory Multiple Myeloma," The New England Journal of Medicine, 2007, 357:2123-2132.
Ding et al., "Somatic mutations affect key pathways in lung adenocarcinoma," Nature., Oct. 23, 2008, 455:1069-1075.
Dovedi and Davies, "Emerging targeted therapies for bladder cancer: a disease waiting for a drug," Cancer Metastasis Rev, 2009, 28:355-367.
Dring et al., "A Global Expression-based Analysis of the Consequences of the t(4;14) Translocation in Myeloma," Clinical Cancer Research, Sep. 2004, 10: 5692-5701.
Drueke et al., "Phosphate binders in CKD: bad news or good news?," Journal of the American Society of Nephrology, Aug. 2012, 23(8):1277-1280.
Dutt et al., "Drug-sensitive FGFR2 mutations in endometrial carcinoma," PNAS, Jun. 24, 2008, 105(25):8713-8717.
Dutt et al., "Drug-sensitive FGFR2 mutations in endometrial carcinoma," Supporting Information, Jun. 2008, 8 pages.
Edmondson et al., "Aminopiperidine-fused imidazoles as dipeptidyl peptidase-IV inhibitors," Bioorg & Med Chem Lett., 2009, 19(15):4097-4101.
Eissa, "Synthesis and evaluation of some surface active agents from long chain fatty amine," Spanish National Research Council, Jan. 2007, 58(4):379-389.
Elsheikh et al., "FGFR1 amplification in breast carcinomas: a chromogenic in situ hybridisation analysis," Breast Cancer Research, Mar. 2007, 9(2): 1-12.
Erian at al., "2-Aryl-1,1-dicyano-3-phenylsulfonylpropenes in heterocyclic synthesis. A synthetic strategy towards heterocyclic sulfones," Monatshefte fuer Chemie, 1998, 129(10):1049-1056.
Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.
Eswarakumar and Schlessinger, "Cellular signaling by fibroblast growth factor receptors," Cytokine & Growth Factor Reviews, 2005, 139-149.
Eurasian Office Action in Eurasian Application No. 201590005, dated Oct. 21, 2015, 6 pages.
Eurasian Office Action in Eurasian Application No. 201590005, dated Mar. 28, 2018, 6 pages.
Eurasian Office Action in Eurasian Application No. 201791866, dated Feb. 19, 2018, 10 pages (English Translation).
Eurasian Office Action in Eurasian Application No. 201791867, dated Apr. 4, 2018, 4 pages (English Translation).
Eurasian Office Action in Eurasian Application No. 202091923, dated Jul. 27, 2021, 6 pages (English Translation).
European Communication pursuant to Article 94(3) EPC in European Application No. 13783125.1, dated Jan. 26, 2016, 4 pages.
European Office Action in European Application No. 18733045.1, dated Jan. 11, 2021, 5 pages.
European Office Action in European Application No. 20192679.7, dated Feb. 11, 2021, 7 pages.
European Office Action in European Application No. 16715139.8, dated May 18, 2021, 9 pages.
European search report in European Application No. 16203866.5, dated Mar. 1, 2017, 7 pages.
European Search Report in European Application No. 17199421.3, dated Jul. 12, 2018, 15 pages.
European Search Report in European Application No. 17199421.3, dated Mar. 12, 2018, 14 pages.
Faul et al., "FGF23 induces left ventricular hypertrophy," The Journal of Clinical Investigation, 2010, 1-16.
FDA.gov, "FDA grants accelerated approval to pemigatinib for cholangiocarcinoma with an FGFR2 rearrangement or fusion," Apr. 20, 2020, [Retrieved on Apr. 27, 2021], retrieved from URL <https://www.fda.gov/drugs/resources-information-approved-drugs/fda-grants-accelerated-approval-pemigatinib-cholangiocarcinoma-fgfr2-rearrangement-or-fusion>, 2 pages.
Feng et al., "Guidance to rational use of pharmaceuticals in gallbladder sarcomatoid carcinoma using patient-derived cancer cells and whole exome sequencing," Oncotarget, 2017, 8(3): 5349-5360.
Feng et al., "Targeting Fibroblast Growth Factor Receptor Signaling Inhibits Prostate Cancer Progression," Clinical Cancer Research, 2012, 1-9.
Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cell lung cancer cells: therapeutic implications and synergism with epidermal growth factor receptor inhibition," Mol Cancer Therapy, 2008, 3408-3419.
French et al., Targeting FGFR4 inhibits hepatocellular carcinoma in preclinical mouse models, PLoS One 2012;7:e36713.
Fricker, "Metal based drugs: from serendipity to design," Dalton Transactions, 2007, 43:4903-4917.
Fricker, "The therapeutic application of lanthanides," Chemical Society Reviews, 2006, 35(6):524-533.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperostosis-hyperphosphatemia syndrome and familial tumoral calcinosis are allelic disorders," J Mol Med, 2005, 83:33-38.
Fu et al., "Intratumoral inorganic phosphate deprivation: A new anticancer strategy," Medical Hypotheses, Feb. 2020, 135:109497.
Fukumoto and Yamashita, "FGF23 is a hormone-regulating phophate metabolism—Unique biological characteristics of FGF23," Bone, 2007, 1190-1195.
Fun et al., "2-7(7,8-Diphenyl-1H-imidazo[4,5-f]-quinoxalin-2-yl)phenol methanol disolvate," Acta Crystallographica Section E Structure Reports Online, 2008, 64(9):o1741-o1742.
Furniss "Acidic/Basic characteristics for purification," Vogel's Textbook of Practical Organic Chemistry, 5th edition, 1989, 131-133, 135-143.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Gallo et al., "Functions of Fibroblast Growth Factor Receptors in cancer defined by novel translocations and mutations," Cytokine & Growth Factor Reviews, 2015, 26(4):425-449.
Garringer et al., "Molecular genetic and biochemical analyses of FGF23 mutations in familial tumoral calcinosis," Am J Physiol Endocrinol Metab, 2008, 929-937.
Gattineni et al., "FGF23 decreases renal NaPi-2a and NaPi-2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gennaro et al., "Pharmaceutical Sciences," Remington's Pharmaceutical Sciences 17th Ed., Jan. 1985, 14-18 and 1409-1423.
Gerby et al., "2-Arylidenedihydroindole-3-ones: Design, synthesis, and biological activity on bladder carcinoma cell lines," Bioorganic & Medicinal Chemistry Letters, 2007, 208-213.
Ghorab et al., "Synthesis of some sulfur containing Tetrahydrobenzoabuthieno[b] Thieno(Pyridines, Quinolines, Oxazines and Pyrimidines) as possible radioprotective and Antineoplastic agents," Phosphorus, Sulfur and Silicon, Jan. 1998, 134/135:57-76.
Gibson, "Pharmaceutical Preformulation and Formulation," CRC Press LLC, 2009, 2nd ed, 559 pages.
Goetz et al., "Isolated C-terminal tail of FGF23 alleviates hypophosphatemia by inhibiting FGF23-FGFR-Klotho complex formation," PNAS, Jan. 2010, 107(1): 407-412.

(56) References Cited

OTHER PUBLICATIONS

Golub et al., "Molecular Classification of Cancer: Class Discovery and Class Prediction by Gene Expression Monitoring," Science, 1999, 286: 531-537.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11): 1045-1089.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Granberg et al., "Strong FGFR3 staining is a marker for FGFR3 fusions in diffuse gliomas," Neuro-Oncology, 2017, 19(9): 1206-1216.
Grand et al., "Targeting FGFR3 in multiple myeloma: inhibition of t(4;14)-positive cells by SU5402 and PD173074," Leukemia, 2004, 18: 962-966.
Greene, T. W. and Wuts, P. G. M., "Protective Groups in Organic Synthesis", 3rd Ed., Wiley & Sons, Inc., New York (1999), 799 pages.
Greulich and Pollock, "Targeting mutant fibroblast growth factor receptors in cancer," Cell Press, May 2011, 17(5): 283-292.
Grose and Dickson, "Fibroblast growth factor signaling in tumorigenesis," Cytokine & Growth Factor Reviews, 2005, 179-186.
Gu et al., "Phosphotyrosine profiling identifies the KG-1 cell line as a model for the study of FGFR1 fusions in acute myeloid leukemia," Blood, Dec. 15, 2006, 108(13):4202-42040.
Guagnano et al., "Discovery of 3-(2,6-Dichloro-3,5-dimethoxy-phenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase," J. Med. Chem., 2011, 54: 7066-7083.
Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.
Gust et al., "Fibroblast Growth Factor Receptor 3 Is a Rational Therapeutic Target in Bladder Cancer," Molecular Cancer Therapeutics, Jul. 2013, 12(7): 1245-1254.
Haas et al., "Recent Developments in Negishi Cross-Coupling Reactions," ACS Catal., 2016, 6(3):1540-1552.
Hackam et al. "Translation of Research Evidence From Animals to Humans," JAMA, 296(14), 2006, 296(14):1731-1732.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 2015, 1-14.
Hara and Saito, "CARD9 versus CARMA1 in innate and adaptive immunity," Cell Press, 2009, 234-242.
Heinrich et al., "Fragment-based discovery of new highly substituted 1H-pyrrolo[2,3-b]- and 3H-imidazolo[4,5-b]-pyridines as focal adhesion kinase inhibitors," J of Med Chem., Jan. 8, 2013, 56(3):1160-1170.
Heinzle C, et al., "Differential Effects of Polymorphic Alleles of FGF Receptor 4 on Colon Cancer Growth and Metastasis," Cancer Research, Nov. 2012, 72(22):5767-5777.
Heinzle et al., "Is fibroblast growth factor receptor 4 a suitable target of cancer therapy?," Cur. Pharm. Des., 2014, 20:2881-2898.
Heinzle et al., "Targeting fibroblast-growth-factor-receptor-dependent signaling for cancer therapy," Expert Opinion, 2011, 1-18.
Helsten et al., "The FGFR Landscape in Cancer: Analysis of 4,853 Tumors by Next-Generation Sequencing," Clin. Cancer Res., Jan. 2016, 22:259-267.
Hideshima and Anderson, "Preclinical Studies of Novel Targeted Therapies," Hematol Oncol Clin N Am, 2007, 1071-1091.
Ho et al., "Fibroblast growth factor receptor 4 regulates proliferation, anti apoptosis and alpha-fetoprotein secretion during hepatocellular carcinoma progression and represents a potential target for therapeutic intervention," J Hepatol, 2009, 50:118-127.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Hu and Cong, "Fibroblast growth factor 19 is correlated with an unfavorable prognosis and promotes progression by activating fibroblast growth factor receptor 4 in advanced-stage serous ovarian cancer," Oncol Rep., Aug. 20, 2015, 34(5):2683-2691.
Huynh, "Tyrosine kinase inhibitors to treat liver cancer," Expert Opinion, 2010, 13-26.
Hynes and Dey, "Potential for Targeting the Fibroblast Growth Factor Receptors in Breast Cancer," Cancer Res, 2010, 70:5199-5202.
ICH Harmonised Tripartite Guideline, "Specifications:Test Procedures and Acceptance Criteria for New Drug Substances and New Drug Products Chemical Substances," ICHTRRPHU, Oct. 6, 1999, 35 pages.
Ichikawa et al., "A homozygous missense mutation in human KLOTHO causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder Is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
Indian Office Action in Indian Application No. 10665/DELNP/2014, dated Jun. 25, 2018, 8 pages.
Indian Office Action in Indian Application No. 201717030265, dated Dec. 12, 2019, 5 pages.
Indian Office Action in Indian Application No. 201717030267, dated Dec. 3, 2019, 7 pages.
Indian Office Action in Indian Application No. 9781/DELNP/2015, dated Jan. 18, 2019, 6 pages.
Indonesian Office Action in Indonesian Application No. P00201507153, dated Apr. 27, 2018, 5 pages (English Translation).
Indonesian Office Action in Indonesian Application No. PID201705977, dated Jun. 5, 2020, 5 pages.
Inokuchi et al., "Therapeutic targeting of fibroblast growth factor receptors in gastric cancer," Gastroenterol Res Pract., Apr. 27, 2015, 2015:796380, 8 pages.
International Invitation to Pay Fees in International Appln. No. PCT/US2019/030633, dated Aug. 12, 2019, 5 pages.
International Preliminary Report on Patentability and Written Opinion in International Application No. PCT/US2011/066473, dated Jun. 25, 2013, 10 pages.
International Preliminary Report on Patentability in International Application No. PCT/US2013/045309, dated Dec. 24, 2014, 11 pages.

(56) References Cited

OTHER PUBLICATIONS

International Preliminary Report on Patentability in International Application No. PCT/US2013/054361, dated Feb. 19, 2015, 7 pages.
International Preliminary Report on Patentability in International Application No. PCT/US2014/034662, dated Oct. 29, 2015, 12 pages.
International Preliminary Report on Patentability in International Application No. PCT/US2015/056583, dated Apr. 25, 2017, 7 pages.
International Preliminary Report on Patentability in International Application No. PCT/US2016/018737, dated Aug. 31, 2017, 8 pages.
International Preliminary Report on Patentability in International Application No. PCT/US2016/018770, dated Aug. 22, 2017, 10 pages.
International Preliminary Report on Patentability in International Application No. PCT/US2016/018787, dated Aug. 22, 2017, 7 pages.
International Preliminary Report on Patentability in International Application No. PCT/US2018/034559, dated Nov. 26, 2019, 8 pages.
International Preliminary Report on Patentability in International Application No. PCT/US2019/030578, dated Nov. 10, 2020, 14 pages.
International Preliminary Report on Patentability in International Application No. PCT/US2019/030633, dated Nov. 10, 2020, 10 pages.
International Search Report and Written Opinion for International Application No. PCT/US2015/056583, dated Dec. 15, 2015, 10 pages.
International Search Report and Written Opinion in International Application No. PCT/US2013/045309, dated Jan. 22, 2014, 19 pages.
International Search Report and Written Opinion in International Application No. PCT/US2013/054361, dated Oct. 16, 2013, 12 pages.
International Search Report and Written Opinion in International Application No. PCT/US2014/034662, dated Oct. 24, 2014, 18 pages.
International Search Report and Written Opinion in International Application No. PCT/US2016/018737, dated Jun. 2, 2016, 12 pages.
International Search Report and Written Opinion in International Application No. PCT/US2016/018770, dated Jun. 2, 2016, 14 pages.
International Search Report and Written Opinion in International Application No. PCT/US2016/018787, dated Jun. 2, 2016, 12 pages.
International Search Report and Written Opinion in International Application No. PCT/US2018/034559, dated Mar. 8, 2019, 14 pages.
International Search Report and Written Opinion in International Application No. PCT/US2019/030578, dated Jul. 11, 2019, 26 pages.
International Search Report and Written Opinion in International Application No. PCT/US2019/030633, dated Nov. 28, 2019, 21 pages.
International Search Report and Written Opinion in International Application No. PCT/US2020/021313, dated Jun. 26, 2020, 19 pages.
International Search Report and Written Opinion in International Application No. PCT/US2020/041104, dated Sep. 4, 2020, 14 pages.
International Search Report and Written Opinion in International Application. No. PCT/US2011/066473, dated Jun. 19, 2012, 15 pages.
International Search Report and Written Opinion in International Appln. No. PCT/US2020/063038, dated Mar. 15, 2021, 16 pages.
International Search Report and Written Opinion in International Appln. No. PCT/US2020/063064, dated Feb. 12, 2021, 13 pages.
International Search Report in International Application No. PCT/US2020/053436, dated Dec. 4, 2020, 15 pages.
International Search Report in Written Opinion in International Application No. PCT/US2020/055547, dated Jan. 11, 2021, 13 pages.
International Search Report in Written Opinion in International Application No. PCT/US2021/013438, dated Apr. 20, 2021, 16 pages.
International Seach Report and Written Opinion in International Application No. PCT/US2020/055735, dated Dec. 15, 2020, 16 pages.
Invitation to Pay Additional Fees and, Where Applicable, Protest Fee in International Application No. PCT/US2013/045309, mailed Nov. 25, 2013, 5 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Israeli Office Action in Israeli Application No. 236,078 dated Mar. 21, 2017, 10 pages (English Translation).
Jackson et al., "8p11 Myeloproliferative syndrome: a review," Human Pathology, Apr. 1, 2010, 41:461-476.
Jan de Beur, "Tumoral Calcinosis: A Look into the Metabolic Mirror of Phosphate Homeostasis," The Journal of Clinical Endocrinology & Metabolism, 2005, 90: 2469-2471.
Japanese Office Action in Japanese Application No. 2015-517376, dated Feb. 21, 2017, 5 pages (with English translation).
Japanese Office Action in Japanese Application No. 2016-509131, dated Feb. 20, 2018, 5 pages (English Translation).
Japanese Office Action in Japanese Application No. 2017-543981, dated Dec. 3, 2019, 4 pages.
Japanese Office Action in Japanese Application No. 2017-544021, dated Nov. 26, 2019, 6 pages.
Japanese Office Action in Japanese Application No. 2018-228352, dated Aug. 20, 2019, 6 pages.
Javidi-Sharifi et al., "Crosstalk between KIT and FGFR3 Promotes Gastrointestinal Stromal Tumor Cell Growth and Drug Resistance," Cancer Research, Mar. 2015, 75(5): 880-892.
Jebar et al., "FGFR3 and Ras gene mutations are mutually exclusive genetic events in urothelial cell carcinoma," Oncogene, 2005, 24: 5218-5225.
Jiang et al., "miR-99a promotes proliferation targeting FGFR3 in human epithelial ovarian cancer cells," Biomedicine & Pharmacotherapy, 2014, 68: 163-169.
Ji et al., "Embase abstract: Modeling and simulation as gating for clinical pharmacology studies of INCB054828," 119th Annual Meeting of the American Society for Clinical Pharmacology and Therapeutics, Mar. 1, 2018, 2 pages.
Johnson et al., "Pharmacological and Functional Comparison of the Polo-like Kinase Family: Insight into Inhibitor and Substrate Specificity," Biochemistry, 2007, 46: 9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Jordan, "Tamoxifen: A Most Unlikely Pioneering Medicine," Nature Reviews: Drug Discovery, Mar. 2003, 2:205-213.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.
Kassack et al., "Structure-activity relationships of analogues of NF449 confirm NF449 as the most potent and selective known $P2X_1$ receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.

(56) References Cited

OTHER PUBLICATIONS

Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kerekes et. al., "Aurora kinase inhibitors based on the imidazo[1,2-a]pyrazine core: fluorine and deuterium incorporation improve oral absorption and exposure," J Med Chem., 2011, 54(1):201-210.
Khojasteh et al., "Chemical inhibitors of cytochrome P450 isoforms in human liver microsomes: a re-evaluation of P450 isoform selectivity," Eur J Drug Metab Pharmacokinet., Mar. 2011, 36:1-16.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.
Kim et al., "The design, synthesis, and biological evaluation of potent receptor tyrosine kinase inhibitors," Bioorganic & Medicinal Chemistry Letters, 2012, 4979-4985.
Klein et al., "FGFR1 Kinase Inhibitors: Close Regioisomers Adopt Divergent Binding Modes and Display Distinct Biophysical Signatures," American Chemical Society, 2014, 166-171.
Knights and Cook, "De-regulated FGF receptors as therapeutic targets in cancer," Pharmacology & Therapeutics, 2010, 125:105-117.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS One, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Korean Office Action in Korean Application No. 10-2015-7000701, dated Aug. 26, 2019, 19 pages.
Korean Office Action in Korean Application No. 10-2015-7032502, dated Sep. 9, 2020, 16 pages.
Korean Office Action in Korean Application No. 10-2020-7021884, dated Oct. 28, 2020, 15 pages.
Kotha et al., "Recent applications of the Suzuki-Miyaura cross-coupling reaction in organic synthesis," Tetrahedron, 2002, 58:9633-9695.
Koziczak and Hynes, "Cooperation between Fibroblast Growth Factor Receptor-4 and ErbB2 in Regulation of CyclinD1 Translation," The Journal of Biological Chemistry, 2004, 279(48): 50004-50011.
Koziczak et al., "Blocking of FGFR signaling inhibits breast cancer cell proliferation through downregulation of D-type cyclins," Oncogene, 2004, 23:3501-3508.
Krejci et al., "Molecular pathology of the fibroblast growth factor family," Hum Mutat, Sep. 2009, 30(9): 1245-1255.
Krejci et al., "NF449 Is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kuroso et al., "Immunohistochemical Detection of Fibroblast Growth Factor Receptor 3 in Human Breast Cancer: Correlation with Clinicopathological/Molecular Parameteres and Prognosis," Pathobiology, Mar. 2010, 77: 231-240.
Kurosu et al., "Regulation of Fibroblast Growth Factor-23 Signaling by Klotho," The Journal of Biological Chemistry, Mar. 2006, 281(10): 6120-6123.
Lala et al., "Role of nitric oxide in tumor progression: Lessons from experimental tumors," Cancer and Metastasis Reviews, 1998, 17: 91-106.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Lamont et al., "Small molecule FGF receptor inhibitors block FGFR-dependent urothelial carcinoma growth in vitro and in vivo," Br. J Cancer, 2011, 104:75-82.
Le Corre et al., "Synthesis and biological evaluation of a triazole-based library of pyrido[2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.
L'Hote and Knowles, "Cell responses to FGFR3 signalling: growth, differentiation and apoptosis," Experimental Cell Research, 2005, 417-431.
Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liang et al., "Anticancer molecules targeting fibroblast growth factor receptors," Cell Press, 2012, 11 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.
Liu et al., "Pathogenic role of Fgf23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Luo et al., "Deficiency of metabolic regulator FGFR4 delays breast cancer progression through systemic and microenvironmental metabolic alterations," Cancer & Metabolism, 2013, 20 pages.
Maeda et al., "Transforming property of TEL-FGFR3 mediated through PI3-K in a T-cell lymphoma that subsequently progressed to AML," Blood, Mar. 2005, 105(5): 2115-2123.
Malaysian Office Action in Malaysian Application No. 2014003396, dated Dec. 15, 2017, 4 pages.
Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Marfe and Stefano, "in vitro Anti-leukaemia Activity of Pyrrolo[1,2-b][1,2,5]benzothiadiaze-pines (PBTDs)," Recent Patents on Anti-Cancer Drug Discovery, 2010, 58-68.
Marks et al., "Mutational Analysis of EGFR and Related Signaling Pathway Genes in Lung Adenocarcinomas Identifies a Novel Somatic Kinase Domain Mutation in FGFR4," PLoS One, May 9, 2007, 2:e426.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
Martino et al., "Mutant fibroblast growth factor receptor 3 induces intracellular signaling and cellular transformation in a cell type- and mutation-specific manner," Oncogene, 2009, 28: 4306-4316.

(56) References Cited

OTHER PUBLICATIONS

Matsuda et al., "Fibroblast Growth Factor Receptor 2 IIIc as a Therapeutic Target for Colorectal Cancer Cells," Mol Cancer Ther., 2012, 52 pages.
McConkey et al., "Molecular genetics of bladder cancer: Emerging mechanisms of tumor initiation and progression," Urologic Oncology: Seminars and Original Investigations, 2010, 429-440.
McMahon, "VEGF Receptor Signaling in Tumor Angiogenesis," Oncologist, 2000, 5(suppl 1):3-10.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5): 566-570.
Metzner, "Fibroblast Growth Factor Receptors as Therapeutic Targets in Human Melanoma: Synergism with BRAF Inhibition," J Investigative Dermatol., 2011, 131:2087-2095.
Mexican Office Action in Mexican Application No. MX/a/2014/015192, dated Jan. 24, 2018, 6 pages.
Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and $G_1/G_0$ Arrest," The Journal of Pharmacology and Experimental Therapeutics, 2010, 332(3):795-802.
Mohammadi et al., "Crystal structure of an angiogenesis inhibitor bound to the FGF receptor tyrosine kinase domain," The EMBO Journal, 1998, 5896-5904.
Mohammadi et al., "Structures of the Tyrosine Kinase Domain of Fibroblast Growth Factor Receptor in Complex with Inhibitors," Science, May 1997, 276:955-960.
Murphy et al., "Evidence for distinct alterations in the FGF axis in prostate cancer progression to an aggressive clinical phenotype," J Pathol., 2010, 220:452-460.
Naito et al., "Progressive tumoral calcinosis as the presenting feature of sarcoidosis in a patient on haemodialysis treatment," Nephrol Dial Transplant, 1999, 14:2716-2719.
Nakatani et al., "In vivo genetic evidence for klotho-dependent, fibroblast growth factor 23 (Fgf23)-mediated regulation of systemic phosphate homeostasis," The FASEB Journal, Feb. 2009, 23:433-441.
Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.
Neidle et al., "Failure Modes in the Discovery Process," Cancer Drug Design, 2008, pp. 427-431.
New Zealand Examination Report in New Zealand Application No. 743274, dated Jul. 18, 2018, 4 pages.
New Zealand Office Action in New Zealand Application No. 702747, dated Mar. 8, 2019, 2 pages.
New Zealand Office Action in New Zealand Application No. 702747, dated Sep. 16, 2016, 3 pages.
New Zealand Office Action in New Zealand Application No. 713074, dated Feb. 18, 2020, 3 pages.
New Zealand Office Action in New Zealand Application No. 743274, dated Jul. 19, 2018, 5 pages.
New Zealand Office Action in New Zealand Application No. 752422, dated Feb. 18, 2020, 2 pages.
Nitta, "Relationship between Fibroblast Growth Factor-23 and Mineral Metabolism in Chronic Kidney Disease," International Journal of Nephrology, 2010, 1-7.
Nomura et al., "FGF10/FGFR20 signal induces cell migration and invasion in pancreatic cancer," Br. J Cancer, 2008, 99:305-313.
Norman et al., "Protein-Ligand Crystal Structures Can Guide the Design of Selective Inhibitors of the FGFR Tyrosine Kinase," J. Med. Chem., 2012, 55(11):5003-5012.
Novelli, "Fosrenol (TM) reduces damaging high levels of phosphate in end-stage kidney disease patients," EurekAlert!, Nov. 2, 2002 [retrieved on Dec. 1, 2020], retrieved from URL <https://www.eurekalert.org/pub_releases/2002-11/pn-fr110202.php>, 4 pages.
Office Action from the Intellectual Property Office of the Philippines in Application No. 1-2014-502772, dated Mar. 17, 2016, 3 pages.
Ornitz et al., "Receptor Specificity of the Fibroblast Growth Factor Family," The Journal of Biological Chemistry, 1996, 271(25): 15292-15297.
Pai et al., "Antibody-Mediated Inhibition of Fibroblast Growth Factor 19 Results in Increased Bile Acids Synthesis and lleal Malabsortion of Bile Acides in Cynomolgus Monkeys," Toxicological Sciences, 2012, 126(2): 446-456.
Pan et al., "MK-2461, a Novel Multitargeted Kinase Inhibitor, Preferentially Inhibits the Activated c-Met Receptor," Cancer Res, Feb. 2010, 1524-1533.
Pandith et al., "Oncogenic role of fibroblast growth factor receptor 3 in tumorigenesis of urinary bladder cancer," Urologic Oncology: Seminars and Original Investigations, 2010, 1-9.
Pandith et al., "Oncogenic role of fibroblast growth factor receptor 3 in tumorigenesis of urinary bladder cancer," Urologic Oncology: Seminars and Original Investigations, 2013, 31: 398-406.
Pardo et al., "The Fibroblast Growth Factor Receptor Inhibitor PD173074 Blocks Small Cell Lung Cancer Growth In vitro and In vivo," Cancer Res, Nov. 2009, 8645-8651.
Paterson et al., "Preclinical studies of fibroblast growth factor receptor 3 as a therapeutic target in multiple myeloma," British Journal of Haematology, 2004, 124:595-603.
Peruvian Office Action in Peruvian Application No. 1424, dated Mar. 12, 2021, 13 pages.
Peruvian Office Action in Peruvian Application No. 1429, dated Mar. 19, 2021, 12 pages.
Peruvian Office Action in Peruvian Application No. 2433, dated Nov. 27, 2018, 13 pages.
Philippine Office Action in Philippine Application No. 1/2017/501483, dated Dec. 12, 2019, 5 pages.
Philippine Office Action in Philippine Application No. 1-2017-501481, dated Oct. 29, 2019, 4 pages.
Philippine Office Action in Philippine Application No. 1/2015/502383, dated Jul. 8, 2019, 7 pages.
Philippine Office Action in the Philippine Application No. 1/2017/501483, dated Aug. 31, 2020, 4 pages.
Piazza et al., "Towards a new age in the treatment of multiple myeloma," Ann Hematol, 2007, 86:159-172.
Pinedo and Slamon, "Translational Research: The Role of VEGF in Tumor Angiogenesis," Oncologist, 2000, 5(suppl 1):1-2.
Piro et al., "An FGFR3 Autocrine Loop Sustains Acquired Resistance to Trastuzumab in Gastric Cancer Patients," Clinical Cancer Research, Dec. 2016, 22(24): 6164-6175.
Platt et al., "Spectrum of Phosphatidylinositol 3-Kinase Pathway Gene Alterations in Bladder Cancer," Clin Cancer Res, Oct. 2009, 6008-6017.
Pliarchopoulou et al., "Current chemotherapeutic options for the treatment of advanced bladder cancer: A review," Urologic Oncology: Seminars and Original Investigations, 2010, 1-9.
Plowright et al., "Ectopic expression of fibroblast growth factor receptor 3 promotes myeloma cell proliferation and prevents apoptosis," Blood, Feb. 2000, 95(3): 992-998.
Podar et al., "Emerging therapies for multiple myeloma," Expert Opin. Emerging Drugs, 2009, 14(1):9-127.
Podar et al., "Targeting signalling pathways for the treatment of multiple myeloma," Expert Opin. Ther. Targets, 2005, 359-381.
Pollett et al., "Overexpression of the myeloma-associated oncogene fibroblast growth factor receptor 3 confers dexamethasone resistance," Blood, Nov. 2002, 100(10): 3819-3821.
Pollock et al., "Frequent activating FGFR2 mutations in endometrial carcinomas parallel germline mutations associated with craniosynostosis and skeletal dysplasia syndromes," Oncogene, 2007, 26:7158-7162.

(56) References Cited

OTHER PUBLICATIONS

Propper et al., "Phase I and Pharmacokinetic Study of PKC412, an Inhibitor of Protein Kinase C," J Clin Oncol, 2001, 19(5):1485-1492.
Qian et al., "Targeting Tumor Angiogenesis with Histone Deacetylase Inhibitors: the Hydroxamic Acid Derivative LBH589," Clin Cancer Res, Jan. 2006, 634-642.
Qing et al., "Antibody-based targeting of FGFR3 in bladder carcinoma and t(4;14)-positive multiple myeloma in mice," The Journal of Clinical Investigation, May 2009, 119(5): 1216-1229.
Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.
Qiu et al., "Over-expression of fibroblast growth factor receptor 3 in human hepatocellular carcinoma," World J Gastroenterol, 2005, 11(34): 5266-5272.
Raab et al., "Multiple myeloma," Lancet, 2009, 374: 324-339.
Ravindranathan et al., "Discovery of Novel Fibroblast Growth Factor Receptor 1 Kinase Inhibitors by Structure-Based Virtual Screening," J. Med. Chem., 2010, 53: 1662-1672.
Razzaque, "FGF23-mediated regulation of systemic phosphate homeostasis: is Klotho an essential player?," Am J Physiol Renal Physiol, 2009, 470-476.
Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.
Reis-Filho et al., "FGFR1 Emerges as a Potential Therapeutic Target for Lobular Breast Carcinomas," Clin Cancer Res, Nov. 2006, 6652-6662.
Reiter et al., "Consistent Fusion of ZNF198 to the Fibroblast Growth Factor Receptor-1 in the t(8;13)(p11;q12) Myeloproliferative Syndrome," Blood, Sep. 1998, 92(5): 1735-1742.
Remington, "The Science and Practice of Pharmacy," Lippincott Williams & Wilkins, 2005, 21st edition *************Too voluminous to provide***********.
Remington's Pharmaceutical Sciences, 17th ed., Mack Publishing Company, Easton, Pa., 1985, p. 1418*.
Renhowe et al., "Design, Structure—Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.
Ribatti et al., "The discovery of basic fibroblast growth factor/fibroblast growth factor-2 and its role in haematological malignancies," Cytokine & Growth Factor Reviews, 2007, 18: 327-334.
Ribatti, "Tyrosine Kinase Inhibitors as Antiangiogenic Drugs in Multiple Myeloma," Pharmaceuticals, 2010, 3: 1225-1231.
Roidl et al., "Resistance to Chemotherapy Is Associated with Fibroblast Growth Factor Receptor 4 Up-Regulation," Clin Cancer Res, Mar. 2009, 2058-2066.
Ronchetti et al., "Deregulated FGFR3 mutants in multiple myeloma cell lines with t(4;14): comparative analysis of Y373C, K650E and the novel G384D mutations," Oncogene, 2001, 20: 3553-3562.
Roumiantsev et al., "Distinct stem cell myeloproliferative/T lymphoma syndromes induced by ZNF198-FGFR1 and BCR-FGFR1 fusion genes from 8p11 translocations," Cancer Cell, Mar. 2004, 5: 287-298.
Rowe et al., "Handbook of Pharmaceutical Additives," The Pharmaceutical Press and the American Pharmaceutical Association, 2009, 3rd ed., *************Too voluminous to provide***********.
Rowe et al., "Handbook of Pharmaceutical Excipients," The Pharmaceutical Press and the American Pharmaceutical Association, 2009, 6th Edition, 917 pages.
Ryan et al., "Toxicologic Pathology of Unique Biotechnology Agents and Biotherapies," Toxicologic Pathology, 1999, 27(1): 78-86.
Sakurai et al., "A novel angiogenesis inhibitor, Ki23057, is useful for preventing the progression of colon cancer and the spreading of cancer cells to the liver," European Journal of Cancer, 2007, 2612-2620.
Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.
Saxty et al., "Fragment-based drug discovery of selective inhibitors of fibroblast growth factor receptor (FGFr)," Cancer Res, Apr. 15, 2010, 70, 5778.
Schenone et al., "Small Molecules ATP-Comptetitive Inhibitors of FLT3: A Chemical Overview," Current Medicinal Chemistry, 2008, 15(29): 3113-3132.
Schlapbach et al., "A novel Pd-catalyzed cyclization rection of ureas for the synthesis of dihydroquinazolinone p38 kinase inhibitors," Bioorg. Med. Chem. Lett., 2004, 357-360.
Science IP Order 3032627, Chemical Structure Search, Science IP, Apr. 2012, 78 pages.
Science IP Order 3101926, Chemical Structure Search, Science IP, Jan. 2015, 50 pages.
Science IP Order 3101983, Chemical Structure Search, Science IP, Jan. 2015, 70 pages.
Science IP Order 3104564, Patent Chemical Structure Search, Science IP, Mar. 2015, 90 pages.
Science IP Order 3104565, Patent Chemical Structure Search, Science IP, Mar. 2015, 521 pages.
Segev et al., "Restrained chondrocyte proliferation and maturation with abnormal growth plate vascularization and ossification in human FRFR-3$^{G380R}$ transgenic mice," Human Molecular Genetics, 2000, 9(2): 249-258.
Seitzer et al., "A single nucleotide change in the mouse genome accelerates breast cancer progression," Cancer Res., Jan. 2010, 70(2):802-812.
Shariat et al., "Association of Angiogenesis Related Markers With Bladder Cancer Outcomes and Other Molecular Markers," The Journal of Urology, May 2010, 183: 1744-1750.
Sharkey et al., "PKC412 demonstrates JNK-dependent activity against human multiple myeloma cells," Blood, Feb. 2007, 109(4): 1712-1719.
Shi et al., "High Expression of FGFR4 Enhances Tumor Growth and Metastasis in Nasopharyngeal Carcinoma," Journal of Cancer, 2015, 6(12): 1245-1254.
Shinya et al., "Fgf signalling through MAPK cascade is required for development of the subpallial telencephalon in zebrafish embryos," Development, 2001, 4153-4164.
sigmaaldrich.com, "4-Chloro-1H-pyrrolo[2,3-b]pyridine-5-carbaldehyde," CAS # 958230-19-8, [retrieved on Feb. 4, 2021] retrieved from URL <https://www.sigmaaldrich.com/catalog/product/aldrich/ade000976?lang=en®ion=US>, 2 pages.
Singh et al., "Transforming Fusions of FGFR and TACC Genes in Human Glioblastoma," Science, Sep. 2012, 337:1231-1235.
Slavin et al., "Familial Tumoral Calcinosis," The American Journal of Surgican Pathology, 1993, 17(8): 188-802.
Smith et al., "Circulating αKlotho influences phosphate handling by controlling FGF23 production," The Journal of Clinical Investigation, Dec. 2012, 122(12): 4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptor 3-lllc mediates colorectal cancer growth and migration," British Journal of Cancer, 2010, 1-12.
Soria, "FGFR inhibition overview of clinical development programs," Presentation, presented at TAT in Washington DC on Mar. 5-7, 2014, 54 pages.
Soverini et al., "Novel mutation and RNA splice variant of fibroblast growth factor receptor 3 in multiple myeloma patients at diagnosis," Haematologica, 2002, 87: 1036-1040.
Specktor et al., "Hyperphosphatemic familial tumoral calcinosis caused by a mutation in GALNT3 in a European kindred," J Hum Genet, 2006, 51:487-490.

(56) References Cited

OTHER PUBLICATIONS

Squires et al., "Development of inhibitors of the fibroblast growth factor receptor (FGFR) kinase using a fragment based approach," Cancer Res 70, Apr. 15, 2010, 3626.
Squires et al., "Development of inhibitors of the fibroblast growth factor receptor (FGFR) kinase using a fragment based approach," Cancer Res, 2008, 1 page.
STN International Search Report for CAS RN 2380276-25-3, dated Nov. 20, 2019, 11 pages.
STN Search Report dated Jan. 6, 2020, 88 pages.
STN Search Report, dated Sep. 11, 2019, 31 pages.
Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases," J. Med. Chem., 2000, 43: 2655-2663.
Sun et al., "Synthesis and Biological Evaluations of 3-Substituated Indolin-2-ones: A Novel Class of Tyrosine Kinase Inhibitors That Exhibit Selectivity toward Particular Receptor Tyrosine Kinases," J. Med. Chem., 1998, 41: 2588-2603.
Surry et al., "Dialkylbiaryl Phosphines in Pd-Catalyzed Amination: A User's Guide," Chem Sci., 2011, 2(1):27-50.
Taiwan Office Action in Taiwan Application No. 103114284, dated Apr. 9, 2018, 4 pages (English Search Report).
Taiwan Office Action in Taiwan Application No. 105104993, dated Feb. 11, 2020, 9 pages.
Taiwan Office Action in Taiwan Application No. 105105018, dated Oct. 22, 2019, 7 pages.
Taiwan Office Action in Taiwan Application No. 107146498, dated Dec. 19, 2019, 7 pages.
Taiwanese Office Action in Taiwan Application No. 102120946, dated Nov. 9, 2016, 9 pages (with English translation).
Taiwanese Office Action in Taiwanese Application No. 102120946, dated Jul. 13, 2017, 7 pages (English Translation).
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Takii et al., "Serotonin Derivative, N-(p-Coumaroyl)serotonin, Isolated from Safflower (*Carthamus tinctorius* L.) Oil Cake Augments the Proliferation of Normal Human and Mouse Fibroblasts in Synergy with Basic Fibroblast Growth Factor (bFGF) or Epidermal Growth Factor (EGF)", J Biochem., 1995, 125(5):910-915.
Tan et al., "Development of covalent inhibitors that can overcome resistance to first-generation FGFR kinase inhibitors," PNAS, Oct. 2014, E4869-E4877.
Tang et al., "Role of fibroblast growth factor receptor 4 in cancer," Cancer Science, Oct. 2018, 109(10):3024-3031.
Taylor et al., "Identification of FGFR4-activating mutations in human rhabdomyasarcomas that promote metastasis in xenotransplanted models," J Clin Invest., Nov. 2009, 119(11):3395-3407.
Taylor, "Inhibitor PD-173074 Bound to the Tyrosine Kinase Domain of FGFR 1," Molecular & Behavioral Neuroscience Institute , Feb. 2006, 1 page.
Taylor, "Inhibitor SU-5402 Bound to the Tyrosine Kinase Domain of FGFR 1," Molecular & Behavioral Neuroscience Institute , Apr. 2006, 1 page.
Terai et al., "Vascular calcification and secondary hyperparathyroidism of severe chronic kidney disease and its relation to serum phosphate and calcium levels," British Journal of Pharmacology, 2009, 156: 1267-1278.
Thai Office Action in Thai Application No. 1401007417, dated Jun. 5, 2016, 7 pages (with English translation).
The Cancer Genome Atlas Research Network, "Comprehensive molecular characterization of urothelial bladder carcinoma," Nature, 2014, 507: 315-22.
Thome and Weil, "Post-translational modifications regulate distinct functions of CARMA1 and BCL10," Trends in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.
Thompson et al., "Photochemical Preparation of a Pyridone Containing Tetracycle: A Jak Protein Kinase Inhibitor," Bioorganic & Medicinal Chemistry Letters 12:1219-1223, 2002.
Thompson et al., "Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Thussbas et al., "FGFR4 Arg388 Allele Is Associated With Resistance to Adjuvant Therapy in Primary Breast Cancer," J. Clin. Oncol., Aug. 10, 2006, 23:3747-3755.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.
Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al., "Inhibition of fibroblast growth factor receptor 3 induces differentiation and apoptosis in t(4;14) myeloma," Blood, May 2004, 103(9):3521-3528.
Trudel et al., "The inhibitory anti-FGFR3 antibody, PRO-001, is cytotoxic to t(4;14) multiple myeloma cells," Blood, May 2006, 107(10): 4039-4046.
Trudel, "CHIR-258, a Novel Multi-targeted Tyrosine Kinaselnhibitor, for the Treatment of t(4;14) Multiple Myeloma," Presentation, Presented at International Myeloma Foundation, Apr. 2005, 18 pages.
Turkington et al., "Fibroblast growth factor receptor 4 (FGFR4): a targetable regulator of drug resistance in colorectal cancer," Cell Death Dis., Feb. 6, 2014, 5:e1046.
Turner and Grose, "Fibroblast growth factor signalling: from development to cancer," Nature Reviews Cancer, 2010, 10:116-129.
Turner et al., "FGFR1 Amplification Drives Endocrine Therapy Resistance and Is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.
Ueno et al., "Enhanced Expression of Fibroblast Growth Factor Receptor 3 IIIc Promotes Human Esophageal Carcinoma Cell Proliferation," Journal of Histochemistry & Cytochemistry, 2016, 64(1):7-17.
Ukraine Office Action in Ukraine Application No. a201500191, dated Dec. 13, 2016, 10 pages (with English translation).
Ukraine Office Action in Ukraine Application No. a201511370, dated Nov. 12, 2018, 6 pages (with English translation).

(56) References Cited

OTHER PUBLICATIONS

Ukraine Office Action in Ukraine Application No. a201709220, dated Dec. 9, 2019, 11 pages.
Ukraine Office Action in Ukraine Application No. a201801562, dated Jul. 28, 2021, 9 pages.
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
Van Oers et al., "FGFR3 Mutations Indicate Better Survival in Invasive Upper Urinary Tract and Bladder Tumours," European Urology, 2009, 650-658.
Våtsveen et al., "FGFR3 is expressed and is important for survival in INA-6, a human myeloma cell line without a t(4;14)," Eur. J. Haematol., 83:5, Jul. 6, 2009, 471-476.
Verstovsek et al., "Interim Results from Fight-203, a Phase 2, Open-Label, Multicenter Study Evaluating the Efficacy and Safety of Pemigatinib (INCB054828) in Patients with Myeloid/Lymphoid Neoplasms with Rearrangement of Fibroblast Growth Factor Receptor 1 (FGFR1)," Blood, Nov. 29, 2018, retrieved from URL <https://ashpublications.org/blood/article/132/Supplement%201/690/266005/Interim-Results-from-Fight203-a-Phase-2-0penLabel>, 132(Supplement 1):690.
Vietnamese Office Action in Vietnamese Application No. 1-2015-00102, dated Mar. 18, 2015, 4 pages.
Vogt et al., "FGF23 and phosphate cardiovascular toxins in ckd," Toxins, Nov. 6, 2019, 11(11):647.
Von Massenhausen et al., "Evaluation of FGFR3 as a Therapeutic Target in Head and Neck Squamous Cell Carcinoma," Targ. Oncol., 2016, 11: 631-642.
Walsky and Obach, "Validated assays for human cytochrome P450 activities," Drug Metab Dispos., 2004, 32(6):647-660.
Walsky et al., "Evaluation of 227 drugs for in vitro inhibition of cytochrome P450 2B6," J Clin Pharmacol., Dec. 2006, 46(12):1426-1438.
Wang and Becker, "Antisense targeting of basic fibroblast growth factor and fibroblast growth factor receptor-1 in human melanomas blocks intratumoral angiogenesis and tumor growth," Nature Medicine, Aug. 1997, 887-893.
Wang and Ding, "Fibroblast growth factor receptors in breast cancer," Tumor Biology, May 2017, 1-10.
Wang et al., "The fibroblast growth factor receptor-4 Arg388 allele is associated with prostate cancer initiation and progression," Clin Cancer Res. 2004, 10:6169-6178.
Ware et al., "Rapidly Acquired Resistance to EFGR Tyrosine Kinase Inhibitors in NSCLC Cell Lines through De-Repression of FGFR2 and FGFR3 Expression," PLoS, Nov. 2010, 5(11): 1-9.
Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.
Williams et al., "Oncogenic FGFR3 gene fusions in bladder cancer," Hum Mol Genet, 2013, 22:795-803.
Wu, "Urothelial Tumorigenesis: A Tale Of Divergent Pathways," Nature Reviews, Sep. 2005, 5:713-725.
Wuts et al., "Greene's Protective Groups in Organic Synthesis," 4th Ed., 2006, Chapter 7, 696-926.
Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFR1 on cell proliferation, survival, and migration in a 3D mammary epithelial cell model," JCB, 2005, 171(4): 663-673.
Xin et al., "CHIR-258 Is Efficacious in A Newly Developed Fibroblast Growth Factor Receptor 3-Expressing Orthotopic Multiple Myeloma Model in Mice," Clin Cancer Res, Aug. 2006, 4908-4915.
Xu et al., "Fibroblast growth factor receptor 4 promotes progression and correlates to poor prognosis in cholangiocarcinoma," Biochemical and Biophysical Research Communications, 2014, 446: 54-60.
Xu et. al. "Design, synthesis and biological evaluation of deuterated nintedanib for improving pharmacokinetic properties," J Label Compd Radiopharm., 2015, 58(7):308-312.
Ying et al., "Genome-wide screening for genetic alterations in esophageal cancer by aCGH identifies 11q13 amplification oncogenes associated with nodal metastasis," PLoS One, Jun. 25, 2012, 7:e39797.
Yu et al., "Analysis of the Biochemical Mechanisms for the Endocrine Actions of Fibroblast Growth Factor-23," Endocrinology, Nov. 2005, 146(11): 4647-4656.
Yu et al., "FGFR-4 Arg(3)(8)(8) enhances prostate cancer progression via extracellular signal-related kinase and serum response factor signaling," Clin Cancer Res., Jul. 2011, 17:4355-4366.
Zaid et al., "Identification of FGFR4 as a Potential Therapeutic Target for Advanced-Stage, High-Grade Serous Ovarian Cancer," Clin Cancer Res, 2013, 19(4): 809-820.
Zhang et al., "AZD4547, a potent and selective FGF-receptor inhibitor induces tumor regressions in a human primary model of FGF-receptor 2 amplified gastric cancer and is efficacious in combination with chemotherapy," 2012, AstraZeneca, 1 page.
Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.
Zhang et al., "Enhanced FGFR signalling predisposes pancreatic cancer to the effect of a potent FGFR inhibitor in preclinical models," British Journal of Cancer, 2014, 110: 320-329.
Zhang et al., "FP-1039 (FGFR1:Fc), A Soluble FGFR1 Receptor Antagonist, Inhibits Tumor Growth and Angiogenesis," Mol Cancer Ther, 6, Nov. 2007, B55.
Zhang et al., "Predicting Drug-Drug Interactions: An FDA Perspective," The AAPS Journal, May 6, 2009, 11(2):300-306.
Zhang et al., "Recent progress in therapeutic and diagnostic applications of lanthanides," Mini-Reviews in Medicinal Chemistry, 2011, 11(8):678-694.
Zhang et al., "Receptor Specificity of the Fibroblast Growth Factor Family," Journal of Biological Chemistry, Jun. 2006, 281(23): 15694-15700.
Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.
Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.
Zhao et al., "Homozygous Deletions and Chromosome Amplifications in Human Lung Carcinomas Revealed by Single Nucleotide Polymorphism Array Analysis," Cancer Res, Jul. 2005, 5561-5570.
Zhou et al., "A Structure-Guided Approach to Creating Covalent FGFR Inhibitors," Chemistry and Biology, Mar. 2010, 285-295.
Zhu et al., "Fibroblast growth factor receptor 3 inhibition by short hairpin RNAs leads to apoptosis in multiple myeloma," Mol Cancer Ther, May 2005, 787-798.
Zieger et al., "Role of Activating Fibroblast Growth Factor Receptor 3 Mutations in the Development of Bladder Tumors," Clin Cancer Res, Nov. 2005, 7709-7719.
Zingone et al., "Ectopic expression of wild-type FGFR3 cooperates with MYC to accelerate development of B-cell lineage neoplasms," Leukemia, 2010, 1171-1178.
Australian Office Action in Australian Application No. 2018272013, dated Sep. 2, 2021, 4 pages.
Australian Office Action in Australian Application No. 2020250211, dated Sep. 13, 2021, 4 pages.
Australian Office Action in Australian Application No. 2020270520, dated Dec. 16, 2021, 4 pages.

(56) References Cited

OTHER PUBLICATIONS

Australian Allowance in Australian Application No. 2020250201, dated Jun. 23, 2022, 4 pages.
Balek, L., "ARQ 087 inhibits FGFR signaling and rescues aberrant cell proliferation and differentiation in experimental models of craniosynostoses and chondrodysplasias caused by activating mutations in FGFR1, FGFR2 and FGFR3," Bone, Dec. 2017, 105:57-66.
Bauer, "Pharmaceutical Solids—The Amorphous Phase", Journal of Validation Technology, 2009, 15(3):63-68.
Byrn et al., "Pharmacautical Solids: A Strategic Approach to Regulatory Considerations," Pharmaceutical Research., Jul. 1995, 12(7):945-954.
Casey et al., "Translating in vivo metabolomic analysis of succinate dehydrogenase deficient tumours into clinical utility," JCO Precis Oncol., Mar. 29, 2018, 2:1-12.
Canada Office Action in Canada Application No. 2,976,788, dated Apr. 7, 2022, 4 pages.
Canada Office Action in Canada Application No. 2,976,790, dated Apr. 25, 2022, 4 pages.
Chilean Office Action in Chilean Application No. 3439-2019, dated Jan. 31, 2022, 15 pages.
Chilean Office Action in Chilean Application No. 2848-2020, dated Mar. 7, 2022, 23 pages.
Chilean Office Action in Chilean Application No. 2839-2020, dated Jan. 31, 2022, 42 pages (with English translation).
Chinese Office Action in Chinese Application No. 201910023729.3, dated Sep. 8, 2021, 11 pages.
Chinese Office Action in Chinese Application No. 201910023729.3, dated Mar. 23, 2022, 11 pages.
Colombian Office Action in Colombian Application No. NC2019/0014699, dated Jun. 6, 2022, 31 pages.
Ecuador Office Action in Ecuador Application No. IEPI-2015-1225, dated May 11, 2022, 18 pages.
Ecuador Office Action in Ecuador Application No. IEPI-2015-1225, dated Dec. 30, 2021, 21 pages.
Ecuador Opposition in Ecuador Application No. SENADI-2020-78226, dated Jun. 2022, 19 pages.
Ecuador Opposition in Ecuador Application No. SENADI-2020-78230, dated Jun. 2022, 21 pages.
Eurasian Office Action in Eurasian Application No. 201992794, dated Sep. 17, 2021, 7 pages.
Eurasian Office Action in Eurasian Application No. 202190877, dated Oct. 6, 2021, 4 pages.
Eurasian Office Action in Eurasian Application No. 202092648, dated Feb. 8, 2022, 7 pages.
Eurasian Office Action in Eurasian Application No. 202091923, dated Apr. 5, 2022, 4 pages.
Eurasian Office Action in Eurasian Application No. 202092649/26, dated Apr. 22, 2022, 6 pages.
European Office Action in European Application No. 19724676.2, dated Aug. 26, 2021, 5 pages.
European Office Action in European Application No. 19724670.5, dated Nov. 9, 2021, 4 pages.
Ezzat et al., "Dual Inhibition of RET and FGFR4 Restrains Medullary Thyroid Cancer Cell Growth," Clinical Cancer Research, 2005, 11:1336-1341.
Goyal et al,. "Polyclonal Secondary FGFR2 Mutations Drive Acquired Resistance to FGFR Inhibition in Patients with FGFR2 Fusion-Positive Cholangiocarcinoma," Cancer Discov., 2016, 7(3):252-263.
Indian Office Action in Indian Application No. 202017052609, dated May 23, 2022, 7 pages.
Indian Office Action in Indian Application No. 202017052853, dated May 13, 2022, 6 pages.
Indian Oral Hearing in Indian Application No. 201717030265, dated Jan. 13, 2022, 2 pages.
International Preliminary Report on Patentability in International Application No. PCT/US2020/021313, dated Aug. 25, 2021, 11 pages.
International Preliminary Report on Patentability in International Application No. PCT/US2020/041104, dated Jan. 11, 2022, 7 pages.
International Preliminary Report on Patentability in International Application No. PCT/US2020/053436, dated Apr. 5, 2022, 8 pages.
International Preliminary Report on Patentability in International Application No. PCT/US2020/055735, dated Apr. 19, 2022, 8 pages.
International Preliminary Report on Patentability in International Application No. PCT/US2020/055547, dated Apr. 19, 2022, 7 pages.
International Preliminary Report on Patentability in International Application No. PCT/US2020/063038, dated Jun. 16, 2022, 8 pages.
International Preliminary Report on Patentability in International Application No. PCT/US2020/063064, dated May 17, 2022, 7 pages.
Israeli Office Action in Israeli Application No. 289834 dated Jul. 14, 2022, 4 pages.
Japanese Office Action in Japanese Application No. 2020-069604, dated Nov. 15, 2021, 7 pages.
Japanese Office Action in Japanese Application No. 2020-093529, dated Mar. 1, 2022, 5 pages.
Japanese Office Action in Japanese Application No. 2019-565177, dated May 13, 2022, 11 pages.
Korean Office Action in Korean Application No. 10-2021-7018897, dated Oct. 1, 2021, 15 pages.
Korean Office Action in Korean Application No. 10-2020-7021884, dated Oct. 25, 2021, 6 pages.
Mexican Office Action in Mexican Application No. MX/a/2019/014097, dated Mar. 15, 2022, 12 pages.
Philippine Office Action in Philippine Application No. 1/2015/502383, dated Nov. 11, 2021, 4 pages.
Philippine Office Action in Philippine Application No. 1/2019/502810, dated Dec. 7, 2021, 4 pages.
Philippine Allowance in Philippine Application No. 1/2015/502383, dated Jun. 6, 2022, 2 pages.
Staerk et al., "Pan-Src Family Kinase Inhibitors Replace Sox2 during the Direct Reprogramming of Somatic Cells," Angewandte Chem., Jun. 14, 2011, 50(25):5734-5736.
Taiwan Office Action in Taiwan Application No. 109132389, dated Aug. 23, 2021, 4 pages.
Ukraine Office Action in Ukraine Application No. a 2019 12195, dated Nov. 11, 2021, 7 pages.
Ye et al., "Combination of the FGFR4 inhibitor PD173074 and 5-fluorouracil reduces proliferation and promotes apoptosis in gastric cancer," Oncol Rep., Dec. 2013, 30(6):2777-2784.
Yu et al., "Amorphous pharmaceutical solids: preparation, characterization and stabilization," Advanced Drug Delivery Reviews, May 16, 2001, 48(1):27-42.

* cited by examiner

BICYCLIC HETEROCYCLES AS FGFR INHIBITORS

PRIORITY CLAIM

This application claims priority to U.S. Provisional Patent Application No. 62/915,750, filed on Oct. 16, 2019, the entirety of which is incorporated by reference herein.

FIELD OF THE INVENTION

The present disclosure relates to bicyclic heterocycles, and pharmaceutical compositions of the same, that are inhibitors of the enzyme FGFR and are useful in the treatment of FGFR-associated diseases such as cancer.

BACKGROUND OF INVENTION

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005, 16, 139-149). Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described (Reviewed in Knights and Cook, Pharmacology & Therapeutics, 2010, 125, 105-117; Turner and Grose, Nature Reviews Cancer, 2010, 10, 116-129). Large scale DNA sequencing of thousands of tumor samples has revealed that FGFR genes are altered in many cancers (Helsten et al. Clin Cancer Res. 2016, 22, 259-267). Some of these activating mutations are identical to germline mutations that lead to skeletal dysplasia syndromes (Gallo et al. Cytokine & Growth Factor Reviews 2015, 26, 425-449). Mechanisms that lead to aberrant ligand-dependent signaling in human disease include overexpression of FGFs and changes in FGFR splicing that lead to receptors with more promiscuous ligand binding abilities. Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, colorectal, endometrial, gastric, head and neck, kidney, lung, ovarian, prostate); hematopoietic malignancies (e.g., multiple myeloma, acute myelogenous leukemia, and myeloproliferative neoplasms); and other neoplasms (e.g., glioblastoma and sarcomas). In addition to a role in oncogenic neoplasms, FGFR activation has also been implicated in skeletal and chondrocyte disorders including, but not limited to, achrondroplasia and craniosynostosis syndromes.

There is a continuing need for the development of new drugs for the treatment of cancer, and the FGFR inhibitors described herein help address this need.

SUMMARY OF INVENTION

The present disclosure is directed to compounds having Formula (I):

(I)

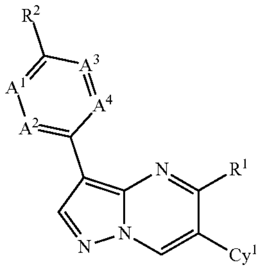

or pharmaceutically acceptable salts thereof, wherein constituent variables are defined herein.

The present disclosure is further directed to pharmaceutical compositions comprising a compound of Formula (I), or a pharmaceutically acceptable salt thereof, and at least one pharmaceutically acceptable carrier.

The present disclosure is further directed to methods of inhibiting an FGFR enzyme (e.g., an FGFR3 enzyme) comprising contacting the enzyme with a compound of Formula (I), or a pharmaceutically acceptable salt thereof.

The present disclosure is further directed to a method of treating a disease associated with abnormal activity or expression of an FGFR enzyme (e.g., an FGFR3 enzyme), comprising administering a compound of Formula (I), or a pharmaceutically acceptable salt thereof, to a patient in need thereof.

The present disclosure is further directed to compounds of Formula (I) for use in treating a disease associated with abnormal activity or expression of an FGFR enzyme (e.g., an FGFR3 enzyme).

The present disclosure is further directed to a method for treating a disorder mediated by an FGFR enzyme (e.g., an FGFR3 enzyme), or a mutant thereof, in a patient in need thereof, comprising the step of administering to said patient a compound of Formula (I), or pharmaceutically acceptable composition thereof.

The present disclosure is further directed to a method for treating a disorder mediated by an FGFR enzyme (e.g., an FGFR3 enzyme), or a mutant thereof, in a patient in need thereof, comprising the step of administering to the patient a compound of Formula (I), or a pharmaceutically acceptable salt thereof, or a composition comprising a compound of Formula (I), or a pharmaceutically acceptable salt thereof, in combination with another therapy or therapeutic agent as described herein.

The present disclosure is further directed to the use of compounds of Formula (I) in the preparation of a medicament for use in therapy.

DETAILED DESCRIPTION

Compounds

In one aspect, the present disclosure provides compounds of Formula (I):

I

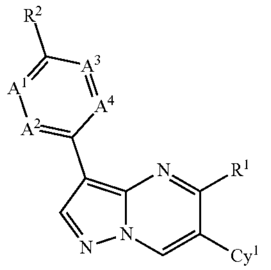

or a pharmaceutically acceptable salt thereof, wherein:

$Cy^1$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

$R^1$ is $OR^3$ or $NR^4R^5$;

$R^2$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a2}$, $SR^{a2}$, $C(O)R^{b2}$, $C(O)NR^{c2}R^{d2}$, $C(O)OR^{a2}$, $NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{20}$;

$A^1$ is N or $CR^6$;

$A^2$ is N or $CR^7$;

$A^3$ is N or $CR^8$;

$A^4$ is N or $CR^9$;

$R^3$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-14 membered heterocycloalkyl, $C_{6-10}$ aryl, 5-10 membered heteroaryl, $C_{3-10}$ cycloalkyl-$C_{1-3}$ alkylene, 4-14 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl is substituted with 1, 2, 3, or 4 substituents independently selected from $R^{30A}$; and wherein said $C_{2-6}$ alkenyl, $C_{2-6}$ alkynyl, $C_{3-10}$ cycloalkyl, 4-14 membered heterocycloalkyl, $C_{6-10}$ aryl, 5-10 membered heteroaryl, $C_{3-10}$ cycloalkyl-$C_{1-3}$ alkylene, 4-14 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{30}$;

$R^4$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-14 membered heterocycloalkyl, $C_{6-10}$ aryl, 5-10 membered heteroaryl, $C_{3-10}$ cycloalkyl-$C_{1-3}$ alkylene, 4-14 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-14 membered heterocycloalkyl, $C_{6-10}$ aryl, 5-10 membered heteroaryl, $C_{3-10}$ cycloalkyl-$C_{1-3}$ alkylene, 4-14 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{40}$;

$R^5$ is selected from H and $C_{1-6}$ alkyl; wherein said $C_{1-6}$ alkyl is optionally substituted with 1 or 2 substituents independently selected from $R^g$;

$R^6$, $R^7$, $R^8$, and $R^9$ are each independently selected from H, D, $C_{1-6}$ alkyl, $C_{2-6}$ alkenyl, $C_{2-6}$ alkynyl, $C_{1-6}$ haloalkyl, $C_{3-10}$cycloalkyl, 4-10 membered heterocycloalkyl, $C_{6-10}$ aryl, 5-10 membered heteroaryl, halo, CN, $OR^{a2}$, $SR^{a2}$, $C(O)R^{b2}$, $C(O)NR^2R^2$, $C(O)OR^{a2}$, $NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{20}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{c1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$ $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$ $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a4}$, $SR^{a4}$, $C(O)R^{b4}$, $C(O)OR^{a4}$, $NR^{c4}R^{d4}$, $NR^{c4}C(O)R^{b4}$ $NR^{4}C(O)OR^{a4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^{30A}$ is independently selected from $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a6}$, $SR^{a6}$, $C(O)R^{b6}$, $C(O)NR^{c6}R^{d6}$, $C(O)OR^{a6}$, $NR^{c6}R^{d6}$ $NR^{6}C(O)R^{b6}$, $NR^{6}C(O)OR^{a6}$, $NR^{c6}S(O)R^{b6}$, $NR^{c6}S(O)_2R^{b6}$, $NR^{6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{31}$;

each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a6}$, $SR^{a6}$, $C(O)R^{b}$, $C(O)NR^{c6}R^{d6}$, $C(O)OR^{a6}$, $NR^{c6}R^{d6}$, $NR^{6}C(O)R^{b6}NR^{c6}C(O)OR^{a6}$, $NR^{6}S(O)R^{b6}$, $NR^{6}S(O)_2R^{b6}$, $NR^{6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{31}$;

each $R^{31}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $NR^{c8}C(O)OR^{a8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, and $S(O)_2NR^{c8}R^{d8}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^{40}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a7}$, $SR^{7}$, $C(O)R^{b7}$, $C(O)NR^{c7}R^{d7}$, $C(O)OR^{a7}$, $NR^{c7}R^{d7}$, $NR^{c7}C(O)R^{b7}$, $NR^{c7}C(O)OR^{a7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, and $S(O)_2NR^{c7}R^{d7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{41}$;

each $R^{41}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a9}$, $SR^{a9}$, $C(O)R^{b9}$, $C(O)NR^{c9}R^{d9}$, $C(O)OR^{a9}$, $NR^{c9}R^{d9}$ $NR^{9}C(O)R^{b9}$, $NR^{c9}C(O)OR^{a9}$ $NR^{9}S(O)R^{b9}$, $NR^{9}S(O)_2R^{9}$, $NR^{9}S(O)_2NR^{c9}R^{d9}$, $S(O)R^{b9}$, $S(O)NR^{c9}R^{d9}$, $S(O)_2R$, and $S(O)_2NR^{c9}R^{d9}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a2}$, $R^{c2}$, and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{20}$;

or any $R^{c2}$ and $R^{d2}$ attached to the same N atom, together with the N atom to which they are attached, form a 4-, 5-, 6- or 7-membered heterocycloalkyl group optionally substituted with 1, 2 or 3 substituents independently selected from $R^{20}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{20}$;

each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

each $R^{a4}$, $R^{c}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^g$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^{a5}$, $R^{c5}$ and $R^{d5}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c5}$ and $R^{d5}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{31}$;

or any $R^{c6}$ and $R^{d6}$ attached to the same N atom, together with the N atom to which they are attached, form a 4-, 5-, 6- or 7-membered heterocycloalkyl group optionally substituted with 1, 2 or 3 substituents independently selected from $R^{31}$;

each $R^{b6}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{31}$;

each $R^{a7}$, $R^{c7}$ and $R^{d7}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{41}$;

or any $R^{c7}$ and $R^{d7}$ attached to the same N atom, together with the N atom to which they are attached, form a 4-, 5-, 6- or 7-membered heterocycloalkyl group optionally substituted with 1, 2 or 3 substituents independently selected from $R^{41}$;

each $R^{b7}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{41}$;

each $R^{a8}$, $R^{c8}$ and $R^{d8}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b8}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a9}$, $R^{c9}$ and $R^{d9}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b9}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $A^1$ is $CR^6$. In some embodiments, $A^1$ is N.

In some embodiments, $A^2$ is $CR^7$. In some embodiments, $A^2$ is N.

In some embodiments, $A^3$ is $CR^8$. In some embodiments, $A^3$ is N.

In some embodiments, $A^4$ is $CR^9$. In some embodiments, $A^4$ is N.

In some embodiments, $A^1$ is $CR^6$; $A^2$ is $CR^7$; $A^3$ is CR; and $A^4$ is $CR^9$.

In some embodiments, $A^1$ is $CR^6$; $A^2$ is $CR^7$; and $A^4$ is $CR^9$.

In some embodiments, $A^1$ is $CR^6$; $A^2$ is $CR^7$; $A^3$ is N; and $A^4$ is $CR^9$.

In some embodiments, $A^2$, $A^3$, and $A^4$ are each CH.

In some embodiments, $A^2$ and $A^3$ are each CH.

In some embodiments, $A^2$ is CH.

In some embodiments, $A^2$ and $A^4$ are each CH.

In some embodiments, $R^6$, $R^7$, $R^8$, and $R^9$ are each independently selected from H, D, $C_{1-6}$ alkyl, $C_{1-6}$ haloalkyl, halo, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein said $C_{1-6}$ alkyl is optionally substituted with 1, 2, 3, or 4 substituents independently selected from $R^{20}$.

In some embodiments, $R^6$, $R^7$, $R^8$, and $R^9$ are each independently selected from H, D, $C_{1-6}$ alkyl, $C_{1-6}$ haloalkyl, 5-10 membered heteroaryl, halo, CN, $OR^{a2}$, $C(O)R^{b2}$, $C(O)NR^{c2}R^{d2}$, $C(O)OR^{a2}$, $NR^{c2}R^{d2}$ $S(O)_2R^{b2}$, and $S(O)_2NR^{c2}R^{d2}$; wherein said $C_{1-6}$ alkyl is optionally substituted with 1, 2, 3, or 4 substituents independently selected from $R^{20}$.

In some embodiments, $R^6$, $R^7$, $R^8$, and $R^9$ are each independently selected from H, D, $C_{1-6}$ alkyl, $C_{1-6}$ haloalkyl, halo, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein said $C_{1-6}$ alkyl is optionally substituted with 1 or 2 substituents independently selected from $R^{20}$.

In some embodiments, $R^6$, $R^7$, $R^8$, and $R^9$ are each independently selected from H, D, $C_{1-6}$ alkyl, $C_{1-6}$ haloalkyl, halo, CN, $OR^{a2}$, $SR^{a2}$, $C(O)R^{b2}$, $C(O)NR^{c2}R^{d2}$, $C(O)OR^{a2}$, $NR^{c2}R^{d2}$, $S(O)R^{b2}$, $S(O)NR^{c2}R^{d2}$, $S(O)_2R^{b2}$, and $S(O)_2NR^{c2}R^{d2}$.

In some embodiments, $R^6$, $R^7$, $R^8$, and $R^9$ are each independently selected from H, D, $C_{1-6}$ alkyl, $C_{1-6}$ haloalkyl, halo, CN, $OR^{a2}$, $C(O)NR^{c2}R^{d2}$, $NR^{c2}R^{d2}$, $S(O)_2R^{b2}$, and $S(O)_2NR^{c2}R^{d2}$.

In some embodiments, $R^6$, $R^7$, $R^8$, and $R^9$ are each independently selected from H, $C_{1-6}$ alkyl, $C_{1-6}$ haloalkyl, halo, CN, $OR^{a2}$, $C(O)NR^{c2}R^{d2}$, and $S(O)_2R^{b2}$.

In some embodiments, $R^6$, $R^7$, $R^8$, and $R^9$ are each independently selected from H, $C_{1-6}$ alkyl, $C_{1-6}$ haloalkyl, 5-10 membered heteroaryl, halo, CN, $OR^a$, $C(O)NR^{c2}R^{d2}$, and $S(O)_2R^{b2}$.

In some embodiments, $R^6$ is selected from H, D, $C_{1-6}$ alkyl, $C_{1-6}$ haloalkyl, halo, CN, $OR^{a2}$, $SR^{a2}$, $C(O)R^{b2}$, $C(O)NR^{c2}R^{d2}$, $C(O)OR^{a2}$, $NR^{c2}R^{d2}$ $S(O)R^{b2}$, $S(O)NR^{c2}R^{d2}$, $S(O)_2R^{b2}$, and $S(O)_2NR^{c2}R^{d2}$.

In some embodiments, $R^6$ is selected from H, D, $C_{1-6}$ alkyl, $C_{1-6}$ haloalkyl, halo, CN, $OR^{a2}$, $C(O)NR^{c2}R^{d2}$, $NR^{c2}R^{d2}$, $S(O)_2R^{b2}$, and $S(O)_2NR^{c2}R^{d2}$.

In some embodiments, $R^6$ is selected from H, $C_{1-6}$ alkyl, $C_{1-6}$ haloalkyl, halo, CN, $OR^{a2}$, $C(O)NR^{c2}R^{d2}$, and $S(O)_2R^{b2}$.

In some embodiments, $R^6$ is H or $C(O)NR^{c2}R^{d2}$. In some embodiments, $R^6$ is H. In some embodiments, $R^6$ is $C(O)NR^{c2}R^{d2}$. In some embodiments, $R^6$ is H or $C(O)NHCH_3$. In some embodiments, $R^6$ is $C(O)NHCH_3$. In some embodiments, $R^6$ is H or 5-10 membered heteroaryl.

In some embodiments, $R^7$ is selected from H, D, $C_{1-6}$ alkyl, $C_{1-6}$ haloalkyl, halo, CN, $OR^{a2}$, $SR^{a2}$, $C(O)R^{b2}$, $C(O)NR^{c2}R^{d2}$, $C(O)OR^{a2}$, $NR^{c2}R^{d2}$ $S(O)R^{b2}$, $S(O)NR^{c2}R^{d2}$, $S(O)_2R^{b2}$, and $S(O)_2NR^{c2}R^{d2}$.

In some embodiments, $R^7$ is selected from H, D, $C_{1-6}$ alkyl, $C_{1-6}$ haloalkyl, halo, CN, $OR^{a2}$, $C(O)NR^{c2}R^{d2}$, $NR^{c2}R^{d2}$, $S(O)_2R^{b2}$, and $S(O)_2NR^{c2}R^{d2}$.

In some embodiments, $R^7$ is selected from H, $C_{1-6}$ alkyl, $C_{1-6}$ haloalkyl, halo, CN, $OR^{a2}$, $C(O)NR^{c2}R^{d2}$, and $S(O)_2R^{b2}$. In some embodiments, $R^7$ is H.

In some embodiments, $R^8$ is selected from H, D, $C_{1-6}$ alkyl, $C_{1-6}$ haloalkyl, halo, CN, $OR^{a2}$, $SR^{a2}$, $C(O)R^{b2}$, $C(O)NR^2R^2$, $C(O)OR^{a2}$, $NR^{c2}R^{d2}$ $S(O)R^{b2}$, $S(O)NR^{c2}R^{d2}$, $S(O)_2R^{b2}$, and $S(O)_2NR^{c2}R^{d2}$.

In some embodiments, $R^8$ is selected from H, D, $C_{1-6}$ alkyl, $C_{1-6}$ haloalkyl, halo, CN, $OR^{a2}$, $C(O)NR^{c2}R^{d2}$, $NR^{c2}R^{d2}S(O)_2R^{b2}$, and $S(O)_2NR^{c2}R^{d2}$.

In some embodiments, $R^8$ is selected from H, $C_{1-6}$ alkyl, $C_{1-6}$ haloalkyl, halo, CN, $OR^{a2}$, $C(O)NR^{c2}R^{d2}$, and $S(O)_2R^{b2}$.

In some embodiments, $R^8$ is H, $C_{1-6}$ alkyl, $C_{1-6}$ haloalkyl, halo, CN, $OR^{a2}$, or $S(O)_2R^{b2}$. In some embodiments, $R^8$ is H, methyl, $CHF_2$, F, CN, OH, or $S(O)_2(CH_3)_2$. In some embodiments, $R^8$ is $C_{1-6}$ alkyl, $C_{1-6}$ haloalkyl, halo, CN, $OR^{a2}$, or $S(O)_2R^{b2}$. In some embodiments, $R^8$ is H.

In some embodiments, $R^9$ is selected from H, D, $C_{1-6}$ alkyl, $C_{1-6}$ haloalkyl, halo, CN, $OR^{a2}$, $SR^{a2}$, $C(O)R^{b2}$, $C(O)NR^{c2}R^{d2}$, $C(O)OR^{a2}$, $NR^{c2}R^{d2}$, $S(O)R^{b2}$, $S(O)NR^{c2}R^{d2}$, $S(O)_2R^{b2}$, and $S(O)_2NR^{c2}R^{d2}$.

In some embodiments, $R^9$ is selected from H, D, $C_{1-6}$ alkyl, $C_{1-6}$ haloalkyl, halo, CN, $OR^{a2}$, $C(O)NR^{c2}R^{d2}$, $NR^{c2}R^{d2}S(O)_2R^{b2}$, and $S(O)_2NR^{c2}R^{d2}$. In some embodiments, $R^9$ is selected from H, $C_{1-6}$ alkyl, $C_{1-6}$ haloalkyl, halo, CN, $OR^{a2}$. $C(O)NR^{c2}R^{d2}$, and $S(O)_2R^{b2}$.

In some embodiments, $R^9$ is H or halo. In some embodiments, $R^9$ is H. In some embodiments, $R^9$ is halo. In some embodiments, $R^9$ is H or F. In some embodiments, $R^9$ is F.

In some embodiments, $R^1$ is $OR^3$.

In some embodiments, $R^1$ is $NR^4R^5$.

In some embodiments, $R^3$ is selected from $C_{1-6}$ alkyl, $C_{1-6}$ haloalkyl, $C_{3-10}$ cycloalkyl, 4-14 membered heterocycloalkyl, $C_{6-10}$ aryl, and 5-10 membered heteroaryl; wherein said $C_{1-6}$ alkyl is substituted with 1, 2, 3, or 4 substituents independently selected from $R^{30A}$ and wherein said 4-14 membered heterocycloalkyl, $C_{6-10}$ aryl, and 5-10 membered heteroaryl are each optionally substituted with 1, 2, 3, or 4 substituents independently selected from $R^{30}$.

In some embodiments, $R^3$ is selected from $C_{1-6}$ alkyl, $C_{1-6}$ haloalkyl, $C_{3-6}$ cycloalkyl, 4-6 membered heterocycloalkyl, phenyl, and 5-6 membered heteroaryl; wherein said $C_{1-6}$ alkyl is substituted with 1, 2, 3, or 4 substituents independently selected from $R^{30A}$ and wherein said 4-6 membered heterocycloalkyl, phenyl, and 5-6 membered heteroaryl are each optionally substituted with 1, 2, 3, or 4 substituents independently selected from $R^{30}$.

In some embodiments, $R^3$ is selected from $C_{1-6}$ alkyl, $C_{1-6}$ haloalkyl, and 4-6 membered heterocycloalkyl; wherein said $C_{1-6}$ alkyl is substituted with 1, 2, 3, or 4 substituents independently selected from $R^{30A}$ and wherein said 4-6 membered heterocycloalkyl is optionally substituted with 1, 2, 3, or 4 substituents independently selected from $R^{30}$.

In some embodiments, $R^3$ is selected from $C_{1-6}$ alkyl, $C_{1-6}$ haloalkyl, and 4-6 membered heterocycloalkyl; wherein said $C_{1-6}$ alkyl is substituted with 1 or 2 substituents independently selected from $R^{30A}$ and wherein said 4-6 membered heterocycloalkyl is optionally substituted with 1 or 2 substituents independently selected from $R^{30}$.

In some embodiments, $R^3$ is selected from 4-14 membered heterocycloalkyl, $C_{6-10}$ aryl, and 5-10 membered heteroaryl; each of which is optionally substituted with 1, 2, 3, or 4 substituents independently selected from $R^{30}$.

In some embodiments, $R^3$ is 4-14 membered heterocycloalkyl optionally substituted with 1, 2, 3, or 4 substituents independently selected from $R^{30}$. In some embodiments, $R^3$ is 4-6 membered heterocycloalkyl optionally substituted with 1, 2, 3, or 4 substituents independently selected from $R^{30}$. In some embodiments, $R^3$ is 4-6 membered heterocycloalkyl optionally substituted with 1 or 2 substituents independently selected from $R^{30}$.

In some embodiments, $R^3$ is tetrahydrofuranyl optionally substituted with 1, 2, 3, or 4 substituents independently selected from $R^{30}$. In some embodiments, $R^3$ is tetrahydrofuran-3-yl optionally substituted with 1, 2, 3, or 4 substituents independently selected from $R^{30}$. In some embodiments, $R^3$ is tetrahydrofuran-3-yl optionally substituted with 1 or 2 substituents independently selected from $R^{30}$.

In some embodiments, $R^3$ is 4-14 membered heterocycloalkyl. In some embodiments, $R^3$ is 4-6 membered heterocycloalkyl. In some embodiments, $R^3$ is 5-6 membered heterocycloalkyl.

In some embodiments, $R^3$ is 5 membered heterocycloalkyl. In some embodiments, $R^3$ is tetrahydrofuranyl.

In some embodiments, $R^3$ is tetrahydrofuran-3-yl.

In some embodiments, $R^4$ is selected from $C_{1-6}$ alkyl, $C_{1-6}$ haloalkyl, $C_{3-10}$ cycloalkyl, 4-14 membered heterocycloalkyl, $C_{6-10}$ aryl, and 5-10 membered heteroaryl; wherein said $C_{1-6}$ alkyl, $C_{3-10}$ cycloalkyl, 4-14 membered heterocycloalkyl, $C_{6-10}$ aryl, and 5-10 membered heteroaryl are each optionally substituted with 1, 2, 3, or 4 substituents independently selected from $R^{40}$.

In some embodiments, $R^4$ is selected from $C_{1-6}$ alkyl, $C_{1-6}$ haloalkyl, $C_{3-6}$ cycloalkyl, 4-6 membered heterocycloalkyl, $C_{6-10}$ aryl, and 5-6 membered heteroaryl; wherein said $C_{1-6}$ alkyl, $C_3$. 6 cycloalkyl, 4-6 membered heterocycloalkyl, $C_{6-10}$ aryl, and 5-6 membered heteroaryl are each optionally substituted with 1, 2, 3, or 4 substituents independently selected from $R^4$.

In some embodiments, $R^4$ is 4-14 membered heterocycloalkyl optionally substituted with 1, 2, 3, or 4 substituents independently selected from $R^{40}$. In some embodiments, $R^4$ is 5-6 membered heterocycloalkyl optionally substituted with 1, 2, 3, or 4 substituents independently selected from $R^{40}$. In some embodiments, $R^4$ is tetrahydrofuranyl optionally substituted with 1, 2, 3, or 4 substituents independently selected from $R^{40}$. In some embodiments, $R^4$ is tetrahydrofuran-3-yl optionally substituted with 1, 2, 3, or 4 substituents independently selected from $R^{40}$.

In some embodiments, $R^4$ is 4-14 membered heterocycloalkyl. In some embodiments, $R^4$ is 4-6 membered heterocycloalkyl optionally substituted with 1, 2, 3, or 4 substituents independently selected from $R^{40}$. In some embodiments, $R^4$ is 5-6 membered heterocycloalkyl. In some embodiments, $R^4$ is 4-6 membered heterocycloalkyl. In some embodiments, $R^4$ is tetrahydrofuranyl.

In some embodiments, $R^4$ is tetrahydrofuran-3-yl.

In some embodiments, $R^5$ is selected from H and $C_{1-6}$ alkyl. In some embodiments, $R^5$ is H.

In some embodiments, $R^2$ is selected from H, D, $C_{1-6}$ alkyl, $C_{1-6}$ haloalkyl, $C_{3-10}$ cycloalkyl, halo, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein said $C_{1-6}$ alkyl is optionally substituted with 1, 2, 3, or 4 substituents independently selected from $R^{20}$.

In some embodiments, $R^2$ is selected from H, D, and halo.

In some embodiments, $R^2$ is selected from H, D, $C_{1-6}$ alkyl, $C_{1-6}$ haloalkyl, $C_{3-10}$ cycloalkyl, halo, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$.

In some embodiments, $R^2$ is selected from H, D, $C_{1-6}$ alkyl, and halo.

In some embodiments, $R^2$ is H.

In some embodiments, $Cy^1$ is selected from phenyl and 5-6 membered heteroaryl; wherein the 5-6 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl is optionally substituted by oxo to form a carbonyl group; and wherein the phenyl and 5-6 membered heteroaryl are each optionally substituted with 1 or 2 substituents independently selected from $R^{10}$.

In some embodiments, $Cy^1$ is selected from phenyl and 5-6 membered heteroaryl; wherein the phenyl and 5-6 membered heteroaryl are each optionally substituted with 1, 2, 3 or 4 substituents independently selected from $R^{10}$. In some embodiments, $Cy^1$ is selected from phenyl and 5-6 membered heteroaryl; wherein the phenyl and 5-6 membered heteroaryl are each optionally substituted with 1 or 2 substituents independently selected from $R^{10}$. In some embodiments, $Cy^1$ is selected from phenyl and 5-6 membered heteroaryl; wherein the phenyl and 5-6 membered heteroaryl are each substituted with 1 or 2 substituents independently selected from $R^{10}$. In some embodiments, $Cy^1$ is selected from phenyl and 5-6 membered heteroaryl; wherein the phenyl and 5-6 membered heteroaryl are each substituted with 1 substituent 15 independently selected from $R^{10}$.

In some embodiments, $Cy^1$ is phenyl, pyrazolyl or pyridinyl, each of which is optionally substituted with 1, 2, 3 or 4 substituents independently selected from $R^{10}$. In some embodiments, $Cy^1$ is phenyl, pyrazolyl or pyridinyl, each of which is optionally substituted with 1 or 2 substituents independently selected from $R^{10}$. In some embodiments, wherein $Cy^1$ is phenyl, pyrazolyl, triazolyl, oxazolyl, 2-oxo-1,2-dihydropyridinyl, pyridazinyl, or pyridinyl, each of which is optionally substituted with 1 or 2 substituents independently selected from $R^{10}$. In some embodiments, $Cy^1$ is phenyl, pyrazolyl or pyridinyl, each of which is substituted with 1 or 2 substituents independently selected from $R^{10}$. In some embodiments, $Cy^1$ is phenyl, pyrazolyl or pyridinyl, each of which is optionally substituted with 1 substituent independently selected from $R^{10}$.

In some embodiments, $Cy^1$ is 5-10 membered heteroaryl optionally substituted with 1, 2, 3 or 4 substituents independently selected from $R^{10}$. In some embodiments, $Cy^1$ is 5-10 membered heteroaryl optionally substituted with 1 or 2 substituents independently selected from $R^{10}$. In some embodiments, $Cy^1$ is 5-10 membered heteroaryl optionally substituted with 1 substituent independently selected from $R^{10}$. In some embodiments, $Cy^1$ is 5-10 membered heteroaryl substituted with 1 or 2 substituents independently selected from $R^{10}$.

In some embodiments, $Cy^1$ is 5-6 membered heteroaryl optionally substituted with 1, 2, 3 or 4 substituents independently selected from $R^{10}$. In some embodiments, $Cy^1$ is 5-6 membered heteroaryl optionally substituted with 1 or 2 substituents independently selected from $R^{10}$. In some embodiments, $Cy^1$ is 5-6 membered heteroaryl optionally substituted with 1 substituent independently selected from $R^{10}$. In some embodiments, $Cy^1$ is 5-6 membered heteroaryl substituted with 1 or 2 substituents independently selected from $R^{10}$.

In some embodiments, $Cy^1$ is pyrazolyl or pyridinyl, each of which is optionally substituted with 1, 2, 3 or 4 substituents independently selected from $R^{10}$. In some embodiments, $Cy^1$ is pyrazolyl or pyridinyl, each of which is optionally substituted with 1 or 2 substituents independently selected from $R^{10}$. In some embodiments, $Cy^1$ is pyrazolyl or pyridinyl, each of which is substituted with 1 or 2 substituents independently selected from $R^{10}$. In some embodiments, $Cy^1$ is pyrazolyl or pyridinyl, each of which is optionally substituted with 1 substituent independently selected from $R^{10}$.

In some embodiments, $Cy^1$ is pyrazol-4-yl, pyridin-3-yl, or pyridin-4-yl, each of which is optionally substituted with 1, 2, 3 or 4 substituents independently selected from $R^{10}$. In some embodiments, $Cy^1$ is pyrazol-4-yl, pyridin-3-yl, or pyridin-4-yl, each optionally substituted with 1 or 2 substituents independently selected from $R^{10}$. In some embodiments, $Cy^1$ is pyrazol-4-yl, pyridin-3-yl, or pyridin-4-yl, each optionally substituted with 1 substituent independently selected from $R^{10}$.

In some embodiments, $Cy^1$ is pyrazolyl optionally substituted with 1, 2, 3 or 4 substituents independently selected from $R^{10}$. In some embodiments, $Cy^1$ is pyrazolyl optionally substituted with 1 or 2 substituents independently selected from $R^{10}$. In some embodiments, $Cy^1$ is pyrazolyl optionally substituted with 1 substituent independently selected from $R^{10}$.

In some embodiments, $Cy^1$ is pyridinyl optionally substituted with 1, 2, 3 or 4 substituents independently selected from $R^{10}$. In some embodiments, $Cy^1$ is pyridinyl optionally substituted with 1 or 2 substituents independently selected from $R^{10}$. In some embodiments, $Cy^1$ is pyridinyl optionally substituted with 1 substituent independently selected from $R^{10}$.

In some embodiments, $Cy^1$ is $C_{6-10}$ aryl optionally substituted with 1, 2, 3 or 4 substituents independently selected from $R^{10}$. In some embodiments, $Cy^1$ is $C_{6-10}$ aryl optionally substituted with 1 or 2 substituents independently selected from $R^{10}$. In some embodiments, $Cy^1$ is $C_{6-10}$ aryl substituted with 1 or 2 substituents independently selected from $R^{10}$. In some embodiments, $Cy^1$ is $C_{6-10}$ aryl substituted with 1 substituent independently selected from $R^{10}$.

In some embodiments, $Cy^1$ is phenyl optionally substituted with 1, 2, 3 or 4 substituents independently selected from $R^{10}$. In some embodiments, $Cy^1$ is phenyl optionally substituted with 1 or 2 substituents independently selected from $R^{10}$. In some embodiments, $Cy^1$ is phenyl substituted with 1 or 2 substituents independently selected from $R^{10}$. In some embodiments, $Cy^1$ is phenyl substituted with 1 substituent independently selected from $R^{10}$.

In some embodiments, each $R^{10}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{11}$.

In some embodiments, each $R^{10}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{3-10}$ cycloalkyl, 4-10 membered heterocycloalkyl, $C_{6-10}$ aryl, and 5-10 membered heteroaryl are each optionally substituted with 1 or 2 substituents independently selected from $R^{11}$.

In some embodiments, each $R^{10}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{3-10}$ cycloalkyl, 4-10 membered heterocycloalkyl, $C_{6-10}$ aryl, and 5-10 membered heteroaryl are each optionally substituted with 1 substituent independently selected from $R^{11}$.

In some embodiments, each $R^{10}$ is independently selected from $C_{1-6}$ alkyl, $C_{3-10}$ cycloalkyl, 4-10 membered heterocycloalkyl, and $NR^{c1}R^{d1}$; wherein said $C_{1-6}$ alkyl, $C_{3-10}$ cycloalkyl, and 4-10 membered heterocycloalkyl are each optionally substituted with 1, 2, 3, or 4 substituents independently selected from $R^{11}$.

In some embodiments, each $R^{10}$ is independently selected from $C_{1-6}$ alkyl, $C_{3-10}$ cycloalkyl, 4-10 membered heterocycloalkyl, and $NR^{c1}R^{d1}$; wherein said $C_{1-6}$ alkyl, $C_{3-10}$ cycloalkyl, and 4-10 membered heterocycloalkyl are each optionally substituted with 1 or 2 substituents independently selected from $R^{11}$.

In some embodiments, each $R^{10}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $S(O)_2R^{b1}$, and $S(O)_2NR^{c1}R^{d1}$; wherein said $C_{1-6}$ alkyl, $C_{3-6}$ cycloalkyl, and 4-6 membered heterocycloalkyl are each optionally substituted with 1 or 2 substituents independently selected from $R^{11}$.

In some embodiments, each $R^{10}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a1}$, and $NR^{c1}R^{d1}$; wherein said $C_{1-6}$ alkyl and 4-6 membered heterocycloalkyl are each optionally substituted with 1 or 2 substituents independently selected from $R^{11}$.

In some embodiments, each $R^{10}$ is independently selected from $C_{1-6}$ alkyl, $C_{3-6}$ cycloalkyl, 4-6 membered heterocycloalkyl, and $NR^{c1}R^{d1}$; wherein said $C_{1-6}$ alkyl, $C_{3-6}$ cycloalkyl, and 4-6 membered heterocycloalkyl are each optionally substituted with 1 or 2 substituents independently selected from $R^{11}$.

In some embodiments, each $R^{10}$ is independently selected from methyl, ethyl, propyl, isopropyl, piperidinyl, piperazinyl, azetidinyl, morpholino, cyclopropyl, and cyclobutyl; each of which is optionally substituted with 1, 2, 3, or 4 substituents independently selected from $R^{11}$. In some embodiments, each $R^{10}$ is independently selected from methyl, ethyl, propyl, isopropyl, piperidinyl, piperazinyl, azetidinyl, morpholino, cyclopropyl, and cyclobutyl; each of which is optionally substituted with 1 or 2 substituents independently selected from $R^{11}$. In some embodiments, each $R^{10}$ is independently selected from methyl, ethyl, propyl, isopropyl, piperidinyl, piperazinyl, azetidinyl, morpholino, cyclopropyl, ethylamino, and cyclobutyl; each of which is optionally substituted with 1 or 2 substituents independently selected from $R^{11}$. In some embodiments, each $R^{10}$ is independently selected from methyl, ethyl, propyl, isopropyl, piperidinyl, piperazinyl, azetidinyl, morpholino, cyclopropyl, and cyclobutyl; each of which is optionally substituted with 1 substituent independently selected from $R^{11}$.

In some embodiments, each $R^{10}$ is independently selected from methyl, isopropyl, 2-hydroxypropan-2-yl, $NH(CH_3)$, methylpiperidin-4-yl, methylpiperazin-1-yl, morpholinoethyl, 1-methylazetidin-3-yl, morpholino, cyclopropyl, and cyclobutyl.

In some embodiments, each $R^{10}$ is independently selected from methyl, ethyl, isopropyl, 2-hydroxypropan-2-yl, $NH(CH_3)$, methylpiperidin-4-yl, methylpiperazin-1-yl, morpholinoethyl, 1-methylazetidin-3-yl, morpholino, cyclopropyl, ethylamino, hydroxyethyl-2-yl, cyanoethyl-2-yl, dimethylamino-2-oxoethyl, 2-hydroxy-2-methylpropyl, 2-methoxyethyl, pyridin-3-ylmethyl, (tetrahydro-2H-pyran-4-yl)methyl, 2-morpholinoethyl, 3-fluoro-1-methylpiperidin-4-yl, ((1R,4R)-2-Oxa-5-azabicyclo[2.2.1]heptan-5-yl)methyl, 1-isopropylpiperidin-4-yl, 4-fluoro-1-methylpiperidin-4-yl, 4-methylpiperazin-1-yl, tetrahydrofuran-3-yl, 1,1-dioxidotetrahydrothiophen-3-yl, and cyclobutyl.

In some embodiments, each $R^{10}$ is $C_{1-6}$ alkyl. In some embodiments, $R^{10}$ is methyl.

In some embodiments, each $R^{11}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{3}C(O)R^{b3}$, $NR^{c3}C(O)OR^{a3}$, $NR^{c3}S(O)_2R^{b3}$ $NR^{c3}S(O)_2NR^{c3}R^{d3}$, $S(O)_2R^{b3}$, and $S(O)_2NR^{c3}R^{d3}$; wherein said $C_{1-6}$ alkyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{12}$.

In some embodiments, each $R^{11}$ is independently selected from $C_{1-6}$ alkyl, $C_{1-6}$ haloalkyl, 20 $C_{3-6}$ cycloalkyl, 4-6 membered heterocycloalkyl, halo, D, CN, $OR^{a3}$, $C(O)R^{b3}$, $C(O)NR^{c3}R^{d3}$, $C(O)OR^{a3}$, $NR^{c3}R^{d3}$ and $S(O)_2R^{3}$.

In some embodiments, each $R^{11}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a3}$, and $NR^{c3}R^{d3}$.

In some embodiments, each $R^{11}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a3}$, $SR^{a3}$, $C(O)R^{b3}$, $C(O)NR^{c3}R^{d3}$, $C(O)OR^{a3}$, $NR^{c3}R^{d3}$ $NR^{c3}C(O)R^{b3}$ $NR^{c3}C(O)OR^{a3}$, (check hold up with missing letter at beginning) $NR^{c3}S(O)_2R^{3}$, $NR^{c3}S(O)_2NR^{c3}R^{d3}$, $S(O)_2R^{b3}$, and $S(O)_2NR^{c3}R^{d3}$.

In some embodiments, each $R^{11}$ is independently selected from $C_{1-6}$ alkyl, 4-10 membered heterocycloalkyl, and $OR^{a3}$; wherein said $C_{1-6}$ alkyl, and 4-10 membered heterocycloalkyl are each optionally substituted with 1, 2, 3, or 4 substituents independently selected from $R^{12}$. In some embodiments, each $R^{11}$ is independently selected from $C_{1-6}$ alkyl, 4-10 membered heterocycloalkyl, and $OR^{a3}$.

In some embodiments, each $R^{11}$ is independently selected from $C_{1-6}$ alkyl, 4-6 membered heterocycloalkyl, and $OR^{a3}$; wherein said $C_{1-6}$ alkyl and 4-6 membered heterocycloalkyl are each optionally substituted with 1 or 2 substituents independently selected from $R^{12}$.

In some embodiments, each $R^{11}$ is independently selected from $C_{1-6}$ alkyl, CN, 4-7 membered heterocycloalkyl, $C(O)NR^{c3}R^{d3}$, halo, 5-10 membered heteroaryl, and $OR^{a3}$; wherein said $C_{1-6}$ alkyl and 4-7 membered heterocycloalkyl are each optionally substituted with 1 or 2 substituents independently selected from $R^{12}$.

In some embodiments, each $R^{11}$ is independently selected from $C_{1-6}$ alkyl, 4-6 membered heterocycloalkyl, and $OR^{a3}$. In some embodiments, each $R^{11}$ is independently selected from $C_{1-6}$ alkyl, CN, 4-7 membered heterocycloalkyl, $C(O)NR^{c3}R^{d3}$, halo, and $OR^{a3}$. In some embodiments, each $R^{11}$ is independently selected from $C_{1-6}$ alkyl, 5-6 membered heterocycloalkyl, and $OR^{a3}$. In some embodiments, each $R^{11}$ is independently selected from $C_{1-6}$ alkyl, 6 membered heterocycloalkyl, and $OR^{a3}$.

In some embodiments, each $R^{11}$ is independently selected from methyl, OH, and morpholino.

In some embodiments, each $R^{11}$ is independently selected from methyl, OH, methoxy, CN, $C(O)N(CH_3)_2$, isopropyl, pyridinyl, tetrahydropyranyl, fluoro, 2-oxa-5-azabicyclo[2.2.1]heptanyl, and morpholino.

In some embodiments, each $R^{11}$ is $C_{1-6}$ alkyl. In some embodiments, each $R^{11}$ is methyl.

In some embodiments, each $R^{11}$ is $C_{1-6}$ alkyl or $OR^{a3}$. In some embodiments, each $R^{11}$ is methyl or OH.

In some embodiments, each $R^{12}$ is independently selected from $C_{1-6}$ alkyl, $C_{1-6}$ haloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$ $NR^{c5}C(O)R^{b5}$, $NR^{c5}C(O)OR^{a5}$, $NR^{c5}S(O)_2R^{b5}$, $NR^{c5}S(O)_2NR^{c5}R^{d5}$, $S(O)_2R^{b5}$, and $S(O)_2NR^{c5}R^{d5}$; wherein said $C_{1-6}$ alkyl is optionally substituted with 1, 2, 3, or 4 substituents independently selected from $R^{g}$.

In some embodiments, each $R^{12}$ is independently selected from $C_{1-6}$ alkyl and halo. In some embodiments, each $R^{12}$ is independently selected from $C_{1-6}$ alkyl.

In some embodiments, each $R^{20}$ is independently selected from $C_{1-6}$ alkyl, $C_{1-6}$ haloalkyl, halo, D, CN, $OR^{a4}$, $SR^{a4}$, $C(O)R^{b4}$, $C(O)OR^{a4}$, $NR^{c4}R^{d4}$ $NR^{4}C(O)R^{b4}$ $NR^{4}S(O)_2R^{b4}$, $S(O)_2R^{b4}$, and $S(O)_2NR^{c4}R^{d4}$; wherein said $C_{1-6}$ alkyl is optionally substituted with 1, 2, 3, or 4 substituents independently selected from $R^{g}$.

In some embodiments, each $R^{20}$ is independently selected from $C_{1-6}$ alkyl and halo. In some embodiments, each $R^{20}$ is independently selected from $C_{1-6}$ alkyl.

In some embodiments, each $R^{20}$ is independently selected from halo, D, CN, $OR^{a4}$, and $NR^{c4}R^{d4}$ In some embodiments, each $R^{20}$ is independently selected from D.

In some embodiments, each $R^{30A}$ is independently selected from $C_{1-6}$ haloalkyl, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{6}C(O)R^{b6}$, $NR^{6}S(O)R^{b6}$, $NR^{c6}S(O)_2R^{b6}$, $S(O)_2R^{b6}$, and $S(O)_2NR^{c6}R^{d6}$.

In some embodiments, each $R^{3A}$ is independently selected from halo, CN, $OR^{a6}$, and $NR^{6}R^{d6}$.

In some embodiments, each $R^{3A}$ is independently selected from halo.

In some embodiments, each $R^{30}$ is independently selected from $C_{1-6}$ alkyl, $C_{1-6}$ haloalkyl halo, D, CN, $OR^{a6}$, $C(O)R^{b6}$, $C(O)NR^{c6}R^{d6}$, $C(O)OR^{a6}$, and $NR^{c6}R^{d6}$.

In some embodiments, each $R^{31}$ is independently selected from $C_{1-6}$ alkyl, $C_{1-6}$ haloalkyl, halo, D, CN, $OR^{a8}$, $C(O)R^{b8}$, $C(O)NR^{c8}R^{d8}$, $C(O)OR^{a8}$, $NR^{c8}R^{d8}$ and $S(O)_2R^{b8}$; wherein said $C_{1-6}$ alkyl, is optionally substituted with 1, 2, 3, or 4 substituents independently selected from $R^{g}$.

In some embodiments, each $R^{31}$ is independently selected from $C_{1-6}$ alkyl and halo. In some embodiments, each $R^{31}$ is independently selected from $C_{1-6}$ alkyl.

In some embodiments, each $R^{40}$ is independently selected from $C_{1-6}$ alkyl, $C_{1-6}$ haloalkyl, halo, D, CN, $OR^{a7}$, $SR^{a7}$, $C(O)R^{b7}$, $C(O)NR^{c7}R^{d7}$, $C(O)OR^{a7}$, $NR^{c7}R^{d7}$ $NR^{c7}C(O)R^{b7}$, $NR^{c7}S(O)_2R^{b7}$, $S(O)_2R^{b7}$, and $S(O)_2NR^{c7}R^{d7}$; wherein said $C_{1-6}$ alkyl is optionally substituted with 1, 2, 3, or 4 substituents independently selected from $R^{41}$.

In some embodiments, each $R^{40}$ is independently selected from $C_{1-6}$ alkyl, $C_{1-6}$ haloalkyl, halo, D, CN, $OR^{a7}$, $C(O)R^{b7}$, $C(O)NR^{c7}R^{d7}$, $C(O)OR^{a7}$, and $NR^{c7}R^{d7}$.

In some embodiments, each $R^{40}$ is independently selected from $C_{1-6}$ alkyl and halo. In some embodiments, each $R^{40}$ is independently selected from $C_{1-6}$ alkyl.

In some embodiments, each $R^{41}$ is independently selected from $C_{1-6}$ alkyl, $C_{1-6}$ haloalkyl, halo, D, CN, $OR^{a9}$, $C(O)R^{b9}$, $C(O)NR^{c9}R^{d9}$, $C(O)OR^{a9}$, $NR^{c9}R^{d9}$ and $S(O)_2R^{b9}$; wherein said $C_{1-6}$ alkyl is optionally substituted with 1, 2, 3, or 4 substituents independently selected from $R^{g}$.

In some embodiments, each $R^{41}$ is independently selected from $C_{1-6}$ alkyl and halo. In some embodiments, each $R^{41}$ is independently selected from $C_{1-6}$ alkyl.

In some embodiments, each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl; or any $R^{c1}$ and $R^{d1}$ attached to the same N atom, together with the N atom to which they are attached, form a 4-, 5-, or 6-membered heterocycloalkyl group optionally substituted with 1, 2, 3, or 4 substituents independently selected from $R^{11}$.

In some embodiments, each $R^{a1}$, $R^{c1}$ and $R^{d1}$ is independently selected from H, $C_{1-6}$ alkyl, and $C_{1-6}$ haloalkyl.

In some embodiments, each $R^{a1}$, $R^{c1}$ and $R^{d1}$ is independently selected from H and $C_{1-6}$ alkyl, wherein said $C_{1-6}$ alkyl is optionally substituted with 1, 2, 3, or 4 substituents independently selected from $R^{11}$. In some embodiments, each $R^{a1}$, $R^{c1}$ and $R^{d1}$ is independently selected from H and $C_{1-6}$ alkyl.

In some embodiments, each $R^{b1}$ is independently selected from $C_{1-6}$ alkyl, $C_{1-6}$ haloalkyl, $C_{3-10}$ cycloalkyl, and 4-10 membered heterocycloalkyl.

In some embodiments, each $R^{b1}$ is independently selected from $C_{1-6}$ alkyl optionally substituted with 1, 2, 3, or 4 substituents independently selected from $R^{11}$. In some embodiments, each $R^{b1}$ is independently selected from $C_{1-6}$ alkyl.

In some embodiments, each $R^{a2}$, $R^{c2}$, and $R^{d2}$ is independently selected from H, $C_{1-6}$ alkyl, and $C_{1-6}$ haloalkyl.

In some embodiments, each $R^{a2}$, $R^{c2}$ and $R^{d2}$ is independently selected from H and $C_{1-6}$ alkyl, wherein said $C_{1-6}$ alkyl is optionally substituted with 1, 2, 3, or 4 substituents independently selected from $R^{20}$. In some embodiments, each $R^{a2}$, $R^{c2}$ and $R^{d2}$ is independently selected from H and $C_{1-6}$ alkyl.

In some embodiments, each $R^{c2}$ and $R^{d2}$ is independently selected from H, $C_{1-6}$ alkyl, and $C_{1-6}$ haloalkyl.

In some embodiments, each $R^{b2}$ is independently selected from $C_{1-6}$ alkyl optionally substituted with 1, 2, 3, or 4 substituents independently selected from $R^{20}$. In some embodiments, each $R^{b2}$ is independently selected from $C_{1-6}$ alkyl.

In some embodiments, each $R^{b2}$ is independently selected from $C_{1-6}$ alkyl and $C_{1-6}$ haloalkyl.

In some embodiments, each $R^{a3}$, $R^{c3}$ and $R^{d3}$, is independently selected from H, $C_{1-6}$ alkyl, and $C_{1-6}$ haloalkyl.

In some embodiments, each $R^{a3}$, $R^{c3}$ and $R^{d3}$ is independently selected from H and $C_{1-6}$ alkyl, wherein said $C_{1-6}$ alkyl is optionally substituted with 1, 2, 3, or 4 substituents independently selected from $R^{12}$. In some embodiments, each $R^{a3}$, $R^{c3}$ and $R^{d3}$ is independently selected from H and $C_{1-6}$ alkyl.

In some embodiments, each $R^{b3}$ is independently selected from $C_{1-6}$ alkyl and $C_{1-6}$ haloalkyl.

In some embodiments, each $R^{b3}$ is independently selected from $C_{1-6}$ alkyl optionally substituted with 1, 2, 3, or 4 substituents independently selected from $R^{12}$. In some embodiments, each $R^{b3}$ is independently selected from $C_{1-6}$ alkyl.

In some embodiments, each $R^{a4}$, $R^{c4}$ and $R^{d4}$, is independently selected from H, $C_{1-6}$ alkyl, and $C_{1-6}$ haloalkyl.

In some embodiments, each $R^{a5}$, $R^{c5}$ and $R^{d5}$ is independently selected from H and $C_{1-6}$ alkyl.

In some embodiments, each $R^{a6}$, $R^{c6}$ and $R^{d6}$ is independently selected from H and $C_{1-6}$ alkyl.

In some embodiments, each $R^{a6}$, $R^{c6}$ and $R^{d6}$, is independently selected from H, $C_{1-6}$ alkyl, and $C_{1-6}$ haloalkyl.

In some embodiments, each $R^{b6}$ is independently selected from $C_{1-6}$ alkyl.

In some embodiments, each $R^{b6}$ is independently selected from $C_{1-6}$ alkyl and $C_{1-6}$ haloalkyl.

In some embodiments, each $R^{a7}$, $R^{c7}$ and $R^{d7}$ is independently selected from H and $C_{1-6}$ alkyl.

In some embodiments, each $R^{a7}$, $R^{c7}$ and $R^{d7}$, is independently selected from H, $C_{1-6}$ alkyl, and $C_{1-6}$ haloalkyl.

In some embodiments, each $R^{b7}$ is independently selected from $C_{1-6}$ alkyl.

In some embodiments, each $R^{b7}$ is independently selected from $C_{1-6}$ alkyl and $C_{1-6}$ haloalkyl.

In some embodiments the compound of Formula I is a compound of Formula IIa:

IIa

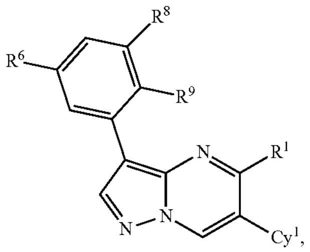

or a pharmaceutically acceptable salt thereof, wherein $Cy^1$, $R^1$, $R^6$, $R^8$, and $R^9$ are as defined herein.

In some embodiments the compound of Formula I is a compound of Formula IIb:

IIb

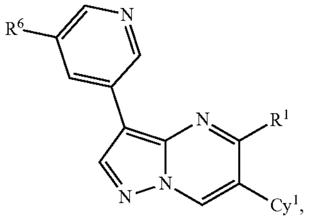

or a pharmaceutically acceptable salt thereof, wherein $Cy^1$, $R^1$, and $R^6$ are as defined herein.

In some embodiments the compound of Formula I is a compound of Formula IIIa:

IIIa

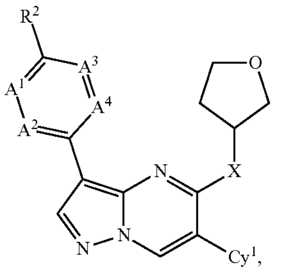

or a pharmaceutically acceptable salt thereof, wherein X is O or NH; and wherein $Cy^1$, $R^2$, $A^1$, $A^2$, $A^3$, and $A^4$ are as defined herein. In some embodiments, X is O. In some embodiments, X is NH.

In some embodiments the compound of Formula I is a compound of Formula IIIb:

IIIb

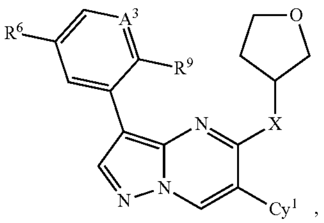

or a pharmaceutically acceptable salt thereof, wherein X is O or NH; and wherein $Cy^1$, $R^6$, $R^9$, and $A^3$ are as defined herein. In some embodiments, X is O. In some embodiments, X is NH.

In some embodiments the compound of Formula I is a compound of Formula IVa:

IVa

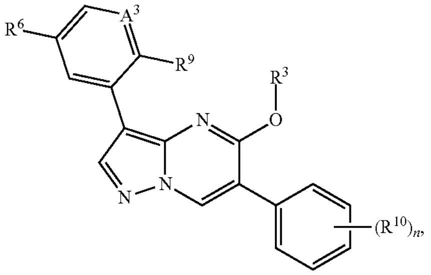

or a pharmaceutically acceptable salt thereof, wherein n is 0, 1, 2, 3, or 4, and wherein $R^3$, $R^6$, $R^9$, $R^{10}$, and $A^3$ are as defined herein. In some embodiments, n is 0, 1, 2 or 3. In some embodiments, n is 0, 1, or 2. In some embodiments, n is 0 or 1. In some embodiments, n is 1 or 2. In some embodiments, n is 0. In some embodiments, n is 1. In some embodiments, n is 2.

In some embodiments the compound of Formula I is a compound of Formula IVb:

IVb

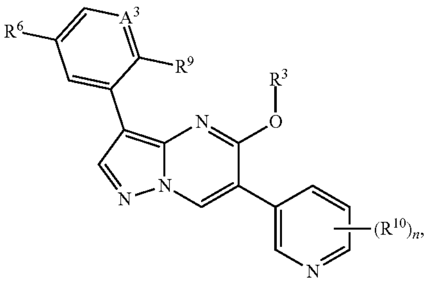

or a pharmaceutically acceptable salt thereof, wherein n is 0, 1, 2, 3, or 4, and wherein $R^3$, $R^6$, $R^9$, $R^{10}$, and $A^3$ are as defined herein. In some embodiments, n is 0, 1, 2 or 3. In some embodiments, n is 0, 1, or 2. In some embodiments, n is 0 or 1. In some embodiments, n is 1 or 2. In some embodiments, n is 0. In some embodiments, n is 1. In some embodiments, n is 2.

In some embodiments the compound of Formula I is a compound of Formula IVc:

IVc

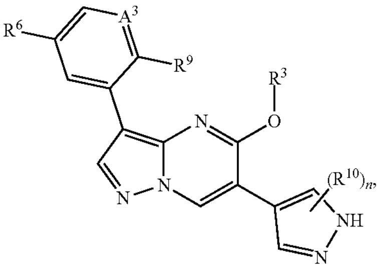

or a pharmaceutically acceptable salt thereof, wherein n is 0, 1, 2, or 3, and wherein $R^3$, $R^6$, $R^9$, $R^{10}$, and $A^3$ are as defined herein. In some embodiments, n is 0, 1, or 2. In some embodiments, n is 0 or 1. In some embodiments, n is 1.

In some embodiments the compound of Formula I is a compound of Formula V:

V

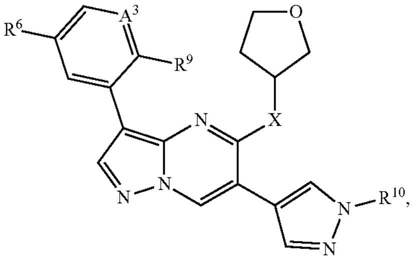

or a pharmaceutically acceptable salt thereof, wherein X is O or NH; and wherein $R^6$, $R^9$, $R^{10}$, and $A^3$ are as defined herein. In some embodiments, X is O. In some embodiments, X is NH.

In some embodiments, provided herein is a compound of Formula (I), wherein:

$Cy^1$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

$R^1$ is $OR^3$ or $NR^4R^5$;

$R^2$ is selected from H, D, and halo;

$A^1$ is selected from N and $CR^6$;

$A^2$ is selected from N and $CR^7$;

$A^3$ is selected from N and $CR^8$;

$A^4$ is selected from N and $CR^9$;

$R^3$ is selected from $C_{1-6}$ alkyl, $C_{1-6}$ haloalkyl, $C_{3-10}$ cycloalkyl, 4-14 membered heterocycloalkyl, $C_{3-10}$ cycloalkyl-$C_{1-3}$ alkylene, 4-14 membered heterocycloalkyl-$C_{1-3}$ alkylene, and $C_{6-10}$ aryl-$C_{1-3}$ alkylene; wherein said $C_{1-6}$ alkyl is substituted with 1, 2, 3, or 4 substituents independently selected from $R^{30A}$ and wherein said $C_{3-10}$ cycloalkyl, 4-14 membered heterocycloalkyl, $C_{3-10}$ cycloalkyl-$C_{1-3}$ alkylene, 4-14 membered heterocycloalkyl-$C_{1-3}$ alkylene, and $C_{6-10}$ aryl-$C_{1-3}$ alkylene are each optionally substituted with 1, 2, 3, or 4 substituents independently selected from $R^{30}$;

$R^4$ is selected from $C_{1-6}$ alkyl, $C_{1-6}$ haloalkyl, $C_{3-10}$ cycloalkyl, 4-14 membered heterocycloalkyl, $C_{3-10}$ cycloalkyl-$C_{1-3}$ alkylene, 4-14 membered heterocycloalkyl-$C_{1-3}$ alkylene, and $C_{6-10}$ aryl-$C_{1-3}$ alkylene; wherein said $C_{1-6}$ alkyl, $C_{3-10}$ cycloalkyl, 4-14 membered heterocycloalkyl, $C_{3-10}$ cycloalkyl-$C_{1-3}$ alkylene, 4-14 membered heterocycloalkyl-$C_{1-3}$ alkylene, and $C_{6-10}$ aryl-$C_{1-3}$ alkylene are each optionally substituted with 1, 2, 3, or 4 substituents independently selected from $R^{40}$;

$R^5$ is H;

$R^6$, $R^7$, $R^8$, and $R^9$ are each independently selected from H, D, $C_{1-6}$ alkyl, $C_{1-6}$ haloalkyl, halo, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein said $C_{1-6}$ alkyl is optionally substituted with 1, 2, 3, or 4 substituents independently selected from $R^{20}$;

each $R^{10}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $S(O)_2R^{b1}$, and $S(O)_2NR^{c1}R^{d1}$; wherein said $C_{1-6}$ alkyl, $C_{3-10}$ cycloalkyl, and 4-10 membered heterocycloalkyl are each optionally substituted with 1, 2, 3, or 4 substituents independently selected from $R^{11}$;

each $R^{11}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a3}$, $C(O)R^{b3}$, $C(O)N^{c3}R^{d3}$, $C(O)OR^{a3}$, $NR^{c3}R^{d3}$, and $S(O)_2R^{b3}$;

each $R^{20}$ is independently selected from halo, D, CN, $OR^{a4}$, and $NR^{c4}R^{d4}$;

each $R^{30A}$ is independently selected from halo, CN, $OR^{a6}$, and $NR^{c6}R^{d6}$;

each $R^{30}$ is independently selected from $C_{1-6}$ alkyl, $C_{1-6}$ haloalkyl halo, D, CN, $OR^{a6}$, $C(O)R^{b6}$, $C(O)NR^{c6}R^{d6}$, $C(O)OR^{a6}$, and $NR^{c6}R^{d6}$;

each $R^{40}$ is independently selected from $C_{1-6}$ alkyl, $C_{1-6}$ haloalkyl, halo, D, CN, $OR^{a7}$, $C(O)R^{b7}$, $C(O)NR^{c7}R^{d7}$, $C(O)OR^{a7}$, and $NR^{c7}R^{d7}$;

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl;

or any $R^{c1}$ and $R^{d1}$ attached to the same N atom, together with the N atom to which they are attached, form a 4-, 5-, or 6-membered heterocycloalkyl group optionally substituted with 1, 2, 3, or 4 substituents independently selected from $R^{11}$;

each $R^{b1}$ is independently selected from $C_{1-6}$ alkyl, $C_{1-6}$ haloalkyl, $C_{3-10}$ cycloalkyl, and 4-10 membered heterocycloalkyl;

each $R^{a2}$, $R^{c2}$, and $R^{d2}$ is independently selected from H, $C_{1-6}$ alkyl, and $C_{1-6}$ haloalkyl; each $R^{b2}$ is independently selected from $C_{1-6}$ alkyl and $C_{1-6}$ haloalkyl;

each $R^{a3}$, $R^{c3}$ and $R^{d3}$, is independently selected from H, $C_{1-6}$ alkyl, and $C_{1-6}$ haloalkyl; each $R^{b3}$ is independently selected from $C_{1-6}$ alkyl and $C_{1-6}$ haloalkyl;

each $R^{a4}$, $R^{c4}$ and $R^{d4}$, is independently selected from H, $C_{1-6}$ alkyl, and $C_{1-6}$ haloalkyl;

each $R^{a6}$, $R^{c6}$ and $R^{d6}$, is independently selected from H, $C_{1-6}$ alkyl, and $C_{1-6}$ haloalkyl;

each $R^{b6}$ is independently selected from $C_{1-6}$ alkyl and $C_{1-6}$ haloalkyl;

each $R^{a7}$, $R^{c7}$ and $R^{d7}$, is independently selected from H, $C_{1-6}$ alkyl, and $C_{1-6}$ haloalkyl; and each $R^{b7}$ is independently selected from $C_{1-6}$ alkyl and $C_{1-6}$ haloalkyl.

In some embodiments, provided herein is a compound of Formula (I), wherein:

$Cy^1$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

$R^1$ is $OR^3$ or $NR^4R^5$;

$R^2$ is selected from H, D, and halo;

$A^1$ is $CR^6$;

$A^2$ is $CR^7$;

$A^3$ is CR or N;

$A^4$ is $CR^9$;

$R^3$ is selected from $C_{1-6}$ alkyl, $C_{1-6}$ haloalkyl, $C_{3-10}$ cycloalkyl, 4-14 membered heterocycloalkyl, $C_{3-10}$ cycloalkyl-$C_{1-3}$ alkylene, 4-14 membered heterocycloalkyl-$C_{1-3}$ alkylene, and $C_{6-10}$ aryl-$C_{1-3}$ alkylene; wherein said $C_{1-6}$ alkyl is substituted with 1, 2, 3, or 4 substituents independently selected from $R^{30A}$ and wherein said $C_{3-10}$ cycloalkyl, 4-14 membered heterocycloalkyl, $C_{3-10}$ cycloalkyl-$C_{1-3}$ alkylene, 4-14 membered heterocycloalkyl-$C_{1-3}$ alkylene, and $C_{6-10}$ aryl-$C_{1-3}$ alkylene are each optionally substituted with 1, 2, 3, or 4 substituents independently selected from $R^{30}$;

$R^4$ is selected from $C_{1-6}$ alkyl, $C_{1-6}$ haloalkyl, $C_{3-10}$ cycloalkyl, 4-14 membered heterocycloalkyl, $C_{3-10}$ cycloalkyl-$C_{1-3}$ alkylene, 4-14 membered heterocycloalkyl-$C_{1-3}$ alkylene, and $C_{6-10}$ aryl-$C_{1-3}$ alkylene; wherein said $C_{1-6}$ alkyl, $C_{3-10}$ cycloalkyl, 4-14 membered heterocycloalkyl, $C_{3-10}$ cycloalkyl-$C_{1-3}$ alkylene, 4-14 membered heterocycloalkyl-$C_{1-3}$ alkylene, and $C_{6-10}$ aryl-$C_{1-3}$ alkylene are each optionally substituted with 1, 2, 3, or 4 substituents independently selected from $R^{40}$;

$R^5$ is H;

$R^6$, $R^7$, $R^8$, and $R^9$ are each independently selected from H, D, $C_{1-6}$ alkyl, $C_{1-6}$ haloalkyl, halo, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein said $C_{1-6}$ alkyl is optionally substituted with 1, 2, 3, or 4 substituents independently selected from $R^{20}$;

each $R^{10}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $S(O)_2R^{b1}$, and $S(O)_2NR^{c1}R^{d1}$; wherein said $C_{1-6}$ alkyl, $C_{3-10}$ cycloalkyl, and 4-10 membered heterocycloalkyl are each optionally substituted with 1, 2, 3, or 4 substituents independently selected from $R^{11}$;

each $R^{11}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a3}$, $C(O)R^{b3}$, $C(O)N^{c3}R^{d3}$, $C(O)OR^{a3}$, $NR^{c3}R^{d3}$ and $S(O)_2R^{b3}$;

each $R^{20}$ is independently selected from halo, D, CN, $OR^{a4}$, and $NR^{c4}R^{d4}$;

each $R^{30A}$ is independently selected from halo, CN, $OR^{a6}$, and $NR^{c6}R^{d6}$;

each $R^{30}$ is independently selected from $C_{1-6}$ alkyl, $C_{1-6}$ haloalkyl halo, D, CN, $OR^{a6}$, $C(O)R^{b6}$, $C(O)NR^{c6}R^{d6}$, $C(O)OR^{a6}$, and $NR^{c6}R^{d6}$;

each $R^{40}$ is independently selected from $C_{1-6}$ alkyl, $C_{1-6}$ haloalkyl, halo, D, CN, $OR^{a7}$, $C(O)R^{b7}$, $C(O)NR^{c7}R^{d7}$, $C(O)OR^{a7}$, and $NR^{c7}R^{d7}$;

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl;

or any $R^{c1}$ and $R^{d1}$ attached to the same N atom, together with the N atom to which they are attached, form a 4-, 5-, or 6-membered heterocycloalkyl group optionally substituted with 1, 2, 3, or 4 substituents independently selected from $R^{11}$;

each $R^{b1}$ is independently selected from $C_{1-6}$ alkyl, $C_{1-6}$ haloalkyl, $C_{3-10}$ cycloalkyl, and 4-10 membered heterocycloalkyl;

each $R^{a2}$, $R^{c2}$, and $R^{d2}$ is independently selected from H, $C_{1-6}$ alkyl, and $C_{1-6}$ haloalkyl;

each $R^{b2}$ is independently selected from $C_{1-6}$ alkyl and $C_{1-6}$ haloalkyl;

each $R^{a3}$, $R^{c3}$ and $R^{d3}$, is independently selected from H, $C_{1-6}$ alkyl, and $C_{1-6}$ haloalkyl;

each $R^{b3}$ is independently selected from $C_{1-6}$ alkyl and $C_{1-6}$ haloalkyl;

each $R^{a4}$, $R^{c4}$ and $R^{d4}$ is independently selected from H, $C_{1-6}$ alkyl, and $C_{1-6}$ haloalkyl;

each $R^{a6}$, $R^{c6}$ and $R^{d6}$ is independently selected from H, $C_{1-6}$ alkyl, and $C_{1-6}$ haloalkyl;

each $R^{b6}$ is independently selected from $C_{1-6}$ alkyl and $C_{1-6}$ haloalkyl;

each $R^{a7}$, $R^{c7}$ and $R^{d7}$ is independently selected from H, $C_{1-6}$ alkyl, and $C_{1-6}$ haloalkyl; and each $R^{b7}$ is independently selected from $C_{1-6}$ alkyl and $C_{1-6}$ haloalkyl.

In some embodiments, provided herein is a compound of Formula (I), wherein:

$Cy^1$ is selected from phenyl and 5-6 membered heteroaryl; wherein the 5-6 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl is optionally substituted by oxo to form a carbonyl group; and wherein the phenyl and 5-6 membered heteroaryl are each optionally substituted with 1 or 2 substituents independently selected from $R^{10}$;

$R^1$ is $OR^3$ or $NR^4R^5$;

$R^2$ is selected from H, D, and halo;

$A^1$ is selected from N and $CR^6$;

$A^2$ is selected from N and $CR^7$;

$A^3$ is selected from N and $CR^8$;

$A^4$ is selected from N and $CR^9$;

$R^3$ is selected from $C_{1-6}$ alkyl, $C_{1-6}$ haloalkyl, $C_{3-6}$ cycloalkyl, 4-6 membered heterocycloalkyl, $C_{3-6}$ cycloalkyl-$C_{1-3}$ alkylene, 4-6 membered heterocycloalkyl-$C_{1-3}$ alkylene, and $C_{6-10}$ aryl-$C_{1-3}$ alkylene; wherein said $C_{1-6}$ alkyl is substituted with 1, 2, 3, or 4 substituents independently selected from $R^{30A}$ and wherein said $C_{3-6}$ cycloalkyl, 4-6 membered heterocycloalkyl, $C_{3-6}$ cycloalkyl-$C_{1-3}$ alkylene, 4-6 membered heterocycloalkyl-$C_{1-3}$ alkylene, and $C_{6-10}$ aryl-$C_{1-3}$ alkylene are each optionally substituted with 1 or 2 substituents independently selected from $R^{30}$;

$R^4$ is selected from $C_{1-6}$ alkyl, $C_{1-6}$ haloalkyl, $C_{3-6}$ cycloalkyl, 4-6 membered heterocycloalkyl, $C_{3-6}$ cycloalkyl-$C_{1-3}$ alkylene, 4-6 membered heterocycloalkyl-$C_{1-3}$ alkylene, and $C_{6-10}$ aryl-$C_{1-3}$ alkylene; wherein said $C_{1-6}$ alkyl, $C_{3-6}$ cycloalkyl, 4-6 membered heterocycloalkyl, $C_{3-6}$ cycloalkyl-$C_{1-3}$ alkylene, 4-6 membered heterocycloalkyl-$C_{1-3}$ alkylene, and $C_{6-10}$ aryl-$C_{1-3}$ alkylene are each optionally substituted with 1 or 2 substituents independently selected from $R^{40}$;

$R^5$ is H;

$R^6$, $R^7$, $R^8$, and $R^9$ are each independently selected from H, D, $C_{1-6}$ alkyl, $C_{1-6}$ haloalkyl, halo, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein said $C_{1-6}$ alkyl is optionally substituted with 1 or 2 substituents independently selected from $R^{20}$;

each $R^{10}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $S(O)_2R^{b1}$, and $S(O)_2NR^{c1}R^{d1}$; wherein said $C_{1-6}$ alkyl, $C_{3-6}$ cycloalkyl, and 4-6 membered heterocycloalkyl are each optionally substituted with 1 or 2 substituents independently selected from $R^{11}$;

each $R^{11}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a3}$, $C(O)R^{b3}$, $C(O)N^{c3}R^{d3}$, $C(O)OR^{a3}$, $NR^{c3}R^{d3}$, and $S(O)_2R^{b3}$;

each $R^{20}$ is independently selected from halo, D, CN, $OR^{a4}$, and $NR^{c4}R^{d4}$;

each $R^{30A}$ is independently selected from halo, CN, $OR^{a6}$, and $NR^{c6}R^{d6}$;

each $R^{30}$ is independently selected from $C_{1-6}$ alkyl, $C_{1-6}$ haloalkyl halo, D, CN, $OR^{a6}$, $C(O)R^{b6}$, $C(O)NR^{c6}R^{d6}$, $C(O)OR^{a6}$, and $NR^{c6}R^{d6}$;

each $R^{40}$ is independently selected from $C_{1-6}$ alkyl, $C_{1-6}$ haloalkyl, halo, D, CN, $OR^{a7}$, $C(O)R^{b7}$, $C(O)NR^{c7}R^{d7}$, $C(O)OR^{a7}$, and $NR^{c7}R^{d7}$;

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl;

or any $R^{c1}$ and $R^{d1}$ attached to the same N atom, together with the N atom to which they are attached, form a 4-, 5-, or 6-membered heterocycloalkyl group optionally substituted with 1, 2, 3, or 4 substituents independently selected from $R^{11}$;

each $R^{b1}$ is independently selected from $C_{1-6}$ alkyl, $C_{1-6}$ haloalkyl, $C_{3-10}$ cycloalkyl, and 4-10 membered heterocycloalkyl;

each $R^{a2}$, $R^{c2}$, and $R^{d2}$ is independently selected from H, $C_{1-6}$ alkyl, and $C_{1-6}$ haloalkyl; each $R^{b2}$ is independently selected from $C_{1-6}$ alkyl and $C_{1-6}$ haloalkyl;

each $R^{a3}$, $R^{c3}$ and $R^{d3}$ is independently selected from H, $C_{1-6}$ alkyl, and $C_{1-6}$ haloalkyl; each $R^{b3}$ is independently selected from $C_{1-6}$ alkyl and $C_{1-6}$ haloalkyl;

each $R^{a4}$, $R^{c4}$ and $R^{d4}$ is independently selected from H, $C_{1-6}$ alkyl, and $C_{1-6}$ haloalkyl;

each $R^{a6}$, $R^{c6}$ and $R^{d6}$ is independently selected from H, $C_{1-6}$ alkyl, and $C_{1-6}$ haloalkyl;

each $R^{b6}$ is independently selected from $C_{1-6}$ alkyl and $C_{1-6}$ haloalkyl;

each $R^{a7}$, $R^{c7}$ and $R^{d7}$ is independently selected from H, $C_{1-6}$ alkyl, and $C_{1-6}$ haloalkyl; and each $R^{b7}$ is independently selected from $C_{1-6}$ alkyl and $C_{1-6}$ haloalkyl.

In some embodiments, provided herein is a compound of Formula (I), wherein:

$Cy^1$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; and wherein the $C_{6-10}$ aryl and 5-10 membered heteroaryl are each optionally substituted with 1 or 2 substituents independently selected from $R^{10}$;

$R^1$ is $OR^3$ or $NR^4R^5$;

$R^2$ is H;

$A^1$ is selected from N and $CR^6$;

$A^2$ is selected from N and $CR^7$;

$A^3$ is selected from N and CR;

$A^4$ is selected from N and $CR^9$;

$R^3$ is 4-14 membered heterocycloalkyl;

$R^4$ is 4-14 membered heterocycloalkyl;

$R^5$ is H;

$R^6$, $R^7$, $R^8$, and $R^9$ are each independently selected from H, D, $C_{1-6}$ alkyl, $C_{1-6}$ haloalkyl, halo, CN, $OR^{a2}$, C(O)$NR^{c2}R^{d2}$, $NR^{c2}R^{d2}$, $S(O)_2R^{b2}$, and $S(O)_2NR^{c2}R^{d2}$;

each $R^{10}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a1}$, and $NR^{c1}R^{d1}$; wherein said $C_{1-6}$ alkyl and 4-10 membered heterocycloalkyl are each optionally substituted with 1 or 2 substituents independently selected from $R^{11}$;

each $R^{11}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a3}$, and $NR^{c3}R^{d3}$;

each $R^{a1}$, $R^{c1}$ and $R^{d1}$ is independently selected from H, $C_{1-6}$ alkyl, and $C_{1-6}$ haloalkyl;

each $R^{c2}$ and $R^{d2}$ is independently selected from H, $C_{1-6}$ alkyl, and $C_{1-6}$ haloalkyl;

each $R^{b2}$ is independently selected from $C_{1-6}$ alkyl and $C_{1-6}$ haloalkyl; and each $R^{a3}$, $R^{c3}$ and $R^{d3}$ is independently selected from H and $C_{1-6}$ alkyl.

In some embodiments, provided herein is a compound of Formula (I), wherein:

$Cy^1$ is selected from phenyl and 5-6 membered heteroaryl; wherein the 5-6 membered heteroaryl has at least one ring-forming carbon atom and 1, 2, 3, or 4 ring-forming heteroatoms independently selected from N, O, and S; and wherein the phenyl and 5-6 membered heteroaryl are each optionally substituted with 1 or 2 substituents independently selected from $R^{10}$;

$R^1$ is $OR^3$ or $NR^4R^5$;

$R^2$ is H;

$A^1$ is selected from N and $CR^6$;

$A^2$ is selected from N and $CR^7$;

$A^3$ is selected from N and CR;

$A^4$ is selected from N and $CR^9$;

$R^3$ is 4-6 membered heterocycloalkyl;

$R^4$ is 4-6 membered heterocycloalkyl;

$R^5$ is H;

$R^6$, $R^7$, $R^8$, and $R^9$ are each independently selected from H, D, $C_{1-6}$ alkyl, $C_{1-6}$ haloalkyl, halo, CN, $OR^{a2}$, C(O)$NR^{c2}R^{d2}$, $NR^{c2}R^{d2}$, $S(O)_2R^{b2}$, and $S(O)_2NR^{c2}R^{d2}$;

each $R^{10}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a1}$, and $NR^{c1}R^{d1}$; wherein said $C_{1-6}$ alkyl and 4-6 membered heterocycloalkyl are each optionally substituted with 1 or 2 substituents independently selected from $R^{11}$;

each $R^{11}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a3}$, and $NR^{c3}R^{d3}$;

each $R^{a1}$, $R^{c1}$ and $R^{d1}$ is independently selected from H, $C_{1-6}$ alkyl, and $C_{1-6}$ haloalkyl;

each $R^{c2}$ and $R^{d2}$ is independently selected from H, $C_{1-6}$ alkyl, and $C_{1-6}$ haloalkyl;

each $R^{b2}$ is independently selected from $C_{1-6}$ alkyl and $C_{1-6}$ haloalkyl; and each $R^{a3}$, $R^{c3}$ and $R^{d3}$ is independently selected from H and $C_{1-6}$ alkyl.

In some embodiments, provided herein is a compound of Formula (I) wherein:

$Cy^1$ is selected from phenyl and 5-6 membered heteroaryl; wherein the 5-6 membered heteroaryl has at least one ring-forming carbon atom and 1, 2, 3, or 4 ring-forming heteroatoms independently selected from N, O, and S; and wherein the phenyl and 5-6 membered heteroaryl are each optionally substituted with 1 or 2 substituents independently selected from $R^{10}$;

$R^1$ is $OR^3$ or $NR^4R^5$;

$R^2$ is H;

$A^1$ is $CR^6$;

$A^2$ is $CR^7$;

$A^3$ is selected from N and $CR^8$;

$A^4$ is $CR^9$;

$R^3$ is 4-6 membered heterocycloalkyl;

$R^4$ is 4-6 membered heterocycloalkyl;

$R^5$ is H;

$R^6$, $R^7$, $R^8$, and $R^9$ are each independently selected from H, D, $C_{1-6}$ alkyl, $C_{1-6}$ haloalkyl, halo, CN, $OR^{a2}$, C(O)$NR^{c2}R^{d2}$, $NR^{c2}R^{d2}$, $S(O)_2R^{b2}$, and $S(O)_2NR^{c2}R^{d2}$;

each $R^{10}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a1}$, and $NR^{c1}R^{d1}$; wherein said $C_{1-6}$ alkyl and 4-6 membered heterocycloalkyl, are each optionally substituted with 1 or 2 substituents independently selected from $R^{11}$;

each $R^{11}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a3}$, and $NR^{c3}R^{d3}$;

each $R^{a1}$, $R^{c1}$ and $R^{d1}$ is independently selected from H, $C_{1-6}$ alkyl, and $C_{1-6}$ haloalkyl;

each $R^{c2}$ and $R^{d2}$ is independently selected from H, $C_{1-6}$ alkyl, and $C_{1-6}$ haloalkyl;

each $R^{b2}$ is independently selected from $C_{1-6}$ alkyl and $C_{1-6}$ haloalkyl; and each $R^{a3}$, $R^{c3}$ and $R^{d3}$ is independently selected from H and $C_{1-6}$ alkyl.

In some embodiments, provided herein is a compound selected from:

N-methyl-3-(6-(1-methyl-1H-pyrazol-4-yl)-5-((tetrahydrofuran-3-yl)oxy)pyrazolo[1,5-a]pyrimidin-3-yl)benzamide;

4-fluoro-N-methyl-3-(6-(1-methyl-1H-pyrazol-4-yl)-5-((tetrahydrofuran-3-yl)oxy)pyrazolo[1,5-a]pyrimidin-3-yl)benzamide;

N-methyl-5-(6-(1-methyl-1H-pyrazol-4-yl)-5-((tetrahydrofuran-3-yl)oxy)pyrazolo[1,5-a]pyrimidin-3-yl)nicotinamide;

4-fluoro-N,3-dimethyl-5-(6-(1-methyl-1H-pyrazol-4-yl)-5-((tetrahydrofuran-3-yl)oxy)pyrazolo[1,5-a]pyrimidin-3-yl)benzamide;

(S)-4-fluoro-N,3-dimethyl-5-(6-(1-methyl-1H-pyrazol-4-yl)-5-((tetrahydrofuran-3-yl)oxy)pyrazolo[1,5-a]pyrimidin-3-yl)benzamide;

(S)-3-cyano-N-methyl-5-(6-(1-methyl-1H-pyrazol-4-yl)-5-((tetrahydrofuran-3-yl)oxy)pyrazolo[1,5-a]pyrimidin-3-yl)benzamide;

(S)—N-methyl-5-(6-(1-methyl-1H-pyrazol-4-yl)-5-((tetrahydrofuran-3-yl)amino)pyrazolo[1,5-a]pyrimidin-3-yl)nicotinamide;

(S)-3-cyano-N-methyl-5-(6-(1-methyl-1H-pyrazol-4-yl)-5-((tetrahydrofuran-3-yl)amino)pyrazolo[1,5-a]pyrimidin-3-yl)benzamide;

(S)-5-(6-(1-isopropyl-1H-pyrazol-4-yl)-5-((tetrahydrofuran-3-yl)oxy)pyrazolo[1,5-a]pyrimidin-3-yl)-N-methylnicotinamide;

(S)-5-(6-(1-isopropyl-1H-pyrazol-4-yl)-5-((tetrahydrofuran-3-yl)amino)pyrazolo[1,5-a]pyrimidin-3-yl)-N-methylnicotinamide;

(S)-3,4-difluoro-N-methyl-5-(6-(1-(1-methylpiperidin-4-yl)-1H-pyrazol-4-yl)-5-((tetrahydrofuran-3-yl)oxy)pyrazolo[1,5-a]pyrimidin-3-yl)benzamide;
(S)-3,4-difluoro-N-methyl-5-(6-(4-(4-methylpiperazin-1-yl)phenyl)-5-((tetrahydrofuran-3-yl)oxy)pyrazolo[1,5-a]pyrimidin-3-yl)benzamide;
(S)-3,4-difluoro-N-methyl-5-(6-(6-(4-methylpiperazin-1-yl)pyridin-3-yl)-5-((tetrahydrofuran-3-yl)oxy)pyrazolo[1,5-a]pyrimidin-3-yl)benzamide
(S)-3,4-difluoro-N-methyl-5-(6-(1-(2-morpholinoethyl)-1H-pyrazol-4-yl)-5-((tetrahydrofuran-3-yl)oxy)pyrazolo[1,5-a]pyrimidin-3-yl)benzamide
(S)-3,4-difluoro-N-methyl-5-(6-(6-methylpyridin-3-yl)-5-((tetrahydrofuran-3-yl)oxy)pyrazolo[1,5-a]pyrimidin-3-yl)benzamide;
(S)-4-fluoro-N,3-dimethyl-5-(6-(1-methyl-1H-pyrazol-4-yl)-5-((tetrahydrofuran-3-yl)amino)pyrazolo[1,5-a]pyrimidin-3-yl)benzamide;
(S)-3,4-difluoro-N-methyl-5-(6-(1-(1-methylazetidin-3-yl)-1H-pyrazol-4-yl)-5-((tetrahydrofuran-3-yl)oxy)pyrazolo[1,5-a]pyrimidin-3-yl)benzamide;
(S)—N-methyl-5-(6-(4-(4-methylpiperazin-1-yl)phenyl)-5-((tetrahydrofuran-3-yl)oxy)pyrazolo[1,5-a]pyrimidin-3-yl)nicotinamide;
(S)—N-methyl-5-(6-(6-(4-methylpiperazin-1-yl)pyridin-3-yl)-5-((tetrahydrofuran-3-yl)oxy)pyrazolo[1,5-a]pyrimidin-3-yl)nicotinamide;
(S)—N-methyl-5-(6-(6-morpholinopyridin-3-yl)-5-((tetrahydrofuran-3-yl)oxy)pyrazolo[1,5-a]pyrimidin-3-yl)nicotinamide;
(S)-5-(6-(1-cyclopropyl-1H-pyrazol-4-yl)-5-((tetrahydrofuran-3-yl)oxy)pyrazolo[1,5-a]pyrimidin-3-yl)-N-methylnicotinamide;
(S)-5-(6-(1-cyclobutyl-1H-pyrazol-4-yl)-5-((tetrahydrofuran-3-yl)oxy)pyrazolo[1,5-a]pyrimidin-3-yl)-N-methylnicotinamide;
(S)-3-(difluoromethyl)-4-fluoro-N-methyl-5-(6-(pyridin-3-yl)-5-((tetrahydrofuran-3-yl)oxy)pyrazolo[1,5-a]pyrimidin-3-yl)benzamide;
(S)-3-(difluoromethyl)-4-fluoro-N-methyl-5-(6-(5-methyl-6-(methylamino)pyridin-3-yl)-5-((tetrahydrofuran-3-yl)oxy)pyrazolo[1,5-a]pyrimidin-3-yl)benzamide;
(S)-3-(difluoromethyl)-4-fluoro-5-(6-(6-(2-hydroxypropan-2-yl)pyridin-3-yl)-5-((tetrahydrofuran-3-yl)oxy)pyrazolo[1,5-a]pyrimidin-3-yl)-N-methylbenzamide;
(S)-3-(difluoromethyl)-4-fluoro-N-methyl-5-(6-(1-(1-methylazetidin-3-yl)-1H-pyrazol-4-yl)-5-((tetrahydrofuran-3-yl)oxy)pyrazolo[1,5-a]pyrimidin-3-yl)benzamide;
(S)-3-cyano-N-methyl-5-(6-(pyridin-3-yl)-5-((tetrahydrofuran-3-yl)oxy)pyrazolo[1,5-a]pyrimidin-3-yl)benzamide;
(S)-3-cyano-N-methyl-5-(6-(6-methylpyridin-3-yl)-5-((tetrahydrofuran-3-yl)oxy)pyrazolo[1,5-a]pyrimidin-3-yl)benzamide;
(S)-3-cyano-N-methyl-5-(6-(5-methylpyridin-3-yl)-5-((tetrahydrofuran-3-yl)oxy)pyrazolo[1,5-a]pyrimidin-3-yl)benzamide;
(S)-3-cyano-N-methyl-5-(6-(pyridin-4-yl)-5-((tetrahydrofuran-3-yl)oxy)pyrazolo[1,5-a]pyrimidin-3-yl)benzamide;
(S)-4-fluoro-3-hydroxy-N-methyl-5-(6-(1-methyl-1H-pyrazol-4-yl)-5-((tetrahydrofuran-3-yl)oxy)pyrazolo[1,5-a]pyrimidin-3-yl)benzamide; and
(S)-3-(6-(1-cyclobutyl-1H-pyrazol-4-yl)-5-((tetrahydrofuran-3-yl)oxy)pyrazolo[1,5-a]pyrimidin-3-yl)-N-methyl-5-(methylsulfonyl)benzamide;

or a pharmaceutically acceptable salt of any of the aforementioned.

In some embodiments, provided herein is a compound selected from:

(S)-3-(1H-Indazol-4-yl)-6-(1-methyl-1H-pyrazol-4-yl)-5-((tetrahydrofuran-3-yl)oxy)pyrazolo[1,5-a]pyrimidine;
(S)-4-Fluoro-N,3-dimethyl-5-(6-(1-(1-methylpiperidin-4-yl)-1H-pyrazol-4-yl)-5-((tetrahydrofuran-3-yl)amino)pyrazolo[1,5-a]pyrimidin-3-yl)benzamide;
(S)-4-Fluoro-N,3-dimethyl-5-(6-(1-(1-methylazetidin-3-yl)-1H-pyrazol-4-yl)-5-((tetrahydrofuran-3-yl)amino)pyrazolo[1,5-a]pyrimidin-3-yl)benzamide;
(S)-4-Fluoro-3-(6-(1-(2-hydroxyethyl)-1H-pyrazol-4-yl)-5-((tetrahydrofuran-3-yl)amino)pyrazolo[1,5-a]pyrimidin-3-yl)-N,5-dimethylbenzamide;
(S)-3-(6-(1-(2-Cyanoethyl)-1H-pyrazol-4-yl)-5-((tetrahydrofuran-3-yl)amino)pyrazolo[1,5-a]pyrimidin-3-yl)-4-fluoro-N,5-dimethylbenzamide;
3-(6-(1-(1,1-Dioxidotetrahydrothiophen-3-yl)-1H-pyrazol-4-yl)-5-(((S)-tetrahydrofuran-3-yl)amino)pyrazolo[1,5-a]pyrimidin-3-yl)-4-fluoro-N,5-dimethylbenzamide;
(S)-3-(6-(1-(2-(Dimethylamino)-2-oxoethyl)-1H-pyrazol-4-yl)-5-((tetrahydrofuran-3-yl)amino)pyrazolo[1,5-a]pyrimidin-3-yl)-4-fluoro-N,5-dimethylbenzamide;
(S)-4-Fluoro-3-(6-(1-(2-hydroxy-2-methylpropyl)-1H-pyrazol-4-yl)-5-((tetrahydrofuran-3-yl)amino)pyrazolo[1,5-a]pyrimidin-3-yl)-N,5-dimethylbenzamide;
4-Fluoro-N,3-dimethyl-5-(6-(1-(tetrahydrofuran-3-yl)-1H-pyrazol-4-yl)-5-(((S)-tetrahydrofuran-3-yl)amino)pyrazolo[1,5-a]pyrimidin-3-yl)benzamide;
(S)-4-Fluoro-N,3-dimethyl-5-(6-(2-methyloxazol-5-yl)-5-((tetrahydrofuran-3-yl)amino)pyrazolo[1,5-a]pyrimidin-3-yl)benzamide;
(S)-3-(6-(1-Ethyl-1H-pyrazol-3-yl)-5-((tetrahydrofuran-3-yl)amino)pyrazolo[1,5-a]pyrimidin-3-yl)-4-fluoro-N,5-dimethylbenzamide;
(S)-4-Fluoro-N,3-dimethyl-5-(6-(pyridazin-4-yl)-5-((tetrahydrofuran-3-yl)amino)pyrazolo[1,5-a]pyrimidin-3-yl)benzamide;
(S)-3-(5-(Ethylsulfonyl)-2,3-difluorophenyl)-6-(1-methyl-1H-pyrazol-4-yl)-N-(tetrahydrofuran-3-yl)pyrazolo[1,5-a]pyrimidin-5-amine;
(S)-3-(5-(Ethylsulfonyl)-2,3-difluorophenyl)-6-(1-methyl-1H-pyrazol-4-yl)-5-((tetrahydrofuran-3-yl)oxy)pyrazolo[1,5-a]pyrimidine;
(S)-3-(Difluoromethyl)-4-fluoro-N-methyl-5-(6-(1-methyl-1H-pyrazol-4-yl)-5-((tetrahydrofuran-3-yl)amino)pyrazolo[1,5-a]pyrimidin-3-yl)benzamide;
(S)-3-(Difluoromethyl)-5-(6-(1-ethyl-1H-pyrazol-4-yl)-5-((tetrahydrofuran-3-yl)amino)pyrazolo[1,5-a]pyrimidin-3-yl)-4-fluoro-N-methylbenzamide;
3-(Difluoromethyl)-4-fluoro-N-methyl-5-(6-(1-(tetrahydrofuran-3-yl)-1H-pyrazol-4-yl)-5-(((S)-tetrahydrofuran-3-yl)amino)pyrazolo[1,5-a]pyrimidin-3-yl)benzamide;
(S)-3-(Difluoromethyl)-4-fluoro-5-(6-(1-(2-methoxyethyl)-1H-pyrazol-4-yl)-5-((tetrahydrofuran-3-yl)amino)pyrazolo[1,5-a]pyrimidin-3-yl)-N-methylbenzamide;
(S)-3-(3-(1H-Pyrazol-3-yl)phenyl)-6-(1-methyl-1H-pyrazol-4-yl)-5-((tetrahydrofuran-3-yl)oxy)pyrazolo[1,5-a]pyrimidine;
(S)-3,4-Difluoro-N-methyl-5-(6-(1-(pyridin-3-ylmethyl)-1H-pyrazol-4-yl)-5-((tetrahydrofuran-3-yl)amino)pyrazolo[1,5-a]pyrimidin-3-yl)benzamide;
(S)-3-(6-(1-Ethyl-1H-pyrazol-4-yl)-5-((tetrahydrofuran-3-yl)amino)pyrazolo[1,5-a]pyrimidin-3-yl)-4,5-difluoro-N-methylbenzamide;

(S)-3,4-Difluoro-N-methyl-5-(6-(1-((tetrahydro-2H-pyran-4-yl)methyl)-1H-pyrazol-4-yl)-5-((tetrahydrofuran-3-yl)amino)pyrazolo[1,5-a]pyrimidin-3-yl)benzamide;

(S)-3,4-Difluoro-N-methyl-5-(6-(1-(2-morpholinoethyl)-1H-pyrazol-4-yl)-5-((tetrahydrofuran-3-yl)amino)pyrazolo[1,5-a]pyrimidin-3-yl)benzamide;

(S)-3,4-Difluoro-5-(6-(1-isopropyl-2-oxo-1,2-dihydropyridin-4-yl)-5-((tetrahydrofuran-3-yl)amino)pyrazolo[1,5-a]pyrimidin-3-yl)-N-methylbenzamide;

(S)-3,4-Difluoro-5-(6-(6-(2-hydroxypropan-2-yl)pyridin-3-yl)-5-((tetrahydrofuran-3-yl)amino)pyrazolo[1,5-a]pyrimidin-3-yl)-N-methylbenzamide;

(S)-3,4-Difluoro-N-methyl-5-(6-(2-methyloxazol-5-yl)-5-((tetrahydrofuran-3-yl)amino)pyrazolo[1,5-a]pyrimidin-3-yl)benzamide;

(S)—N-Methyl-5-(6-(1-methyl-1H-pyrazol-3-yl)-5-((tetrahydrofuran-3-yl)amino)pyrazolo[1,5-a]pyrimidin-3-yl)nicotinamide;

(S)—N-Methyl-5-(6-(2-methyl-2H-1,2,3-triazol-4-yl)-5-((tetrahydrofuran-3-yl)amino)pyrazolo[1,5-a]pyrimidin-3-yl)nicotinamide;

(S)—N-Ethyl-5-(6-(1-methyl-1H-pyrazol-3-yl)-5-((tetrahydrofuran-3-yl)amino)pyrazolo[1,5-a]pyrimidin-3-yl)nicotinamide;

(S)—N-Isopropyl-5-(6-(1-methyl-1H-pyrazol-3-yl)-5-((tetrahydrofuran-3-yl)amino)pyrazolo[1,5-a]pyrimidin-3-yl)nicotinamide;

(S)-5-(6-(1-Isopropyl-1H-pyrazol-4-yl)-5-((tetrahydrofuran-3-yl)oxy)pyrazolo[1,5-a]pyrimidin-3-yl)-N-(methyl-$d_3$)nicotinamide;

4-Fluoro-3-(6-(1-((3R,4R)-3-fluoro-1-methylpiperidin-4-yl)-1H-pyrazol-4-yl)-5-(((S)-tetrahydrofuran-3-yl)oxy)pyrazolo[1,5-a]pyrimidin-3-yl)-5-methyl-N-(methyl-$d_3$)benzamide;

4-Fluoro-3-(6-(1-((3R,4R)-3-fluoro-1-methylpiperidin-4-yl)-1H-pyrazol-4-yl)-5-(((S)-tetrahydrofuran-3-yl)amino)pyrazolo[1,5-a]pyrimidin-3-yl)-N,5-dimethylbenzamide;

3-(6-(6-(((1R,4R)-2-Oxa-5-azabicyclo[2.2.1]heptan-5-yl)methyl)pyridin-3-yl)-5-(((S)-tetrahydrofuran-3-yl)oxy)pyrazolo[1,5-a]pyrimidin-3-yl)-5-(difluoromethyl)-4-fluoro-N-(methyl-$d_3$)benzamide;

(S)-4-Fluoro-3-(6-(2-(1-isopropylpiperidin-4-yl)-2H-1,2,3-triazol-4-yl)-5-((tetrahydrofuran-3-yl)amino)pyrazolo[1,5-a]pyrimidin-3-yl)-5-methyl-N-(methyl-$d_3$)benzamide;

(S)-4-Fluoro-3-(6-(2-(1-isopropylpiperidin-4-yl)oxazol-5-yl)-5-((tetrahydrofuran-3-yl)amino)pyrazolo[1,5-a]pyrimidin-3-yl)-5-methyl-N-(methyl-$d_3$)benzamide;

(S)-4-Fluoro-3-(6-(2-(4-fluoro-1-methylpiperidin-4-yl)oxazol-5-yl)-5-((tetrahydrofuran-3-yl)amino)pyrazolo[1,5-a]pyrimidin-3-yl)-N,5-dimethylbenzamide; and (S)-4-Fluoro-N,3-dimethyl-5-(6-(2-(4-methylpiperazin-1-yl)oxazol-5-yl)-5-((tetrahydrofuran-3-yl)amino)pyrazolo[1,5-a]pyrimidin-3-yl)benzamide;

or a pharmaceutically acceptable salt of any of the aforementioned.

In some embodiments, or a pharmaceutically acceptable salt thereof, wherein:

$Cy^1$ is selected from $C_{6-10}$ aryl and 5-10 membered heteroaryl; wherein each 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

$R^1$ is $OR^3$ or $NR^4R^5$;

$R^2$ is selected from H, D, and halo;

$A^1$ is $CR^6$;

$A^2$ is $CR^7$;

$A^3$ is selected from N and $CR^8$;

$A^4$ is $CR^9$;

$R^3$ is selected from $C_{1-6}$ alkyl, $C_{1-6}$ haloalkyl, $C_{3-10}$ cycloalkyl, 4-14 membered heterocycloalkyl, wherein said $C_{3-10}$ cycloalkyl, and 4-14 membered heterocycloalkyl, are each optionally substituted with 1, 2, 3, or 4 substituents independently selected from $R^{30}$;

$R^4$ is selected from $C_{1-6}$ alkyl, $C_{1-6}$ haloalkyl, $C_{3-10}$ cycloalkyl, and 4-14 membered heterocycloalkyl; wherein said $C_{1-6}$ alkyl, $C_{3-10}$ cycloalkyl, and 4-14 membered heterocycloalkyl, are each optionally substituted with 1, 2, 3, or 4 substituents independently selected from $R^{40}$;

$R^5$ is H;

each $R^6$, $R^7$, $R^8$, and $R^9$ is independently selected from H, D, $C_{1-6}$ alkyl, $C_{1-6}$ haloalkyl, 5-10 membered heteroaryl, halo, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein said $C_{1-6}$ alkyl and 5-10 membered heteroaryl are each optionally substituted with 1, 2, 3, or 4 substituents independently selected from $R^{20}$;

each $R^{10}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, and $S(O)_2R^{b1}$; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$;

each $R^{11}$ is independently selected from $C_{1-6}$ alkyl, $C_{1-6}$ haloalkyl, $C_{3-10}$ cycloalkyl, 4-10 membered heterocycloalkyl, 5-10 membered heteroaryl, halo, D, CN, $OR^{a3}$, $C(O)R^{b3}$, $C(O)NR^{c3}R^{d3}$, $C(O)OR^{a3}$, $NR^{c3}R^{d3}$, and $S(O)_2R^{b3}$; wherein said $C_{1-6}$ alkyl, $C_{3-10}$ cycloalkyl, 4-10 membered heterocycloalkyl, and 5-10 membered heteroaryl are each optionally substituted with 1, 2, 3, or 4 substituents independently selected from $R^{12}$;

each $R^{12}$ is independently selected from $C_{1-6}$ alkyl, $C_{1-6}$ haloalkyl, halo, D, CN, $OR^{a5}$, and $NR^{c5}R^{d5}$.

each $R^{20}$ is independently selected from $C_{1-6}$ alkyl, $C_{1-6}$ haloalkyl, halo, D, CN, $OR^{a4}$, and $NR^{c4}R^{d4}$;

each $R^{30}$ is independently selected from $C_{1-6}$ alkyl, $C_{1-6}$ haloalkyl halo, D, CN, $OR^{a6}$, and $NR^{c6}R^{d6}$;

each $R^{40}$ is independently selected from $C_{1-6}$ alkyl, $C_{1-6}$ haloalkyl, halo, D, CN, $OR^{a7}$, and $NR^{c7}R^{d7}$;

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl;

or any $R^{c1}$ and $R^{d1}$ attached to the same N atom, together with the N atom to which they are attached, form a 4-, 5-, or 6-membered heterocycloalkyl group optionally substituted with 1, 2, 3, or 4 substituents independently selected from $R^{11}$;

each $R^{b1}$ is independently selected from $C_{1-6}$ alkyl, $C_{1-6}$ haloalkyl, $C_{3-10}$ cycloalkyl, and 4-10 membered heterocycloalkyl;

each $R^{a2}$, $R^{c2}$, and $R^{d2}$ is independently selected from H, $C_{1-6}$ alkyl, and $C_{1-6}$ haloalkyl; wherein said $C_{1-6}$ alkyl, is optionally substituted with 1, 2, 3, or 4 substituents independently selected from $R^{20}$;

each $R^{b2}$ is independently selected from $C_{1-6}$ alkyl, and $C_{1-6}$ haloalkyl;

each $R^{a3}$, $R^{c3}$ and $R^{d3}$, is independently selected from H, $C_{1-6}$ alkyl, and $C_{1-6}$ haloalkyl; each $R^{b3}$ is independently selected from $C_{1-6}$ alkyl and $C_{1-6}$ haloalkyl;

each $R^{a4}$, $R^{c4}$ and $R^{d4}$, is independently selected from H, $C_{1-6}$ alkyl, and $C_{1-6}$ haloalkyl;

each $R^{a5}$, $R^{c5}$ and $R^{d}$s, is independently selected from H, $C_{1-6}$ alkyl, and $C_{1-6}$ haloalkyl;

each $R^{a6}$, $R^{c6}$ and $R^{d6}$, is independently selected from H, $C_{1-6}$ alkyl, and $C_{1-6}$ haloalkyl; and each $R^{a7}$, $R^{c7}$ and $R^{d7}$, is independently selected from H, $C_{1-6}$ alkyl, and $C_{1-6}$ haloalkyl.

In some embodiments, or a pharmaceutically acceptable salt thereof, wherein:

$Cy^1$ is selected from phenyl and 5-10 membered heteroaryl; wherein each 5-10 membered heteroaryl has at least one ring-forming carbon atom and 1, 2, 3, or 4 ring-forming heteroatoms independently selected from N, O, and S; and wherein the phenyl and 5-10 membered heteroaryl are each optionally substituted with 1, 2 or 3 substituents independently selected from $R^{10}$;

$R^1$ is $OR^3$ or $NR^4R^5$;

$R^2$ is H;

A1 is $CR^6$;

A2 is $CR^7$;

A3 is selected from N and $CR^8$;

A4 is $CR^9$;

$R^3$ is 4-6 membered heterocycloalkyl;

$R^4$ is 4-6 membered heterocycloalkyl;

$R^5$ is H;

$R^6$, $R^7$, $R^8$, and $R^9$ is independently selected from H, D, $C_{1-6}$ alkyl, $C_{1-6}$ haloalkyl, 5-6 membered heteroaryl, halo, CN, $OR^{a2}$, $C(O)NR^{c2}R^{d2}$, $NR^{c2}R^{d2}$, $S(O)_2R^{b2}$, and $S(O)_2NR^{c2}R^{d2}$;

each $R^{10}$ is independently selected from $C_{1-6}$ alkyl, $C_{1-6}$ haloalkyl, $C_{3-6}$ cycloalkyl, 4-7 membered heterocycloalkyl, halo, D, CN, $OR^{a1}$, and $NR^{c1}R^{d1}$; wherein said $C_{1-6}$ alkyl and $C_{3-10}$ cycloalkyl, and 4-10 membered heterocycloalkyl, are each optionally substituted with 1 or 2 substituents independently selected from $R^{11}$;

each $R^{11}$ is independently selected from $C_{1-6}$ alkyl, $C_{1-6}$ haloalkyl, $C_{3-10}$ cycloalkyl, 4-7 membered heterocycloalkyl, 5-6 membered heteroaryl, halo, D, CN, $OR^{a3}$, $C(O)NR^{c3}R^{d3}$, and $NR^{c3}R^{d3}$.

each $R^{20}$ is independently selected from D;

each $R^{a1}$, $R^{c1}$ and $R^{d1}$ is independently selected from H, $C_{1-6}$ alkyl, and $C_{1-6}$ haloalkyl;

each $R^{a2}$, $R^{c2}$, and $R^{d2}$ is independently selected from H, $C_{1-6}$ alkyl, and $C_{1-6}$ haloalkyl; wherein said $C_{1-6}$ alkyl, is optionally substituted with 1, 2, or 3 substituents independently selected from $R^{20}$;

each $R^{b2}$ is independently selected from $C_{1-6}$ alkyl, and $C_{1-6}$ haloalkyl; and each $R^{a3}$, $R^{c3}$ and $R^{d3}$, is independently selected from H, $C_{1-6}$ alkyl, and $C_{1-6}$ haloalkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. A single divalent substituent, e.g., oxo, can replace two hydrogen atoms.

As used herein, the term "$C_{i-j}$," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. An alkyl group formally corresponds to an alkane with one C—H bond replaced by the point of attachment of the alkyl group to the remainder of the compound. In some embodiments, the alkyl group contains 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like. In some embodiments, the alkyl group is methyl, ethyl, or propyl.

As used herein, the term "$C_{i-j}$ alkylene," employed alone or in combination with other terms, means a saturated divalent linking hydrocarbon group that may be straight-chain or branched, having i to j carbons. In some embodiments, the alkylene group contains from 1 to 4 carbon atoms, from 1 to 3 carbon atoms, or from 1 to 2 carbon atoms. Examples of alkylene moieties include, but are not limited to, chemical groups such as methylene, ethylene, 1,1-ethylene, 1,2-ethylene, 1,3-propylene, 1,2-propylene, 1,1-propylene, isopropylene, and the like.

As used herein, "alkenyl," employed alone or in combination with other terms, refers to a straight-chain or branched hydrocarbon group corresponding to an alkyl group having one or more carbon-carbon double bonds. An alkenyl group formally corresponds to an alkene with one C—H bond replaced by the point of attachment of the alkenyl group to the remainder of the compound. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl," employed alone or in combination with other terms, refers to a straight-chain or branched hydrocarbon group corresponding to an alkyl group having one or more carbon-carbon triple bonds. An alkynyl group formally corresponds to an alkyne with one C—H bond replaced by the point of attachment of the alkyl group to the remainder of the compound. In some embodiments, the alkynyl moiety contains 2 to 6 or 2 to 4 carbon atoms. Example alkynyl groups include, but are not limited to, ethynyl, propyn-1-yl, propyn-2-yl, and the like.

As used herein, "halo" or "halogen", employed alone or in combination with other terms, includes fluoro, chloro, bromo, and iodo. In some embodiments, halo is F or Cl. In some embodiments, halo is F.

As used herein, the term "haloalkyl," employed alone or in combination with other terms, refers to an alkyl group in which one or more of the hydrogen atoms has been replaced by a halogen atom, having up to the full valency of halogen atom substituents, which may either be the same or different. In some embodiments, the halogen atoms are fluoro atoms. In some embodiments, the alkyl group has 1 to 6, 1 to 4, or 1 to 3 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. In some embodiments, the alkyl group has 1 to 6, 1 to 4, or 1 to 3 carbon atoms. Example alkoxy groups include methoxy, ethoxy, propoxy (e.g., n-propoxy and isopropoxy), t-butoxy, and the like. In some embodiments, alkoxy is methoxy.

As used herein, "haloalkoxy," employed alone or in combination with other terms, refers to a group of formula —O-(haloalkyl). In some embodiments, the alkyl group has 1 to 6, 1 to 4, or 1 to 3 carbon atoms. An example haloalkoxy group is $—OCF_3$.

As used herein, "amino," employed alone or in combination with other terms, refers to $NH_2$.

As used herein, the term "alkylamino," employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino," employed alone or in combination with other terms, refers to a group of formula $—N(alkyl)_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "alkylthio," employed alone or in combination with other terms, refers to a group of formula —S-alkyl. In some embodiments, the alkyl group has 1 to 6 or 1 to 4 carbon atoms.

As used herein, the term "cycloalkyl," employed alone or in combination with other terms, refers to a non-aromatic cyclic hydrocarbon including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. A cycloalkyl group containing a fused aromatic ring can be attached through any ring-forming atom including a ring-forming atom of the fused aromatic ring. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5]octane and the like). In some embodiments, the cycloalkyl group has 3 to 10 ring members, or 3 to 7 ring members, or 3 to 6 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus, and which has 4-14 ring members, 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or polycyclic (e.g., having 2, 3 or 4 fused, bridged, or spiro rings) or spirocyclic ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, 4 to 10 ring-forming atoms, or 3 to 8 ring forming atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, dihydropyran ring, tetrahydropyran ring, tetrahyropyridine, azetidine ring, or tetrahydrofuran ring. In some embodiments, the heterocycloalkyl is a 4-7 membered heterocycloalkyl moiety having carbon and 1, 2, or 3 heteroatoms independently selected from N, O and S. In some embodiments, the heterocycloalkyl is 4-10 membered heterocycloalkyl moiety having carbon and 1, 2, or 3 heteroatoms independently selected from N, O and S.

As used herein, the term "aryl," employed alone or in combination with other terms, refers to a monocyclic or polycyclic (e.g., having 2 fused rings) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl.

As used herein, the term "heteroaryl" or "heteroaromatic" employed alone or in combination with other terms, refers to a monocyclic or polycyclic (e.g., having 2 or 3 fused rings) aromatic hydrocarbon moiety, having one or more heteroatom ring members independently selected from nitrogen, sulfur and oxygen. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In one embodiment the heteroaryl group is a 5 to 10 membered heteroaryl group. In another embodiment the heteroaryl group is a 5 to 6 membered heteroaryl group. In some embodiments, the heteroaryl is a 5-6 membered heteroaryl moiety having carbon and 1, 2, or 3 heteroatoms independently selected from N, O and S. In some embodiments, the heteroaryl is a 5-10 membered heteroaryl moiety having carbon and 1, 2, or 3 heteroatoms independently selected from N, O and S. In some embodiments, the heteroaryl has 5-6 ring atoms and 1 or 2 heteroatom ring members independently selected from nitrogen, sulfur and oxygen. In some embodiments, no more than 2 heteroatoms of a 5-membered heteroaryl moiety are N.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized π (pi) electrons where n is an integer).

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term, "compound," as used herein is meant to include all stereoisomers, geometric iosomers, tautomers, and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., in the form of hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The following abbreviations may be used herein: AcOH (acetic acid); $Ac_2O$ (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DEAD (diethyl azodicarboxylate); DIAD (N,N'-diisopropyl azidodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography—mass spectrometry); m (multiplet); M (molar); mCPBA (3-chloroperoxybenzoic acid); $MgSO_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); $NaHCO_3$ (sodium bicarbonate); NaOH (sodium hydroxide); $Na_2SO_4$ (sodium sulfate); $NH_4Cl$ (ammonium chloride); $NH_4OH$ (ammonium hydroxide); NIS (N-iodosuccinimide); nM (nanomolar); NMR (nuclear magnetic resonance spectroscopy); OTf (trifluoromethanesulfonate); Pd (palladium); Ph (phenyl); pM (picomolar); PMB (para-methoxybenzyl), $POCl_3$ (phosphoryl chloride); RP-HPLC (reverse phase high performance liquid chromatography); s (singlet); SEM (2-trimethylsilylethoxymethyl); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); μg (microgram(s)); μL (microliter(s)); μM (micromolar); wt % (weight percent).

Synthesis

Compounds of the invention, including salts thereof, can be prepared using known organic synthesis techniques and according to various possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "r.t.", as used herein, are understood in the art, and refer generally to a temperature, e.g. a reaction temperature, that is about the temperature of the room in which the reaction is carried out, for example, a temperature from about 20° C. to about 30° C.

Compounds of Formula (I) can be prepared as shown in Scheme 1. Halogenation of commercially available heterocycles 1-1 (wherein Z=halogen (F, Cl, Br, I) or pseudohalogen (e.g., OTf)) with a suitable halogenating reagent (e.g., NBS, NCS, etc.) affords intermediates 1-2. Nucleophilic aromatic substitution with ammonia then affords amines 1-3, which can undergo selective halogenation to provide intermediates 1-4. Removal of the amino group under reductive deamination conditions (e.g. alkyl nitrite in an appropriate solvent at elevated temperature) affords intermediates 1-5, which can undergo selective cross-coupling with M-$Cy^1$ (wherein M is $B(OH)_2$, Bpin, $BF_3K$, $Sn(Bu)_3$, or Zn) to give intermediates 1-6. Nucleophilic aromatic substitution with $R^{1'}$—XH (wherein X=O or NH) provides intermediates 1-7, which can undergo cross-coupling with intermediates 1-8 under standard Suzuki conditions (Tetrahedron 2002, 58, 9633-9695) (e.g., in the presence of a palladium catalyst, such as [1,1'-bis(diphenylphosphino)-ferrocene]dichloropalladium(II), complex with dichloromethane or bis(di-tert-butyl(4-dimethyl-aminophenyl)phosphine)-dichloropalladium(II) and a base (e.g., a carbonate base or cesium fluoride)), or standard Stille conditions (ACS Catalysis 2015, 5, 3040-3053) (e.g., in the presence of a palladium(0) catalyst, such as tetrakis(triphenylphosphine)-palladium(0)), or standard Negishi conditions (ACS Catalysis 2016, 6, 1540-1552) (e.g., in the presence of a palladium catalyst, such as tetrakis(triphenylphosphine)palladium(0) or [1,1'-bis(diphenylphosphino)-ferrocene]-dichloropalladium (II)), to afford compounds of the Formula Ia.

Scheme 1.

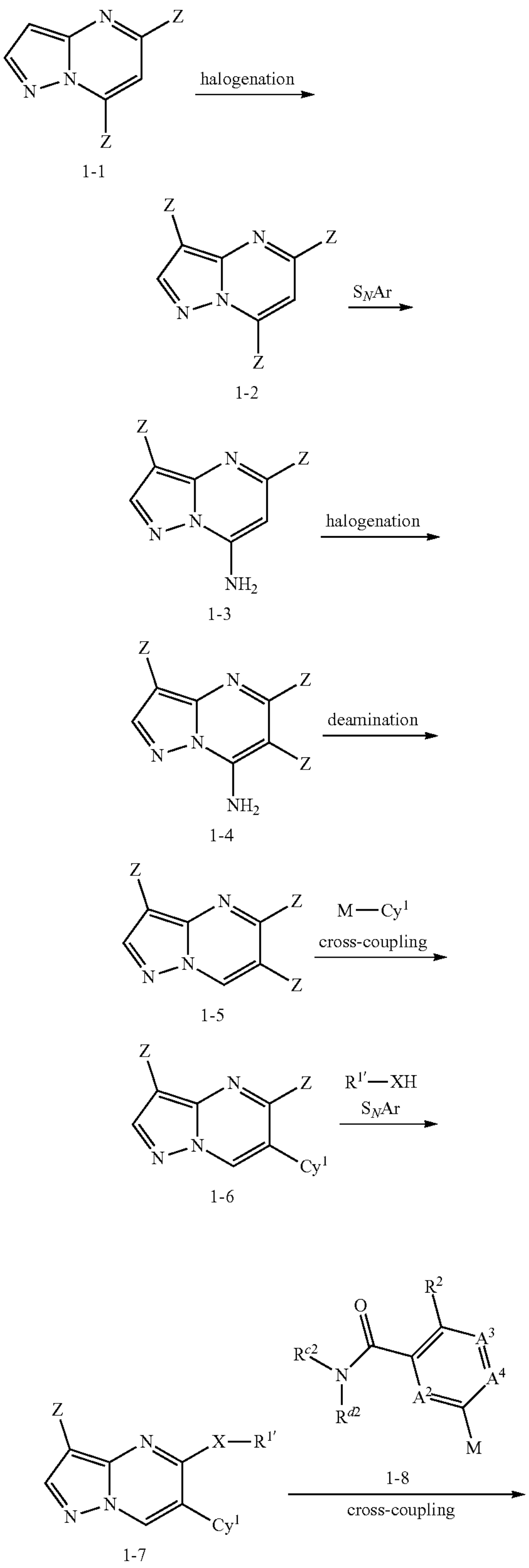

-continued

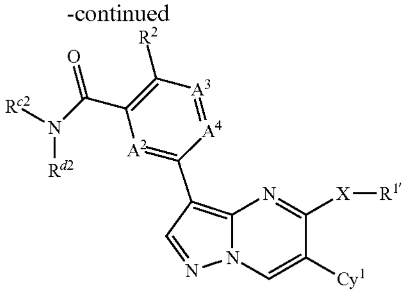

Formula Ia

Compounds of Formula I can also be prepared as shown in Scheme 2. From intermediates 1-5 (Scheme 1), nucleophilic aromatic substitution with $R^{1'}$—XH (wherein X═O or NH) provides intermediates 2-1, which can undergo selective cross-coupling with intermediates 1-8 to afford compounds 2-2. Cross coupling of 2-2 with M-$Cy^1$ then affords compounds of Formula Ib.

Scheme 2.

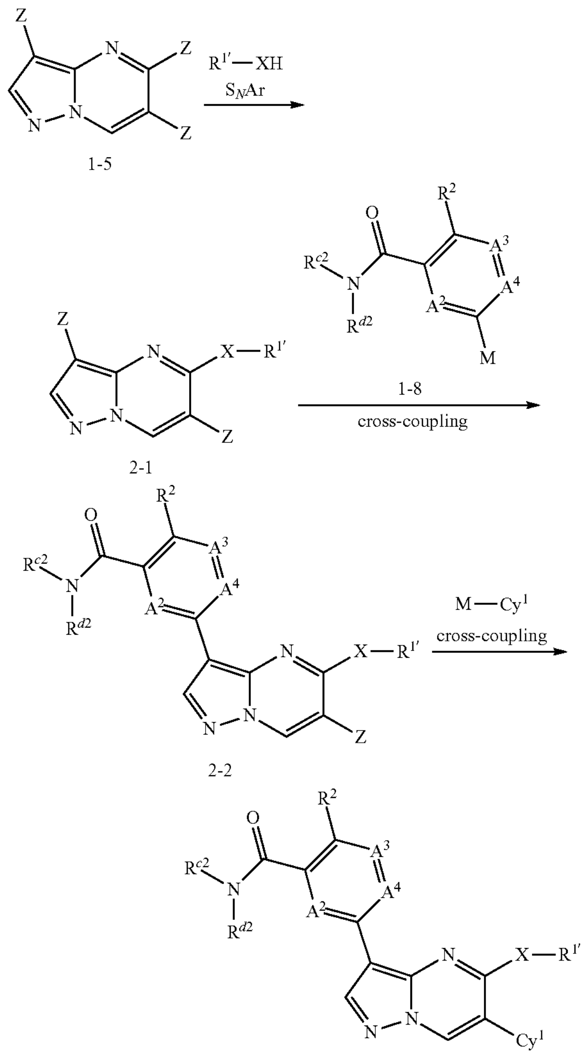

Formula Ib

Methods of Use

Compounds of the present disclosure can inhibit the activity of the FGFR enzyme. For example, compounds of the present disclosure can be used to inhibit activity of an FGFR enzyme in a cell or in an individual or patient in need of inhibition of the enzyme by administering an inhibiting amount of one or more compounds of the present disclosure to the cell, individual, or patient.

As FGFR inhibitors, the compounds of the present disclosure are useful in the treatment of various diseases associated with abnormal expression or activity of the FGFR enzyme or FGFR ligands. Compounds which inhibit FGFR will be useful in providing a means of preventing the growth or inducing apoptosis in tumors, particularly by inhibiting angiogenesis. It is therefore anticipated that compounds of the present disclosure will prove useful in treating or preventing proliferative disorders such as cancers. In particular, tumors with activating mutants of receptor tyrosine kinases or upregulation of receptor tyrosine kinases may be particularly sensitive to the inhibitors.

In certain embodiments, the disclosure provides a method for treating a FGFR-mediated disorder in a patient in need thereof, comprising the step of administering to said patient a compound according to the invention, or a pharmaceutically acceptable composition thereof.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

In some embodiments, said cancer is selected from hepatocellular cancer, bladder cancer, breast cancer, cervical cancer, colorectal cancer, endometrial cancer, gastric cancer, head and neck cancer, kidney cancer, liver cancer, cholangiocarcinoma, lung cancer, ovarian cancer, prostate cancer, esophageal cancer, gall bladder cancer, pancreatic cancer, thyroid cancer, skin cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, hairy cell lymphoma, Burkett's lymphoma, glioblastoma, melanoma, and rhabdosarcoma. In some embodiments, said cancer is selected from bladder cancer, breast cancer, colorectal cancer, endometrial cancer, gastric cancer, head and neck cancer, kidney cancer, liver cancer, cholangiocarcinoma, lung cancer, ovarian cancer, pancreatic cancer, glioblastoma, melanoma, and rhabdosarcoma.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET), 8p11 myeloproliferative syndrome), myelodysplasia syndrome (MDS), T-cell acute lymphoblastic lymphoma (T-ALL), multiple myeloma, cutaneous T-cell lymphoma, adult T-cell leukemia, Waldenstrom's Macroglubulinemia, hairy cell lymphoma, marginal zone lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, lymphosarcoma, leiomyosarcoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, mesothelioma, pavicellular and non-pavicellular carcinoma, bronchial adenoma and pleuropulmonary blastoma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (exocrine pancreatic carcinoma, ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer, gall bladder cancer and anal cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) and urothelial carcinoma.

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors, neuro-ectodermal tumors), and spinal cord (neurofibroma, meningioma, glioma, sarcoma), neuroblastoma, Lhermitte-Duclos disease and pineal tumors.

Exemplary gynecological cancers include cancers of the breast (ductal carcinoma, lobular carcinoma, breast sarcoma, triple-negative breast cancer, HER2-positive breast cancer, inflammatory breast cancer, papillary carcinoma), uterus (endometrial carcinoma), cervix (cervical carcinoma, pretumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers, tumors of the eye, tumors of the lips and mouth and squamous head and neck cancer.

The compounds of the present disclosure can also be useful in the inhibition of tumor metastases.

In addition to oncogenic neoplasms, the compounds of the invention are useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes. In some embodiments, the present disclosure provides a method for treating a patient suffering from a skeletal and chondrocyte disorder.

In some embodiments, compounds described herein can be used to treat Alzheimer's disease, HIV, or tuberculosis.

As used herein, the term "8p11 myeloproliferative syndrome" is meant to refer to myeloid/lymphoid neoplasms associated with eosinophilia and abnormalities of FGFR1.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR enzyme with a compound described herein includes the administration of a compound described herein to an individual or patient, such as a human, having FGFR, as well as, for example, introducing a compound described herein into a sample containing a cellular or purified preparation containing the FGFR enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005*; Handbook of Pharmaceutical Excipients,* 6th ed.; Rowe et al., Eds.; The Pharmaceutical Press and the American Pharmaceutical Association: 2009*; Handbook of Pharmaceutical Additives,* 3rd ed.; Ash and Ash Eds.; Gower Publishing Company: 2007*; Pharmaceutical Preformulation and Formulation,* 2nd ed.; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with compounds described herein for treatment of FGFR-associated diseases, disorders or conditions, or diseases or conditions as described herein. The agents can be combined with the present compounds in a single dosage form, or the agents can be administered simultaneously or sequentially as separate dosage forms.

Compounds described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf Additionally, the solid forms of the FGFR inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, compounds described herein can be used in combination with one or more inhibitors of the enzyme or protein receptors such as HPK1, SBLB, TUT4, A2A/A2B, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, compounds described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, compounds described herein can be used in combination with targeted therapies, including JAK kinase inhibitors (Ruxolitinib, additional JAK1/2 and JAK1-selective, baricitinib or INCB39110), Pim kinase inhibitors (e.g., LGH447, INCB053914 and SGI-1776), PI3 kinase inhibitors including PI3K-delta selective and broad spectrum PI3K inhibitors (e.g., INCB50465 and INCB54707), PI3K-gamma inhibitors such as PI3K-gamma selective inhibitors, MEK inhibitors, CSF1R inhibitors (e.g., PLX3397 and LY3022855), TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as OTX015, CPI-0610, INCB54329 or INCB57643), LSD1 inhibitors (e.g., GSK2979552, INCB59872 and INCB60003), arginase inhibitors (e.g., INCB1158), indoleamine 2,3-dioxygenase inhibitors (e.g., epacadostat, NLG919 or BMS-986205), PARP inhibiors (e.g., olaparib or rucaparib), and inhibitors of BTK such as ibrutinib. For treating cancer and other proliferative diseases, compounds described herein can be used in combination with targeted therapies, including c-MET inhibitors (e.g., capmatinib), an ALK2 inhibitor (e.g., INCB00928), or combinations thereof.

For treating cancer and other proliferative diseases, compounds described herein can be used in combination with chemotherapeutic agents, agonists or antagonists of nuclear receptors, or other anti-proliferative agents. Compounds described herein can also be used in combination with a medical therapy such as surgery or radiotherapy, e.g., gamma-radiation, neutron beam radiotherapy, electron beam radiotherapy, proton therapy, brachytherapy, and systemic radioactive isotopes.

Examples of suitable chemotherapeutic agents include any of abarelix, abiraterone, afatinib, aflibercept, aldesleukin, alemtuzumab, alitretinoin, allopurinol, altretamine, amidox, amsacrine, anastrozole, aphidicolon, arsenic trioxide, asparaginase, axitinib, azacitidine, bevacizumab, bexarotene, baricitinib, bendamustine, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, didox, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lonafarnib, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, niraparib, nofetumomab, oserelin, oxaliplatin, paclitaxel, pamidronate, panitumumab, panobinostat, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, rucaparib, ruxolitinib, sorafenib, streptozocin, sunitinib, sunitinib maleate, tamoxifen, tegafur, temozolomide, teniposide, testolactone, tezacitabine, thalidomide, thioguanine, thiotepa, tipifarnib, topotecan, toremifene, tositumomab, trastuzumab, tretinoin, triapine, trimidox, triptorelin, uracil mustard, valrubicin, vandetanib, vinblastine, vincristine, vindesine, vinorelbine, vorinostat, veliparib, talazoparib, and zoledronate.

In some embodiments, compounds described herein can be used in combination with immune checkpoint inhibitors. In some embodiments, the inhibitor of an immune checkpoint molecule is an inhibitor of CD19, e.g., an anti-CD19 antibody. In some embodiments, the anti-CD19 antibody is tafasitamab. In some embodiments, the anti-PD-1 monoclonal antibody is MGA012 (retifanlimab). Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is a small molecule PD-L1 inhibitor. In some embodiments, the small molecule PD-L1 inhibitor has an IC50 less than 1 μM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is MGA012, nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is nivolumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab.

In some embodiments, the compounds of the disclosure can be used in combination with INCB086550.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of 20 GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

In some embodiments, the compounds described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with compounds described herein for the treatment of cancer include chemotherapeutic agents, targeted cancer therapies, immunotherapies or radiation therapy. Compounds described herein may be effective in combination with antihormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds described herein. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280.

Agents against Abl (or Bcr-Abl) include imatinib, dasatinib, nilotinib, and ponatinib and those against Alk (or EML4-ALK) include crizotinib. Angiogenesis inhibitors may be efficacious in some tumors in combination with FGFR inhibitors. These include antibodies against VEGF or VEGFR or kinase inhibitors of VEGFR.

Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with FGFR inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds described herein. In some embodiments, the JAK inhibitor is selective for JAK1 over JAK2 and JAK3.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds described herein include steroids including 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure can be used in combination with bone marrow transplant for the treatment of a variety of tumors of hematopoietic origin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

When employed as pharmaceuticals, compounds described herein can be administered in the form of pharmaceutical compositions which refers to a combination of one or more compounds described herein, and at least one pharmaceutically acceptable carrier or excipient. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, one or more compounds described herein in combination with one or more pharmaceutically acceptable carriers or excipients. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is suitable for topical administration.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from, for example, about 5 mg to about 1000 mg, about 5 mg to about 100 mg, about 100 mg to about 500 mg or about 10 to about 30 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid pre-formulation composition containing a homogeneous mixture of one or more compounds described herein. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds, or compositions as described herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of the compounds in a pharmaceutical composition can vary depending upon a number of factors including dosage, chemical characteristics (e.g., hydrophobicity), and the route of administration. For example, compounds of the present disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Compounds described herein can also be formulated in combination with one or more additional active ingredients, which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to labeled compounds of the disclosure (radio-labeled, fluorescent-labeled, etc.) that would be useful not only in imaging techniques but also in assays, both in vitro and in vivo, for localizing and quantitating FGFR3 protein in tissue samples, including human, and for identifying FGFR3 ligands by inhibition binding of a labeled compound. Substitution of one or more of the atoms of the compounds of the present disclosure can also be useful in generating differentiated ADME (Adsorption, Distribution, Metabolism and Excretion). Accordingly, the present invention includes FGFR binding assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}$. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups in Formula (I) can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. J. *Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro adenosine receptor labeling and competition assays, compounds that incorporate $^{3}H$, $^{14}C$, $^{82}Br$, $^{125}$, $^{131}$ or $^{35}S$ can be useful. For radio-imaging applications $^{11}C$, $^{18}F$, $^{125}$, $^{123}$, $^{124}$, $^{131}$, $^{75}Br$, $^{76}Br$ or $^{77}Br$ can be useful.

It is understood that a "radio-labeled" or "labeled compound" is a compound that has incorporated at least one radionuclide. In some embodiments, the radionuclide is selected from the group consisting of $^{3}H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the invention can be used in a screening assay to identify and/or evaluate compounds. For example, a newly synthesized or identified compound (i.e., test compound) which is labeled can be evaluated for its ability to bind an FGFR3 protein by monitoring its concentration variation when contacting with the FGFR3, through tracking of the labeling. For example, a test compound (labeled) can be evaluated for its ability to reduce binding of another compound which is known to bind to a FGFR3 protein (i.e., standard compound). Accordingly, the ability of a test compound to compete with the standard compound for binding to the FGFR3 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of FGFR-associated diseases or disorders, such as cancer and other diseases referred to herein which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of FGFR3 as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.,* 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.,* 5, 670 (2003); and "Preparative LC-MS Purification: Improved Compound Specific Method Optimization", K. Blom, B. Glass, R. Sparks, A. Combs, *J. Combi. Chem.,* 6, 874-883 (2004). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.,* 6, 874-883 (2004)]. Typically, the flow rate used with the 30×100 mm column was 60 mL/minute.

pH=10 purifications: Waters XBridge $C_{18}$ 5 μm, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.,* 6, 874-883 (2004)]. Typically, the flow rate used with 30×100 mm column was 60 mL/minute.

Intermediate A. 3,4-Difluoro-N-methyl-5-(4,4,5,5-tetramethyl-1,3,2-dioxaborolan-2-yl)benzamide

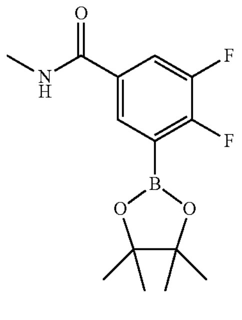 [SMILES: CNC(=O)c1cc(F)c(F)c(B2OC(C)(C)C(C)(C)O2)c1]

Step 1.3-Bromo-4,5-difluorobenzoic Acid

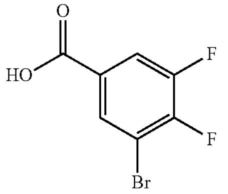 [SMILES: O=C(O)c1cc(F)c(F)c(Br)c1]

A sample of 3,4-difluorobenzoic acid (2.01 g, 12.7 mmol) was dissolved in sulfuric acid (25 ml) and treated with NBS (2.49 g, 14.0 mmol). The solution was warmed to 60° C. and stirred for 16 hours. The reaction was poured into ice water (250 mL) and diluted with EtOAc (250 mL). The phases were separated and the aqueous portion was extracted with additional EtOAc. The organic fractions were combined, dried with magnesium sulfate, filtered, and concentrated in vacuo. The resulting material (initially an oil, crystallizes over several days) was collected to provide crude 3-bromo-4,5-difluorobenzoic acid (1.27 g, 5.36 mmol, 42% yield). Compound does not ionize by LCMS and structure was confirmed by subsequent steps.

Step 2.3-Bromo-4,5-difluoro-N-methylbenzamide

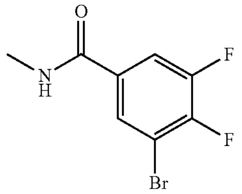

A sample of 3-bromo-4,5-difluorobenzoic acid (1.27 g, 5.36 mmol) was dissolved in DCM (26.8 ml). This solution was treated with DIPEA (1.872 ml, 10.72 mmol), and HATU (2.241 g, 5.89 mmol), and stirred for 15 minutes. Lastly, methylamine (8.04 ml, 2M in THF, 16.08 mmol) was added and the mixture was stirred at 22° C. After 40 minutes, the reaction mixture was treated with saturated aqueous ammonium chloride (50 mL) and diluted with EtOAc (100 mL). The phases were separated and the aqueous phase was extracted with additional EtOAc. The organic fractions were combined, dried with magnesium sulfate, filtered, and concentrated in vacuo. The residue was purified by flash chromatography (0-15% EtOAc in DCM) to provide 3-bromo-4,5-difluoro-N-methylbenzamide (0.403 g, 1.612 mmol, 30% yield). LCMS calculated for $C_8H_7BrF_2NO$ $(M+H)^+$: m/z=250.0; found: 249.9.

Step 3. 3,4-difluoro-N-methyl-5-(4,4,5,5-tetramethyl-1,3,2-dioxaborolan-2-yl)

A sample of 3-bromo-4,5-difluoro-N-methylbenzamide (402 mg, 1.608 mmol) was suspended in toluene and treated with potassium acetate (316 mg, 3.22 mmol) and bis(pinacolato)diboron (694 mg, 2.73 mmol). The solvent was removed in vacuo, and the residue was azeotroped twice more with toluene. Anhydrous dioxane (16.08 ml) was added and the mixture was stirred to dissolve. The solution was degassed by bubbling with nitrogen for 5 mins. [1,1'-Bis(diphenylphosphino)-ferrocene]dichloropalladium(II) (131 mg, 0.161 mmol) was added and the reaction was warmed to 100° C. and stirred for 2 hours. After cooling to room temperature, the reaction was diluted with DCM and filtered to remove the potassium acetate. The filtrate was concentrated in vacuo, and the residue was purified by flash chromatography (0-100% EtOAc/DCM) to afford 3,4-difluoro-N-methyl-5-(4,4,5,5-tetramethyl-1,3,2-dioxaborolan-2-yl)benzamide (500 mg, 1.683 mmol, quant. yield). The following data is reported for the corresponding boronic acid, which was the only observable species by LCMS. LCMS calculated for $C_8H_9BF_2NO_3$ $(M+H)^+$: m/z=216.1; found: 216.1.

Intermediate B. 4-Fluoro-N,3-dimethyl-5-(4,4,5,5-tetramethyl-1,3,2-dioxaborolan-2-yl)benzamide

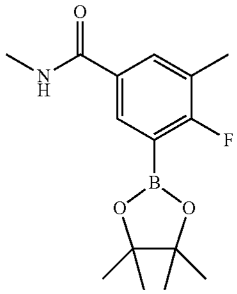 [SMILES: CNC(=O)c1cc(C)c(F)c(B2OC(C)(C)C(C)(C)O2)c1]

Step 1. 3-Bromo-4-fluoro-5-methylbenzoic Acid

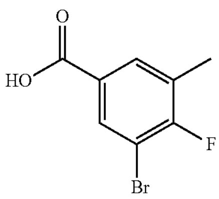

A sample of 4-fluoro-3-methylbenzoic acid (2.03 g, 13.17 mmol) was dissolved in sulfuric acid (26.3 ml) and treated with NBS (2.58 g, 14.49 mmol). The solution was warmed to 60° C. and stirred for 16 hours. The reaction was poured into ice water (500 mL) and stirred for an hour. The sample was filtered and the solid was collected to provide crude 3-bromo-4-fluoro-5-methylbenzoic acid (3.29 g, 14.12 mmol, >100% theoretical yield). Compound does not ionize by LCMS and structure was confirmed by subsequent steps; subsequent steps also indicate an unidentified dibrominated product.

Step 2. 3-Bromo-4-fluoro-5-formyl-N-methylbenzamide

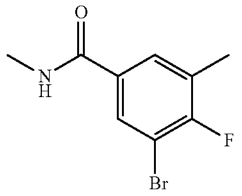

A sample of crude 3-bromo-4-fluoro-5-methylbenzoic acid (3.29 g, 14.12 mmol) was suspended in DCM (70.6 ml). This suspension was treated with DIPEA (4.93 ml, 28.2 mmol), causing complete dissolution of the starting material. The solution was then treated with HATU (5.90 g, 15.53 mmol), and stirred for 15 minutes. Lastly, methylamine (21.18 ml, 2M in THF, 42.4 mmol) was added and the mixture was stirred at 22° C. After 40 minutes, the reaction mixture was treated with saturated aqueous ammonium chloride (50 mL) and diluted with EtOAc (100 mL). The phases were separated and the aqueous phase was extracted with additional EtOAc. The organic fractions were combined, dried with magnesium sulfate, filtered, and concentrated in vacuo. The residue was purified by flash chromatography (0-100% EtOAc in Hexanes) to provide 3-bromo-4-fluoro-N,5-dimethylbenzamide (1.4 g, 5.69 mmol, 40.3% yield). LCMS calculated for $C_9H_{10}BrFNO$ $(M+H)^+$: m/z=246.0; found: 245.9.

Step 3. 4-fluoro-N,3-dimethyl-5-(4,4,5,5-tetramethyl-1,3,2-dioxaborolan-2-yl)benzamide A sample of 3-bromo-4-fluoro-N,5-dimethylbenzamide (95 mg, 0.386 mmol) was suspended in toluene and treated with potassium acetate (114 mg, 1.158 mmol) and bis (pinacolato)diboron (147 mg, 0.579 mmol). The solvent was removed in vacuo, and the residue was azeotroped twice more with toluene. Anhydrous dioxane (3.86 ml) was added and the mixture was stirred to dissolve. The solution was degassed by bubbling with nitrogen for 5 minutes. [1,1'-Bis (diphenylphosphino)ferrocene]dichloropalladium(II) (47.3 mg, 0.058 mmol) was added and the reaction was warmed to 110° C. and stirred for 2 hours. The reaction was diluted with DCM and filtered to remove solid potassium acetate. The filtrate was concentrated in vacuo and the residue was purified by flash column chromatography (0-100% EtOAc/DCM) to provide 4-fluoro-N,3-dimethyl-5-(4,4,5,5-tetramethyl-1,3,2-dioxaborolan-2-yl)benzamide (99 mg, 0.338 mmol, 87% yield). The following data is reported for the corresponding boronic acid, which was the only observable species by LCMS. LCMS calculated for $C_9H_{12}BFNO_3$ $(M+H)^+$: m/z=212.1; found: 212.2.

Intermediate C. 3-(Difluoromethyl)-4-fluoro-N-methyl-5-(4,4,5,5-tetramethyl-1,3,2-dioxaborolan-2-yl)benzamide

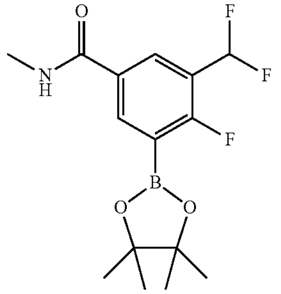 [SMILES: CNC(=O)c1cc(B2OC(C)(C)C(C)(C)O2)c(F)c(C(F)F)c1]

Step 1. 3-Bromo-4-fluoro-5-formylbenzoic Acid

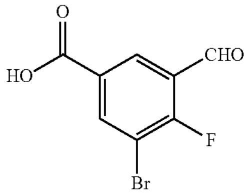 [SMILES: O=Cc1cc(C(=O)O)cc(Br)c1F]

A sample of 4-fluoro-3-formylbenzoic acid (2.07 g, 12.31 mmol) was dissolved in sulfuric acid (24.62 ml) and treated with NBS (2.41 g, 13.54 mmol). The solution was warmed to 60° C. and stirred for 16 hours. The reaction was poured into ice water (500 mL) and stirred for an hour. The sample was filtered and the solid was collected to provide 3-bromo-4-fluoro-5-formylbenzoic acid (2.63 g, 10.65 mmol, 86% yield). Compound does not ionize by LCMS and structure was confirmed by subsequent steps.

Step 2. 3-Bromo-4-fluoro-5-formyl-N-methylbenzamide

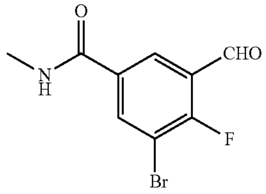

To a solution of 3-bromo-4-fluoro-5-formylbenzoic acid (400 mg, 1.62 mmol) and HATU (739 mg, 1.94 mmol) in DMF (6 ml) was added DIPEA (0.42 mL, 2.43 mmol), and the reaction mixture was stirred at room temperature for 5 min. Methylamine (2M/THF) (1.2 mL, 2.43 mmol) was added and stirring was continued for an additional 30 min. The reaction mixture was partitioned between water and EtOAc, and the phases were separated. The aqueous phase was extracted with EtOAc and the combined organic phases were washed with brine, dried over $MgSO_4$, filtered, and concentrated. The product was purified by flash chromatography (0-100% EtOAc/hexanes) to afford the title compound (176 mg, 42%). LCMS calculated for $C_9H_8BrFNO_2$ $(M+H)^+$: m/z=260.0; found: 260.0.

Step 3. 3-Bromo-5-(difluoromethyl)-4-fluoro-N-methylbenzamide

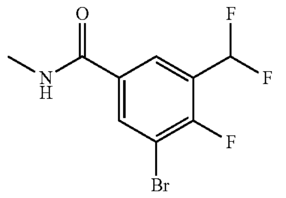

To a solution of 3-bromo-4-fluoro-5-formyl-N-methylbenzamide (176 mg, 0.68 mmol) in DCM (4 ml) was added DAST (179 μl, 1.35 mmol) at 0° C., and the reaction mixture was allowed to warm to room temp. After 30 min, more DAST (179 μl, 1.35 mmol) was added and stirring was continued for 1 h. The reaction mixture was cooled to 0° C., carefully quenched with 5 saturated aqueous $NaHCO_3$, and extracted with DCM. The phases were separated and the organic phase was washed with brine, dried over $MgSO_4$, filtered and concentrated. The product was purified by flash chromatography (0-100% EtOAc/hexanes). LCMS calculated for $C_9H_8BrF_3NO$ $(M+H)^+$: m/z=282.0; found: 282.0.

Step 4. 3-(Difluoromethyl)-4-fluoro-N-methyl-5-(4,4,5,5-tetramethyl-1,3,2-dioxaborolan-2-yl)benzamide 3-Bromo-5-(difluoromethyl)-4-fluoro-N-methylbenzamide (191 mg, 0.68 mmol) was combined with bis(pinacolato)diboron (430 mg, 1.69 mmol), dichloro[1,1'-bis(diphenyl-phosphino)ferrocene]palladium (II) dichloromethane adduct (27.6 mg, 0.034 mmol) and potassium acetate (199 mg, 2.03 mmol) in dioxane (5 ml) and the mixture was sparged with $N_2$, then heated to 100° C. for 6 h. The reaction mixture was diluted with EtOAc, filtered, and concentrated. The residue was purified by flash chromatography (0-100% EtOAc/hexanes) to afford the title compound (223 mg, 100%). The following data is reported for the corresponding boronic acid, which was the only observable species by LCMS. LCMS calculated for $C_9H_{10}BF_3NO_3$ $(M+H)^+$: m/z=248.1; found: 248.1.

Intermediate D. 3-Cyano-N-methyl-5-(4,4,5,5-tetramethyl-1,3,2-dioxaborolan-2-yl)benzamide

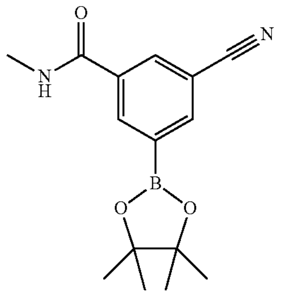 [SMILES: CNC(=O)c1cc(C#N)cc(B2OC(C)(C)C(C)(C)O2)c1]

Step 1. 3-Bromo-5-cyano-N-methylbenzamide

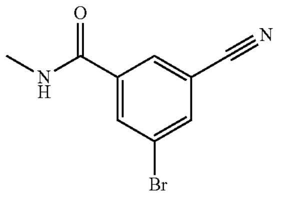

To a solution of 3-bromo-5-cyanobenzoic acid (500 mg, 2.21 mmol) and HATU (1.0 g, 2.65 mmol) in DMF (10 ml) was added DIPEA (580 μl, 3.32 mmol), and the reaction mixture was stirred at room temp for 5 min. Methylamine (2M/THF) (1.66 mL, 3.32 mmol) was added and the reaction mixture was stirred for an additional 30 min. Ice chips and water were added and the mixture was stirred overnight. The resulting precipitate was filtered, washed with water, and air dried to afford the title compound (263 mg, 50%). LCMS calculated for $C_9H_8BrN_2O$ $(M+H)^+$: m/z=239.0; found: 239.0.

Step 2. 3-Cyano-N-methyl-5-(4,4,5,5-tetramethyl-1,3,2-dioxaborolan-2-yl)benzamide This compound was synthesized by a procedure analogous to that reported for Intermediate C, Step 4. The following data is reported for the corresponding boronic acid, which was the only observable species by LCMS. LCMS calculated for $C_9H_{10}BN_2O_3$ $(M+H)^+$: m/z=205.1; found: 205.0.

Intermediate E. N-(Methyl-$d_5$)-5-(4,4,5,5-tetramethyl-1,3,2-dioxaborolan-2-yl)nicotinamide

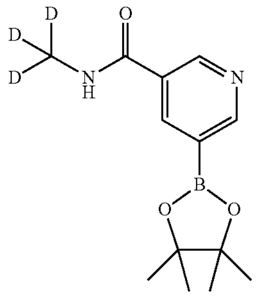 [SMILES: [2H]C([2H])([2H])NC(=O)c1cncc(B2OC(C)(C)C(C)(C)O2)c1]

Step 1. 5-Bromo-N-(methyl-$d_3$)nicotinamide

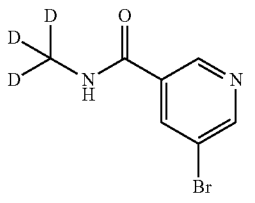 [SMILES: [2H]C([2H])([2H])NC(=O)c1cncc(Br)c1]

To a solution of 5-bromonicotinic acid (100 mg, 0.49 mmol) and HATU (226 mg, 0.59 mmol) in DMF (4 ml) was added DIPEA (259 μl, 1.49 mmol), and the reaction mixture was stirred at room temperature for 5 min. Methylamine-$d_3$ hydrochloride (41.9 mg, 0.59 mmol) was added and stirring was continued for an additional 30 min. The reaction mixture was partitioned between water and EtOAc, and the phases were separated. The aqueous phase was extracted with EtOAc and the combined organic phases were washed with brine, dried over $MgSO_4$, filtered, and concentrated. The product was purified by flash chromatography (0-100% EtOAc/hexanes) to afford the title compound (94 mg, 87%) as a white solid. LCMS calculated for $C_7H_5D_3BrN_2O$ $(M+H)^+$: m/z=218.0; found: 218.0.

Step 2. N-(Methyl-$d_3$)-5-(4,4,5,5-tetramethyl-1,3,2-dioxaborolan-2-yl)nicotinamide 5-Bromo-N-(methyl-$d_3$)nicotinamide (94 mg, 0.43 mmol) was combined with bis(pinacolato)diboron (164 mg, 0.65 mmol), dichloro[1,1'-bis(diphenylphosphino)ferrocene]palladium (II) dichloromethane adduct (17.6 mg, 0.02 mmol) and potassium acetate (127 mg, 1.30 mmol) in dioxane (3 ml) and the mixture was sparged with $N_2$ for 5 min. The reaction was heated to 100° C. for 3 h. The reaction mixture was diluted with EtOAc, filtered, and concentrated. The product was used without purification, assuming quantitative yield. The following data is reported for the corresponding boronic acid, which was the only observable species by LCMS. LCMS calculated for $C_7H_7D_3BN_2O_3$ $(M+H)^+$: m/z=184.1; found: 184.2.

Intermediate F. 4-Fluoro-3-methyl-N-(methyl-$d_3$)-5-(4,4,5,5-tetramethyl-1,3,2-dioxaborolan-2-yl)benzamide

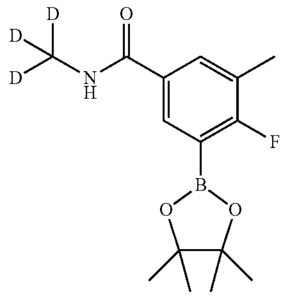 [SMILES: [2H]C([2H])([2H])NC(=O)c1cc(C)c(F)c(B2OC(C)(C)C(C)(C)O2)c1]

Prepared by an identical procedure to that described for Intermediate B, utilizing methylamine-$d_3$ instead of methylamine in Step 2. The following data is reported for the corresponding boronic acid, which was the only observable species by LCMS. LCMS calculated for $C_9H_9D_3BFNO_3$ $(M+H)^+$: m/z=215.1; found: 215.1.

Intermediate G. 3-(Difluoromethyl)-4-fluoro-N-(methyl-d3)-5-(4,4,5,5-tetramethyl-1,3,2-dioxaborolan-2-yl)benzamide

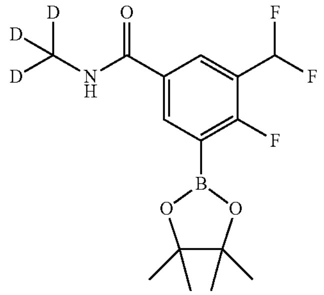 [SMILES: [2H]C([2H])([2H])NC(=O)c1cc(B2OC(C)(C)C(C)(C)O2)c(F)c(C(F)F)c1]

Prepared by an identical procedure to that described for Intermediate C, utilizing methylamine-$d_3$ instead of methylamine in Step 2. The following data is reported for the corresponding boronic acid, which was the only observable species by LCMS. LCMS calculated for $C_9H_7D_3BF_3NO_3$ $(M+H)^+$: m/z=251.1; found: 251.1.

Example 1. N-Methyl-3-(6-(1-methyl-1H-pyrazol-4-yl)-5-((tetrahydrofuran-3-yl)oxy)pyrazolo[1,5-a]pyrimidin-3-yl)benzamide (racemic)

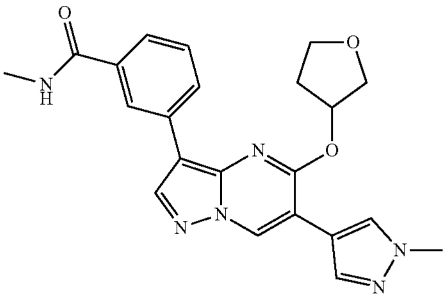

Step 1. 3,5,7-Trichloropyrazolo[1,5-a]pyrimidine

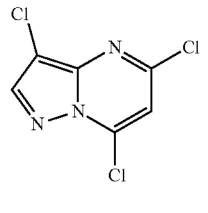 [SMILES: Clc1cc(Cl)n2ncc(Cl)c2n1]

To a solution of 5,7-dichloropyrazolo[1,5-a]pyrimidine (500 mg, 2.66 mmol, Combi-Blocks ST-4256) in DMF (5 ml) was added NCS (391 mg, 2.93 mmol) and the reaction mixture was stirred at 60° C. for 1 h. After cooling to room temperature, ice chips and water were added. The resulting precipitate was filtered, washed with water, and air dried to afford the title compound (460 mg, 78%) as an off-white solid. LCMS calculated for $C_6H_3Cl_3N_3$ $(M+H)^+$: m/z=221.9; found: 221.9.

Step 2. 3,5-Dichloropyrazolo[1,5-a]pyrimidin-7-amine

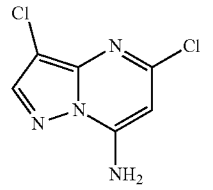 [SMILES: Nc1cc(Cl)nc2c(Cl)cnn12]

A suspension of 3,5,7-trichloropyrazolo[1,5-a]pyrimidine (460 mg, 2.07 mmol) in concentrated ammonium hydroxide (10 ml, 145 mmol) was heated to 100° C. in a heavy walled sealed tube for 1 h. After cooling to room temperature, the reaction mixture was diluted with cold water and filtered. The collected solid was then washed with cold water and air dried to afford the title compound (355 mg, 85%). LCMS calculated for $C_6H_5Cl_2N_4$ $(M+H)^+$: m/z=203.0; found: 203.0.

Step 3. 3,5-Dichloro-6-iodopyrazolo[1,5-a]pyrimidin-7-amine

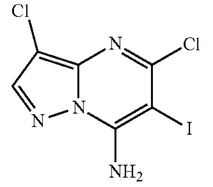 [SMILES: Nc1c(I)c(Cl)nc2c(Cl)cnn12]

To a solution of 3,5-dichloropyrazolo[1,5-a]pyrimidin-7-amine (355 mg, 1.75 mmol) in DMF (5 ml) was added NIS (590 mg, 2.62 mmol) and the reaction mixture was stirred at 50° C. for 1 h. After cooling to room temperature, ice chips and water were added. The resulting precipitate was filtered, washed with water, and air dried to afford the title compound (489 mg, 85%). LCMS calculated for $C_6H_4Cl_2IN_4$ $(M+H)^+$: m/z=328.9; found: 328.8.

Step 4. 3,5-Dichloro-6-iodopyrazolo[1,5-a]pyrimidine

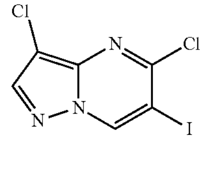 [SMILES: Clc1nc2c(Cl)cnn2cc1I]

To a solution of 3,5-dichloro-6-iodopyrazolo[1,5-a]pyrimidin-7-amine (489 mg, 1.49 mmol) in THF (4 ml) was added tert-butyl nitrite (0.88 ml, 7.43 mmol), and the reaction mixture was heated to 80° C. for 2 h. The reaction mixture was concentrated and purified by flash chromatography (0-50% EtOAc/hexanes) to afford the title compound (217 mg, 47%). LCMS calculated for $C_6H_3Cl_2IN_3$ $(M+H)^+$: m/z=313.9; found: 313.7.

Step 5. 3,5-Dichloro-6-(1-methyl-1H-pyrazol-4-yl)pyrazolo[1,5-a]pyrimidine

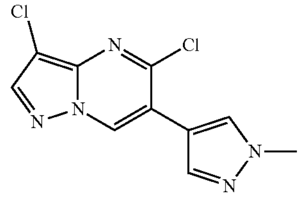 [SMILES: Cn1cc(-c2cn3ncc(Cl)c3nc2Cl)cn1]

A mixture of 3,5-dichloro-6-iodopyrazolo[1,5-a]pyrimidine (217 mg, 0.69 mmol), 1-methyl-4-(4,4,5,5-tetramethyl-1,3,2-dioxaborolan-2-yl)-1H-pyrazole (158 mg, 0.760 mmol), $PdCl_2(dppf)-CH_2Cl_2$ adduct (28 mg, 35 μmol), and sodium carbonate (220 mg, 2.07 mmol) in dioxane (3 ml) and water (1 ml) was sparged with $N_2$ and heated to 80° C. for 2 h. The reaction mixture was diluted with EtOAc and water, and filtered through celite. The phases were separated and the organic phase was washed with brine, dried over $MgSO_4$, filtered and concentrated. The residue was purified by flash chromatography (0-100% EtOAc/hexanes) to afford the title compound (126 mg, 68%). LCMS calculated for $C_{10}H_8Cl_2N_5$ $(M+H)^+$: m/z=268.0; found: 268.0.

Step 6. 3-Chloro-6-(1-methyl-1H-pyrazol-4-yl)-5-((tetrahydrofuran-3-yl)oxy)pyrazolo[1,5-a]pyrimidine (Racemic)

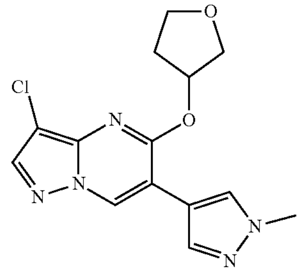 [SMILES: Cn1cc(-c2cn3ncc(Cl)c3nc2OC2CCOC2)cn1]

To a solution of 3,5-dichloro-6-(1-methyl-1H-pyrazol-4-yl)pyrazolo[1,5-a]pyrimidine (40 mg, 0.15 mmol) in DMF (1 ml) was added tetrahydrofuran-3-ol (60 μl, 0.75 mmol), followed by cesium carbonate (146 mg, 0.45 mmol) at room temperature. The reaction mixture was heated to 90° C. for 1 h. The reaction mixture was cooled to room temperature, diluted with DMF and filtered. The solution of the product in DMF was used directly in Step 7. LCMS calculated for $C_{14}H_{15}ClN_5O_2(M+H)^+$: m/z=320.1; found: 320.1.

Step 7. N-Methyl-3-(6-(1-methyl-1H-pyrazol-4-yl)-5-((tetrahydrofuran-3-yl)oxy)pyrazolo[1,5-a]pyrimidin-3-yl)benzamide (Racemic)

A mixture of 3-chloro-6-(1-methyl-H-pyrazol-4-yl)-5-((tetrahydrofuran-3-yl)oxy)pyrazolo[1,5-a]pyrimidine (10 mg, 0.03 mmol), (3-(methylcarbamoyl)phenyl)boronic acid (8.4 mg, 0.05 mmol), XPhos Pd G2 (1.2 mg, 1.6 μmol), and cesium carbonate (31 mg, 0.09 mmol) in DMF (1 ml) and water (0.5 ml) was sparged with $N_2$ and heated to 100° C. for 1 h. The reaction mixture was diluted with MeOH and filtered through a thiol siliaprep cartridge. The product was purified by prep HPLC (pH 2). The product was isolated as the TFA salt. LCMS calculated for $C_{22}H_{23}N_6O_3$ $(M+H)^+$: m/z=419.2; found: 419.1. $^1H$ NMR (500 MHz, DMSO) δ 9.32 (s, 1H), 8.61 (s, 2H), 8.44 (q, J=4.4 Hz, 1H), 8.19 (s, 1H), 8.17 (s, 1H), 8.05 (s, 1H), 7.64 (d, J=7.7 Hz, 1H), 7.50 (t, J=7.7 Hz, 1H), 5.78 (td, J=4.8, 2.5 Hz, 1H), 4.19 (dd, J=10.7, 4.9 Hz, 1H), 4.07 (d, J=10.6 Hz, 1H), 3.96 (q, J=7.7 Hz, 1H), 3.92 (s, 3H), 3.86 (td, J=8.2, 4.7 Hz, 1H), 2.83 (d, J=4.5 Hz, 3H), 2.46 (dt, J=14.6, 7.4 Hz, 1H), 2.36-2.27 (m, 1H).

Example 2. 4-Fluoro-N-methyl-3-(6-(1-methyl-1H-pyrazol-4-yl)-5-((tetrahydrofuran-3-yl)oxy)pyrazolo[1,5-a]pyrimidin-3-yl)benzamide (racemic)

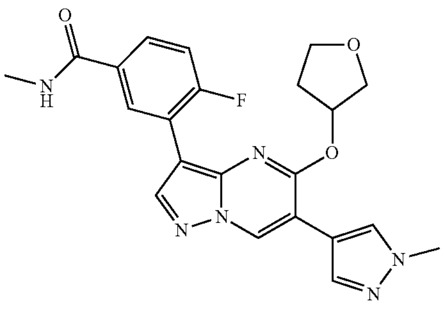

This compound was prepared by a procedure analogous to that described for Example 1, utilizing (2-fluoro-5-(methylcarbamoyl)phenyl)boronic acid instead of (3-(methylcarbamoyl)-phenyl)boronic acid in Step 7. The product was isolated as the TFA salt. LCMS calculated for $C_{22}H_{21}FN_6O_3$ $(M+H)^+$: m/z=437.2; found: 437.1.

Example 3. N-Methyl-5-(6-(1-methyl-1H-pyrazol-4-yl)-5-((tetrahydrofuran-3-yl)oxy)pyrazolo[1,5-a]pyrimidin-3-yl)nicotinamide (Racemic)

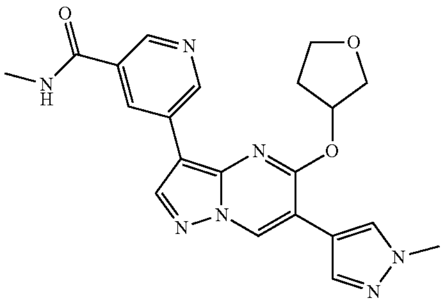

This compound was prepared by a procedure analogous to that described for Example 1, utilizing (5-(methylcarbamoyl)pyridin-3-yl)boronic acid instead of (3-(methylcarbamoyl)-phenyl)boronic acid in Step 7. The product was isolated as the TFA salt. LCMS calculated for $C_{21}H_{22}N_7O_3$ $(M+H)^+$: m/z=420.2; found: 420.1.

Example 4. 4-Fluoro-N,3-dimethyl-5-(6-(1-methyl-1H-pyrazol-4-yl)-5-((tetrahydrofuran-3-yl)oxy)pyrazolo[1,5-a]pyrimidin-3-yl)benzamide (Racemic)

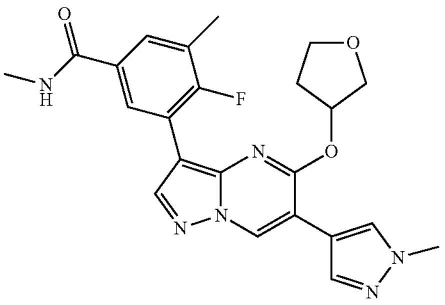

This compound was prepared by a procedure analogous to that described for Example 1, utilizing 4-fluoro-N,3-dimethyl-5-(4,4,5,5-tetramethyl-1,3,2-dioxaborolan-2-yl)benzamide (Intermediate B) instead of (3-(methylcarbamoyl)-phenyl)boronic acid in Step 7. The product was isolated as the TFA salt. LCMS calculated for $C_{23}H_{24}FN_6O_3$ $(M+H)^+$: m/z=451.2; found: 451.2.

Example 5. (S)-4-Fluoro-N,3-dimethyl-5-(6-(1-methyl-1H-pyrazol-4-yl)-5-((tetrahydrofuran-3-yl)oxy)pyrazolo[1,5-a]pyrimidin-3-yl)benzamide

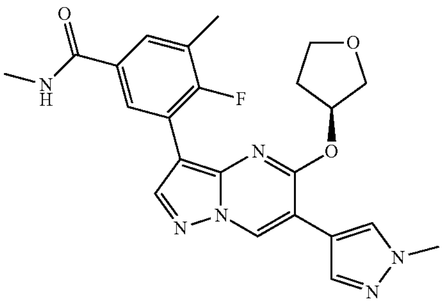

This compound was prepared by a procedure identical to that described for Example 4, utilizing (S)-tetrahydrofuran-3-ol instead of racemic tetrahydrofuran-3-ol in Step 6. The product was isolated as the TFA salt. LCMS calculated for $C_{23}H_{24}FN_6O_3$ $(M+H)^+$: m/z=451.2; found: 451.2.

Example 6. (S)-3-Cyano-N-methyl-5-(6-(1-methyl-1H-pyrazol-4-yl)-5-((tetrahydrofuran-3-yl)oxy)pyrazolo[1,5-a]pyrimidin-3-yl)benzamide

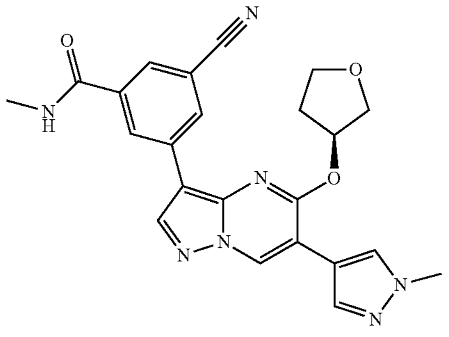

Step 1. 5,6-Dichloro-3-iodopyrazolo[1,5-a]pyrimidine

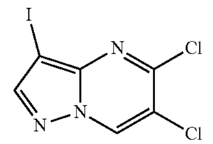 [SMILES: Clc1cn2ncc(I)c2nc1Cl]

This compound was prepared by a procedure analogous to that described for 3,5-dichloro-6-iodopyrazolo[1,5-a]pyrimidine (Example 1, Step 4), utilizing NIS instead of NCS in Step 1 and NCS instead of NIS in Step 3. LCMS calculated for $C_6H_3Cl_2IN_3$ $(M+H)^+$: m/z=313.9; found: 313.8.

Step 2. (S)-6-Chloro-3-iodo-5-((tetrahydrofuran-3-yl)oxy)pyrazolo[1,5-a]pyrimidine

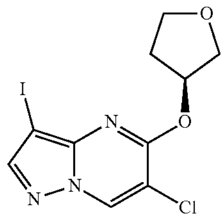 [SMILES: Clc1cn2ncc(I)c2nc1O[C@H]1CCOC1]

To a solution of 5,6-dichloro-3-iodopyrazolo[1,5-a]pyrimidine (391 mg, 1.25 mmol) in DMF (3.5 ml) was added (S)-tetrahydrofuran-3-ol (503 µl, 6.23 mmol), followed by cesium carbonate (609 mg, 1.87 mmol) at room temperature. The reaction mixture was heated to 90° C. for 1 h. After cooling to room temperature, the reaction mixture was partitioned between water and EtOAc, and the phases were separated. The organic phase was washed with brine, dried over $MgSO_4$, filtered, and concentrated. The residue was purified by flash chromatography (0-50% EtOAc/hexanes) to afford the title compound (48 mg, 11%). LCMS calculated for $C_{10}H_{10}ClIN_3O_2$ $(M+H)^+$: m/z=366.0; found: 366.0.

Step 3. (S)-3-(6-Chloro-5-((tetrahydrofuran-3-yl)oxy)pyrazolo[1,5-a]pyrimidin-3-yl)-5-cyanobenzoic Acid

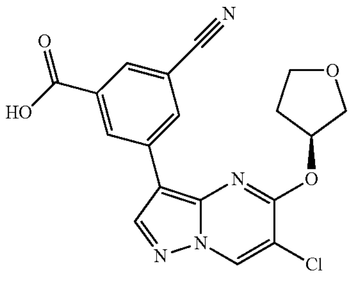 [SMILES: N#Cc1cc(C(=O)O)cc(-c2cnn3cc(Cl)c(O[C@H]4CCOC4)nc23)c1]

A mixture of (S)-6-chloro-3-iodo-5-((tetrahydrofuran-3-yl)oxy)pyrazolo[1,5-a]pyrimidine (15 mg, 0.04 mmol), methyl 3-cyano-5-(4,4,5,5-tetramethyl-1,3,2-dioxaborolan-2-yl)benzoate (13 mg, 0.05 mmol), $PdCl_2(dppf)-CH_2Cl_2$ adduct (1.7 mg, 2.1 µmol), and sodium carbonate (13 mg, 0.12 mmol) in dioxane (1 ml) and water (0.5 ml) was sparged with $N_2$ and heated to 80° C. for 2 h. The solution was then treated with an excess of NaOH and stirred at room temperature until the methyl ester was fully hydrolyzed to the acid. The reaction mixture was acidified to pH 1 with 1M HCl and filtered through a siliaprep thiol cartridge. The filtrate was partitioned between water and EtOAc, and the phases were separated. The aqueous phase was extracted with EtOAc and the combined organic phases were washed with brine, dried over $MgSO_4$, filtered, and concentrated. The product was used without further purification. LCMS calculated for $C_{18}H_{14}ClN_4O_4$ $(M+H)^+$: m/z=385.1; found: 385.1.

Step 4. (S)-3-(6-Chloro-5-((tetrahydrofuran-3-yl)oxy)pyrazolo[1,5-a]pyrimidin-3-yl)-5-cyano-N-methylbenzamide

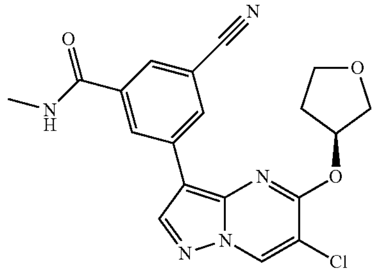 [SMILES: CNC(=O)c1cc(C#N)cc(-c2cnn3cc(Cl)c(O[C@H]4CCOC4)nc23)c1]

To a solution of (S)-3-(6-chloro-5-((tetrahydrofuran-3-yl)oxy)pyrazolo[1,5-a]pyrimidin-3-yl)-5-cyanobenzoic acid (15 mg, 0.039 mmol) and HATU (17.8 mg, 0.047 mmol) in DMF (2 ml) was added DIPEA (10 µl, 0.06 mmol), and the reaction mixture was stirred for 5 min at room temperature. Methylamine (2M/THF) (59 µl, 0.12 mmol) was added, and the reaction mixture was stirred at room temperature for an additional 30 min. The reaction mixture was partitioned between water and EtOAc, and the phases were separated. The aqueous phase was extracted with EtOAc and the combined organic phases were washed with brine, dried over $MgSO_4$, filtered, and concentrated. The product was used without further purification. LCMS calculated for $C_{19}H_{17}ClN_5O_3$ $(M+H)^+$: m/z=398.1; found: 398.2.

Step 5. (S)-3-Cyano-N-methyl-5-(6-(1-methyl-1H-pyrazol-4-yl)-5-((tetrahydrofuran-3-yl)oxy)pyrazolo[1,5-a]pyrimidin-3-yl)benzamide A mixture of (S)-3-(6-chloro-5-((tetrahydrofuran-3-yl)oxy)pyrazolo[1,5-a]pyrimidin-3-yl)-5-cyano-N-methylbenzamide (15 mg, 0.038 mmol), 1-methyl-4-(4,4,5,5-tetramethyl-1,3,2-dioxaborolan-2-yl)-1H-pyrazole (9.4 mg, 0.045 mmol), XPhos Pd G3 (1.6 mg, 1.9 μmol), and sodium carbonate (12 mg, 0.11 mmol) in dioxane (1.5 ml) and water (0.5 ml) was sparged with $N_2$ and heated to 90° C. for 2 h. The reaction mixture was diluted with MeOH, filtered through a siliaprep thiol cartridge, and the product was purified by prep HPLC (pH 2). The product was isolated as the TFA salt. LCMS calculated for $C_{23}H_{22}N_7O_3$ $(M+H)^+$: m/z=444.2; found: 444.2.

Example 7. (S)—N-Methyl-5-(6-(1-methyl-1H-pyrazol-4-yl)-5-((tetrahydrofuran-3-yl)amino)pyrazolo[1,5-a]pyrimidin-3-yl)nicotinamide

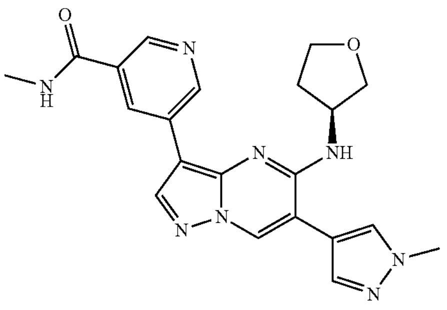

Step 1. (S)-3-Chloro-6-(1-methyl-1H-pyrazol-4-yl)-N-(tetrahydrofuran-3-yl)pyrazolo[1,5-a]pyrimidin-5-amine

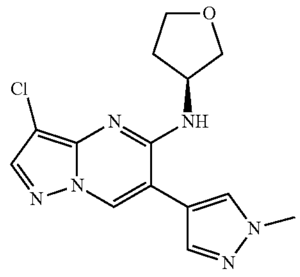 [SMILES: Cn1cc(-c2cn3ncc(Cl)c3nc2N[C@H]2CCOC2)cn1]

To a solution of 3,5-dichloro-6-(1-methyl-1H-pyrazol-4-yl)pyrazolo[1,5-a]pyrimidine (10 mg, 0.037 mmol, Example 1, Step 5) in DMF (0.5 ml) was added (S)-tetrahydrofuran-3-amine (16 mg, 0.19 mmol), followed by cesium carbonate (37 mg, 0.11 mmol) at room temperature. The reaction mixture was heated to 80° C. for 1 h. After cooling to room temperature, the reaction mixture was partitioned between water and EtOAc, and the phases were separated. The organic phase was washed with brine, dried over $MgSO_4$, filtered, and concentrated. The product was used without further purification. LCMS calculated for $C_{14}H_{16}ClN_6O$ $(M+H)^+$: m/z=319.1; found: 319.0.

Step 2. (S)—N-Methyl-5-(6-(1-methyl-1H-pyrazol-4-yl)-5-((tetrahydrofuran-3-yl)amino)pyrazolo[1,5-a]pyrimidin-3-yl)nicotinamide A mixture of (S)-3-chloro-6-(1-methyl-1H-pyrazol-4-yl)-N-(tetrahydrofuran-3-yl)pyrazolo[1,5-a]pyrimidin-5-amine (10 mg, 0.031 mmol), N-methyl-5-(4,4,5,5-tetramethyl-1,3,2-dioxaborolan-2-yl)nicotinamide (9.9 mg, 0.038 mmol), XPhos Pd G2 (1.2 mg, 1.6 μmol), and sodium carbonate (10 mg, 0.094 mmol) in dioxane (1 ml) and water (0.5 ml) was sparged with $N_2$ and heated to 100° C. for 2 h. The reaction mixture was diluted with MeOH and filtered through a thiol siliaprep cartridge. The product was purified by prep HPLC (pH 2). The product was isolated as the TFA salt. LCMS calculated for $C_{21}H_{23}N_8O_2$ $(M+H)^+$: m/z=419.2; found: 419.2.

Example 8. (S)-3-Cyano-N-methyl-5-(6-(1-methyl-1H-pyrazol-4-yl)-5-((tetrahydrofuran-3-yl)amino)pyrazolo[1,5-a]pyrimidin-3-yl)benzamide

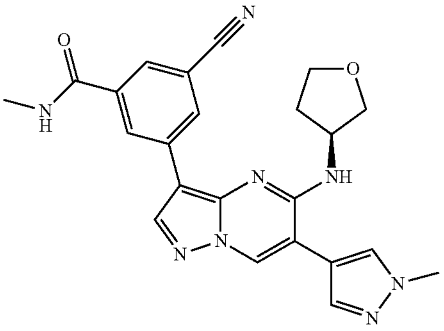

Step 1. (S)-3-Cyano-5-(6-(1-methyl-1H-pyrazol-4-yl)-5-((tetrahydrofuran-3-yl)amino)pyrazolo[1,5-a]pyrimidin-3-yl)benzoic Acid

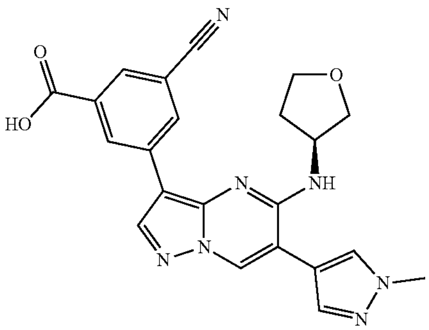 [SMILES: Cn1cc(-c2cn3ncc(-c4cc(C#N)cc(C(=O)O)c4)c3nc2N[C@H]2CCOC2)cn1]

A mixture of (S)-3-chloro-6-(1-methyl-1H-pyrazol-4-yl)-N-(tetrahydrofuran-3-yl)pyrazolo[1,5-a]pyrimidin-5-amine (15 mg, 0.047 mmol, Example 7, Step 1), methyl 3-cyano-5-(4,4,5,5-tetramethyl-1,3,2-dioxaborolan-2-yl)benzoate (16.2 mg, 0.056 mmol), XPhos Pd G2 (1.9 mg, 2.4 μmol), and sodium carbonate (15 mg, 0.14 mmol) in dioxane (1.5 ml) and water (0.5 ml) was sparged with $N_2$ and heated to 100° C. for 2 h. The reaction mixture was acidified to pH 1 with 1M HCl, diluted with EtOAc, and filtered through a thiol siliaprep cartridge. The phases were separated and the organic phase was washed with brine, dried over $MgSO_4$, filtered and concentrated. The product was used without purification. LCMS calculated for $C_{22}H_{20}N_7O_3$ $(M+H)^+$: m/z=430.2; found: 430.1.

Step 2. (S)-3-Cyano-N-methyl-5-(6-(1-methyl-1H-pyrazol-4-yl)-5-((tetrahydrofuran-3-yl)amino)pyrazolo[1,5-a]pyrimidin-3-yl)benzamide To a mixture of (S)-3-cyano-5-(6-(1-methyl-1H-pyrazol-4-yl)-5-((tetrahydrofuran-3-yl)amino)pyrazolo[1,5-a]pyrimidin-3-yl)benzoic acid (20 mg, 0.047 mmol) and HATU (21.4 mg, 0.056 mmol) in DMF (3 ml) was added DIPEA (24 μl, 0.14 mmol), and the reaction mixture was stirred at room temp for 5 min. Methylamine (2M/THF) (70 μl, 0.14 mmol) was added, and the reaction mixture was stirred at room temperature for an additional 30 min. The reaction mixture was partitioned between water and EtOAc, and the phases were separated. The organic phase was washed with brine, dried over $MgSO_4$, filtered, and concentrated. The product was purified by prep HPLC (pH 2). The product was isolated as the TFA salt. LCMS calculated for $C_{23}H_{23}N_8O_2$ $(M+H)^+$: m/z=443.2; found: 443.4.

Example 9. (S)-5-(6-(1-Isopropyl-1H-pyrazol-4-yl)-5-((tetrahydrofuran-3-yl)oxy)pyrazolo[1,5-a]pyrimidin-3-yl)-N-methylnicotinamide

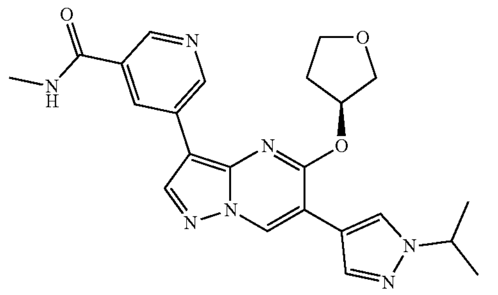 [SMILES: CNC(=O)c1cncc(-c2cnn3cc(-c4cnn(C(C)C)c4)c(O[C@H]4CCOC4)nc23)c1]

Step 1. 3,5-Dichloro-6-(1-isopropyl-1H-pyrazol-4-yl)pyrazolo[1,5-a]pyrimidine

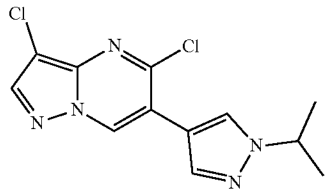 [SMILES: CC(C)n1cc(-c2cn3ncc(Cl)c3nc2Cl)cn1]

A mixture of 3,5-dichloro-6-iodopyrazolo[1,5-a]pyrimidine (100 mg, 0.32 mmol, Example 1, Step 4), 1-isopropyl-4-(4,4,5,5-tetramethyl-1,3,2-dioxaborolan-2-yl)-1H-pyrazole (75 mg, 0.32 mmol), $PdCl_2(dppf)$-$CH_2Cl_2$ adduct (13 mg, 0.016 mmol), and sodium carbonate (101 mg, 0.96 mmol) in dioxane (2 ml) and water (0.5 ml) was sparged with $N_2$ and heated to 80° C. for 1 h. The reaction mixture was diluted with EtOAc and water. The phases were separated and the organic phase was washed with brine, dried over $MgSO_4$, filtered and concentrated. The residue was purified by flash chromatography (0-100% EtOAc/hexanes) to afford the title compound (77 mg, 82%). LCMS calculated for $C_{12}H_{12}Cl_2N_5$ $(M+H)^+$: m/z=296.0; found: 296.2.

Step 2. (S)-3-Chloro-6-(1-isopropyl-1H-pyrazol-4-yl)-5-((tetrahydrofuran-3-yl)oxy)pyrazolo[1,5-a]pyrimidine

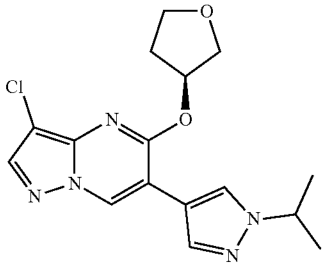 [SMILES: CC(C)n1cc(-c2cn3ncc(Cl)c3nc2O[C@H]2CCOC2)cn1]

To a solution of 3,5-dichloro-6-(1-isopropyl-H-pyrazol-4-yl)pyrazolo[1,5-a]pyrimidine (10 mg, 0.034 mmol) in DMF (1 ml) was added (S)-tetrahydrofuran-3-ol (14 mg, 0.17 mmol), followed by cesium carbonate (16.5 mg, 0.051 mmol) at room temperature. The reaction mixture was heated to 80° C. for 1 h; then cooled to room temperature. The solution of the product in DMF was used directly for the next reaction. LCMS calculated for $C_{16}H_{19}ClN_5O_2$ $(M+H)^+$: m/z=348.1; found: 348.1.

Step 3. (S)-5-(6-(1-Isopropyl-1H-pyrazol-4-yl)-5-((tetrahydrofuran-3-yl)oxy)pyrazolo[1,5-a]pyrimidin-3-yl)-N-methylnicotinamide A mixture of (S)-3-chloro-6-(1-isopropyl-1H-pyrazol-4-yl)-5-((tetrahydrofuran-3-yl)oxy)pyrazolo[1,5-a]pyrimidine (12 mg, 0.035 mmol), N-methyl-5-(4,4,5,5-tetramethyl-1,3,2-dioxaborolan-2-yl)nicotinamide (10.9 mg, 0.041 mmol), XPhos Pd G2 (1.4 mg, 1.7 μmol), and cesium carbonate (34 mg, 0.10 mmol) in DMF (1 ml) and water (0.5 ml) was sparged with $N_2$ and heated to 100° C. for 2 h. The reaction was diluted with MeOH, filtered through a siliaprep thiol cartridge, and the product was purified by prep HPLC (pH 2). The product was isolated as the TFA salt. LCMS calculated for $C_{23}H_{26}N_7O_3$ $(M+H)^+$: m/z=448.2; found: 448.4. $^1H$ NMR (500 MHz, DMSO) δ 9.39 (d, J=2.1 Hz, 1H), 9.38 (s, 1H), 9.00 (t, J=2.1 Hz, 1H), 8.85 (d, J=2.0 Hz, 1H), 8.74 (s, 1H), 8.72 (q, J=4.9, 4.4 Hz, 1H), 8.28 (s, 1H), 8.06 (s, 1H), 5.79 (td, J=4.7, 2.4 Hz, 1H), 4.58 (p, J=6.7 Hz, 1H), 4.17 (dd, J=10.7, 4.7 Hz, 1H), 4.11-4.05 (m, 1H), 3.96 (q, J=8.1 Hz, 1H), 3.88 (td, J=8.3, 4.7 Hz, 1H), 2.86 (d, J=4.5 Hz, 3H), 2.46 (dt, J=14.6, 7.3 Hz, 1H), 2.36-2.26 (m, 1H), 1.47 (d, J=6.6 Hz, 6H).

Example 10. (S)-5-(6-(1-Isopropyl-1H-pyrazol-4-yl)-5-((tetrahydrofuran-3-yl)amino)pyrazolo[1,5-a]pyrimidin-3-yl)-N-methylnicotinamide

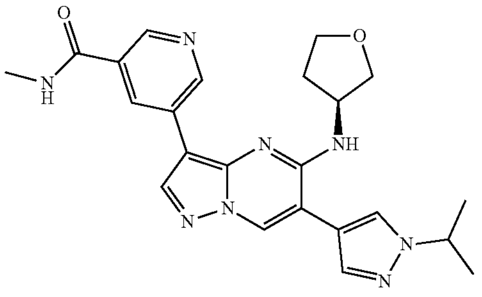 [SMILES: CNC(=O)c1cncc(-c2cnn3cc(-c4cnn(C(C)C)c4)c(N[C@H]4CCOC4)nc23)c1]

Step 1. (S)-3-Chloro-6-(1-Isopropyl-1H-pyrazol-4-yl)-N-(tetrahydrofuran-3-yl)pyrazolo[1,5-a]pyrimidin-5-amine

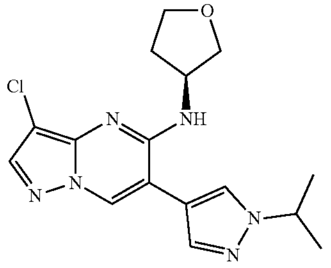

To a solution of 3,5-dichloro-6-(1-isopropyl-H-pyrazol-4-yl)pyrazolo[1,5-a]pyrimidine (10 mg, 0.034 mmol, Example 9, Step 1) in DMF (1 ml) was added (S)-tetrahydrofuran-3-amine (15 mg, 0.17 mmol), followed by cesium carbonate (16.5 mg, 0.051 mmol) at room temperature. The reaction mixture was heated to 80° C. for 1 h, then cooled to room temperature. The reaction mixture was partitioned between water and EtOAc, and the phases were separated. The organic phase was washed with brine, dried over $MgSO_4$, filtered, and concentrated. The residue was used without purification. LCMS calculated for $C_{16}H_{20}ClN_6O$ $(M+H)^+$: m/z=347.1; found: 347.2.

Step 2. (S)-5-(6-(1-Isopropyl-1H-pyrazol-4-yl)-5-((tetrahydrofuran-3-yl)amino)pyrazolo[1,5-a]pyrimidin-3-yl)-N-methylnicotinamide This compound was synthesized by a procedure analogous to that described in Example 9, Step 3. The product was isolated as the TFA salt. LCMS calculated for $C_{23}H_{27}NO_2$ $(M+H)^+$: m/z=447.2; found: 447.4.

Example 11. (S)-3,4-Difluoro-N-methyl-5-(6-(1-(1-methylpiperidin-4-yl)-1H-pyrazol-4-yl)-5-((tetrahydrofuran-3-yl)oxy)pyrazolo[1,5-a]pyrimidin-3-yl)benzamide

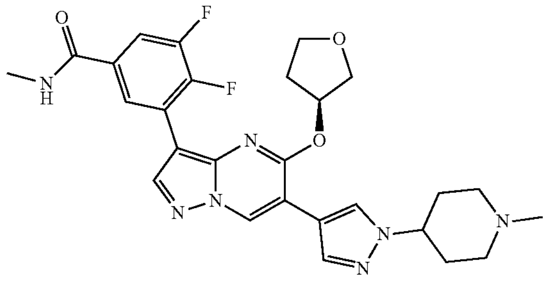

Step 1. 3-Bromo-5,6-dichloropyrazolo[1,5-a]pyrimidine

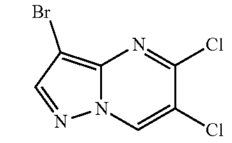 [SMILES: Clc1cn2ncc(Br)c2nc1Cl]

This compound was prepared by a procedure analogous to that described for 3,5-dichloro-6-iodopyrazolo[1,5-a]pyrimidine (Example 1, Step 4), utilizing NBS instead of NCS in Step 1 and NCS instead of NIS in Step 3. LCMS calculated for $C_6H_3BrCl_2N_3$ $(M+H)^+$: m/z=265.9; found: 265.9.

Step 2. (S)-3-Bromo-6-chloro-5-((tetrahydrofuran-3-yl)oxy)pyrazolo[1,5-a]pyrimidine

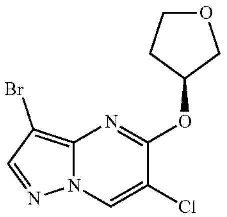

A mixture of 3-bromo-5,6-dichloropyrazolo[1,5-a]pyrimidine (340 mg, 1.27 mmol), (S)-tetrahydrofuran-3-ol (515 μl, 6.37 mmol), and cesium carbonate (623 mg, 1.91 mmol) in THF (6 ml) was heated to 80° C. for 2 h. The reaction mixture was cooled to room temperature, diluted with EtOAc, and filtered. The filtrate was concentrated in vacuo and the residue was purified by flash chromatography (0-50% EtOAc/hexanes) to afford the title compound (271 mg, 67%) as a light yellow solid. LCMS calculated for $C_{10}H_{10}BrClN_3O_2$ $(M+H)^+$: m/z=318.0; found: 317.9.

Step 3. (S)-3-(6-Chloro-5-((tetrahydrofuran-3-yl)oxy)pyrazolo[1,5-a]pyrimidin-3-yl)-4,5-difluoro-N-methylbenzamide

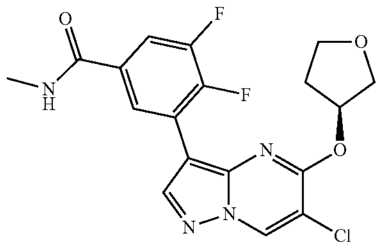 [SMILES: CNC(=O)c1cc(F)c(F)c(-c2cnn3cc(Cl)c(O[C@H]4CCOC4)nc23)c1]

A mixture of (S)-3-bromo-6-chloro-5-((tetrahydrofuran-3-yl)oxy)pyrazolo[1,5-a]pyrimidine (30 mg, 0.094 mmol), 3,4-difluoro-N-methyl-5-(4,4,5,5-tetramethyl-1,3,2-dioxaborolan-2-yl)benzamide (33 mg, 0.11 mmol, Intermediate A), $PdCl_2(dppf)$-$CH_2Cl_2$ adduct (7.7 mg, 9.4 μmol), and sodium carbonate (30 mg, 0.28 mmol) in dioxane (1.5 ml) and water (0.5 ml) was sparged with $N_2$ and heated to 100° C. for 2 h. More 3,4-difluoro-N-methyl-5-(4,4,5,5-tetramethyl-1,3,2-dioxaborolan-2-yl)benzamide (33 mg, 0.11 mmol, Intermediate A) was added and heating was continued for an additional 1 h. The reaction mixture was diluted with EtOAc and filtered through a siliaprep thiol cartridge. The filtrate was partitioned between water and EtOAc, and the phases were separated. The aqueous phase was extracted with EtOAc and the combined organic phases were washed with brine, dried over $MgSO_4$, filtered, and concentrated. The residue was purified by flash chromatography (0-100% EtOAc/hexanes) to afford the title compound. LCMS calculated for $C_{18}H_{16}ClF_2N_4O_3$ $(M+H)^+$: m/z=409.1; found: 409.2.

Step 4. (S)-3,4-Difluoro-N-methyl-5-(6-(1-(1-methylpiperidin-4-yl)-1H-pyrazol-4-yl)-5-((tetrahydrofuran-3-yl)oxy)pyrazolo[1,5-a]pyrimidin-3-yl)benzamide A mixture of (S)-3-(6-chloro-5-((tetrahydrofuran-3-yl)oxy)pyrazolo[1,5-a]pyrimidin-3-yl)-4,5-difluoro-N-methylbenzamide (10 mg, 0.02 mmol), 1-methyl-4-(4-(4,4,5,5-tetramethyl-1,3,2-dioxaborolan-2-yl)-1H-pyrazol-1-yl)piperidine (6 mg, 0.02 mmol), XPhos Pd G2 (1.9 mg, 2.5 μmol), and cesium carbonate (24 mg, 0.073 mmol) in dioxane (1 ml) and water (0.5 ml) was sparged with $N_2$ and heated to 100° C. for 2 h. The reaction mixture was diluted with MeOH and filtered through a thiol siliaprep cartridge. The product was purified by prep HPLC (pH 2). The product was isolated as the TFA salt. LCMS calculated for $C_{27}H_{30}F_2N_7O_3$ $(M+H)^+$: m/z=538.2; found: 538.3.

Examples 12-15

The compounds in the following table were synthesized according to the procedure described for Example 11, utilizing the appropriate commercially available boronate or boronic acid in Step 4. The products were isolated as TFA salts.

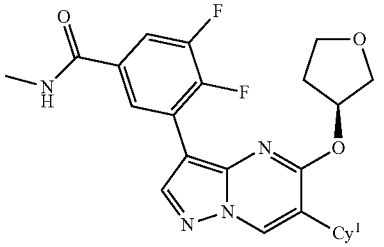

| Example No. and Compound Name | $Cy^1$ | LCMS |
|---|---|---|
| 12. (S)-3,4-Difluoro-N-methyl-5-(6-(4-(4-methylpiperazin-1-yl)phenyl)-5-((tetrahydrofuran-3-yl)oxy)pyrazolo[1,5-a]pyrimidin-3-yl)benzamide | 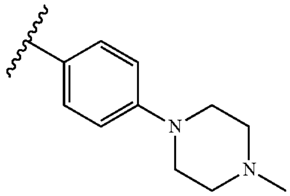 [SMILES: *c1ccc(N2CCN(C)CC2)cc1] | LCMS calculated for $C_{29}H_{31}F_2N_6O_3$ $(M + H)^+$: m/z = 549.2; found: 549.3. |
| 13. (S)-3,4-Difluoro-N-methyl-5-(6-(6-(4-methylpiperazin-1-yl)pyridin-3-yl)-5-((tetrahydrofuran-3-yl)oxy)pyrazolo[1,5-a]pyrimidin-3-yl)benzamide | 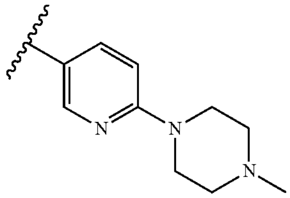 [SMILES: *c1ccc(N2CCN(C)CC2)nc1] | LCMS calculated for $C_{28}H_{30}F_2N_7O_3$ $(M + H)^+$: m/z = 550.2; found: 550.3. |
| 14. (S)-3,4-Difluoro-N-methyl-5-(6-(1-(2-morpholinoethyl)-1H-pyrazol-4-yl)-5-((tetrahydrofuran-3-yl)oxy)pyrazolo[1,5-a]pyrimidin-3-yl)benzamide | 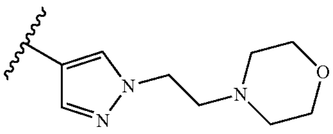 [SMILES: *c1cnn(CCN2CCOCC2)c1] | LCMS calculated for $C_{27}H_{30}F_2N_7O_4$ $(M + H)^+$: m/z = 554.2; found: 554.3. |

-continued

| Example No. and Compound Name | Cy[1] | LCMS |
|---|---|---|
| 15. (S)-3,4-Difluoro-N-methyl-5-(6-(6-methylpyridin-3-yl)-5-((tetrahydrofuran-3-yl)oxy)pyrazolo[1,5-a]pyrimidin-3-yl)benzamide | 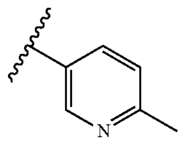 [SMILES: *c1ccc(C)nc1] | LCMS calculated for $C_{24}H_{22}F_2N_5O_3$ (M + H)$^+$: m/z = 466.2; found: 466.2. |

Example 16. (S)-4-Fluoro-N,3-dimethyl-5-(6-(1-methyl-1H-pyrazol-4-yl)-5-((tetrahydrofuran-3-yl)amino)pyrazolo[1,5-a]pyrimidin-3-yl)benzamide

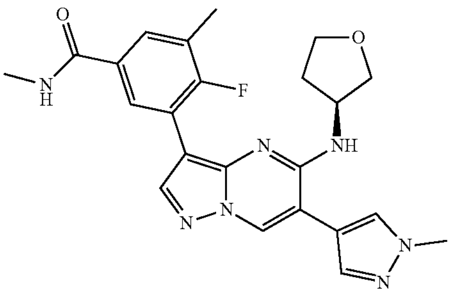

Step 1. (S)-4-Fluoro-3-methyl-5-(6-(1-methyl-1H-pyrazol-4-yl)-5-((tetrahydrofuran-3-yl)amino)pyrazolo[1,5-a]pyrimidin-3-yl)benzoic Acid

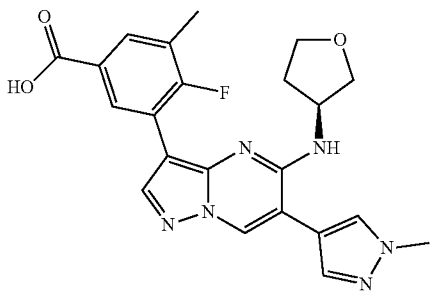 [SMILES: Cc1cc(C(=O)O)cc(-c2cnn3cc(-c4cnn(C)c4)c(N[C@H]4CCOC4)nc23)c1F]

A mixture of (S)-3-chloro-6-(1-methyl-1H-pyrazol-4-yl)-N-(tetrahydrofuran-3-yl)pyrazolo[1,5-a]pyrimidin-5-amine (15 mg, 0.047 mmol, Example 7, Step 1), 4-fluoro-3-methyl-5-(4,4,5,5-tetramethyl-1,3,2-dioxaborolan-2-yl)benzoic acid (15.8 mg, 0.056 mmol, Combi-Blocks), XPhos Pd G2 (1.9 mg, 2.4 μmol), and sodium carbonate (15 mg, 0.14 mmol) in dioxane (1.5 ml) and water (0.5 ml) was sparged with $N_2$ and heated to 100° C. for 2 h. The reaction mixture was diluted with MeOH, filtered through a siliaprep thiol cartridge, and the product was purified by prep HPLC (pH 2) to afford the title compound (5 mg, 24%). LCMS calculated for $C_{22}H_{22}FN_6O_3$ (M+H)$^+$: m/z=437.2; found: 437.2.

Step 2. (S)-4-Fluoro-N,3-dimethyl-5-(6-(1-methyl-1H-pyrazol-4-yl)-5-((tetrahydrofuran-3-yl)amino)pyrazolo[1,5-a]pyrimidin-3-yl)benzamide To a mixture of (S)-4-fluoro-3-methyl-5-(6-(1-methyl-1H-pyrazol-4-yl)-5-((tetrahydrofuran-3-yl)amino)pyrazolo[1,5-a]pyrimidin-3-yl)benzoic acid (5 mg, 0.011 mmol) and HATU (8.7 mg, 0.023 mmol) in DMF (2 ml) was added DIPEA (6 μl, 0.03 mmol), and the reaction mixture was stirred at room temp for 5 min. Methylamine (2M/THF) (17 μl, 0.034 mmol) was added and the reaction mixture was stirred for an additional 30 min. The reaction mixture was diluted with methanol and the product was purified by prep HPLC (pH 2). The product was isolated as the TFA salt. LCMS calculated for $C_{23}H_{25}FN_7O_2$ (M+H)$^+$: m/z=450.2; found: 450.2.

Example 17. (S)-3,4-Difluoro-N-methyl-5-(6-(1-(1-methylazetidin-3-yl)-1H-pyrazol-4-yl)-5-((tetrahydrofuran-3-yl)oxy)pyrazolo[1,5-a]pyrimidin-3-yl)benzamide

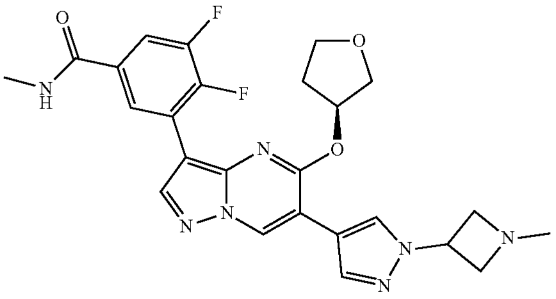

Step 1. tert-Butyl(S)-3-(4-(3-(2,3-difluoro-5-(methylcarbamoyl)phenyl)-5-((tetrahydrofuran-3-yl)oxy)pyrazolo[1,5-a]pyrimidin-6-yl)-1H-pyrazol-1-yl)azetidine-1-carboxylate

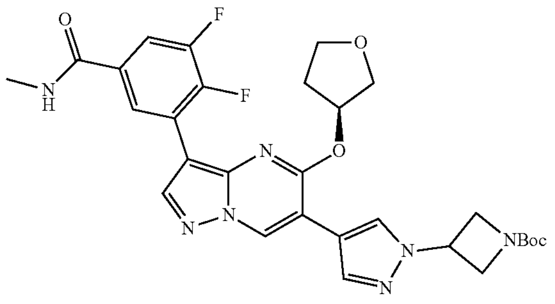 [SMILES: CNC(=O)c1cc(F)c(F)c(-c2cnn3cc(-c4cnn(C5CN(C(=O)OC(C)(C)C)C5)c4)c(O[C@H]4CCOC4)nc23)c1]

A mixture of (S)-3-(6-chloro-5-((tetrahydrofuran-3-yl)oxy)pyrazolo[1,5-a]pyrimidin-3-yl)-4,5-difluoro-N-methylbenzamide (10 mg, 0.024 mmol, Example 11, Step 3), tert-butyl 3-(4-(4,4,5,5-tetramethyl-1,3,2-dioxaborolan-2-yl)-1H-pyrazol-1-yl)azetidine-1-carboxylate (10.3 mg, 0.029 mmol), XPhos Pd G2 (1.9 mg, 2.5 μmol), and cesium carbonate (24 mg, 0.073 mmol) in dioxane (1 ml) and water (0.5 ml) was sparged with $N_2$ and heated to 100° C. for 2 h. The reaction was diluted with MeOH and filtered through a thiol siliaprep cartridge. The filtrate was concentrated and the residue was used without further purification. LCMS calculated for $C_{29}H_{32}F_2N_7O_5$ $(M+H)^+$: m/z=596.2; found: 596.4.

Step 2. (S)-3,4-Difluoro-N-methyl-5-(6-(1-(1-methylazetidin-3-yl)-1H-pyrazol-4-yl)-5-((tetrahydrofuran-3-yl)oxy)pyrazolo[1,5-a]pyrimidin-3-yl)benzamide To a solution of tert-butyl (S)-3-(4-(3-(2,3-difluoro-5-(methylcarbamoyl)phenyl)-5-((tetrahydrofuran-3-yl)oxy)pyrazolo[1,5-a]pyrimidin-6-yl)-1H-pyrazol-1-yl)azetidine-1-carboxylate (15 mg, 0.025 mmol) in DCM (1.5 ml) was added TFA (0.5 ml, 6.5 mmol) and the reaction mixture was stirred at room temp for 30 min. The reaction mixture was concentrated, dissolved in MeOH (2 ml), and treated sequentially with formaldehyde (0.094 ml, 1.26 mmol) and sodium cyanoborohydride (7.9 mg, 0.126 mmol). After stirring for 3 h, the reaction mixture was diluted with MeOH and purified by prep HPLC (pH 2). The product was isolated as the TFA salt. LCMS calculated for $C_{25}H_{26}F_2N_7O_3$ $(M+H)^+$: m/z=510.2; found: 510.5.

Example 18. (S)—N-Methyl-5-(6-(4-(4-methylpiperazin-1-yl)phenyl)-5-((tetrahydrofuran-3-yl)oxy)pyrazolo[1,5-a]pyrimidin-3-yl)nicotinamide

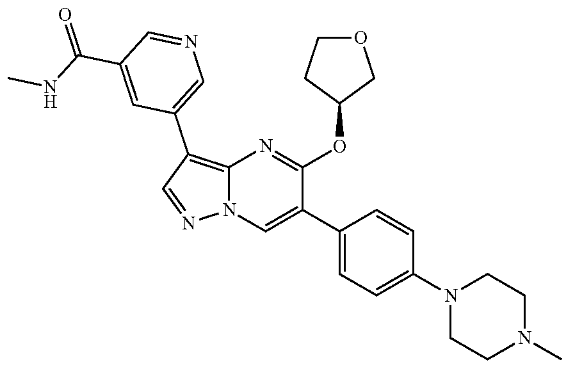

Step 1. (S)-5-(6-Chloro-5-((tetrahydrofuran-3-yl)oxy)pyrazolo[1,5-a]pyrimidin-3-yl)-N-methylnicotinamide

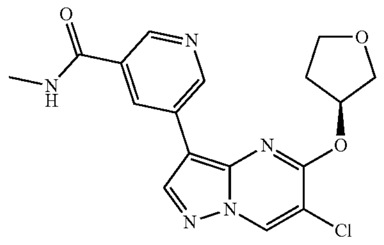 [SMILES: CNC(=O)c1cncc(-c2cnn3cc(Cl)c(O[C@H]4CCOC4)nc23)c1]

A mixture of (S)-3-bromo-6-chloro-5-((tetrahydrofuran-3-yl)oxy)pyrazolo[1,5-a]pyrimidine (60 mg, 0.19 mmol, Example 11, Step 2), N-methyl-5-(4,4,5,5-tetramethyl-1,3,2-dioxaborolan-2-yl)nicotinamide (59 mg, 0.23 mmol), $PdCl_2(dppf)$-$CH_2Cl_2$ adduct (7.7 mg, 9.4 μmol), and sodium carbonate (60 mg, 0.57 mmol) in dioxane (1.5 ml) and water (0.5 ml) was sparged with $N_2$ and heated to 100° C. for 2 h. The reaction mixture was diluted with EtOAc and filtered through a siliaprep thiol cartridge. The filtrate was washed with water and brine, and the phases were separated. The organic phase was dried over $MgSO_4$, filtered, and concentrated. The residue was used without further purification. LCMS calculated for $C_{17}H_{17}ClN_5O_3$ $(M+H)^+$: m/z=374.1; found: 374.1.

Step 2. (S)—N-Methyl-5-(6-(4-(4-methylpiperazin-1-yl)phenyl)-5-((tetrahydrofuran-3-yl)oxy)pyrazolo[1,5-a]pyrimidin-3-yl)nicotinamide A mixture of (S)-5-(6-chloro-5-((tetrahydrofuran-3-yl)oxy)pyrazolo[1,5-a]pyrimidin-3-yl)-N-methylnicotinamide (10 mg, 0.027 mmol), 1-methyl-4-(4-(4,4,5,5-tetramethyl-1,3,2-dioxaborolan-2-yl)phenyl)piperazine (12 mg, 0.04 mmol), XPhos Pd G2 (2.1 mg, 2.7 μmol), and cesium carbonate (26 mg, 0.08 mmol) in dioxane (1 ml) and water (0.5 ml) was sparged with $N_2$ and heated to 100° C. for 2 h. The reaction mixture was diluted with MeOH and filtered through a thiol siliaprep cartridge. The product was purified by prep HPLC (pH 2). The product was isolated as the TFA salt. LCMS calculated for $C_{28}H_{31}N_7O_3$ $(M+H)^+$: m/z=514.3; found: 514.2.

Examples 19-22

The compounds in the following table were synthesized according to the procedure described for Example 18, utilizing the appropriate commercially available boronate or boronic acid in Step 2. The products were isolated as TFA salts.

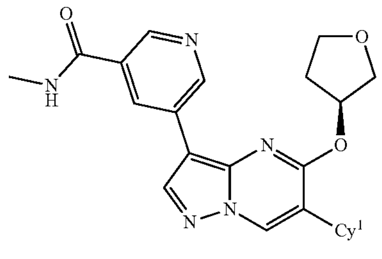

| Example No. | $Cy^1$ | LCMS |
| --- | --- | --- |
| 19. (S)-N-Methyl-5-(6-(6-(4-methylpiperazin-1-yl)pyridin-3-yl)-5-((tetrahydrofuran-3-yl)oxy)pyrazolo[1,5-a]pyrimidin-3-yl)nicotinamide | 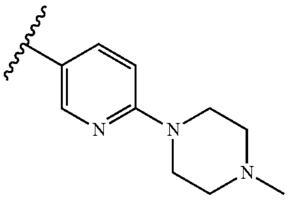 [SMILES: *c1ccc(N2CCN(C)CC2)nc1] | LCMS calculated for $C_{27}H_{31}N_8O_3$ $(M + H)^+$: m/z = 515.2; found: 515.2. |
| 20. (S)-N-Methyl-5-(6-(6-morpholinopyridin-3-yl)-5-((tetrahydrofuran-3-yl)oxy)pyrazolo[1,5-a]pyrimidin-3-yl)nicotinamide | 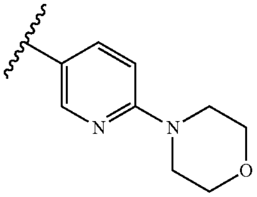 [SMILES: *c1ccc(N2CCOCC2)nc1] | LCMS calculated for $C_{26}H_{28}N_7O_4$ $(M + H)^+$: m/z = 502.2; found: 502.2. |
| 21.(S)-5-(6-(1-Cyclopropyl-1H-pyrazol-4-yl)-5-((tetrahydrofuran-3-yl)oxy)pyrazolo[1,5-a]pyrimidin-3-yl)-N-methylnicotinamide | 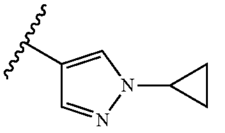 [SMILES: *c1cnn(C2CC2)c1] | LCMS calculated for $C_{23}H_{24}N_7O_3$ $(M + H)^+$: m/z = 446.2; found: 446.3. |
| 22. (S)-5-(6-(1-Cyclobutyl-1H-pyrazol-4-yl)-5-((tetrahydrofuran-3-yl)oxy)pyrazolo[1,5-a]pyrimidin-3-yl)-N-methylnicotinamide | 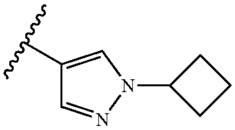 [SMILES: *c1cnn(C2CCC2)c1] | LCMS calculated for $C_{24}H_{26}N_7O_3$ $(M + H)^+$: m/z = 460.2; found: 460.3. |

Example 23. (S)-3-(Difluoromethyl)-4-fluoro-N-methyl-5-(6-(pyridin-3-yl)-5-((tetrahydrofuran-3-yl)oxy)pyrazolo[1,5-a]pyrimidin-3-yl)benzamide

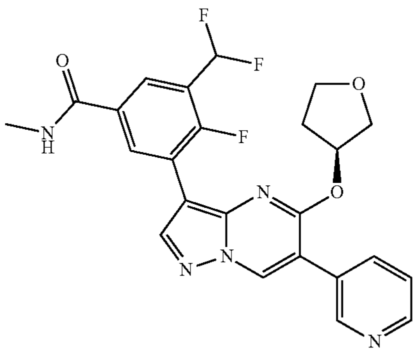 [SMILES: CNC(=O)c1cc(-c2cnn3cc(-c4cccnc4)c(O[C@H]4CCOC4)nc23)c(F)c(C(F)F)c1]

Step 1. (S)-3-(6-Chloro-5-((tetrahydrofuran-3-yl)oxy)pyrazolo[1,5-a]pyrimidin-3-yl)-5-(difluoromethyl)-4-fluoro-N-methylbenzamide

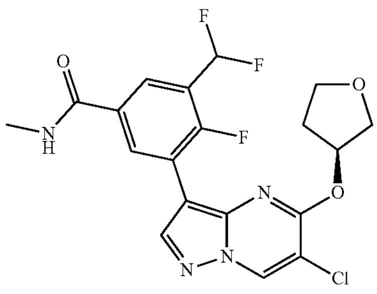 [SMILES: CNC(=O)c1cc(-c2cnn3cc(Cl)c(O[C@H]4CCOC4)nc23)c(F)c(C(F)F)c1]

A mixture of (S)-3-bromo-6-chloro-5-((tetrahydrofuran-3-yl)oxy)pyrazolo[1,5-a]pyrimidine (50 mg, 0.16 mmol), 3-(difluoromethyl)-4-fluoro-N-methyl-5-(4,4,5,5-tetramethyl-1,3,2-dioxaborolan-2-yl)benzamide (46.5 mg, 0.19 mmol, Intermediate C), $PdCl_2$(dppf)-$CH_2Cl_2$ adduct (6.4 mg, 7.9 μmol), and sodium carbonate (50 mg, 0.47 mmol) in dioxane (1 ml) and water (0.5 ml) was thoroughly deoxygenated by two freeze-pump-thaw cycles, and heated to 100° C. for 2 h. The reaction mixture was diluted with EtOAc and filtered through a siliaprep thiol cartridge. The filtrate was concentrated and the residue was purified by flash chromatography (0-100% EtOAc/hexanes) to afford the title compound (41 mg, 59%), which was contaminated with ~30% of protodeborylated by-product. LCMS calculated for $C_{19}H_{17}CF_3N_4O_3$ $(M+H)^+$: m/z=441.1; found: 441.1.

Step 2. (S)-3-(Difluoromethyl)-4-fluoro-N-methyl-5-(6-(pyridin-3-yl)-5-((tetrahydrofuran-3-yl)oxy)pyrazolo[1,5-a]pyrimidin-3-yl)benzamide A mixture of (S)-3-(6-chloro-5-((tetrahydrofuran-3-yl)oxy)pyrazolo[1,5-a]pyrimidin-3-yl)-5-(difluoromethyl)-4-fluoro-N-methylbenzamide (10 mg, 0.023 mmol), 3-(4,4,5,5-tetramethyl-1,3,2-dioxaborolan-2-yl)pyridine (9.3 mg, 0.045 mmol), XPhos Pd G2 (1.8 mg, 2.3 μmol), and cesium carbonate (22 mg, 0.068 mmol) in dioxane (1.5 ml) and water (0.5 ml) was sparged with $N_2$ and heated to 100° C. for 2 h. The reaction mixture was diluted with MeOH and filtered through a thiol siliaprep cartridge. The product was purified by prep HPLC (pH 2). The product was isolated as the TFA salt. LCMS calculated for $C_{24}H_{21}F_3N_5O_3$ $(M+H)^+$: m/z=484.2; found: 484.2.

Example 24. (S)-3-(Difluoromethyl)-4-fluoro-N-methyl-5-(6-(5-methyl-6-(methylamino)pyridin-3-yl)-5-((tetrahydrofuran-3-yl)oxy)pyrazolo[1,5-a]pyrimidin-3-yl)benzamide

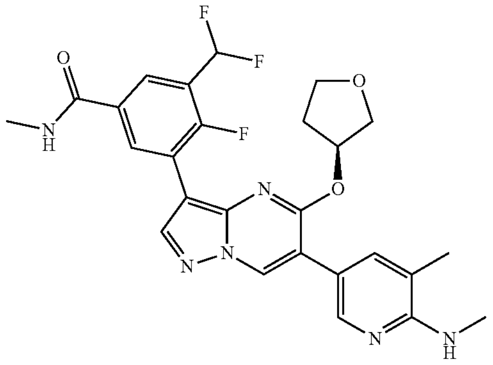

This compound was synthesized by a procedure analogous to that described for Example 23, utilizing N,3-dimethyl-5-(4,4,5,5-tetramethyl-1,3,2-dioxaborolan-2-yl)pyridin-2-amine instead of 3-(4,4,5,5-tetramethyl-1,3,2-dioxaborolan-2-yl)pyridine in Step 2. The product was isolated as the TFA salt. LCMS calculated for $C_{26}H_{26}F_3N_6O_3$ $(M+H)^+$: m/z=527.2; found: 527.3.

Example 25. (S)-3-(Difluoromethyl)-4-fluoro-5-(6-(6-(2-hydroxypropan-2-yl)pyridin-3-yl)-5-((tetrahydrofuran-3-yl)oxy)pyrazolo[1,5-a]pyrimidin-3-yl)-N-methylbenzamide

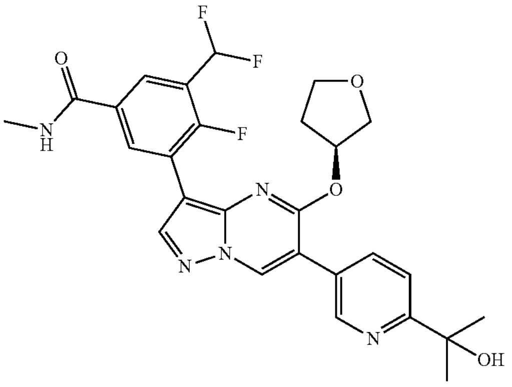 [SMILES: CNC(=O)c1cc(-c2cnn3cc(-c4ccc(C(C)(C)O)nc4)c(O[C@H]4CCOC4)nc23)c(F)c(C(F)F)c1]

This compound was synthesized by a procedure analogous to that described for Example 23, utilizing 2-(5-(4,4,5,5-tetramethyl-1,3,2-dioxaborolan-2-yl)pyridin-2-yl)propan-2-ol instead of 3-(4,4,5,5-tetramethyl-1,3,2-dioxaborolan-2-yl)pyridine in Step 2. The product was isolated as the TFA salt. LCMS calculated for $C_{27}H_{27}F_3N_5O_4$ $(M+H)^+$: m/z=542.2; found: 542.2.

Example 26. (S)-3-(Difluoromethyl)-4-fluoro-N-methyl-5-(6-(1-(1-methylazetidin-3-yl)-1H-pyrazol-4-yl)-5-((tetrahydrofuran-3-yl)oxy)pyrazolo[1,5-a]pyrimidin-3-yl)benzamide

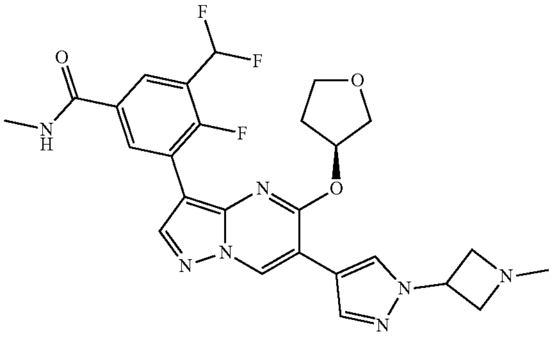

This compound was synthesized by a procedure analogous to that described for Example 17, utilizing (S)-3-(6-chloro-5-((tetrahydrofuran-3-yl)oxy)pyrazolo[1,5-a]pyrimidin-3-yl)-5-(difluoromethyl)-4-fluoro-N-methylbenzamide instead of (S)-3-(6-chloro-5-((tetrahydrofuran-3-yl)oxy)pyrazolo[1,5-a]pyrimidin-3-yl)-4,5-difluoro-N-methylbenzamide in Step 1. The product was isolated as the TFA salt. LCMS calculated for $C_{26}H_{27}F_3N_7O_3$ $(M+H)^+$: m/z=542.2; found: 542.3.

Example 27. (S)-3-Cyano-N-methyl-5-(6-(pyridin-3-yl)-5-((tetrahydrofuran-3-yl)oxy)pyrazolo[1,5-a]pyrimidin-3-yl)benzamide

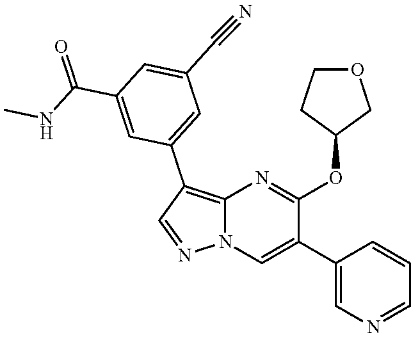 [SMILES: CNC(=O)c1cc(C#N)cc(-c2cnn3cc(-c4cccnc4)c(O[C@H]4CCOC4)nc23)c1]

Step 1. (S)-3-(6-Chloro-5-((tetrahydrofuran-3-yl)oxy)pyrazolo[1,5-a]pyrimidin-3-yl)-5-cyano-N-methylbenzamide

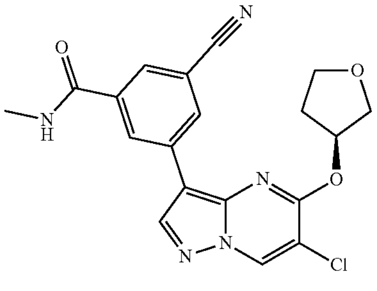 [SMILES: CNC(=O)c1cc(C#N)cc(-c2cnn3cc(Cl)c(O[C@H]4CCOC4)nc23)c1]

A mixture of (S)-3-bromo-6-chloro-5-((tetrahydrofuran-3-yl)oxy)pyrazolo[1,5-a]pyrimidine (50 mg, 0.16 mmol, Example 11, Step 2), 3-cyano-N-methyl-5-(4,4,5,5-tetramethyl-1,3,2-dioxaborolan-2-yl)benzamide (64 mg, 0.31 mmol, Intermediate D), $PdCl_2(dppf)-CH_2Cl_2$ adduct (6.4 mg, 7.9 μmol), and sodium carbonate (50 mg, 0.47 mmol) in dioxane (2 ml) and water (0.5 ml) was sparged with $N_2$ and heated to 100° C. for 2 h. The reaction mixture was diluted with EtOAc and filtered through a siliaprep thiol cartridge. The filtrate was concentrated and the residue was used without purification. LCMS calculated for $C_{19}H_{17}ClN_5O_3$ $(M+H)^+$: m/z=398.1; found: 398.1.

Step 2. (S)-3-Cyano-N-methyl-5-(6-(pyridin-3-yl)-5-((tetrahydrofuran-3-yl)oxy)pyrazolo[1,5-a]pyrimidin-3-yl)benzamide A mixture of (S)-3-(6-chloro-5-((tetrahydrofuran-3-yl)oxy)pyrazolo[1,5-a]pyrimidin-3-yl)-5-cyano-N-methylbenzamide (15 mg, 0.038 mmol), 3-(4,4,5,5-tetramethyl-1,3,2-dioxaborolan-2-yl)pyridine (23.2 mg, 0.11 mmol), XPhos Pd G2 (1.5 mg, 1.9 μmol), and cesium 20 carbonate (37 mg, 0.11 mmol) in DMF (1.5 ml) and Water (0.5 ml) was sparged with $N_2$ and heated to 100° C. for 2 h. The reaction mixture was diluted with MeOH and filtered through a thiol siliaprep cartridge. The product was purified by prep HPLC (pH 2). The product was isolated as the TFA salt. LCMS calculated for $C_{24}H_{21}N_6O_3$ $(M+H)^+$: m/z=441.2; found: 441.2.

Examples 28-30

The compounds in the following table were synthesized according to the procedure described for Example 27, utilizing the appropriate commercially available boronate or boronic acid in Step 2. The products were isolated as TFA salts.

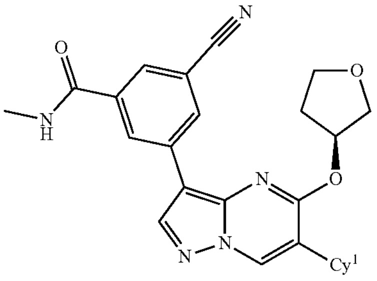

| Example No. | $Cy^1$ | LCMS |
|---|---|---|
| 28. (S)-3-Cyano-N-methyl-5-(6-(6-methylpyridin-3-yl)-5-((tetrahydrofuran-3-yl)oxy)pyrazolo[1,5-a]pyrimidin-3-yl)benzamide | 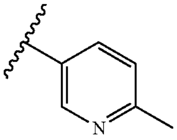 [SMILES: *c1ccc(C)nc1] | LCMS calculated for $C_{25}H_{22}N_6O_3$ $(M + H)^+$: m/z = 455.2; found: 455.2. |
| 29. (S)-3-Cyano-N-methyl-5-(6-(5-methylpyridin-3-yl)-5-((tetrahydrofuran-3-yl)oxy)pyrazolo[1,5-a]pyrimidin-3-yl)benzamide | 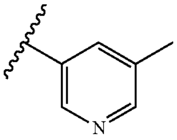 [SMILES: *c1cncc(C)c1] | LCMS calculated for $C_{25}H_{22}N_6O_3$ $(M + H)^+$: m/z = 455.2; found: 455.3. |
| 30. (S)-3-Cyano-N-methyl-5-(6-(pyridin-4-yl)-5-((tetrahydrofuran-3-yl)oxy)pyrazolo[1,5-a]pyrimidin-3-yl)benzamide | 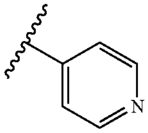 [SMILES: *c1ccncc1] | LCMS calculated for $C_{24}H_{21}N_6O_3$ $(M + H)^+$: m/z = 441.2; found: 441.2. |

Example 31. (S)-4-Fluoro-3-hydroxy-N-methyl-5-(6-(1-methyl-1H-pyrazol-4-yl)-5-((tetrahydrofuran-3-yl)oxy)pyrazolo[1,5-a]pyrimidin-3-yl)benzamide

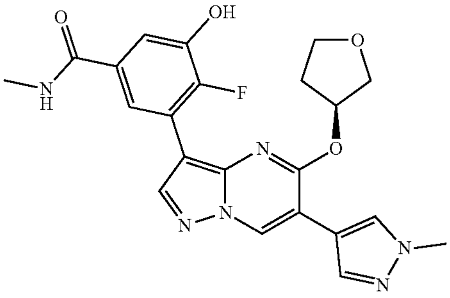

Step 1. 3-Bromo-4-fluoro-5-iodobenzoic Acid

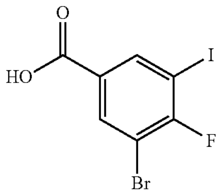 [SMILES: O=C(O)c1cc(Br)c(F)c(I)c1]

To a mixture of 3-bromo-4-fluorobenzoic acid (500 mg, 2.28 mmol) in sulfuric acid (5 mL, 94 mmol) at 0° C. was added NIS (514 mg, 2.28 mmol) and the reaction mixture was allowed to warm to room temperature. After stirring for 1 h, a thick precipitate formed and stirring became very difficult. At this point, the reaction was quenched with ice water and the precipitate was filtered. The solid was washed with water, saturated $NaS_2O_3$, and air dried. LCMS indicated one peak but the product did not ionize. The LCMS was compared to an LCMS of the starting material and the change in retention time was consistent with the desired product.

Step 2. 3-Bromo-4-fluoro-5-hydroxybenzoic Acid

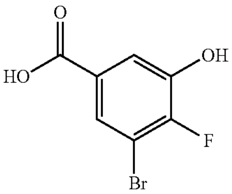 [SMILES: O=C(O)c1cc(O)c(F)c(Br)c1]

A mixture of 3-bromo-4-fluoro-5-iodobenzoic acid (739 mg, 2.14 mmol), copper(I) oxide (36.8 mg, 0.26 mmol), and sodium hydroxide (428 mg, 10.7 mmol) in water (10 ml) was heated to 100° C. overnight. LCMS indicated several products, all of which did not ionize and could not be identified by mass. After cooling to room temperature, the reaction mixture was adjusted to pH 1 with 6M HCl and the aqueous solution was extracted with EtOAc three times. The organic phase was washed with brine, dried over $MgSO_4$, filtered, and concentrated. The residue was used without further purification.

Step 3. 3-Bromo-4-fluoro-5-hydroxy-N-methylbenzamide

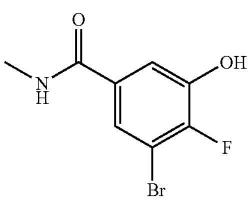

To a solution of 3-bromo-4-fluoro-5-hydroxybenzoic acid (500 mg, 2.13 mmol) and HATU (809 mg, 2.13 mmol) in DMF (10 ml) was added DIPEA (0.82 mL, 4.68 mmol), and the reaction mixture was stirred at room temperature for 5 min. Methylamine (2M/THF) (1.60 mL, 3.19 mmol) was added and stirring was continued for an additional 30 min. The reaction mixture was partitioned between water and EtOAc, and the phases were separated. The aqueous phase was extracted with EtOAc and the combined organic phases were washed with brine, dried over $MgSO_4$, filtered, and concentrated. The product was purified by flash chromatography (0-100% EtOAc/hexanes) followed by 0-20% MeOH/DCM to afford the title compound (164 mg, 31%, yield over 2 steps). LCMS calculated for $C_8H_8BrFNO_2(M+H)^+$: m/z=248.0; found: 248.0.

Step 4. 3-Bromo-4-fluoro-5-((4-methoxybenzyl)oxy)-N-methylbenzamide

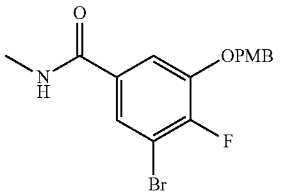

To a solution of 3-bromo-4-fluoro-5-hydroxy-N-methylbenzamide (40 mg, 0.16 mmol) in DMF (1 ml) was added potassium carbonate (33 mg, 0.24 mmol) and 1-(chloromethyl)-4-methoxybenzene (22 µl, 0.16 mmol), and the reaction mixture was heated to reflux for 2 h. The reaction mixture was partitioned between water and EtOAc, and the phases were separated. The aqueous phase was extracted with EtOAc and the combined organic phases were washed with brine, dried over $MgSO_4$, filtered, and concentrated. The product was purified by flash chromatography (0-70% EtOAc/hexanes) to afford the title compound (41 mg, 69%). LCMS calculated for $C_{16}H_{16}BrFNO_3$ $(M+H)^+$: m/z=368.0; found: 368.0.

Step 5. 4-Fluoro-3-((4-methoxybenzyl)oxy)-N-methyl-5-(4,4,5,5-tetramethyl-1,3,2-dioxaborolan-2-yl)benzamide

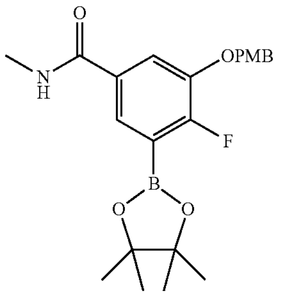

3-Bromo-4-fluoro-5-((4-methoxybenzyl)oxy)-N-methylbenzamide (41 mg, 0.11 mmol) was combined with bis(pinacolato)diboron (71 mg, 0.28 mmol), dichloro[1,1'-bis(diphenylphosphino)ferrocene]palladium (II) dichloromethane adduct (4.5 mg, 5.5 µmol) and potassium acetate (33 mg, 0.33 mmol) in dioxane (1.5 ml) and the mixture was sparged with $N_2$. The reaction was heated to 100° C. for 4 h. The reaction mixture was diluted with EtOAc, filtered through a siliaprep thiol cartridge, and concentrated. The product was used without further purification. The following data is reported for the corresponding boronic acid, which was the only observable species by LCMS. LCMS calculated for $C_{16}H_{18}BFNO_5$ $(M+H)^+$: m/z=334.1; found: 334.2.

Step 6. (S)-3-(6-Chloro-5-((tetrahydrofuran-3-yl)oxy)pyrazolo[1,5-a]pyrimidin-3-yl)-4-fluoro-5-((4-methoxybenzyl)oxy)-N-methylbenzamide

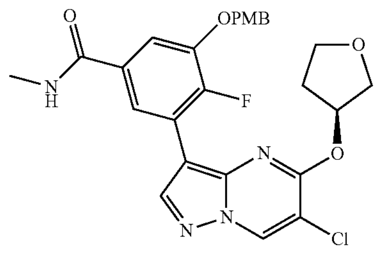

A mixture of (S)-3-bromo-6-chloro-5-((tetrahydrofuran-3-yl)oxy)pyrazolo[1,5-a]pyrimidine (30 mg, 0.094 mmol), (2-fluoro-3-((4-methoxybenzyl)oxy)-5-(methylcarbamoyl)phenyl)boronic acid (38 mg, 0.11 mmol), $PdCl_2$(dppf)-$CH_2Cl_2$ adduct (3.9 mg, 4.7 μmol), and sodium carbonate (30 mg, 0.29 mmol) in dioxane (1 ml) and water (0.5 ml) was sparged with $N_2$ and heated to 100° C. for 2 h. The reaction mixture was diluted with EtOAc and filtered through a siliaprep thiol cartridge. The filtrate was concentrated and the residue was used without further purification. LCMS calculated for $C_{26}H_{25}ClFN_4O_5$ $(M+H)^+$: m/z=527.1; found: 527.1.

Step 7. (S)-4-Fluoro-3-hydroxy-N-methyl-5-(6-(1-methyl-1H-pyrazol-4-yl)-5-((tetrahydrofuran-3-yl)oxy)pyrazolo[1,5-a]pyrimidin-3-yl)benzamide A mixture of (S)-3-(6-chloro-5-((tetrahydrofuran-3-yl)oxy)pyrazolo[1,5-a]pyrimidin-3-yl)-4-fluoro-5-hydroxy-N-methylbenzamide (10 mg, 0.025 mmol), 1-methyl-4-(4,4,5,5-tetramethyl-1,3,2-dioxaborolan-2-yl)-1H-pyrazole (7.7 mg, 0.037 mmol), XPhos Pd G2 (1.0 mg, 1.2 μmol), and cesium carbonate (24 mg, 0.07 mmol) in dioxane (1 ml) and water (0.5 ml) was sparged with $N_2$ and heated to 100° C. for 2 h. The reaction mixture was diluted with MeOH and filtered through a thiol siliaprep cartridge and the filtrate was concentrated.

The residue was dissolved in DCM (3 mL) and treated with TFA (0.5 mL). After stirring for 30 min at room temperature, the reaction mixture was concentrated. The residue was dissolved in MeOH and purified by prep HPLC (pH 2). The product was isolated as the TFA salt. LCMS calculated for $C_{22}H_{22}FN_6O_4$ $(M+H)^+$: m/z=453.2; found: 453.2.

Example 32. (S)-3-(6-(1-Cyclobutyl-1H-pyrazol-4-yl)-5-((tetrahydrofuran-3-yl)oxy)pyrazolo[1,5-a]pyrimidin-3-yl)-N-methyl-5-(methylsulfonyl)benzamide

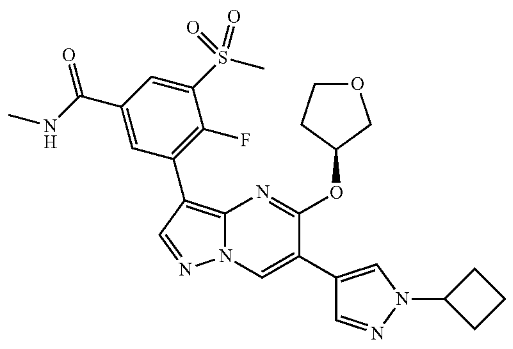 [SMILES: CNC(=O)c1cc(-c2cnn3cc(-c4cnn(C5CCC5)c4)c(O[C@H]4CCOC4)nc23)c(F)c(S(C)(=O)=O)c1]

Step 1. 3-Bromo-N-methyl-5-(methylsulfonyl)benzamide

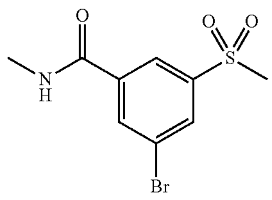

To a solution of 3-bromo-5-(methylsulfonyl)benzoic acid (200 mg, 0.72 mmol) and HATU (327 mg, 0.86 mmol) in DMF (5 ml) was added DIPEA (0.19 mL, 1.08 mmol), and the reaction mixture was stirred at room temperature for 5 min. Methylamine (2M/THF) (0.54 mL, 1.08 mmol) was added and the reaction mixture was stirred for an additional 30 min. The reaction mixture was partitioned between water and EtOAc, and the phases were separated. The aqueous phase was extracted with EtOAc and the combined organic phases were washed with brine, dried over $MgSO_4$, filtered, and concentrated. The product was purified by flash chromatography (0-100% EtOAc/hexanes). LCMS calculated for $C_9H_{11}BrNO_3S$ $(M+H)^+$: m/z=292.0; found: 291.9.

Step 2. N-Methyl-3-(methylsulfonyl)-5-(4,4,5,5-tetramethyl-1,3,2-dioxaborolan-2-yl)benzamide

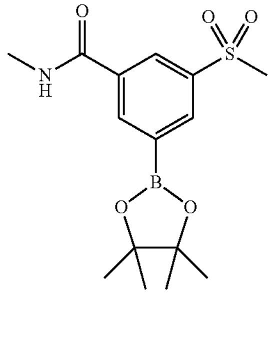

3-Bromo-N-methyl-5-(methylsulfonyl)benzamide (209 mg, 0.72 mmol) was combined with bis(pinacolato)diboron (273 mg, 1.07 mmol), dichloro[1,1'-bis(diphenylphosphino)-ferrocene]palladium (II) dichloromethane adduct (29.2 mg, 0.036 mmol) and potassium acetate (211 mg, 2.15 mmol) in dioxane (5 ml) and the mixture was sparged with $N_2$. The reaction was heated to 100° C. for 3 h. The reaction mixture was diluted with EtOAc, filtered, and concentrated. The product was purified by flash chromatography (0-100% EtOAc/hexanes) to afford the title compound (236 mg, 97%). The following data is reported for the corresponding boronic acid, which was the only observable species by LCMS. LCMS calculated for $C_9H_{13}BNO_5S$ $(M+H)^+$: m/z=258.1; found: 258.1.

Step 3. (S)-3-(6-Chloro-5-((tetrahydrofuran-3-yl)oxy)pyrazolo[1,5-a]pyrimidin-3-yl)-N-methyl-5-(methylsulfonyl)benzamide

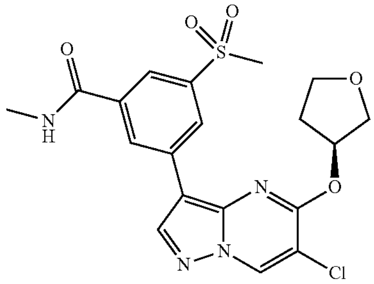 [SMILES: CNC(=O)c1cc(-c2cnn3cc(Cl)c(O[C@H]4CCOC4)nc23)cc(S(C)(=O)=O)c1]

A mixture of (S)-3-bromo-6-chloro-5-((tetrahydrofuran-3-yl)oxy)pyrazolo[1,5-a]pyrimidine (37 mg, 0.12 mmol), N-methyl-3-(methylsulfonyl)-5-(4,4,5,5-tetramethyl-1,3,2-dioxaborolan-2-yl)benzamide (47.3 mg, 0.14 mmol), $PdCl_2$(dppf)-$CH_2Cl_2$ adduct (4.7 mg, 5.8 μmol), and sodium carbonate (37 mg, 0.35 mmol) in dioxane (1 ml) and water (0.5 ml) was sparged with $N_2$ and heated to 100° C. for 2 h. The reaction mixture was diluted with EtOAc and filtered through a siliaprep thiol cartridge. The filtrate was concentrated and the residue was used without further purification. LCMS calculated for $C_{19}H_{20}ClN_4O_5S$ $(M+H)^+$: m/z=451.1; found: 451.1.

Step 4. (S)-3-(6-(1-Cyclobutyl-1H-pyrazol-4-yl)-5-((tetrahydrofuran-3-yl)oxy)pyrazolo[1,5-a]pyrimidin-3-yl)-N-methyl-5-(methylsulfonyl)benzamide A mixture of (S)-3-(6-chloro-5-((tetrahydrofuran-3-yl)oxy)pyrazolo[1,5-a]pyrimidin-3-yl)-N-methyl-5-(methylsulfonyl)benzamide (10 mg, 0.022 mmol), 1-cyclobutyl-4-(4,4,5,5-tetramethyl-1,3,2-dioxaborolan-2-yl)-1H-pyrazole (11 mg, 0.04 mmol), XPhos Pd G2 (0.9 mg, 1.1 μmol), and cesium carbonate (22 mg, 0.07 mmol) in DMF (1.5 ml) and water (0.5 ml) was sparged with $N_2$ and heated to 100° C. for 2 h. The reaction mixture was diluted with MeOH and filtered through a thiol siliaprep cartridge. The product was purified by prep HPLC (pH 2). The product was isolated as the TFA salt. LCMS calculated for $C_{26}H_{29}N_6O_5S$ $(M+H)^+$: m/z=537.2; found: 537.2.

Example 33. (S)-3-(1H-Indazol-4-yl)-6-(1-methyl-1H-pyrazol-4-yl)-5-((tetrahydrofuran-3-yl)oxy)pyrazolo[1,5-a]pyrimidine

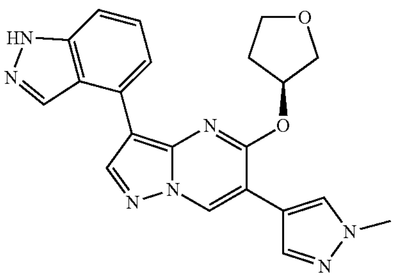 [SMILES: Cn1cc(-c2cn3ncc(-c4cccc5[nH]ncc45)c3nc2O[C@H]2CCOC2)cn1]

Step 1. (S)-6-Chloro-3-(1H-indazol-4-yl)-5-((tetrahydrofuran-3-yl)oxy)pyrazolo[1,5-a]pyrimidine

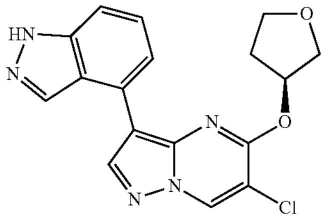 [SMILES: Clc1cn2ncc(-c3cccc4[nH]ncc34)c2nc1O[C@H]1CCOC1]

A mixture of (S)-3-bromo-6-chloro-5-((tetrahydrofuran-3-yl)oxy)pyrazolo[1,5-a]pyrimidine (10 mg, 0.03 mmol, Example 11, Step 2), (1-(tert-butoxycarbonyl)-1H-indazol-4-yl)boronic acid (9.9 mg, 0.04 mmol), $PdCl_2$(dppf)-$CH_2Cl_2$ adduct (1.3 mg, 1.6 μmol), and potassium phosphate, dibasic (16.4 mg, 0.10 mmol) in dioxane (1 ml) and water (0.5 ml) was sparged with $N_2$ and heated to 100° C. for 2 h. The reaction mixture was diluted with EtOAc and filtered through a siliaprep thiol cartridge. The filtrate was concentrated and the residue was used without purification. LCMS calculated for $C_{17}H_{15}ClN_5O_2$$(M+H)^+$: m/z=356.1; found: 356.1.

Step 2. (S)-3-(1H-Indazol-4-yl)-6-(1-methyl-1H-pyrazol-4-yl)-5-((tetrahydrofuran-3-yl)oxy)pyrazolo[1,5-a]pyrimidine A mixture of (S)-6-chloro-3-(1H-indazol-4-yl)-5-((tetrahydrofuran-3-yl)oxy)pyrazolo[1,5-a]pyrimidine (10 mg, 0.03 mmol), 1-methyl-4-(4,4,5,5-tetramethyl-1,3,2-dioxaborolan-2-yl)-1H-pyrazole (8.8 mg, 0.04 mmol), XPhos Pd G2 (1.1 mg, 1.4 μmol), and cesium carbonate (27.5 mg, 0.08 mmol) in dioxane (3 ml) and water (0.5 ml) was sparged with $N_2$ and heated to 100° C. for 2 h. The reaction was diluted with MeOH and filtered through a thiol siliaprep cartridge. The product was purified by prep HPLC (pH 2). LCMS calculated for $C_{21}H_{20}N_7O_2$ $(M+H)^+$: m/z=402.2; found: 402.2.

Example 34. (S)-4-Fluoro-N,3-dimethyl-5-(6-(1-(1-methylpiperidin-4-yl)-1H-pyrazol-4-yl)-5-((tetrahydrofuran-3-yl)amino)pyrazolo[1,5-a]pyrimidin-3-yl)benzamide

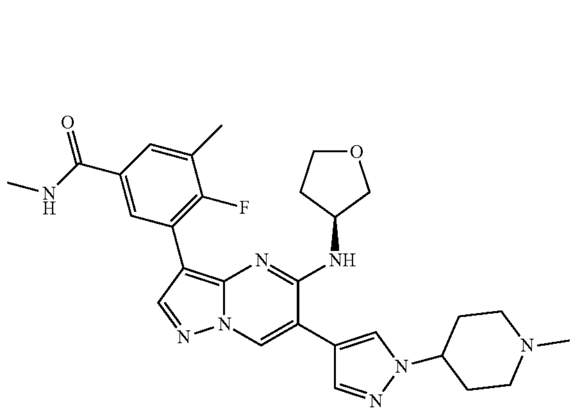

Step 1. (S)-3-Bromo-6-chloro-N-(tetrahydrofuran-3-yl)pyrazolo[1,5-a]pyrimidin-5-amine

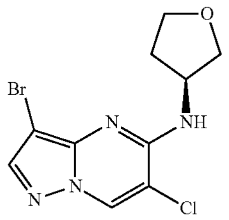 [SMILES: Clc1cn2ncc(Br)c2nc1N[C@H]1CCOC1]

A mixture of 3-bromo-5,6-dichloropyrazolo[1,5-a]pyrimidine (500 mg, 1.87 mmol, Example 11, Step 1), (S)-tetrahydrofuran-3-amine (485 μl, 5.62 mmol), and cesium carbonate (732 mg, 2.25 mmol) in THE (6 ml) was heated to 80° C. for 2 h. The reaction mixture was cooled to room temperature, diluted with EtOAc, and filtered. The filtrate was concentrated in vacuo and the residue was purified by flash chromatography (0-50% EtOAc/hexanes) to afford the title compound (414 mg, 70%) as a light yellow solid. LCMS calculated for $C_{10}H_{11}BrClN_4O$ $(M+H)^+$: m/z=317.0; found: 316.8.

Step 2. (S)-3-(6-Chloro-5-((tetrahydrofuran-3-yl)amino)pyrazolo[1,5-a]pyrimidin-3-yl)-4-fluoro-N,5-dimethylbenzamide

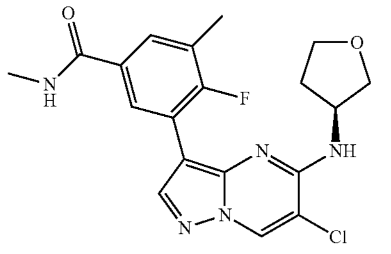 [SMILES: CNC(=O)c1cc(C)c(F)c(-c2cnn3cc(Cl)c(N[C@H]4CCOC4)nc23)c1]

A mixture of (S)-3-bromo-6-chloro-N-(tetrahydrofuran-3-yl)pyrazolo[1,5-a]pyrimidin-5-amine (97.5 mg, 0.31 mmol, Example 34, Step 1), 4-fluoro-N,3-dimethyl-5-(4,4,5,5-tetramethyl-1,3,2-dioxaborolan-2-yl)benzamide (135 mg, 0.46 mmol, Intermediate B), bis(di-tert-butyl(4-dimethylaminophenyl)phosphine)dichloropalladium(II) (21.7 mg, 0.03 mmol), and cesium fluoride (140 mg, 0.92 mmol) in n-BuOH (2.5 ml) and water (0.5 ml) was sparged with $N_2$ and heated to 70° C. for 1 h. The reaction mixture was cooled to room temperature and dry loaded onto silica gel. The product was purified by flash chromatography (0-100% EtOAc/hexanes followed by 0-15% MeOH/DCM) to afford the title compound (86 mg, 69%). LCMS calculated for $C_{19}H_{20}ClFN_5O_2$ $(M+H)^+$: m/z=404.1; found: 404.2.

Step 3. tert-Butyl(S)-4-(4-(3-(2-fluoro-3-methyl-5-(methylcarbamoyl)phenyl)-5-((tetrahydrofuran-3-yl)amino)pyrazolo[1,5-a]pyrimidin-6-yl)-1H-pyrazol-1-yl)piperidine-1-carboxylate

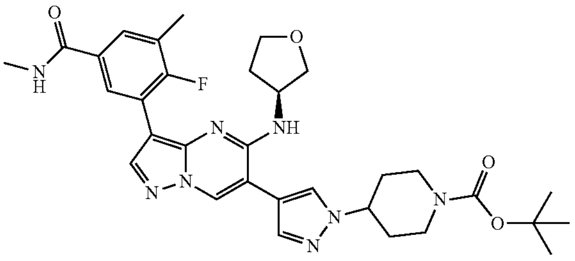 [SMILES: CNC(=O)c1cc(C)c(F)c(-c2cnn3cc(-c4cnn(C5CCN(C(=O)OC(C)(C)C)CC5)c4)c(N[C@H]4CCOC4)nc23)c1]

A mixture of (S)-3-(6-chloro-5-((tetrahydrofuran-3-yl)amino)pyrazolo[1,5-a]pyrimidin-3-yl)-4-fluoro-N,5-dimethylbenzamide (10 mg, 0.03 mmol), tert-butyl 4-(4-(4,4,5,5-tetramethyl-1,3,2-dioxaborolan-2-yl)-1H-pyrazol-1-yl)piperidine-1-carboxylate (14 mg, 0.04 mmol), XPhos Pd G2 (0.9 mg, 1.3 μmol), and cesium carbonate (24 mg, 0.07 mmol) in dioxane (1 ml) and water (0.5 ml) was sparged with $N_2$ and heated to 100° C. for 2 h. The reaction mixture was diluted with MeOH and filtered through a thiol siliaprep cartridge. The filtrate was concentrated and the product was used without purification. LCMS calculated for $C_{32}H_{40}FN_8O_4$ $(M+H)^+$: m/z=619.3; found: 619.4.

Step 4. (S)-4-Fluoro-N,3-dimethyl-5-(6-(1-(1-methylpiperidin-4-yl)-1H-pyrazol-4-yl)-5-((tetrahydrofuran-3-yl)amino)pyrazolo[1,5-a]pyrimidin-3-yl)benzamide To a solution of tert-butyl (S)-4-(4-(3-(2-fluoro-3-methyl-5-(methylcarbamoyl)phenyl)-5-((tetrahydrofuran-3-yl)amino)pyrazolo[1,5-a]pyrimidin-6-yl)-1H-pyrazol-1-yl)piperidine-1-carboxylate (14 mg, 0.02 mmol) in DCM (1.5 ml) was added HCl (4M/dioxane, 2 mL, 8.0 mmol) and the reaction mixture was stirred at room temperature for 30 min. The reaction mixture was triturated with EtOAc, redissolved in MeOH (2 ml), and treated sequentially with formaldehyde (84 μL, 1.1 mmol) and sodium cyanoborohydride (7.1 mg, 0.1 mmol). After stirring for 2 h, the reaction mixture was diluted with MeOH and purified by prep HPLC. LCMS calculated for $C_{28}H_{34}FN_8O_2$ $(M+H)^+$: m/z=533.3; found: 533.3. $^1H$ NMR (500 MHz, DMSO-$d_6$) δ 9.58 (s, 1H), 8.99 (dd, J=7.2, 2.3 Hz, 1H), 8.68 (s, 1H), 8.35-8.30 (m, 1H), 8.29 (d, J=3.8 Hz, 1H), 8.18 (s, 1H), 7.87 (s, 1H), 7.53 (dd, J=6.7, 2.3 Hz, 1H), 6.66 (d, J=5.6 Hz, 1H), 4.73-4.65 (m, 1H), 4.52 (tt, J=11.8, 4.1 Hz, 1H), 4.12 (dd, J=9.1, 6.5 Hz, 1H), 3.87 (q, J=7.6 Hz, 1H), 3.79-3.71 (m, 2H), 3.61 (d, J=12.3 Hz, 2H), 3.25-3.14 (m, 2H), 2.87-2.83 (m, 2H), 2.78 (d, J=4.5 Hz, 2H), 2.43-2.35 (m, 2H), 2.34 (s, 3H), 2.28-2.12 (m, 2H), 2.07-1.99 (m, 1H).

Example 35. (S)-4-Fluoro-N,3-dimethyl-5-(6-(1-(1-methylazetidin-3-yl)-1H-pyrazol-4-yl)-5-((tetrahydrofuran-3-yl)amino)pyrazolo[1,5-a]pyrimidin-3-yl)benzamide

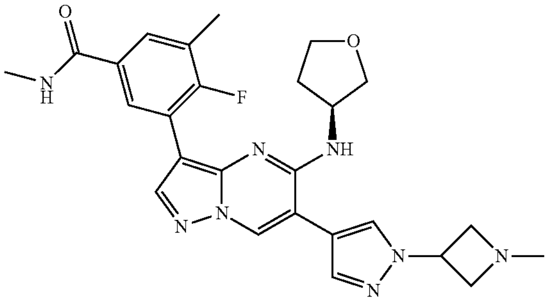

This compound was prepared by a procedure identical to that described for (S)-4-fluoro-N,3-dimethyl-5-(6-(1-(1-methylpiperidin-4-yl)-1H-pyrazol-4-yl)-5-((tetrahydrofuran-3-yl)amino)pyrazolo[1,5-a]pyrimidin-3-yl)benzamide (Example 33), utilizing tert-butyl 3-(4-(4,4,5,5-tetramethyl-1,3,2-dioxaborolan-2-yl)-1H-pyrazol-1-yl)azetidine-1-carboxylate instead of tert-butyl 4-(4-(4,4,5,5-tetramethyl-1,3,2-dioxaborolan-2-yl)-1H-pyrazol-1-yl)piperidine-1-carboxylate in Step 3. LCMS calculated for $C_{26}H_{30}FN_8O_2$ $(M+H)^+$: m/z=505.2; found: 505.3.

Example 36. (S)-4-Fluoro-3-(6-(1-(2-hydroxyethyl)-1H-pyrazol-4-yl)-5-((tetrahydrofuran-3-yl)amino)pyrazolo[1,5-a]pyrimidin-3-yl)-N,5-dimethylbenzamide

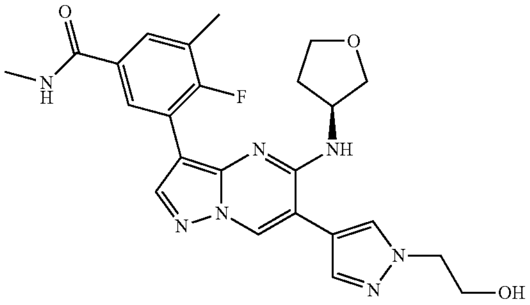 [SMILES: CNC(=O)c1cc(C)c(F)c(-c2cnn3cc(-c4cnn(CCO)c4)c(N[C@H]4CCOC4)nc23)c1]

A mixture of(S)-3-(6-chloro-5-((tetrahydrofuran-3-yl)amino)pyrazolo[1,5-a]pyrimidin-3-yl)-4-fluoro-N,5-dimethylbenzamide (10 mg, 0.03 mmol, Example 34, Step 2), 2-(4-(4,4,5,5-tetramethyl-1,3,2-dioxaborolan-2-yl)-1H-pyrazol-1-yl)ethan-1-ol (8.8 mg, 0.04 mmol), XPhos Pd G2 (1.0 mg, 1.2 μmol), and cesium carbonate (24 mg, 0.07 mmol) in dioxane (1 ml) and water (0.5 ml) was sparged with $N_2$ and heated to 100° C. for 2 h. The reaction mixture was diluted with MeOH and filtered through a thiol siliaprep cartridge. The product was purified by prep HPLC (pH 2). LCMS calculated for $C_{24}H_{27}FN_7O_3$ $(M+H)^+$: m/z=480.2; found: 480.2.

Examples 37-44

The compounds in the following table were prepared by a procedure analogous to that described for Example 36, utilizing the appropriate commercially available boronate.

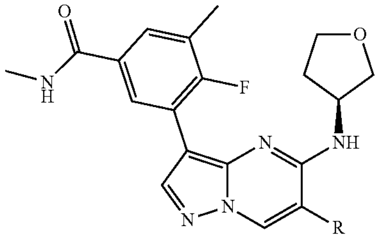

| Example No. | R | LCMS |
|---|---|---|
| 37. (S)-3-(6-(1-(2-Cyanoethyl)-1H-pyrazol-4-yl)-5-((tetrahydrofuran-3-yl)amino)pyrazolo[1,5-a]pyrimidin-3-yl)-4-fluoro-N,5-dimethylbenzamide | 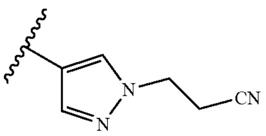 [SMILES: *c1cnn(CCC#N)c1] | Calculated for $C_{25}H_{26}FN_8O_2$ $(M+H)^+$: m/z = 489.2; found: 489.2. |

-continued

| Example No. | R | LCMS |
|---|---|---|
| 38. 3-(6-(1-(1,1-Dioxidotetrahydrothiophen-3-yl)-1H-pyrazol-4-yl)-5-(((S)-tetrahydrofuran-3-yl)amino)pyrazolo[1,5-a]pyrimidin-3-yl)-4-fluoro-N,5-dimethylbenzamide | 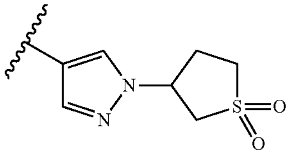 [SMILES: *c1cnn(C2CCS(=O)(=O)C2)c1] | Calculated for $C_{26}H_{29}FN_7O_4$ $(M + H)^+$: m/z = 554.2; found: 554.3. |
| 39. (S)-3-(6-(1-(2-(Dimethylamino)-2-oxoethyl)-1H-pyrazol-4-yl)-5-((tetrahydrofuran-3-yl)amino)pyrazolo[1,5-a]pyrimidin-3-yl)-4-fluoro-N,5-dimethylbenzamide | 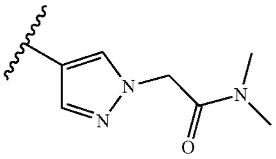 [SMILES: *c1cnn(CC(=O)N(C)C)c1] | Calculated for $C_{26}H_{30}FN_8O_3$ $(M + H)^+$: m/z = 521.2; found: 521.3. |
| 40. (S)-4-Fluoro-3-(6-(1-(2-hydroxy-2-methylpropyl)-1H-pyrazol-4-yl)-5-((tetrahydrofuran-3-yl)amino)pyrazolo[1,5-a]pyrimidin-3-yl)-N,5-dimethylbenzamide | 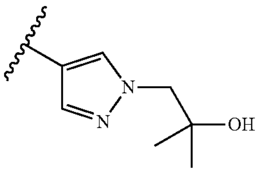 [SMILES: *c1cnn(CC(C)(C)O)c1] | Calculated for $C_{26}H_{31}FN_7O_3$ $(M + H)^+$: m/z = 508.2; found: 508.2. |
| 41. 4-Fluoro-N,3-dimethyl-5-(6-(1-(tetrahydrofuran-3-yl)-1H-pyrazol-4-yl)-5-(((S)-tetrahydrofuran-3-yl)amino)pyrazolo[1,5-a]pyrimidin-3-yl)benzamide | 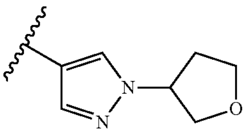 [SMILES: *c1cnn(C2CCOC2)c1] | Calculated for $C_{26}H_{29}FN_7O_3$ $(M + H)^+$: m/z = 506.2; found: 506.5. |
| 42. (S)-4-Fluoro-N,3-dimethyl-5-(6-(2-methyloxazol-5-yl)-5-((tetrahydrofuran-3-yl)amino)pyrazolo[1,5-a]pyrimidin-3-yl)benzamide | 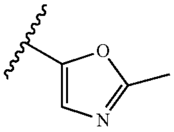 [SMILES: *c1cnc(C)o1] | Calculated for $C_{23}H_{24}FN_6O_3$ (M + H):$^+$: m/z = 451.2; found: 451.1. |
| 43. (S)-3-(6-(1-Ethyl-1H-pyrazol-3-yl)-5-((tetrahydrofuran-3-yl)amino)pyrazolo[1,5-a]pyrimidin-3-yl)-4-fluoro-N,5-dimethylbenzamide | 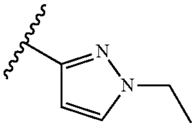 [SMILES: *c1ccn(CC)n1] | Calculated for $C_{24}H_{27}FN_7O_2$ $(M + H)^+$: m/z = 464.2; found: 464.3. |
| 44. (S)-4-Fluoro-N,3-dimethyl-5-(6-(pyridazin-4-yl)-5-((tetrahydrofuran-3-yl)amino)pyrazolo[1,5-a]pyrimidin-3-yl)benzamide | 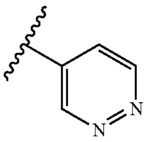 [SMILES: *c1ccnnc1] | Calculated for $C_{23}H_{23}FN_7O_2$ $(M + H)^+$: m/z = 448.2; found: 448.2. |

Example 45. (S)-3-(5-(Ethylsulfonyl)-2,3-difluorophenyl)-6-(1-methyl-1H-pyrazol-4-yl)-N-(tetrahydrofuran-3-yl)pyrazolo[1,5-a]pyrimidin-5-amine

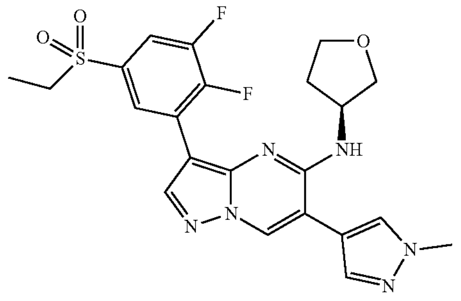 [SMILES: CCS(=O)(=O)c1cc(F)c(F)c(-c2cnn3cc(-c4cnn(C)c4)c(N[C@H]4CCOC4)nc23)c1]

Step 1. (3-Bromo-4,5-difluorophenyl)(ethyl)sulfane

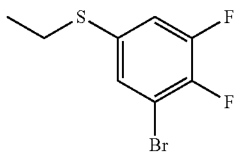

To a solution of 3-bromo-4,5-difluoroaniline (200 mg, 0.96 mmol) in MeCN (5 ml) was added 1,2-diethyldisulfane (142 μl, 1.15 mmol), followed by dropwise addition of tert-butyl nitrite (152 μl, 1.15 mmol), and the reaction mixture was stirred at 80° C. for 1 h. The reaction mixture was concentrated and the product was purified by flash chromatography (100% hexanes) to afford the title compound (131 mg, 54%). The product did not ionize on LCMS. $^1$H NMR (400 MHz, Chloroform-d) δ 7.28 (q, J=2.2 Hz, 1H), 7.11 (ddd, J=9.6, 7.3, 2.2 Hz, 1H), 2.94 (q, J=7.3 Hz, 2H), 1.34 (t, J=7.3 Hz, 3H).

Step 2. 1-Bromo-5-(ethylsulfonyl)-2,3-difluorobenzene

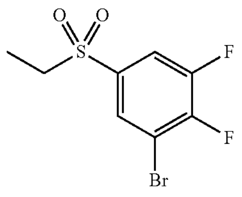

To a solution of (3-bromo-4,5-difluorophenyl)(ethyl)sulfane (130 mg, 0.51 mmol) in DCM (3 ml) was added m-CPBA (345 mg, 1.54 mmol), and the reaction mixture was stirred at room temperature for 2 h, at which point TLC indicated complete consumption of starting material. The reaction mixture was diluted with DCM, treated with saturated $Na_2S_2O_3$ and saturated $NaHCO_3$, and the biphasic mixture was vigorously stirred for 30 min. The phases were separated and the organic phase was dried over $MgSO_4$, filtered, and concentrated. The product was purified by flash chromatography (0-100% EtOAc/hexanes). LMCS: No ionization. Characteristic peaks in $^1$H NMR (400 MHz, Chloroform-d) δ 3.17 (q, J=7.5 Hz, 2H), 1.34 (t, J=7.4 Hz, 3H).

Step 3. 2-(5-(Ethylsulfonyl)-2,3-difluorophenyl)-4,4,5,5-tetramethyl-1,3,2-dioxaborolane

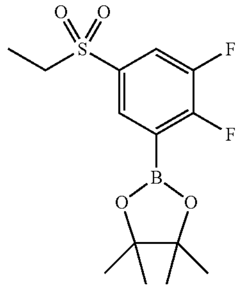 [SMILES: CCS(=O)(=O)c1cc(F)c(F)c(B2OC(C)(C)C(C)(C)O2)c1]

1-Bromo-5-(ethylsulfonyl)-2,3-difluorobenzene (120 mg, 0.421 mmol) was combined with bis(pinacolato)diboron (160 mg, 0.63 mmol), dichloro[1,1'-bis(diphenylphosphino)ferrocene]palladium(II) dichloromethane adduct (17 mg, 0.02 mmol) and potassium acetate (124 mg, 1.26 mmol) in dioxane (4 ml) and the mixture was degassed under a stream of $N_2$. The reaction was heated to 100° C. overnight. The reaction mixture was diluted with EtOAc, filtered, and concentrated. The product was purified by flash chromatography (0-100% EtOAc/hexanes). The product did not ionize on LCMS, but disappearance of SM and appearance of a single new peak indicated the reaction proceeded. The structure was confirmed by utilizing the product in the next step and successfully obtaining the desired product.

Step 4. (S)-6-Chloro-3-(5-(ethylsulfonyl)-2,3-difluorophenyl)-N-(tetrahydrofuran-3-yl)pyrazolo[1,5-a]pyrimidin-5-amine

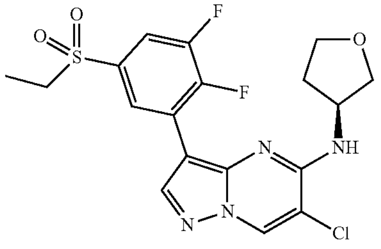 [SMILES: CCS(=O)(=O)c1cc(F)c(F)c(-c2cnn3cc(Cl)c(N[C@H]4CCOC4)nc23)c1]

A mixture of(S)-3-bromo-6-chloro-N-(tetrahydrofuran-3-yl)pyrazolo[1,5-a]pyrimidin-5-amine (54 mg, 0.17 mmol, Example 34, Step 1), 2-(5-(ethylsulfonyl)-2,3-difluorophenyl)-4,4,5,5-tetramethyl-1,3,2-dioxaborolane (85 mg, 0.26 mmol), $PdCl_2$(dppf)-$CH_2Cl_2$ adduct (14 mg, 0.02 mmol), and sodium carbonate (54 mg, 0.51 mmol) in dioxane (2 ml) and water (0.5 ml) was thoroughly deoxygenated by three freeze-pump-thaw cycles, and heated to 100° C. for 2 h. The reaction mixture was diluted with EtOAc and filtered through a siliaprep thiol cartridge. The filtrate was concentrated and the product was purified by flash chromatography (0-100% EtOAc/hexanes followed by 0-10% MeOH/DCM). Approximately 50 mg of product was obtained, that contained about 30% of desired product and about 70% of dehalogenated by-product. LCMS calculated for $C_{18}H_{18}ClF_2N_4O_3S$ (M+H)$^+$: m/z=443.1; found: 443.1.

Step 5. (S)-3-(5-(Ethylsulfonyl)-2,3-difluorophenyl)-6-(1-methyl-1H-pyrazol-4-yl)-N-(tetrahydrofuran-3-yl)pyrazolo[1,5-a]pyrimidin-5-amine A mixture of (S)-6-chloro-3-(5-(ethylsulfonyl)-2,3-difluorophenyl)-N-(tetrahydrofuran-3-yl)pyrazolo[1,5-a]pyrimidin-5-amine (8 mg, 0.02 mmol), 1-methyl-4-(4,4,5,5-tetramethyl-1,3,2-dioxaborolan-2-yl)-1H-pyrazole (11 mg, 0.05 mmol), XPhos Pd G2 (0.7 mg, 0.9 μmol), and cesium carbonate (18 mg, 0.05 mmol) in dioxane (1 ml) and water (0.5 ml) was sparged with $N_2$ and heated to 100° C. for 2 h. The reaction was diluted with MeOH and filtered through a thiol siliaprep cartridge. The product was purified by prep HPLC (pH 2). LCMS calculated for $C_{22}H_{23}F_2N_6O_3S$ (M+H)$^+$: m/z=489.1; found: 489.2.

Example 46. (S)-3-(5-(Ethylsulfonyl)-2,3-difluorophenyl)-6-(1-methyl-1H-pyrazol-4-yl)-5-((tetrahydrofuran-3-yl)oxy)pyrazolo[1,5-a]pyrimidine

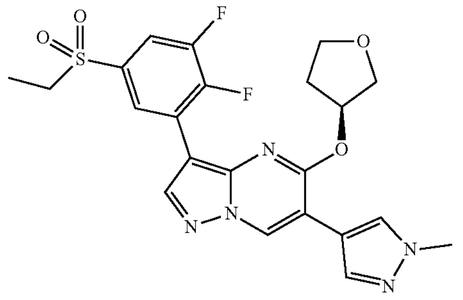 [SMILES: CCS(=O)(=O)c1cc(F)c(F)c(-c2cnn3cc(-c4cnn(C)c4)c(O[C@H]4CCOC4)nc23)c1]

This compound was synthesized by a procedure analogous to that described for Example 45, utilizing (S)-3-bromo-6-chloro-5-((tetrahydrofuran-3-yl)oxy)pyrazolo[1,5-a]pyrimidine (Example 11, Step 2) in Step 4. LCMS calculated for $C_{22}H_{22}F_2N_5O_4S$ (M+H)$^+$: m/z=490.1; found: 490.1.

Example 47. (S)-3-(Difluoromethyl)-4-fluoro-N-methyl-5-(6-(1-methyl-1H-pyrazol-4-yl)-5-((tetrahydrofuran-3-yl)amino)pyrazolo[1,5-a]pyrimidin-3-yl)benzamide

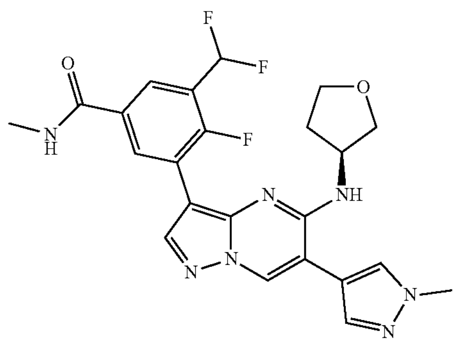

Step 1. (S)-3-(6-Chloro-5-((tetrahydrofuran-3-yl)amino)pyrazolo[1,5-a]pyrimidin-3-yl)-5-(difluoromethyl)-4-fluoro-N-methylbenzamide

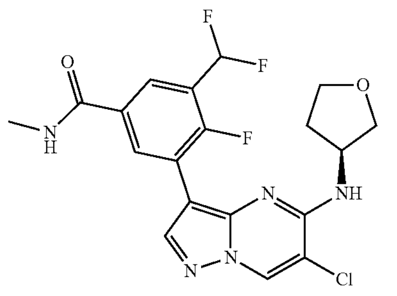 [SMILES: CNC(=O)c1cc(-c2cnn3cc(Cl)c(N[C@H]4CCOC4)nc23)c(F)c(C(F)F)c1]

This compound was prepared by a procedure analogous to that described in Example 34, Step 2, utilizing 3-(difluoromethyl)-4-fluoro-N-methyl-5-(4,4,5,5-tetramethyl-1,3,2-dioxaborolan-2-yl)benzamide (Intermediate C). LCMS calculated for $C_{19}H_{18}ClF_3N_5O_2$(M+H)$^+$: m/z=440.1; found: 440.1.

Step 2. (S)-3-(Difluoromethyl)-4-fluoro-N-methyl-5-(6-(1-methyl-1H-pyrazol-4-yl)-5-((tetrahydrofuran-3-yl)amino)pyrazolo[1,5-a]pyrimidin-3-yl)benzamide This compound was prepared by a procedure analogous to that described in Example 34, Step 3, utilizing 1-methyl-4-(4,4,5,5-tetramethyl-1,3,2-dioxaborolan-2-yl)-1H-pyrazole. LCMS calculated for $C_{23}H_{23}F_3N_7O_2$ (M+H)$^+$: m/z=486.2; found: 486.2.

Examples 48-51

The compounds in the following table were prepared by a procedure analogous to that described for Example 47, utilizing the appropriate commercially available boronate or boronic acid in Step 2.

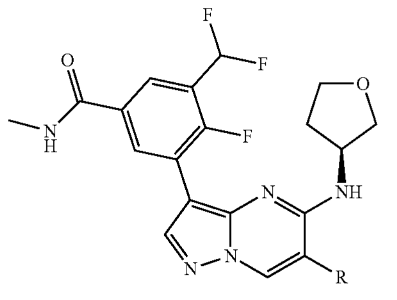

| Example | R | LCMS |
|---|---|---|
| 48. (S)-3-(Difluoromethyl)-5-(6-(1-ethyl-1H-pyrazol-4-yl)-5-((tetrahydrofuran-3-yl)amino)pyrazolo[1,5-a]pyrimidin-3-yl)-4-fluoro-N-methylbenzamide | 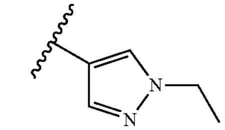 [SMILES: *c1cnn(CC)c1] | Calculated for $C_{24}H_{25}F_3N_7O_2$ $(M + H)^+$: m/z = 500.2; found: 500.2. |
| 49. 3-(Difluoromethyl)-4-fluoro-N-methyl-5-(6-(1-(tetrahydrofuran-3-yl)-1H-pyrazol-4-yl)-5-(((S)-tetrahydrofuran-3-yl)amino)pyrazolo[1,5-a]pyrimidin-3-yl)benzamide | 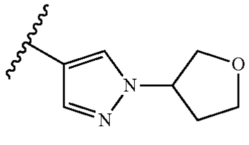 [SMILES: *c1cnn(C2CCOC2)c1] | Calculated for $C_{26}H_{27}F_3N_7O_3$ $(M + H)^+$: m/z = 542.2; found: 542.1. |
| 50. (S)-3-(Difluoromethyl)-4-fluoro-5-(6-(1-(2-methoxyethyl)-1H-pyrazol-4-yl)-5-((tetrahydrofuran-3-yl)amino)pyrazolo[1,5-a]pyrimidin-3-yl)-N-methylbenzamide | 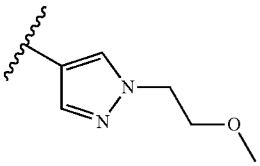 [SMILES: *c1cnn(CCOC)c1] | Calculated for $C_{25}H_{27}F_3N_7O_3$ $(M + H)^+$: m/z = 530.2; found: 530.1. |

Example 51. (S)-3-(3-(1H-Pyrazol-3-yl)phenyl)-6-(1-methyl-1H-pyrazol-4-yl)-5-((tetrahydrofuran-3-yl)oxy)pyrazolo[1,5-a]pyrimidine

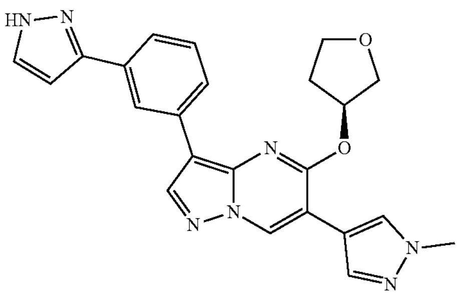 [SMILES: Cn1cc(-c2cn3ncc(-c4cccc(-c5cc[nH]n5)c4)c3nc2O[C@H]2CCOC2)cn1]

Step 1. (S)-3-Chloro-6-(1-methyl-1H-pyrazol-4-yl)-5-((tetrahydrofuran-3-yl)oxy)pyrazolo[1,5-a]pyrimidine

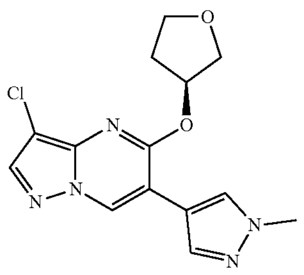 [SMILES: Cn1cc(-c2cn3ncc(Cl)c3nc2O[C@H]2CCOC2)cn1]

A mixture of 3,5-dichloro-6-(1-methyl-1H-pyrazol-4-yl)pyrazolo[1,5-a]pyrimidine(86 mg, 0.32 mmol, Example 1, Step 5), (S)-tetrahydrofuran-3-ol (130 μl, 1.60 mmol), and cesium carbonate (157 mg, 0.48 mmol) in DMF (1.5 ml) was heated to 80° C. for 2 h. The reaction mixture was cooled to room temperature, diluted with DMF to a final concentration of 10 mg/mL, and filtered. The solution of the product in DMF was used directly for the next reactions. LCMS calculated for $C_{14}H_{15}ClN_5O_2$ $(M+H)^+$: m/z=320.1; found: 320.0.

Step 2. (S)-3-(3-(1H-Pyrazol-3-yl)phenyl)-6-(1-methyl-1H-pyrazol-4-yl)-5-((tetrahydrofuran-3-yl)oxy)pyrazolo[1,5-a]pyrimidine A mixture of (S)-3-chloro-6-(1-methyl-1H-pyrazol-4-yl)-5-((tetrahydrofuran-3-yl)oxy)pyrazolo[1,5-a]pyrimidine (10 mg, 0.031 mmol), (3-(1H-pyrazol-3-yl)phenyl)boronic acid (9 mg, 0.05 mmol), XPhos Pd G2 (1.2 mg, 1.6 μmol), and cesium carbonate (30 mg, 0.09 mmol) in dioxane (1 ml) and water (0.5 ml) was sparged with $N_2$ and heated to 100° C. for 2 h. The reaction was diluted with MeOH and filtered through a thiol siliaprep cartridge. The product was purified by prep HPLC (pH 2). LCMS calculated for $C_{23}H_{22}N_7O_2$ $(M+H)^+$: m/z=428.2; found: 428.3.

Example 52. (S)-3,4-Difluoro-N-methyl-5-(6-(1-(pyridin-3-ylmethyl)-1H-pyrazol-4-yl)-5-((tetrahydrofuran-3-yl)amino)pyrazolo[1,5-a]pyrimidin-3-yl)benzamide

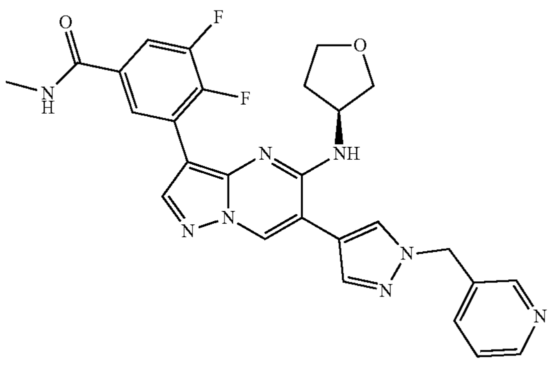 [SMILES: CNC(=O)c1cc(F)c(F)c(-c2cnn3cc(-c4cnn(Cc5cccnc5)c4)c(N[C@H]4CCOC4)nc23)c1]

Step 1. (S)-3-(6-Chloro-5-((tetrahydrofuran-3-yl)amino)pyrazolo[1,5-a]pyrimidin-3-yl)-4,5-difluoro-N-methylbenzamide

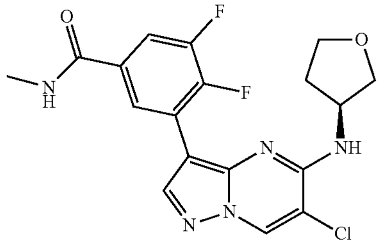 [SMILES: CNC(=O)c1cc(F)c(F)c(-c2cnn3cc(Cl)c(N[C@H]4CCOC4)nc23)c1]

This compound was prepared by a procedure analogous to that described for Example 34, Step 2, utilizing Intermediate A instead of Intermediate B. LCMS calculated for $C_{18}H_{17}ClF_2N_5O_2(M+H)^+$: m/z=408.1; found: 408.2.

Step 2. (S)-3,4-Difluoro-N-methyl-5-(6-(1-(pyridin-3-ylmethyl)-1H-pyrazol-4-yl)-5-((tetrahydrofuran-3-yl)amino)pyrazolo[1,5-a]pyrimidin-3-yl)benzamide This compound was prepared by a procedure analogous to that described for Example 34, Step 3, utilizing 3-((4-(4,4,5,5-tetramethyl-1,3,2-dioxaborolan-2-yl)-1H-pyrazol-1-yl)methyl)pyridine for the Suzuki coupling. LCMS calculated for $C_{27}H_{24}F_2N_8O_2$ $(M+H)^+$: m/z=531.2; found: 531.2.

Examples 53-58

The compounds in the following table were prepared by a procedure analogous to that described for Example 52, utilizing the appropriate boronate or boronic acid in Step 2.

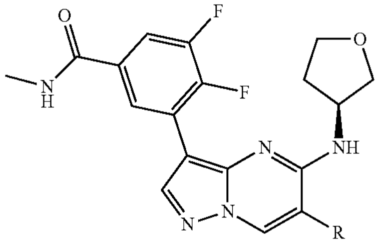

| Example | R | LCMS |
|---|---|---|
| 53. (S)-3-(6-(1-Ethyl-1H-pyrazol-4-yl)-5-((tetrahydrofuran-3-yl)amino)pyrazolo[1,5-a]pyrimidin-3-yl)-4,5-difluoro-N-methylbenzamide | 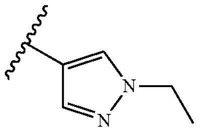 [SMILES: *c1cnn(CC)c1] | Calculated for $C_{23}H_{24}F_2N_7O_2$ $(M + H)^+$: m/z = 468.2; found: 468.2. |
| 54. (S)-3,4-Difluoro-N-methyl-5-(6-(1-((tetrahydro-2H-pyran-4-yl)methyl)-1H-pyrazol-4-yl)-5-((tetrahydrofuran-3-yl)amino)pyrazolo[1,5-a]pyrimidin-3-yl)benzamide | 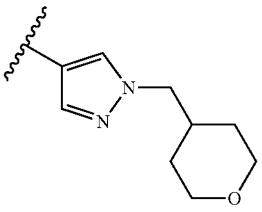 [SMILES: *c1cnn(CC2CCOCC2)c1] | Calculated for $C_{27}H_{30}F_2N_7O_3$ $(M + H)^+$: m/z = 538.2; found: 538.2. |
| 55. (S)-3,4-Difluoro-N-methyl-5-(6-(1-(2-morpholinoethyl)-1H-pyrazol-4-yl)-5-((tetrahydrofuran-3-yl)amino)pyrazolo[1,5-a]pyrimidin-3-yl)benzamide | 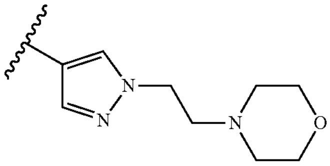 [SMILES: *c1cnn(CCN2CCOCC2)c1] | Calculated for $C_{27}H_{31}F_2N_8O_3$ $(M + H)^+$: m/z = 553.2; found: 553.2. |
| 56. (S)-3,4-Difluoro-5-(6-(1-isopropyl-2-oxo-1,2-dihydropyridin-4-yl)-5-((tetrahydrofuran-3-yl)amino)pyrazolo[1,5-a]pyrimidin-3-yl)-N-methylbenzamide | 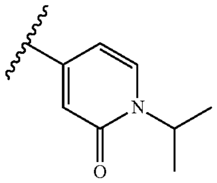 [SMILES: *c1ccn(C(C)C)c(=O)c1] | Calculated for $C_{26}H_{27}F_2N_6O_3$ $(M + H)^+$: m/z = 509.2; found: 509.1. |
| 57. (S)-3,4-Difluoro-5-(6-(6-(2-hydroxypropan-2-yl)pyridin-3-yl)-5-((tetrahydrofuran-3-yl)amino)pyrazolo[1,5-a]pyrimidin-3-yl)-N-methylbenzamide | 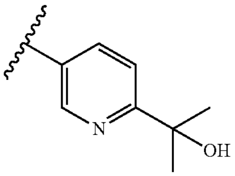 [SMILES: *c1ccc(C(C)(C)O)nc1] | Calculated for $C_{26}H_{27}F_2N_6O_3$ $(M + H)^+$: m/z = 509.2; found: 509.3. |

-continued

| Example | R | LCMS |
|---|---|---|
| 58. (S)-3,4-Difluoro-N-methyl-5-(6-(2-methyloxazol-5-yl)-5-((tetrahydrofuran-3-yl)amino)pyrazolo[1,5-a]pyrimidin-3-yl)benzamide | 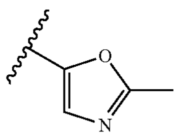 [SMILES: *c1cnc(C)o1] | Calculated for $C_{22}H_{21}F_2N_6O_3$ $(M + H)^+$: m/z = 455.2; found: 455.2. |

Example 59. (S)—N-Methyl-5-(6-(1-methyl-1H-pyrazol-3-yl)-5-((tetrahydrofuran-3-yl)amino)pyrazolo[1,5-a]pyrimidin-3-yl)nicotinamide

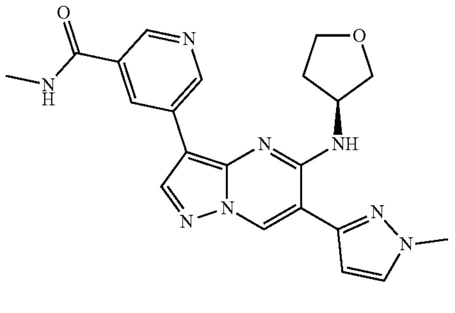

Step 1. (S)-5-(6-Chloro-5-((tetrahydrofuran-3-yl)amino)pyrazolo[1,5-a]pyrimidin-3-yl)-N-methylnicotinamide

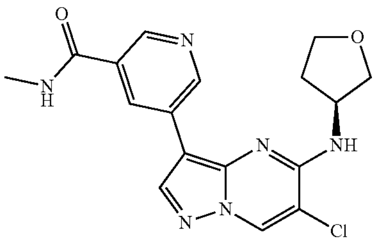 [SMILES: CNC(=O)c1cncc(-c2cnn3cc(Cl)c(N[C@H]4CCOC4)nc23)c1]

A mixture of (S)-3-bromo-6-chloro-N-(tetrahydrofuran-3-yl)pyrazolo[1,5-a]pyrimidin-5-amine (60 mg, 0.19 mmol, Example 34, Step 1), N-methyl-5-(4,4,5,5-tetramethyl-1,3,2-dioxaborolan-2-yl)nicotinamide (99 mg, 0.38 mmol), $PdCl_2$(dppf)-$CH_2Cl_2$ adduct (15 mg, 0.02 mmol), and sodium carbonate (60 mg, 0.57 mmol) in dioxane (1.5 ml) and water (0.5 ml) was sparged with $N_2$ and heated to 100° C. for 2 h. The reaction mixture was adsorbed onto silica gel directly. The product was purified by flash chromatography (0-100% EtOAc/hexanes followed by 0-20% MeOH/DCM) to afford the title compound (41 mg, 58%). LCMS calculated for $C_{17}H_{18}ClN_6O_2$ $(M+H)^+$: m/z=373.1; found: 373.1.

Step 2. (S)—N-Methyl-5-(6-(1-methyl-1H-pyrazol-3-yl)-5-((tetrahydrofuran-3-yl)amino)pyrazolo[1,5-a]pyrimidin-3-yl)nicotinamide A mixture of (S)-5-(6-chloro-5-((tetrahydrofuran-3-yl)amino)pyrazolo[1,5-a]pyrimidin-3-yl)-N-methylnicotinamide (10 mg, 0.03 mmol), 1-methyl-3-(4,4,5,5-tetramethyl-1,3,2-dioxaborolan-2-yl)-1H-pyrazole (11 mg, 0.05 mmol), XPhos Pd G2 (1.0 mg, 1.3 μmol), and cesium carbonate (26 mg, 0.08 mmol) in dioxane (1 ml) and water (0.5 ml) was sparged with $N_2$ and heated to 100° C. for 2 h. The reaction was diluted with MeOH and filtered through a thiol siliaprep cartridge. The product was purified by prep HPLC (pH 2). LCMS calculated for $C_{21}H_{23}N_8O_2$ $(M+H)^+$: m/z=419.2; found: 419.2.

Example 60. (S)—N-Methyl-5-(6-(2-methyl-2H-1,2,3-triazol-4-yl)-5-((tetrahydrofuran-3-yl)amino)pyrazolo[1,5-a]pyrimidin-3-yl)nicotinamide

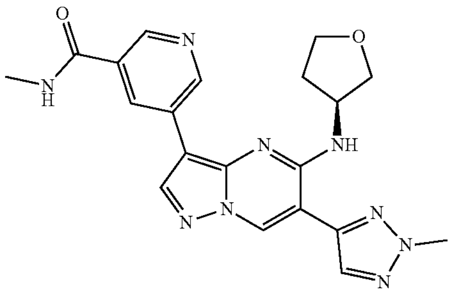

This compound was prepared according to a procedure analogous to that described for Example 59, utilizing 2-methyl-4-(4,4,5,5-tetramethyl-1,3,2-dioxaborolan-2-yl)-2H-1,2,3-triazole in Step 2. LCMS calculated for $C_{20}H_{22}N_9O_2(M+H)^+$: m/z=420.2; found: 420.2.

Example 61. (S)—N-Ethyl-5-(6-(1-methyl-1H-pyrazol-3-yl)-5-((tetrahydrofuran-3-yl)amino)pyrazolo[1,5-a]pyrimidin-3-yl)nicotinamide

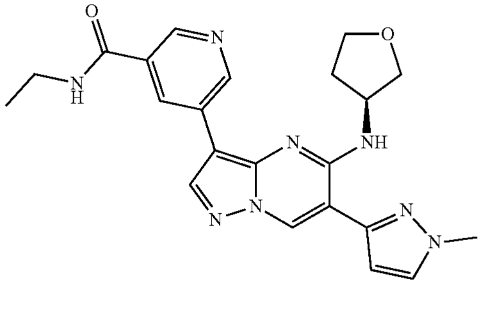 [SMILES: CCNC(=O)c1cncc(-c2cnn3cc(-c4ccn(C)n4)c(N[C@H]4CCOC4)nc23)c1]

Step 1. 5-Bromo-N-ethylnicotinamide

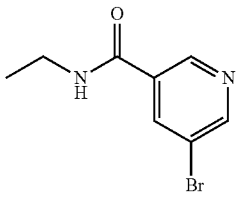

To a suspension of 5-bromonicotinoyl chloride (200 mg, 0.91 mmol) in DCM (6 ml) was added DIPEA (190 μl, 1.09 mmol) and ethylamine (2M/THF, 544 μl, 1.09 mmol) at 0° C., and the reaction mixture was allowed to warm to room temperature. The reaction was quenched with saturated $NaHCO_3$ and extracted with DCM. The phases were separated and the organic phase was washed with brine, dried over $MgSO_4$, filtered and concentrated. The product was used without purification. LCMS calculated for $C_8H_{10}BrN_2O$ $(M+H)^+$: m/z=229.0; found: 229.0.

Step 2. N-Ethyl-5-(4,4,5,5-tetramethyl-1,3,2-dioxaborolan-2-yl)nicotinamide

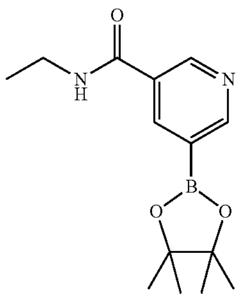 [SMILES: CCNC(=O)c1cncc(B2OC(C)(C)C(C)(C)O2)c1]

5-Bromo-N-ethylnicotinamide (50 mg, 0.22 mmol) was combined with bis(pinacolato)diboron (83 mg, 0.33 mmol), dichloro[1,1'-bis(diphenylphosphino)ferrocene]palladium (II) dichloromethane adduct (9 mg, 11 μmol) and potassium acetate (64 mg, 0.66 mmol) in dioxane (3 ml) and the mixture was sparged with $N_2$ for 5 min. The reaction was heated to 100° C. for 3 h. The reaction mixture was diluted with EtOAc, filtered, and concentrated. The product was used without purification. The following data is reported for the corresponding boronic acid, which was the only observable species by LCMS. LCMS calculated for $C_8H_{12}BN_2O_3$ $(M+H)^+$: m/z=195.1; found: 195.1.

Step 3. (S)—N-Ethyl-5-(6-(1-methyl-1H-pyrazol-3-yl)-5-((tetrahydrofuran-3-yl)amino)pyrazolo[1,5-a]pyrimidin-3-yl)nicotinamide This compound was prepared according to the procedure described for Example 59, utilizing N-ethyl-5-(4,4,5,5-tetramethyl-1,3,2-dioxaborolan-2-yl)nicotinamide. LCMS calculated for $C_{22}H_{25}N_8O_2$ $(M+H)^+$: m/z=433.2; found: 433.2.

Example 62. (S)—N-Isopropyl-5-(6-(1-methyl-1H-pyrazol-3-yl)-5-((tetrahydrofuran-3-yl)amino)pyrazolo[1,5-a]pyrimidin-3-yl)nicotinamide

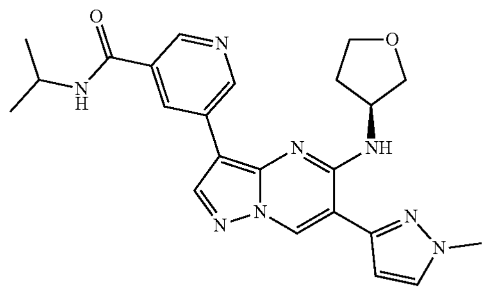 [SMILES: CC(C)NC(=O)c1cncc(-c2cnn3cc(-c4ccn(C)n4)c(N[C@H]4CCOC4)nc23)c1]

This compound was prepared according the procedure described for Example 61, utilizing isopropylamine instead of ethylamine in Step 1. LCMS calculated for $C_{23}H_{27}NO_2$ $(M+H)^+$: m/z=447.2; found: 447.2.

Example 63. (S)-5-(6-(1-Isopropyl-1H-pyrazol-4-yl)-5-((tetrahydrofuran-3-yl)oxy)pyrazolo[1,5-a]pyrimidin-3-yl)-N-(methyl-$d_3$)nicotinamide

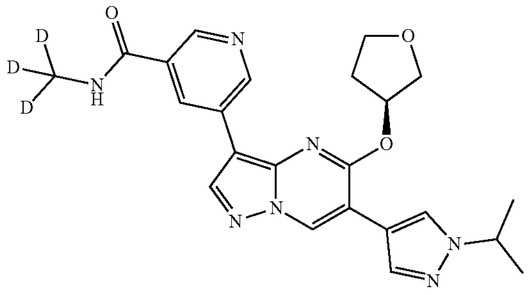 [SMILES: [2H]C([2H])([2H])NC(=O)c1cncc(-c2cnn3cc(-c4cnn(C(C)C)c4)c(O[C@H]4CCOC4)nc23)c1]

This compound was prepared by an identical procedure to that described for Example 9, utilizing Intermediate E in Step 3. LCMS calculated for $C_{23}H_{23}D_3N_7O_3$ $(M+H)^+$: m/z=451.2; found: 451.2. $^1H$ NMR (600 MHz, DMSO-$d_6$) δ 9.40 (s, 2H), 8.99 (t, J=2.2 Hz, 1H), 8.84 (s, 1H), 8.75 (s, 1H), 8.68 (s, 1H), 8.29 (s, 1H), 8.07 (s, 1H), 5.80 (m, J=6.7, 4.4, 2.0 Hz, 1H), 4.59 (hept, J=6.7 Hz, 1H), 4.18 (dd, J=10.7, 4.8 Hz, 1H), 4.08 (dd, J=10.7, 1.9 Hz, 1H), 3.96 (q, J=7.9 Hz, 1H), 3.88 (td, J=8.4, 4.7 Hz, 1H), 2.50-2.42 (m, 1H), 2.32 (m, J=13.9, 6.9, 4.7, 1.9 Hz, 1H), 1.47 (d, J=6.7 Hz, 6H).

Example 64. 4-Fluoro-3-(6-(1-((3R,4R)-3-fluoro-1-methylpiperidin-4-yl)-1H-pyrazol-4-yl)-5-(((S)-tetrahydrofuran-3-yl)oxy)pyrazolo[1,5-a]pyrimidin-3-yl)-5-methyl-N-(methyl-$d_3$)benzamide

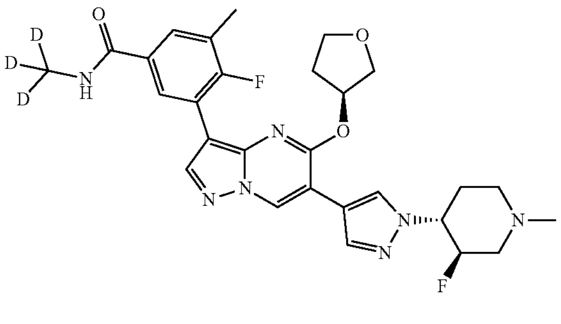 [SMILES: [2H]C([2H])([2H])NC(=O)c1cc(C)c(F)c(-c2cnn3cc(-c4cnn([C@@H]5CCN(C)C[C@H]5F)c4)c(O[C@H]4CCOC4)nc23)c1]

Step 1. tert-Butyl(3R,4S)-3-fluoro-4-((methylsulfonyl)oxy)piperidine-1-carboxylate

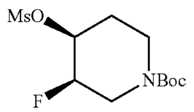 [SMILES: CC(C)(C)OC(=O)N1CC[C@H](OS(C)(=O)=O)[C@H](F)C1]

To a solution of tert-butyl(3R,4S)-3-fluoro-4-hydroxypiperidine-1-carboxylate(200 mg, 0.91 mmol) in DCM (5 ml) at 0° C. was added DIPEA (239 μl, 1.37 mmol) and methanesulfonyl chloride (107 μl, 1.37 mmol), and the reaction mixture was allowed to warm to room temperature. After stirring for 30 min, TLC indicated the reaction was complete. The reaction mixture was quenched with saturated $NaHCO_3$ and extracted with DCM. The organic phase was dried over $MgSO_4$, filtered and concentrated. The product was purified by flash chromatography (0-50% EtOAc/hexanes) to afford the title compound (271 mg, quant.) as a white solid. LCMS calculated for $C_7H_{13}FNO_5S$ $(M-C_4H_7)^+$: m/z=242.0; found: 242.1.

Step 2. tert-Butyl (3R,4R)-3-fluoro-4-(4-(4,4,5,5-tetramethyl-1,3,2-dioxaborolan-2-yl)-1H-pyrazol-1-yl)piperidine-1-carboxylate

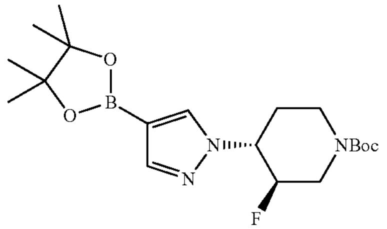 [SMILES: CC(C)(C)OC(=O)N1CC[C@@H](n2cc(B3OC(C)(C)C(C)(C)O3)cn2)[C@H](F)C1]

To a solution of tert-butyl (3R,4S)-3-fluoro-4-((methylsulfonyl)oxy)piperidine-1-carboxylate (191 mg, 0.64 mmol) and 4-(4,4,5,5-tetramethyl-1,3,2-dioxaborolan-2-yl)-1H-pyrazole (125 mg, 0.64 mmol) in acetonitrile (2 ml) was added cesium carbonate (419 mg, 1.29 mmol) and the reaction mixture was stirred at 120° C. in the microwave for 1 h. The reaction mixture was diluted with EtOAc, filtered, and concentrated. The residue was purified by flash chromatography (0-100% EtOAc/hexanes; slow gradient) to afford the title compound (62 mg, 24%). LCMS calculated for $C_{19}H_{32}BFN_3O_4$ $(M+H)^+$: m/z=396.2; found: 396.3.

Step 3. (S)-3-(6-Chloro-5-((tetrahydrofuran-3-yl)oxy)pyrazolo[1,5-a]pyrimidin-3-yl)-4-fluoro-5-methyl-N-(methyl-d3)benzamide

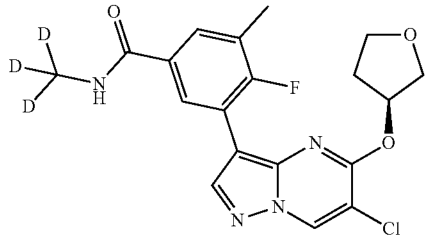 [SMILES: [2H]C([2H])([2H])NC(=O)c1cc(C)c(F)c(-c2cnn3cc(Cl)c(O[C@H]4CCOC4)nc23)c1]

A mixture of(S)-3-bromo-6-chloro-5-((tetrahydrofuran-3-yl)oxy)pyrazolo[1,5-a]pyrimidine (56 mg, 0.176 mmol, Example 11, Step 2), 4-fluoro-3-methyl-N-(methyl-$d_3$)-5-(4,4,5,5-tetramethyl-1,3,2-dioxaborolan-2-yl)benzamide (63 mg, 0.21 mmol), bis(di-tert-butyl(4-dimethylaminophenyl)phosphine)dichloropalladium(II) (12.5 mg, 0.018 mmol), and cesium fluoride (80 mg, 0.53 mmol) in n-BuOH (1.5 ml) and water (0.5 ml) was sparged with $N_2$ and heated to 65° C. for 1 h. The reaction mixture was dry loaded onto silica gel and the product was purified by flash chromatography (0-100% EtOAc/hexanes followed by 0-20% MeOH/DCM) to afford the title compound (45 mg, 63%). LCMS calculated for $C_{19}H_{16}D_3ClFN_4O_3$ $(M+H)^+$: m/z=408.1; found: 408.4.

Step 4. tert-Butyl (3R,4R)-3-fluoro-4-(4-(3-(2-fluoro-3-methyl-5-((methyl-d3)carbamoyl)phenyl)-5-(((S)-tetrahydrofuran-3-yl)oxy)pyrazolo[1,5-a]pyrimidin-6-yl)-1H-pyrazol-1-yl)piperidine-1-carboxylate

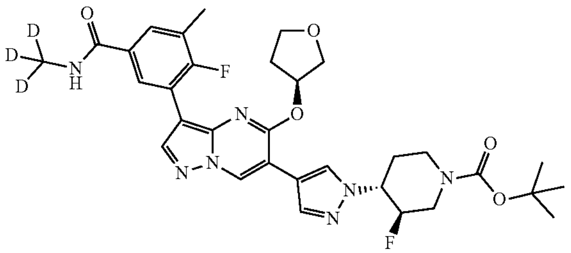 [SMILES: [2H]C([2H])([2H])NC(=O)c1cc(C)c(F)c(-c2cnn3cc(-c4cnn([C@@H]5CCN(C(=O)OC(C)(C)C)C[C@H]5F)c4)c(O[C@H]4CCOC4)nc23)c1]

A mixture of (S)-3-(6-chloro-5-((tetrahydrofuran-3-yl)oxy)pyrazolo[1,5-a]pyrimidin-3-yl)-4-fluoro-5-methyl-N-(methyl-$d_3$)benzamide (15 mg, 0.04 mmol), tert-butyl (3R,4R)-3-fluoro-4-(4-(4,4,5,5-tetramethyl-1,3,2-dioxaborolan-2-yl)-1H-pyrazol-1-yl)piperidine-1-carboxylate (16 mg, 0.04 mmol), XPhos Pd G2 (1.4 mg, 1.8 μmol), and cesium carbonate (36 mg, 0.11 mmol) in dioxane (2 ml) and water (0.5 ml) was sparged with $N_2$ and heated to 100° C. for 1 h. The reaction mixture was filtered through a thiol siliaprep cartridge, concentrated, and the product was used without purification. LCMS calculated for $C_{32}H_{35}D_3F_2N_7O_5$ $(M+H)^+$: m/z=641.3; found: 641.3.

Step 5. 4-Fluoro-3-(6-(1-((3R,4R)-3-fluoro-1-methylpiperidin-4-yl)-1H-pyrazol-4-yl)-5-(((S)-tetrahydrofuran-3-yl)oxy)pyrazolo[1,5-a]pyrimidin-3-yl)-5-methyl-N-(methyl-$d_3$)benzamide A solution of tert-butyl (3R,4R)-3-fluoro-4-(4-(3-(2-fluoro-3-methyl-5-((methyl-$d_3$)carbamoyl)phenyl)-5-(((S)-tetrahydrofuran-3-yl)oxy)pyrazolo[1,5-a]pyrimidin-6-yl)-1H-pyrazol-1-yl)piperidine-1-carboxylate (24 mg, 0.04 mmol) in MeOH (2 ml) was treated with HCl (4M/dioxane, 3 ml) and stirred at room temperature for 30 min. The reaction mixture was concentrated and the product was used without purification.

The amine obtained above was dissolved in MeOH (2 ml) and formaldehyde (37 wt % in water, 28 μl, 0.38 mmol) was added, followed by sodium cyanoborohydride (24 mg, 0.38 mmol). The reaction mixture was stirred at room temperature for 1 h, then filtered and purified by prep HPLC (pH 2) to afford the title compound (7.1 mg, 34%). LCMS calculated for $C_{28}H_{29}D_3F_2N_7O_3$ $(M+H)^+$: m/z=555.3; found: 555.1.

Example 65. 4-Fluoro-3-(6-(1-((3R,4R)-3-fluoro-1-methylpiperidin-4-yl)-1H-pyrazol-4-yl)-5-(((S)-tetrahydrofuran-3-yl)amino)pyrazolo[1,5-a]pyrimidin-3-yl)-N,5-dimethylbenzamide

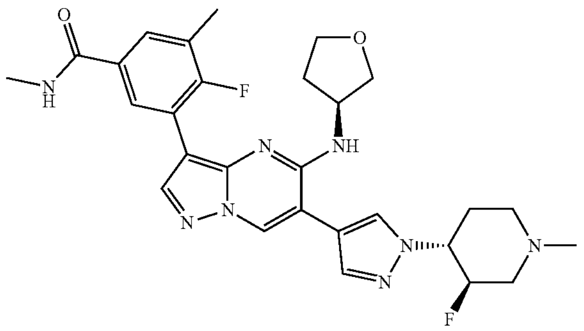

This compound was prepared by an identical procedure to that described for Example 64, utilizing (S)-3-(6-chloro-5-((tetrahydrofuran-3-yl)amino)pyrazolo[1,5-a]pyrimidin-3-yl)-4-fluoro-N,5-dimethylbenzamide (Example 34, Step 2) in Step 4. LCMS calculated for $C_{28}H_{33}F_2N_8O_2$ $(M+H)^+$: m/z=551.3; found: 551.3.

Example 66. 3-(6-(6-(((1R,4R)-2-Oxa-5-azabicyclo[2.2.1]heptan-5-yl)methyl)pyridin-3-yl)-5-(((S)-tetrahydrofuran-3-yl)oxy)pyrazolo[1,5-a]pyrimidin-3-yl)-5-(difluoromethyl)-4-fluoro-N-(methyl-$d_3$)benzamide

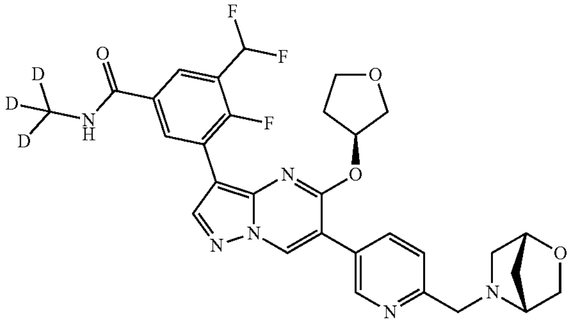 [SMILES: [2H]C([2H])([2H])NC(=O)c1cc(-c2cnn3cc(-c4ccc(CN5C[C@H]6C[C@@H]5CO6)nc4)c(O[C@H]4CCOC4)nc23)c(F)c(C(F)F)c1]

Step 1. (1R,4R)-5-((5-Bromopyridin-2-yl)methyl)-2-oxa-5-azabicyclo[2.2.1]heptane

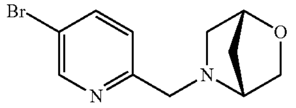 [SMILES: Brc1ccc(CN2C[C@H]3C[C@@H]2CO3)nc1]

To a solution of 5-bromopicolinaldehyde (50 mg, 0.27 mmol) in DCE (1 ml) was added (1R,4R)-2-oxa-5-azabicyclo[2.2.1]heptane hydrochloride (36 mg, 0.27 mmol), sodium triacetoxyborohydride (85 mg, 0.40 mmol), and triethylamine (37 μl, 0.27 mmol), and the reaction mixture was stirred at room temp for 3 h. The reaction was quenched with saturated $NaHCO_3$ and extracted with DCM. The organic phase was dried over $MgSO_4$, filtered, and concentrated. The product was used without purification. LCMS calculated for $C_{11}H_{14}BrN_2O$ $(M+H)^+$: m/z=269.1; found: 269.0.

Step 2. (1R,4R)-5-((5-(4,4,5,5-Tetramethyl-1,3,2-dioxaborolan-2-yl)pyridin-2-yl)methyl)-2-oxa-5-azabicyclo[2.2.1]heptane

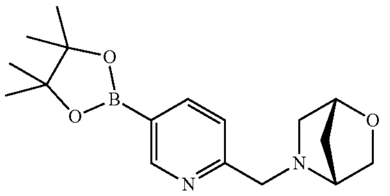 [SMILES: CC1(C)OB(c2ccc(CN3C[C@H]4C[C@@H]3CO4)nc2)OC1(C)C]

(1R,4R)-5-((5-Bromopyridin-2-yl)methyl)-2-oxa-5-azabicyclo[2.2.1]heptane (72 mg, 0.29 mmol) was combined with bis(pinacolato)diboron (102 mg, 0.40 mmol), dichloro[1,1'-bis(diphenylphosphino)ferrocene]palladium (II) dichloromethane adduct (11 mg, 0.01 mmol) and potassium acetate (79 mg, 0.80 mmol) in dioxane (3 ml) and the mixture was sparged with $N_2$. The reaction was heated to 100° C. for 3 h. The reaction mixture was diluted with EtOAc, filtered, concentrated. The product was used without purification. The following data is reported for the corresponding boronic acid, which was the only observable species by LCMS. LCMS calculated for $C_{11}H_{16}BN_2O_3$ $(M+H)^+$: m/z=235.1; found: 235.2.

Step 3. (S)-3-(6-Chloro-5-((tetrahydrofuran-3-yl)oxy)pyrazolo[1,5-a]pyrimidin-3-yl)-5-(difluoromethyl)-4-fluoro-N-(methyl-$d_3$)benzamide

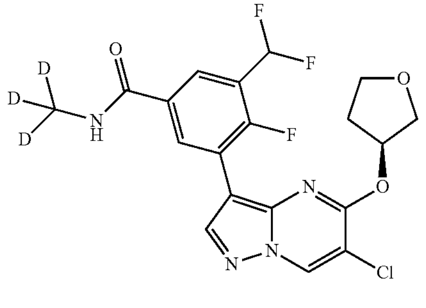 [SMILES: [2H]C([2H])([2H])NC(=O)c1cc(-c2cnn3cc(Cl)c(O[C@H]4CCOC4)nc23)c(F)c(C(F)F)c1]

This compound was prepared by an identical procedure to that described for Example 23, Step 1, utilizing Intermediate G instead of Intermediate C. LCMS calculated for $C_{19}H_{14}D_3ClF_3N_4O_3$ $(M+H)^+$: m/z=444.1; found: 444.1.

Step 4. 3-(6-(6-(((1R,4R)-2-Oxa-5-azabicyclo[2.2.1]heptan-5-yl)methyl)pyridin-3-yl)-5-(((S)-tetrahydrofuran-3-yl)oxy)pyrazolo[1,5-a]pyrimidin-3-yl)-5-(difluoromethyl)-4-fluoro-N-(methyl-$d_3$)benzamide A mixture of (S)-3-(6-chloro-5-((tetrahydrofuran-3-yl)oxy)pyrazolo[1,5-a]pyrimidin-3-yl)-5-(difluoromethyl)-4-fluoro-N-(methyl-$d_3$)benzamide (45 mg, 0.10 mmol), (1R,4R)-5-((5-(4,4,5,5-tetramethyl-1,3,2-dioxaborolan-2-yl)pyridin-2-yl)methyl)-2-oxa-5-azabicyclo[2.2.1]heptane (48 mg, 0.15 mmol), XPhos Pd G2 (4 mg, 5.0 μmol), and cesium carbonate (99 mg, 0.30 mmol) in dioxane (1.5 ml) and water (0.5 ml) was sparged with $N_2$ and heated to 100° C. for 1 h. The reaction mixture was diluted with MeOH, filtered through a thiol siliaprep cartridge, and the product was purified by prep HPLC. LCMS calculated for $C_{30}H_{27}D_3F_3N_6O_4$ $(M+H)^+$: m/z=598.2; found: 598.3. $^1$H NMR (500 MHz, DMSO-$d_6$) δ 9.31 (s, 1H), 9.18 (dd, J=7.1, 2.2 Hz, 1H), 8.98 (d, J=2.3 Hz, 1H), 8.56 (d, J=3.2 Hz, 1H), 8.48 (s, 1H), 8.25 (dd, J=8.1, 2.3 Hz, 1H), 8.02-7.97 (m, 1H), 7.68 (d, J=8.1 Hz, 1H), 7.32 (t, J=54.3 Hz, 1H), 5.80 (td, J=5.0, 2.5 Hz, 1H), 4.78 (d, J=14.7 Hz, 1H), 4.71 (d, J=2.5 Hz, 1H), 4.66 (d, J=14.6 Hz, 1H), 4.53 (s, 1H), 4.26 (d, J=9.9 Hz, 1H), 4.14 (dd, J=10.7, 4.9 Hz, 1H), 3.97 (dd, J=10.7, 1.9 Hz, 1H), 3.89-3.78 (m, 3H), 3.52-3.39 (m, 2H), 2.50-2.43 (m, 1H), 2.39 (d, J=11.8 Hz, 1H), 2.19-2.09 (m, 2H).

Example 67. (S)-4-Fluoro-3-(6-(2-(1-isopropylpiperidin-4-yl)-2H-1,2,3-triazol-4-yl)-5-((tetrahydrofuran-3-yl)amino)pyrazolo[1,5-a]pyrimidin-3-yl)-5-methyl-N-(methyl-$d_3$)benzamide

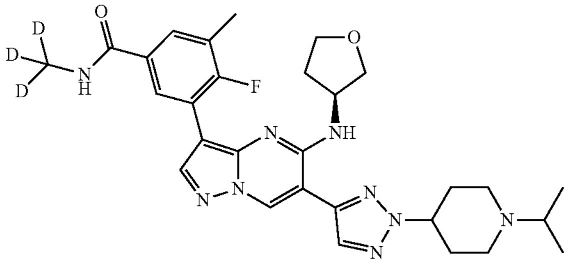 [SMILES: [2H]C([2H])([2H])NC(=O)c1cc(C)c(F)c(-c2cnn3cc(-c4cnn(C5CCN(C(C)C)CC5)n4)c(N[C@H]4CCOC4)nc23)c1]

Step 1. tert-Butyl 4-(4,5-dibromo-2H-1,2,3-triazol-2-yl)piperidine-1-carboxylate

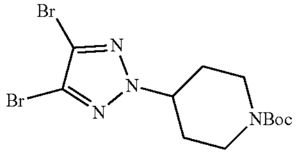 [SMILES: CC(C)(C)OC(=O)N1CCC(n2nc(Br)c(Br)n2)CC1]

A mixture of 4,5-dibromo-2H-1,2,3-triazole (100 mg, 0.44 mmol), tert-butyl 4-((methylsulfonyl)oxy)piperidine-1-carboxylate (148 mg, 0.53 mmol), and cesium carbonate (172 mg, 0.53 mmol) in DMF (4 ml) was heated to 100° C. for 3 h. The reaction mixture was filtered and concentrated to dryness. The residue was purified by flash chromatography (0-100% EtOAc/hexanes) to afford the title compound (140 mg, 77%). LCMS calculated for $C_8H_{11}Br_2N_4O_2$$(M-C_4H_7)^+$: m/z=352.9; found: 352.9.

Step 2. tert-Butyl 4-(4-bromo-2H-1,2,3-triazol-2-yl)piperidine-1-carboxylate

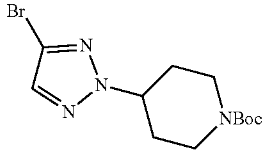 [SMILES: CC(C)(C)OC(=O)N1CCC(n2ncc(Br)n2)CC1]

To a solution of tert-butyl 4-(4,5-dibromo-2H-1,2,3-triazol-2-yl)piperidine-1-carboxylate (140 mg, 0.34 mmol) in THF (3 ml) at −78° C. was added n-butyllithium (143 μl, 0.36 mmol) and the reaction mixture was stirred at −78° C. for 20 min. LCMS indicated about equal ratios of starting material, desired product, and an unknown by-product. Additional n-butyllithium (143 μl, 0.36 mmol) was added and stirring was continued at −78° C. for another 20 min. The reaction mixture was quenched with saturated $NH_4Cl$, warmed to room temperature, and extracted with EtOAc. The layers were separated and the organic phase was washed with brine, dried over $MgSO_4$, filtered and concentrated. The product was purified by flash chromatography (0-50%

EtOAc/hexanes) to afford the title compound (37 mg, 32%). LCMS calculated for $C_8H_{12}BrN_4O_2$ (M-$C_4H_7$)$^+$: m/z=275.0; found: 275.1.

Step 3. tert-Butyl 4-(4-(4,4,5,5-tetramethyl-1,3,2-dioxaborolan-2-yl)-2H-1,2,3-triazol-2-yl)piperidine-1-carboxylate

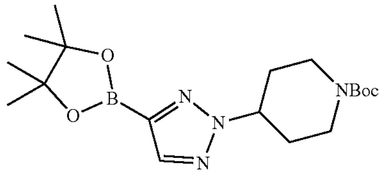 [SMILES: CC(C)(C)OC(=O)N1CCC(n2ncc(B3OC(C)(C)C(C)(C)O3)n2)CC1]

To a solution of tert-butyl 4-(4-bromo-2H-1,2,3-triazol-2-yl)piperidine-1-carboxylate (36 mg, 0.11 mmol) in THE (3 ml) at −78° C. was added n-butyllithium (65 μl, 0.16 mmol) and the reaction mixture was stirred at −78° C. for 15 min. 2-Isopropoxy-4,4,5,5-tetramethyl-1,3,2-dioxaborolane (44 μl, 0.22 mmol) was added and the reaction mixture was stirred while the temperature gradually warmed to room temperature over 2 h. The reaction was quenched with saturated $NH_4Cl$. EtOAc was added and layers were separated. The organic phase was washed with brine, dried over $MgSO_4$, filtered and concentrated. The product was used without purification. The following data is reported for the corresponding boronic acid, which was the only observable species by LCMS. LCMS calculated for $C_{12}H_{22}BN_4O_4$ (M-$C_4H_7$)$^+$: m/z=297.2; found: 297.2.

Step 4. (S)-3-(6-Chloro-5-((tetrahydrofuran-3-yl)amino)pyrazolo[1,5-a]pyrimidin-3-yl)-4-fluoro-5-methyl-N-(methyl-$d_3$)benzamide

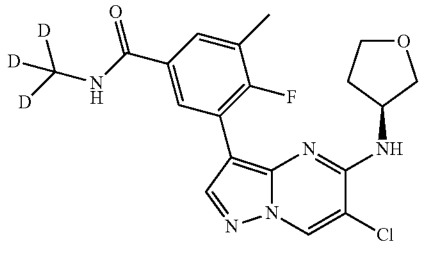 [SMILES: [2H]C([2H])([2H])NC(=O)c1cc(C)c(F)c(-c2cnn3cc(Cl)c(N[C@H]4CCOC4)nc23)c1]

A mixture of (S)-3-bromo-6-chloro-N-(tetrahydrofuran-3-yl)pyrazolo[1,5-a]pyrimidin-5-amine (85 mg, 0.27 mmol, Example 34, Step 1), 4-fluoro-3-methyl-N-(methyl-$d_3$)-5-(4,4,5,5-tetramethyl-1,3,2-dioxaborolan-2-yl)benzamide (95 mg, 0.32 mmol), bis(di-tert-butyl(4-dimethylaminophenyl)phosphine)dichloropalladium(II) (19 mg, 2.7 μmol), and cesium fluoride (122 mg, 0.80 mmol) in BuOH (3.5 ml) and water (0.5 ml) was sparged with $N_2$ and heated to 70° C. for 1 h. The reaction mixture was directly dry loaded onto silica gel and purified by flash chromatography (0-100% EtOAc/hexanes followed by 0-20% MeOH/DCM) to afford the title compound (63 mg, 58%). LCMS calculated for $C_{19}H_{17}D_3ClFN_5O_2$ (M+H)$^+$: m/z=407.1; found: 407.2.

Step 5. tert-Butyl(S)-4-(4-(3-(2-fluoro-3-methyl-5-((methyl-$d_3$)carbamoyl)phenyl)-5-((tetrahydrofuran-3-yl)amino)pyrazolo[1,5-a]pyrimidin-6-yl)-2H-1,2,3-triazol-2-yl)piperidine-1-carboxylate

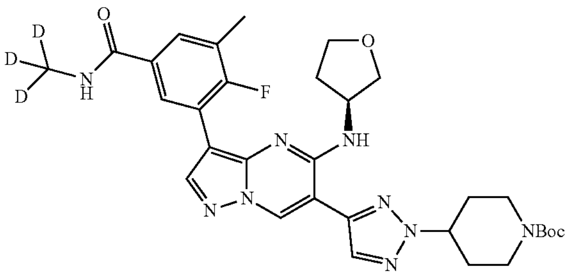 [SMILES: [2H]C([2H])([2H])NC(=O)c1cc(C)c(F)c(-c2cnn3cc(-c4cnn(C5CCN(C(=O)OC(C)(C)C)CC5)n4)c(N[C@H]4CCOC4)nc23)c1]

A mixture of (S)-3-(6-chloro-5-((tetrahydrofuran-3-yl)amino)pyrazolo[1,5-a]pyrimidin-3-yl)-4-fluoro-5-methyl-N-(methyl-$d_3$)benzamide (20 mg, 0.05 mmol), tert-butyl 4-(4-(4,4,5,5-tetramethyl-1,3,2-dioxaborolan-2-yl)-2H-1,2,3-triazol-2-yl)piperidine-1-carboxylate (28 mg, 0.07 mmol), XPhos Pd G2 (1.9 mg, 2.5 μmol), and cesium carbonate (48 mg, 0.15 mmol) in dioxane (2.5 ml) and water (0.5 ml) was sparged with $N_2$ and heated to 100° C. for 1 h. The reaction mixture was diluted with MeOH, filtered through a thiol siliaprep cartridge, and concentrated. The product was used without purification. LCMS calculated for $C_{31}H_{36}D_3FN_9O_4$ (M+H)$^+$: m/z=623.3; found: 623.4.

Step 6. (S)-4-Fluoro-3-(6-(2-(1-isopropylpiperidin-4-yl)-2H-1,2,3-triazol-4-yl)-5-((tetrahydrofuran-3-yl)amino)pyrazolo[1,5-a]pyrimidin-3-yl)-5-methyl-N-(methyl-$d_3$)benzamide A solution of tert-butyl (S)-4-(4-(3-(2-fluoro-3-methyl-5-((methyl-$d_3$)carbamoyl)phenyl)-5-((tetrahydrofuran-3-yl)amino)pyrazolo[1,5-a]pyrimidin-6-yl)-2H-1,2,3-triazol-2-yl)piperidine-1-carboxylate (22 mg, 0.04 mmol) in MeOH (2 ml) was treated with HCl (4M/dioxane, 2 ml) and stirred at room temperature for 30 min. The reaction mixture was concentrated and the product was used without purification.

The amine obtained above was dissolved in MeOH (2 ml). Acetone (52 μL, 0.71 mmol) was added, followed by sodium cyanoborohydride (22 mg, 35 μmol). The reaction mixture was stirred at room temperature for 4 h, then filtered and purified by prep HPLC. LCMS calculated for $C_{29}H_{34}D_3FN_9O_2$ (M+H)$^+$: m/z=565.3; found: 565.4.

Example 68. (S)-4-Fluoro-3-(6-(2-(1-isopropylpiperidin-4-yl)oxazol-5-yl)-5-((tetrahydrofuran-3-yl)amino)pyrazolo[1,5-a]pyrimidin-3-yl)-5-methyl-N-(methyl-$d_3$)benzamide

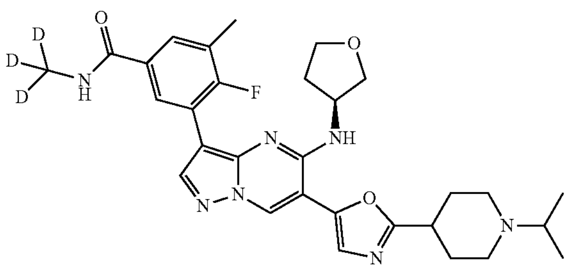 [SMILES: [2H]C([2H])([2H])NC(=O)c1cc(C)c(F)c(-c2cnn3cc(-c4cnc(C5CCN(C(C)C)CC5)o4)c(N[C@H]4CCOC4)nc23)c1]

Step 1. Benzyl 4-((2,2-dimethoxyethyl)carbamoyl) piperidine-1-carboxylate

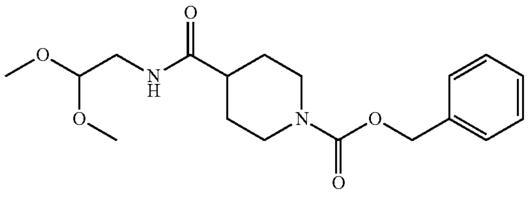 [SMILES: COC(CNC(=O)C1CCN(C(=O)OCc2ccccc2)CC1)OC]

To a solution of 1-((benzyloxy)carbonyl)piperidine-4-carboxylic acid (200 mg, 0.76 mmol) and HATU (318 mg, 0.84 mmol) in DMF (5 ml) was added DIPEA (265 μl, 1.52 mmol), followed by 2,2-dimethoxyethan-1-amine (103 μl, 0.84 mmol), and the reaction mixture was stirred at room temperature for 30 min. The reaction was quenched with water and extracted with EtOAc. The layers were separated and the organic phase was washed with brine, dried over $MgSO_4$, filtered and concentrated. The residue was purified by flash chromatography (0-100% EtOAc/hexanes) to afford the title compound (220 mg, 83%) as a colorless oil. LCMS calculated for $C_{18}H_{26}N_2O_5Na$ $(M+Na)^+$: m/z=373.2; found: 373.3.

Step 2. 2-(Piperidin-4-yl)oxazole

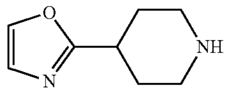 [SMILES: c1coc(C2CCNCC2)n1]

Benzyl 4-((2,2-dimethoxyethyl)carbamoyl)piperidine-1-carboxylate (200 mg, 0.57 mmol) was dissolved in Eaton's reagent (3 mL, 18.9 mmol) and heated to 130° C. for 6 h. The reaction mixture was cooled to 0° C. and quenched with 1M NaOH. The aqueous phase was washed with EtOAc and concentrated. The product was used without purification. LCMS calculated for $C_8H_{13}N_2O$ $(M+H)^+$: m/z=153.1; found: 153.0.

Step 3. tert-Butyl 4-(oxazol-2-yl)piperidine-1-carboxylate

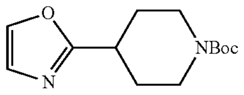 [SMILES: CC(C)(C)OC(=O)N1CCC(c2ncco2)CC1]

To a solution of 2-(piperidin-4-yl)oxazole (90 mg, 0.59 mmol) in THF (3 ml)/water (3 ml) was added sodium carbonate (75 mg, 0.71 mmol) and di-tert-butyl dicarbonate (165 μl, 0.71 mmol). The reaction mixture was stirred for 30 min at room temperature. The reaction mixture was partitioned between water and EtOAc, and the layers were separated. The aqueous phase was extracted with EtOAc and the combined organic layers were washed with brine, dried over $MgSO_4$, filtered, and concentrated. The residue was purified by flash chromatography (0-50% EtOAc/hexanes) to afford the title compound (71 mg, 48% over 2 steps). LCMS calculated for $C_9H_{12}N_2O_3$ $(M-C_4H_7)^+$: m/z=197.1; found: 197.2.

Step 3. tert-Butyl 4-(5-(4,4,5,5-tetramethyl-1,3,2-dioxaborolan-2-yl)oxazol-2-yl)piperidine-1-carboxylate

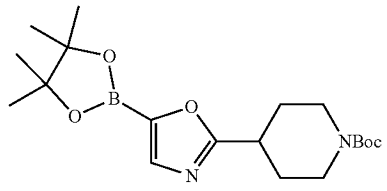 [SMILES: CC(C)(C)OC(=O)N1CCC(c2ncc(B3OC(C)(C)C(C)(C)O3)o2)CC1]

To a solution of tert-butyl 4-(oxazol-2-yl)piperidine-1-carboxylate (20 mg, 0.08 mmol) in THE (3 ml) at −78° C. was added n-butyllithium (48 μl, 0.12 mmol), and the reaction mixture was stirred at −78° C. for 20 min. 2-Isopropoxy-4,4,5,5-tetramethyl-1,3,2-dioxaborolane (32 μl, 0.16 mmol) was added and the reaction mixture was allowed to warm to room temperature. The reaction was quenched with saturated $NH_4Cl$ and extracted with EtOAc. The layers were separated and the organic phase was washed with brine, dried over $MgSO_4$, filtered and concentrated. The product was used without purification. The following data is reported for the corresponding boronic acid, which was the only observable species by LCMS. LCMS calculated for $C_9H_{14}BN_2O_5$ $(M-C_4H_7)^+$: m/z=241.1; found: 241.1.

Step 4. tert-Butyl (S)-4-(5-(3-(2-fluoro-3-methyl-5-((methyl-$d_3$)carbamoyl)phenyl)-5-((tetrahydrofuran-3-yl)amino)pyrazolo[1,5-a]pyrimidin-6-yl)oxazol-2-yl)piperidine-1-carboxylate

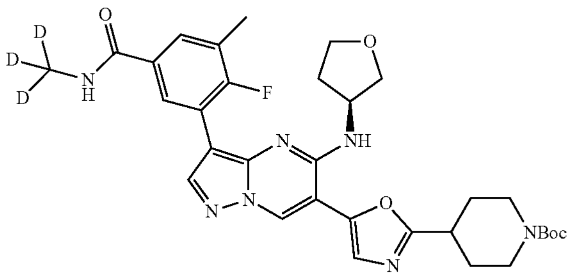 [SMILES: [2H]C([2H])([2H])NC(=O)c1cc(C)c(F)c(-c2cnn3cc(-c4cnc(C5CCN(C(=O)OC(C)(C)C)CC5)o4)c(N[C@H]4CCOC4)nc23)c1]

A mixture of (S)-3-(6-chloro-5-((tetrahydrofuran-3-yl)amino)pyrazolo[1,5-a]pyrimidin-3-yl)-4-fluoro-5-methyl-N-(methyl-$d_3$)benzamide (15 mg, 0.04 mmol), tert-butyl 4-(5-(4,4,5,5-tetramethyl-1,3,2-dioxaborolan-2-yl)oxazol-2-yl)piperidine-1-carboxylate (21 mg, 0.06 mmol), XPhos Pd G2 (2.9 mg, 3.7 μmol), and cesium carbonate (36 mg, 0.11 mmol) in dioxane (2.5 ml) and water (0.5 ml) was sparged with $N_2$ and heated to 100° C. for 1 h. The reaction mixture was partitioned between water and EtOAc, and the layers were separated. The aqueous phase was extracted with EtOAc and the combined organic layers were washed with brine, dried over $MgSO_4$, filtered, and concentrated. The product used without purification. LCMS calculated for $C_{32}H_{36}D_3FN_7O_5$ $(M+H)^+$: m/z=623.3; found: 623.4.

Step 5. (S)-4-Fluoro-3-(6-(2-(1-isopropylpiperidin-4-yl)oxazol-5-yl)-5-((tetrahydrofuran-3-yl)amino)pyrazolo[1,5-a]pyrimidin-3-yl)-5-methyl-N-(methyl-$d_3$)benzamide A solution of tert-butyl (S)-4-(5-(3-(2-fluoro-3-methyl-5-((methyl-$d_3$)carbamoyl)phenyl)-5-((tetrahydrofuran-3-yl)amino)pyrazolo[1,5-a]pyrimidin-6-yl)oxazol-2-yl)piperidine-1-carboxylate (22 mg, 0.04 mmol) in MeOH (2 ml) was treated with HCl (4M/dioxane, 2 ml) and stirred at room temperature for 30 min. The reaction mixture was concentrated and the product was used without purification.

The amine obtained above was dissolved in MeOH (2 ml). Acetone (52 μl, 0.7 mmol) was added, followed by sodium cyanoborohydride (22 mg, 0.4 mmol). The reaction mixture was stirred at room temperature overnight, then filtered and purified by prep HPLC. LCMS calculated for $C_{30}H_{34}D_3FN_7O_3$ $(M+H)^+$: m/z=565.3; found: 565.4.

Example 69. (S)-4-Fluoro-3-(6-(2-(4-fluoro-1-methylpiperidin-4-yl)oxazol-5-yl)-5-((tetrahydrofuran-3-yl)amino)pyrazolo[1,5-a]pyrimidin-3-yl)-N,5-dimethylbenzamide

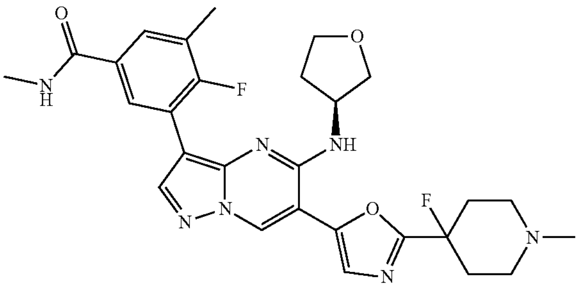

Step 1. tert-Butyl 4-hydroxy-4-(oxazol-2-yl)piperidine-1-carboxylate

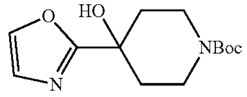 [SMILES: CC(C)(C)OC(=O)N1CCC(O)(c2ncco2)CC1]

To a solution of oxazole (100 mg, 1.45 mmol) in THE (6 ml) at room temperature was added borane tetrahydrofuran complex (1.45 ml, 1.45 mmol) dropwise. The reaction mixture was stirred at room temperature for 30 min and cooled to −78° C. Next, n-butyllithium (2.5M/hexanes, 0.58 ml, 1.45 mmol) was added dropwise, and the reaction was stirred at this temperature for 30 min. A solution of tert-butyl 4-oxopiperidine-1-carboxylate (289 mg, 1.45 mmol) in THF (3 mL) was then slowly added, and the reaction mixture was stirred for an additional 30 min at −78° C. The reaction was quenched with 5% AcOH/EtOH (2 mL total) and allowed to warm to room temperature. The reaction mixture was partitioned between water and EtOAc, and the layers were separated. The aqueous phase was extracted with EtOAc and the combined organic layers were washed with brine, dried over $MgSO_4$, filtered, and concentrated. The residue was purified by flash chromatography (0-100% EtOAc/hexanes)

to afford the title compound (330 mg, 85%). LCMS calculated for $C_9H_{13}N_2O_4$ $(M-C_4H_7)^+$: m/z=213.1; found: 213.2.

Step 2. tert-Butyl 4-fluoro-4-(oxazol-2-yl)piperidine-1-carboxylate

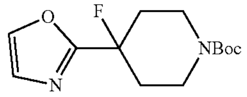 [SMILES: CC(C)(C)OC(=O)N1CCC(F)(c2ncco2)CC1]

To a solution of tert-butyl 4-hydroxy-4-(oxazol-2-yl)piperidine-1-carboxylate (110 mg, 0.41 mmol) in DCM (3 ml) at 0° C. was added DAST (108 μl, 0.82 mmol) and the reaction mixture was stirred at 0° C. for 15 min before being warmed to room temperature. After 1 h, the solution was cooled back to 0° C., quenched with saturated $NaHCO_3$, and extracted with DCM. The organic phase was dried over $MgSO_4$, filtered, and concentrated. The product was purified by flash chromatography (0-100% EtOAc/hexanes) to afford the title compound (76 mg, 69%). LCMS calculated for $C_9H_{12}FN_2O_3$ $(M-C_4H_7)^+$: m/z=215.1; found: 215.1.

Step 3. tert-Butyl 4-fluoro-4-(5-(4,4,5,5-tetramethyl-1,3,2-dioxaborolan-2-yl)oxazol-2-yl)piperidine-1-carboxylate

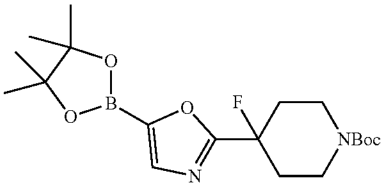 [SMILES: CC(C)(C)OC(=O)N1CCC(F)(c2ncc(B3OC(C)(C)C(C)(C)O3)o2)CC1]

To a solution of tert-butyl 4-fluoro-4-(oxazol-2-yl)piperidine-1-carboxylate (76 mg, 0.28 mmol) in THE (3 ml) at −78° C. was added n-butyllithium (225 μl, 0.56 mmol) (color change observed) and the reaction mixture was stirred at this temperature for 20 min. 2-Isopropoxy-4,4,5,5-tetramethyl-1,3,2-dioxaborolane (143 μl, 0.70 mmol) was added and stirred while the reaction mixture gradually warmed to room temperature over 2 h. The reaction was quenched with saturated $NH_4Cl$. EtOAc was added and the layers were separated. The organic phase was washed with brine, dried over $MgSO_4$, filtered and concentrated. The product was used without purification. The following data is reported for the corresponding boronic acid, which was the only observable species by LCMS. LCMS calculated for $C_9H_{13}BFN_2O_5$ $(M-C_4H_7)^+$: m/z=259.1; found: 259.1.

Step 4. tert-Butyl (S)-4-fluoro-4-(5-(3-(2-fluoro-3-methyl-5-(methylcarbamoyl)phenyl)-5-((tetrahydrofuran-3-yl)amino)pyrazolo[1,5-a]pyrimidin-6-yl)oxazol-2-yl)piperidine-1-carboxylate

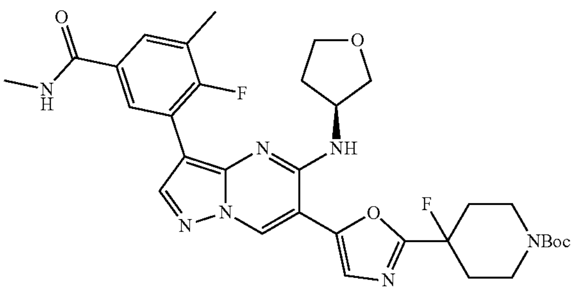 [SMILES: CNC(=O)c1cc(C)c(F)c(-c2cnn3cc(-c4cnc(C5(F)CCN(C(=O)OC(C)(C)C)CC5)o4)c(N[C@H]4CCOC4)nc23)c1]

This compound was prepared according to the procedure described in Example 68, Step 4, utilizing tert-butyl 4-fluoro-4-(5-(4,4,5,5-tetramethyl-1,3,2-dioxaborolan-2-yl)oxazol-2-yl)piperidine-1-carboxylate, (S)-3-(6-chloro-5-((tetrahydrofuran-3-yl)amino)pyrazolo[1,5-a]pyrimidin-3-yl)-4-fluoro-5-methyl-N-(methyl)benzamide, XPhos Pd G2, and cesium carbonate in dioxane and water. LCMS calculated for $C_{32}H_{38}F_2N_7O_5$ $(M+H)^+$: m/z=638.3; found: 638.4.

Step 5. (S)-4-Fluoro-3-(6-(2-(4-fluoro-1-methylpiperidin-4-yl)oxazol-5-yl)-5-((tetrahydrofuran-3-yl)amino)pyrazolo[1,5-a]pyrimidin-3-yl)-N,5-dimethylbenzamide This compound was prepared according to the procedure described in Example 68, Step 5, utilizing formaldehyde instead of acetone for the reductive amination. LCMS calculated for $C_{28}H_{32}F_2N_7O_3$ $(M+H)^+$: m/z=552.3; found: 552.4.

Example 70. (S)-4-Fluoro-N,3-dimethyl-5-(6-(2-(4-methylpiperazin-1-yl)oxazol-5-yl)-5-((tetrahydrofuran-3-yl)amino)pyrazolo[1,5-a]pyrimidin-3-yl)benzamide

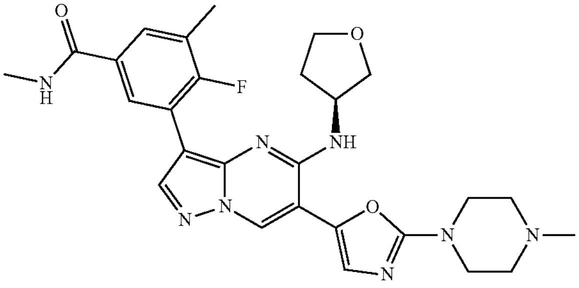

Step 1. tert-Butyl 4-(oxazol-2-yl)piperazine-1-carboxylate

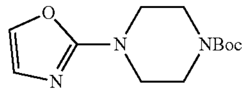 [SMILES: CC(C)(C)OC(=O)N1CCN(c2ncco2)CC1]

A mixture of 2-chlorooxazole hydrochloride (100 mg, 0.72 mmol), tert-butyl piperazine-1-carboxylate (200 mg, 1.07 mmol), RuPhos Pd G4 (30 mg, 0.04 mmol), and cesium carbonate (698 mg, 2.14 mmol) in dioxane (3 ml) was heated to 100° C. for 1 h. The reaction mixture was diluted with EtOAc, filtered and concentrated. The product was purified by flash chromatography (0-100% EtOAc/hexanes) to afford the title compound (72 mg, 40%). LCMS calculated for $C_{12}H_{20}N_3O_3$ $(M+H)^+$: m/z=254.1; found: 254.2.

Step 2. tert-Butyl 4-(5-(4,4,5,5-tetramethyl-1,3,2-dioxaborolan-2-yl)oxazol-2-yl)piperazine-1-carboxylate

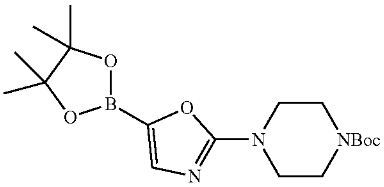 [SMILES: CC(C)(C)OC(=O)N1CCN(c2ncc(B3OC(C)(C)C(C)(C)O3)o2)CC1]

To a solution of tert-butyl 4-(oxazol-2-yl)piperazine-1-carboxylate (7' mg, 0.28 mmol) in THF (3 ml) at −78° C. was added n-butyllithium (221 μl, 0.55 mmol), and the reaction mixture was stirred at −78° C. for 20 min. 2-Isopropoxy-4,4,5,5-tetramethyl-1,3,2-dioxaborolane (141 μl, 0.69 mmol) was added and the reaction mixture was allowed to warm to room temperature. The reaction was quenched with saturated $NH_4Cl$ and extracted with EtOAc. The layers were separated and the organic phase was washed with brine, dried over $MgSO_4$, filtered and concentrated. The product was used without purification. The following data is reported for the corresponding boronic acid, which was the only observable species by LCMS. LCMS calculated for $C_{12}H_{21}BN_3O_5$ $(M+H)^+$: m/z=298.2; found: 298.1.

Step 3. tert-Butyl (S)-4-(5-(3-(2-fluoro-3-methyl-5-(methylcarbamoyl)phenyl)-5-((tetrahydrofuran-3-yl)amino)pyrazolo[1,5-a]pyrimidin-6-yl)oxazol-2-yl)piperazine-1-carboxylate

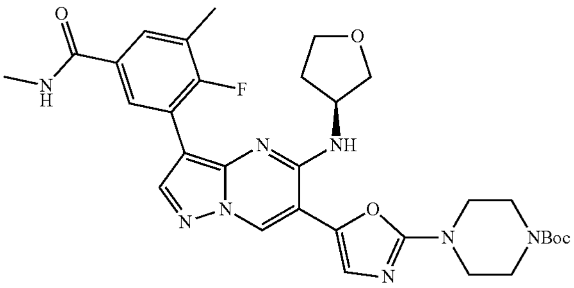 [SMILES: CNC(=O)c1cc(C)c(F)c(-c2cnn3cc(-c4cnc(N5CCN(C(=O)OC(C)(C)C)CC5)o4)c(N[C@H]4CCOC4)nc23)c1]

This compound was prepared according to the procedure described in Example 68, Step 4, utilizing tert-butyl 4-(5-(4,4,5,5-tetramethyl-1,3,2-dioxaborolan-2-yl)oxazol-2-yl)piperazine-1-carboxylate, (S)-3-(6-chloro-5-((tetrahydrofuran-3-yl)amino)pyrazolo[1,5-a]pyrimidin-3-yl)-4-fluoro-5-methyl-N-(methyl)benzamide, XPhos Pd G2, and cesium carbonate in dioxane and water. LCMS calculated for $C_{31}H_{38}FN_8O_5$ $(M+H)^+$: m/z=621.3; found: 621.4.

Step 4. (S)-4-Fluoro-N,3-dimethyl-5-(6-(2-(4-methylpiperazin-1-yl)oxazol-5-yl)-5-((tetrahydrofuran-3-yl)amino)pyrazolo[1,5-a]pyrimidin-3-yl)benzamide This compound was prepared according to the procedure described in Example 68, Step 5, utilizing formaldehyde instead of acetone for the reductive amination. LCMS calculated for $C_{27}H_{32}FN_8O_3$ $(M+H)^+$: m/z=535.3; found: 535.4.

Example A: FGFR Enzymatic Assay

The inhibitor potency of the exemplified compounds was determined in an enzyme discontinuous assay that measures peptide phosphorylation using FRET measurements to detect product formation. Inhibitors were serially diluted in DMSO and a volume of 0.2 μL was transferred to the wells of a 384-well plate. A 5 μL/well volume of enzyme isoforms of FGFR (-1, -2, -3 wild-type and mutant isoforms, -4) including phosphorylated and un-phosphorylated proteins diluted in assay buffer (50 mM HEPES, 10 mM $MgCl_2$, 1 mM EGTA, 0.01% Tween-20, 5 mM DTT, pH 7.5) was added to the plate and pre-incubated with inhibitor for 5 to 15 minutes at ambient temperature. Appropriate controls (enzyme blank and enzyme with no inhibitor) were included on the plate. The reaction was initiated by the addition of a 5 μL/well volume containing both biotinylated EQEDEPEGDYFEWLE peptide substrate (SEQ ID NO: 1) and ATP in assay buffer. The 10 μL/well reaction concentration of the peptide substrate was 500 nM whereas the ATP concentration was maintained near or below the ATP Km. The ATP Km values were pre-determined in a separate series of experiments. The reaction plate was incubated at 25° C. for 1 hr and the reactions were ended with the addition of 5 μL/well of quench solution (50 mM Tris, 150 mM NaCl, 0.5 mg/mL BSA, pH 7.8; 45 mM EDTA, 600 nM staurosporin, with Perkin Elmer Lance Reagents at 3.75 nM Eu-antibody PY20 and 180 nM APC-Streptavidin). The plate was allowed to equilibrate for ~10 minutes at ambient temperature before scanning on a PheraStar plate reader (BMG Labtech) instrument.

Either GraphPad prism or XLfit was used to analyze the data. The $IC_{50}$ values were derived by fitting the data to a four parameter logistic equation producing a sigmoidal dose-response curve with a variable Hill coefficient. Prism equation: Y=Bottom+(Top− Bottom)/(1+10^((Log $IC_{50}$−X)*Hill slope)); XLfit equation: Y=(A+((B−A)/(1+((X/C)^D)))) where X is the logarithm of inhibitor concentration and Y is the response. Compounds having an $IC_{50}$ of 1 μM or less are considered active.

Table 1 provides $IC_{50}$ data for compounds of the invention assayed in the FGFR Enzymatic Assay after dilution in assay buffer, added to the plate and pre-incubated for 4 hours.

The symbol: "+" indicates an $IC_{50}$ less than 10 nM; "++" indicates an $IC_{50}$ greater than or equal to 10 nM but less than 30 nM; "+++" indicates an $IC_{50}$ greater than or equal to 30 nM but less than 200 nM; and "++++" indicates an $IC_{50}$ greater than or equal to 200 nM.

The FGFR3 data in Table 1 was measured in wild-type un-phosphorylated FGFR3 protein.

TABLE 1

| Example No. | FGFR3 $IC_{50}$ (nM) | FGFR1 $IC_{50}$ (nM) | FGFR2 $IC_{50}$ (nM) | FGFR4 $IC_{50}$ (nM) |
|---|---|---|---|---|
| 1 | + | +++ | + | |
| 2 | + | +++ | + | |
| 3 | + | +++ | + | ++++ |
| 4 | + | +++ | + | +++ |
| 5 | + | + | + | |
| 6 | + | ++ | + | |
| 7 | + | +++ | | |
| 8 | + | +++ | | |
| 9 | + | ++ | + | |
| 10 | + | +++ | | |
| 11 | + | + | + | |
| 12 | + | + | + | |
| 13 | + | ++ | + | |
| 14 | + | + | + | |
| 15 | + | +++ | + | |
| 16 | + | +++ | + | |
| 17 | + | + | + | |
| 18 | + | +++ | + | |
| 19 | + | +++ | + | |
| 20 | + | +++ | + | |
| 21 | + | +++ | + | |
| 22 | + | ++ | + | |
| 23 | + | +++ | + | |
| 24 | ++ | ++++ | ++ | |
| 25 | + | +++ | + | |
| 26 | + | + | + | |
| 27 | ++ | ++++ | ++ | |
| 28 | + | ++++ | ++ | |
| 29 | +++ | ++++ | +++ | |
| 30 | + | +++ | ++ | |
| 31 | + | ++ | + | |
| 32 | ++++ | ++++ | +++ | |
| 33 | + | ++ | + | +++ |
| 34 | + | ++ | + | +++ |
| 35 | + | ++ | + | ++++ |
| 36 | + | +++ | + | |
| 37 | + | ++ | + | |
| 38 | + | +++ | + | |
| 39 | + | ++ | + | |
| 40 | + | ++ | + | +++ |
| 41 | + | +++ | + | +++ |
| 42 | + | ++ | + | +++ |
| 43 | + | ++ | + | +++ |
| 44 | ++ | ++++ | ++ | |
| 45 | + | ++ | + | ++++ |
| 46 | ++ | ++ | + | ++++ |
| 47 | + | ++ | + | |
| 48 | + | ++ | + | |
| 49 | + | ++ | + | |
| 50 | + | ++ | + | |
| 51 | + | ++ | + | ++++ |
| 52 | + | + | + | |
| 53 | + | ++ | + | ++++ |
| 54 | + | + | + | |
| 55 | + | + | + | +++ |
| 56 | + | ++ | + | |
| 57 | + | +++ | + | |
| 58 | + | + | + | +++ |
| 59 | + | + | + | ++ |
| 60 | + | +++ | + | ++++ |
| 61 | + | +++ | + | +++ |
| 62 | ++ | +++ | ++ | ++++ |
| 63 | + | ++ | + | +++ |
| 64 | + | + | + | ++ |
| 65 | + | ++ | + | +++ |
| 66 | + | +++ | + | +++ |
| 67 | + | + | + | |
| 68 | + | +++ | + | |
| 69 | + | +++ | + | |
| 70 | + | +++ | + | |

Example B: Luminescent Viability Assay

RT112 cells are purchased from ATCC (Manassas, Va.) and maintained in RPMI, 10% FBS (Gibco/Life Technologies). To measure the effect of test compounds on the viability of cells, the cells are plated with RPMI 10% FBS ($5\times10^3$ cells/well/in 50 μL) into black 96-well Greiner polystyrene in the presence or absence of 50 ul of a concentration range of test compounds. After 3 days, 100 ul of CellTiter-Glo Reagent (Promega) is added. Luminescence is read with a TopCount (PerkinElmer). $IC_{50}$ determination is performed by fitting the curve of percent inhibition versus the log of the inhibitor concentration using the GraphPad Prism 5.0 software.

Example C: pFGFR2 and pFGFR1,3 Functional Cell HTRF Assay

To measure phosphorylated Fibroblast Growth Factor Receptor 2 (FGFR2), KATOIII cells (Human Gastric Carcinoma) are purchased from ATCC and maintained in Iscove's with 20% FBS (Gibco/Life Technologies). For the pFGFR2 assay, KATOIII cells are plated overnight in 5% FBS and Iscove's medium at $5\times10^4$ cells/well into Corning 96-well flat-bottom tissue culture treated plates. The next morning, 50 μl of fresh media with 0.5% FBS is incubated in the presence or absence of a concentration range of test compounds also at 50 ul, for 1 hour at 37° C., 5% CO2. Cell are washed with PBS, lysed with Cell Signaling Lysis Buffer with standard Protease inhibitors for 45 min at room temperature. 4 μl total of Cis Bio Anti Phospho-YAP d2 and Cis Bio Anti Phospho-YAP Cryptate together are added to the lysate and mixed well (following directions of the kit). 16 μl is then transferred to 384 well Greiner white plates and stored at 4° C. overnight in the dark. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 5.0 software.

To measure phosphorylated Fibroblast Growth Factor Receptor 3 (FGFR3), in house stable cell lines BAF3-TEL-FGFR1 or BAF3-TEL-FGFR3 are maintained in RPMI with 10% FBS and 1 ug/ml puromycin (Gibco/Life Technologies). For the assay, 12 nl of BAF3-TEL-FGFR1 or BAF3-TEL-FGFR3 cells in serum free and puromycin free RPMI media at $1\times10^6$ cell/ml are added to 384 Greiner white plate already containing 20 nl dots of compounds at a concentration range. The plates are gently shaken (100 rpm) for 2 minutes at room temperature to mix well and incubate for 2 hours in a single layer at 37° C., 5% CO2. 4 μl/well of 1/25 dilution of lysis buffer #3 (Cis Bio) is added with standard Protease inhibitors and shaken at 200 rpm at room temperature for 20 minutes. 4 μl total of the Cis Bio Tb-pFGFR Ab (Ong) and d2-FGFR3 (ing) together are added to the lysate and mixed well. The plates are sealed and incubated at room temperature overnight in the dark. The plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 5.0 software.

Example D: pFGFR3 Functional Whole Blood HTRF Assay

To measure phosphorylated Fibroblast Growth Factor Receptor 3 (FGFR3) in a whole blood assay, in house stable cell lines BAF3-TEL-FGFR3 are maintained in RPMI with 10% FBS and 1 μg/ml puromycin (Gibco/Life Technologies). For the assay, 100 ul BAF3-TEL-FGFR3 cells in 10% FBS and puromycin free RPMI media at $5\times10^4$ cell/well are added to fibronectin coated 96 well tissue culture plate (5 ug/ml) overnight at 37° C., 5% CO2. The next day, serum is separated from the top of the blood by a low speed spin, 1200, RPM, and heat inactivated by incubating at 56° C. for 15 minutes. 30 μl of the cooled serum is added to a 96 well plate pre dotted with 70 nM dots of compounds at a concentration range. Cell plates are washed gently with media, all the blood/compound mixture is added to the plates, and the plates are incubated for 2 hours at 37° C., 5% CO2. Blood from the plate is gently washed twice by adding media to the side of the wells and then dumping media from the plate, and allowing the plate to briefly sit on a paper towel to drain. 70 μl/well of 1× of lysis buffer #1 (Cis Bio) are added with standard Protease inhibitors, and are shaken at 400 rpm at room temperature for 30 minutes. Following lysis, the plate is spun down for 5 minutes and 16 uL of lysate is transferred into a 384-well small volume plate. 4 μl total of the Cis Bio Tb-pFGFR Ab (Ong) and d2-FGFR3 (Ing) together are added to the lysate and mixed well. The plates are sealed and incubated at room temperature overnight in the dark. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 5.0 software.

Example E: KATOIII Whole Blood pFGFR2α ELISA Assay

To measure tyrosine-phosphorylated Fibroblast Growth Factor Receptor 2 alpha (FGFR2α) in KATO III spiked whole blood assay, KATO III cells are purchased from ATCC and maintained in Iscove's medium with 20% FBS (Gibco/Life Technologies). To measure the inhibition of FGFR2α activity of test compounds, the cells are resuspended with Iscove's, 0.2% FBS at $5\times10^6$ cells/ml. 50 μL of the cells are then spiked into a 96-deep well 2 ml polypropylene assay block (Costar,) in the presence or absence of a concentration range of test compounds and 300 ul human heparinized whole blood (Biological Specialty Corp, Colmar Pa.). After 4 hours incubation in 37° C., the red cells are lysed using Qiagen EL buffer and the cell lysates are resuspended in lysis buffer (Cell Signaling) containing standard protease inhibitor cocktail (Calbiochem/EMD,) and PMSF (Sigma) for 30 minutes ice. The lysates are transferred to a standard V bottom propylene tissue culture plate and frozen overnight at −80° C. Samples are tested an in an R & D Systems DuoSet IC Human Phospho-FGF R2α ELISA and the plate is measured using a SpectraMax M5 microplate set to 450 nm with a wavelength correction of 540. $IC_{50}$ determination is performed by fitting the curve of inhibitor percent inhibition versus the log of the inhibitor concentration using the GraphPad Prism 5.0 software.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula (I):

I

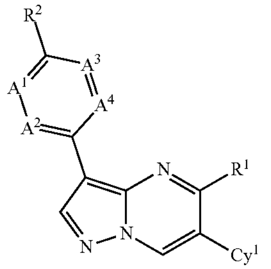

or a pharmaceutically acceptable salt thereof, wherein:

$Cy^1$ is selected from $C_{6-10}$ aryl and 5-10 membered heteroaryl; wherein the 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

$R^1$ is $OR^3$ or $NR^4R^5$;

$R^2$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a2}$, $SR^{a2}$, $C(O)R^{b2}$, $C(O)NR^{c2}R^{d2}$, $C(O)OR^{a2}$, $NR^{c2}R^{d2}$ $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{20}$;

$A^1$ is selected from N and $CR^6$;

$A^2$ is selected from N and $CR^7$;

$A^3$ is selected from N and $CR^8$;

$A^4$ is selected from N and $CR^9$;

$R^3$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-14 membered heterocycloalkyl, $C_{6-10}$ aryl, 5-10 membered heteroaryl, $C_{3-10}$ cycloalkyl-$C_{1-3}$ alkylene, 4-14 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl is substituted with 1, 2, 3, or 4 substituents independently selected from $R^{30A}$; and wherein said $C_{2-6}$ alkenyl, $C_{2-6}$ alkynyl, $C_{3-10}$ cycloalkyl, 4-14 membered heterocycloalkyl, $C_{6-10}$ aryl, 5-10 membered heteroaryl, $C_{3-10}$ cycloalkyl-$C_{1-3}$ alkylene, 4-14 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{30}$;

$R^4$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-14 membered heterocycloalkyl, $C_{6-10}$ aryl, 5-10 membered heteroaryl, $C_{3-10}$ cycloalkyl-$C_{1-3}$ alkylene, 4-14 membered heterocycloalkyl-$C_{1-3}$ alkylene, $C_{6-10}$ aryl-$C_{1-3}$ alkylene, and 5-10 membered heteroaryl-$C_{1-3}$ alkylene; wherein said $C_{1-6}$ alkyl, $C_{2-6}$ alkenyl, $C_{2-6}$ alkynyl, $C_{3-10}$ cycloalkyl, 4-14 membered heterocycloalkyl, $C_{6-10}$ aryl, 5-10 membered heteroaryl, $C_{3-10}$ cycloalkyl-$C_{1-3}$ alkylene, 4-14 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{40}$;

$R^5$ is selected from H and $C_{1-6}$ alkyl; wherein said $C_{1-6}$ alkyl is optionally substituted with 1 or 2 substituents independently selected from $R^g$;

$R^6$, $R^7$, $R^8$, and $R^9$ are each independently selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a2}$, $SR^{a2}$, $C(O)R^{b2}$, $C(O)NR^{c2}R^{d2}$, $C(O)OR^{a2}$, $NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{20}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$alkylene, $C_{6-10}$ aryl-$C_{1-3}$alkylene, 5-10 membered heteroaryl-$C_{1-3}$ alkylene, halo, D, CN, $NO_2$, $OR^{a1}$ $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}$ $S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$ $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$,$NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a4}$, $SR^{a4}$, $C(O)R^{b4}$, $C(O)OR^{a4}$, $NR^{c4}R^{d4}$, $NR^{c4}C(O)R^{b4}$, $NR^{c4}C(O)OR^{a4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^{30A}$ is independently selected from $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a6}$, $SR^{a6}$, $C(O)R^{b6}$, $C(O)NR^{c6}R^{d6}$, $C(O)OR^{a6}$, $NR^{c6}R^{d6}$ $NR^{c6}C(O)R^{b6}$, $NR^{c6}C(O)OR^{a6}$, $NR^{c6}$ $S(O)R^{b6}$, $NR^{c6}$ $S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{31}$;

each $R^{30}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}S(O)R^{b6}$, $NR^{c6}S(O)_2R^{b6}$, $NR^{c6}$ $S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{31}$;

each $R^{31}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $NR^{c8}C(O)OR^{a8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, and $S(O)_2NR^{c8}$ $R^{d8}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^{40}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a7}$, $SR^{a7}$, $C(O)R^{b7}$, $C(O)NR^{c7}R^{d7}$, $C(O)OR^{a7}$, $NR^{c7}R^{d7}$ $NR^{c7}C(O)R^{b7}$, $NR^{c7}C(O)OR^{a7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, and $S(O)_2NR^{c7}R^{d7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{41}$;

each $R^{41}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a9}$, $SR^{a9}$, $C(O)R^{b9}$, $C(O)NR^{c9}R^{d9}$, $C(O)OR^{a9}$, $NR^{c9}R^{d9}$, $NR^{c9}C(O)R^{b9}$, $NR^{c9}C(O)OR^{a9}$,$NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

or any $R^{c1}$ and $R^{d1}$ attached to the same N atom, together with the N atom to which they are attached, form a 4–, 5–, 6– or 7– membered heterocycloalkyl group optionally substituted with 1, 2, 3, or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, amino sulfonyl, $C_{1-6}$ alkylaminosulfonyl and di($C_{1-6}$ alkyl)aminosulfonyl;

each $R^{a2}$, $R^{c2}$, and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{20}$;

or any $R^{c2}$ and $R^{d2}$ attached to the same N atom, together with the N atom to which they are attached, form a 4-, 5-, 6- or 7- membered heterocycloalkyl group optionally substituted with 1, 2 or 3 substituents independently selected from $R^{20}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{20}$;

each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7- membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

or any $R^{c4}$ and $R^{d4}$ attached to the same N atom, together with the N atom to which they are attached, form a 4-, 5-, 6- or 7- membered heterocycloalkyl group optionally substituted with 1, 2 or 3 substituents independently selected from $R^g$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^{a5}$, $R^{c5}$ and $R^{d5}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c5}$ and $R^{d5}$ attached to the same N atom, together with the N atom to which they are attached, form a 4-, 5-, 6- or 7- membered heterocycloalkyl group optionally substituted with 1, 2, 3, or 4 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{31}$;

or any $R^{c6}$ and $R^{d6}$ attached to the same N atom, together with the N atom to which they are attached, form a 4-, 5-, 6- or 7- membered heterocycloalkyl group optionally substituted with 1, 2 or 3 substituents independently selected from $R^{31}$;

each $R^{b6}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{31}$;

each $R^{a7}$, $R^{c7}$ and $R^{d7}$is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{41}$;

or any $R^{c7}$and $R^{d7}$attached to the same N atom, together with the N atom to which they are attached, form a 4-, 5-, 6- or 7- membered heterocycloalkyl group optionally substituted with 1, 2 or 3 substituents independently selected from $R^{41}$;

each $R^{b7}$is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{41}$;

each $R^{a8}$, $R^{c8}$ and $R^{d8}$is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b8}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a9}$, $R^{c9}$ and $R^{d9}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b9}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO-$C_{1-3}$ alkoxy, HO-$C_{1-3}$ alkyl, cyano-$C_{1-3}$ alkyl, $H_2N$-$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The compound of claim 1, or a pharmaceutically acceptable salt thereof, wherein $A^1$ is $CR^6$.

3. The compound of claim 1, or a pharmaceutically acceptable salt thereof, wherein $A^2$ is $CR^7$.

4. The compound of claim 1, or a pharmaceutically acceptable salt thereof, wherein $A^3$ is $CR^8$.

5. The compound of claim 1, or a pharmaceutically acceptable salt thereof, wherein $A^3$ is N.

6. The compound of claim 1, or a pharmaceutically acceptable salt thereof, wherein $A^4$ is $CR^9$.

7. The compound of claim 1, or a pharmaceutically acceptable salt thereof, wherein $A^1$ is $CR^6$; $A^2$ is $CR^7$; $A^3$ is $CR^8$; and $A^4$ is $CR^9$.

8. The compound of claim 1, or a pharmaceutically acceptable salt thereof, wherein $A^1$ is $CR^6$; $A^2$ is $CR^7$; $A^3$ is N; and $A^4$ is $CR^9$.

9. The compound of claim 1, or a pharmaceutically acceptable salt thereof, wherein $A^1$ is $CR^6$; $A^2$ is $CR^7$; and $A^4$ is $CR^9$.

10. The compound of claim 1, or a pharmaceutically acceptable salt thereof, wherein $R^6$, $R^7$, $R^8$, and $R^9$ are each independently selected from H, D, $C_{1-6}$ alkyl, $C_{1-6}$ haloalkyl, halo, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein said $C_{1-6}$ alkyl is optionally substituted with 1, 2, 3, or 4 substituents independently selected from $R^{20}$.

11. The compound of claim 1, or a pharmaceutically acceptable salt thereof, wherein $R^6$, $R^7$, $R^8$, and $R^9$ are each independently selected from H, D, $C_{1-6}$ alkyl, $C_{1-6}$ haloalkyl, 5-10 membered heteroaryl, halo, CN, $OR^{a2}$, $C(O)R^{b2}$, $C(O)NR^{c2}R^{d2}$, $C(O)OR^{a2}$, $NR^{c2}R^{d2}$ $S(O)_2R^{b2}$, and $S(O)_2NR^{c2}R^{d2}$; wherein said $C_{1-6}$ alkyl is optionally substituted with 1, 2, 3, or 4 substituents independently selected from $R^{20}$.

12. The compound of claim 1, or a pharmaceutically acceptable salt thereof, wherein $R^6$, $R^7$, $R^8$, and $R^9$ are each independently selected from H, $C_{1-6}$ alkyl, $C_{1-6}$ haloalkyl, halo, CN, $OR^{a2}$, $C(O)NR^{c2}R^{d2}$, and $S(O)_2R^{b2}$.

13. The compound of claim 1, or a pharmaceutically acceptable salt thereof, wherein $R^6$, $R^7$, $R^8$, and $R^9$ are each independently selected from H, $C_{1-6}$ alkyl, $C_{1-6}$ haloalkyl, 5-10 membered heteroaryl, halo, CN, $OR^{a2}$, $C(O)NR^{c2}R^{d2}$, and $S(O)_2R^{b2}$.

14. The compound of claim 1, or a pharmaceutically acceptable salt thereof, wherein $R^6$ is H or $C(O)NR^{c2}R^{d2}$.

15. The compound of claim 1, or a pharmaceutically acceptable salt thereof, wherein $R^6$ is H or $C(O)NHCH_3$.

16. The compound of claim 1, or a pharmaceutically acceptable salt thereof, wherein $R^6$ is H or 5-10 membered heteroaryl.

17. The compound of claim 1, or a pharmaceutically acceptable salt thereof, wherein $R^7$ is H.

18. The compound of claim 1, or a pharmaceutically acceptable salt thereof, wherein $R^8$ is H, $C_{1-6}$ alkyl, $C_{1-6}$ haloalkyl, halo, CN, $OR^{a2}$, or $S(O)_2R^{b2}$.

19. The compound of claim 1, or a pharmaceutically acceptable salt thereof, wherein $R^8$ is H, methyl, $CHF_2$, F, CN, OH, or $S(O)_2(CH_3)_2$.

20. The compound of claim 1, or a pharmaceutically acceptable salt thereof, wherein $R^9$ is H or halo.

21. The compound of claim 1, or a pharmaceutically acceptable salt thereof, wherein $R^9$ is H or F.

22. The compound of claim 1, or a pharmaceutically acceptable salt thereof, wherein $R^1$ is $OR^3$.

23. The compound of claim 1, or a pharmaceutically acceptable salt thereof, wherein $R^1$ is $NR^4R^5$.

24. The compound of claim 1, or a pharmaceutically acceptable salt thereof, wherein $R^3$ is selected from $C_{1-6}$ alkyl, $C_{1-6}$ haloalkyl, $C_{3-6}$ cycloalkyl, 4-6 membered heterocycloalkyl, phenyl, and 5-6 membered heteroaryl; wherein said $C_{1-6}$ alkyl is substituted with 1, 2, 3, or 4 substituents independently selected from $R^{30A}$ and wherein said 4-6 membered heterocycloalkyl, phenyl, and 5-6 membered heteroaryl are each optionally substituted with 1, 2, 3, or 4 substituents independently selected from $R^{30}$.

25. The compound of claim 1, or a pharmaceutically acceptable salt thereof, wherein $R^3$ is 4-6 membered heterocycloalkyl optionally substituted with 1 or 2 substituents independently selected from $R^{30}$.

26. The compound of claim 1, or a pharmaceutically acceptable salt thereof, wherein $R^3$ is tetrahydrofuran-3-yl optionally substituted with 1 or 2 substituents independently selected from $R^{30}$.

27. The compound of claim 1, or a pharmaceutically acceptable salt thereof, wherein $R^3$ is tetrahydrofuran-3-yl.

28. The compound of claim 1, or a pharmaceutically acceptable salt thereof, wherein $R^4$ is selected from $C_{1-6}$ alkyl, $C_{1-6}$ haloalkyl, $C_{3-6}$ cycloalkyl, 4-6 membered heterocycloalkyl, $C_{6-10}$ aryl, and 5-6 membered heteroaryl; wherein said $C_{1-6}$ alkyl, $C_{3-6}$ cycloalkyl, 4-6 membered heterocycloalkyl, $C_{6-10}$ aryl, and 5-6 membered heteroaryl are each optionally substituted with 1, 2, 3, or 4 substituents independently selected from $R^{40}$.

29. The compound of claim 1, or a pharmaceutically acceptable salt thereof, wherein $R^4$ is 4-6 membered heterocycloalkyl optionally substituted with 1, 2, 3, or 4 substituents independently selected from $R^{40}$.

30. The compound of claim 1, or a pharmaceutically acceptable salt thereof, wherein $R^4$ is tetrahydrofuran-3-yl.

31. The compound of claim 1, or a pharmaceutically acceptable salt thereof, wherein $R^5$ is H.

32. The compound of claim 1, or a pharmaceutically acceptable salt thereof, wherein $R^2$ is H.

33. The compound of claim 1, or a pharmaceutically acceptable salt thereof, wherein $Cy^1$ is 5-6 membered heteroaryl optionally substituted with 1 or 2 substituents independently selected from $R^{10}$.

34. The compound of claim 1, or a pharmaceutically acceptable salt thereof, wherein $Cy^1$ is phenyl optionally substituted with 1 or 2 substituents independently selected from $R^{10}$.

35. The compound of claim 1, or a pharmaceutically acceptable salt thereof, wherein $Cy^1$ is selected from phenyl and 5-6 membered heteroaryl; wherein the phenyl and 5-6 membered heteroaryl are each optionally substituted with 1 or 2 substituents independently selected from $R^{10}$.

36. The compound of claim 1, or a pharmaceutically acceptable salt thereof, wherein $Cy^1$ is phenyl, pyrazolyl or pyridinyl, each of which is optionally substituted with 1 or 2 substituents independently selected from $R^{10}$.

37. The compound of claim 1, or a pharmaceutically acceptable salt thereof, wherein $Cy^1$ is phenyl, pyrazolyl, triazolyl, oxazolyl, 2-oxo-1,2-dihydropyridinyl, pyridazinyl, or pyridinyl, each of which is optionally substituted with 1 or 2 substituents independently selected from $R^{10}$.

38. The compound of claim 1, or a pharmaceutically acceptable salt thereof, wherein $Cy^1$ is pyrazolyl optionally substituted with 1 or 2 substituents independently selected from $R^{10}$.

39. The compound of claim 1, or a pharmaceutically acceptable salt thereof, wherein each $R^{10}$ is independently selected from $C_{1-6}$ alkyl, $C_{1-6}$ haloalkyl, $C_{3-6}$ cycloalkyl, 4-6 membered heterocycloalkyl, halo, D, CN, $OR^{a1}$, and $NR^{c1}R^{d1}$; wherein said $C_{1-6}$ alkyl and 4-6 membered heterocycloalkyl are each optionally substituted with 1 or 2 substituents independently selected from $R^{11}$.

40. The compound of claim 1, or a pharmaceutically acceptable salt thereof, wherein each $R^{10}$ is independently selected from methyl, ethyl, propyl, isopropyl, piperidinyl, piperazinyl, azetidinyl, morpholino, cyclopropyl, and cyclobutyl; each of which is optionally substituted with 1 or 2 substituents independently selected from $R^{11}$.

41. The compound of claim 1, or a pharmaceutically acceptable salt thereof, wherein each $R^{10}$ is independently selected from methyl, ethyl, propyl, isopropyl, piperidinyl, piperazinyl, azetidinyl, morpholino, cyclopropyl, ethylamino, and cyclobutyl; each of which is optionally substituted with 1 or 2 substituents independently selected from $R^{11}$.

42. The compound of claim 1, or a pharmaceutically acceptable salt thereof, wherein each $R^{10}$ is independently selected from methyl, isopropyl, 2-hydroxypropan-2-yl, $NH(CH_3)$, methylpiperidin-4-yl, methylpiperazin-1-yl, morpholinoethyl, 1-methylazetidin-3-yl, morpholino, cyclopropyl, and cyclobutyl.

43. The compound of claim 1, or a pharmaceutically acceptable salt thereof, wherein each $R^{10}$ is independently selected from methyl, ethyl, isopropyl, 2-hydroxypropan-2-yl, $NH(CH_3)$, methylpiperidin-4-yl, methylpiperazin-1-yl, morpholinoethyl, 1-methylazetidin-3-yl, morpholino, cyclopropyl, ethylamino, hydroxyethyl-2-yl, cyanoethyl-2-yl, dimethylamino-2-oxoethyl, 2-hydroxy-2-methylpropyl, 2-methoxyethyl, pyridin-3-ylmethyl, (tetrahydro-2H-pyran-4-yl)methyl, 2-morpholinoethyl, 3-fluoro-1-methylpiperidin-4-yl, ((1R,4R)-2-Oxa-5-azabicyclo[2.2.1]heptan-5-yl) methyl, 1-isopropylpiperidin-4-yl, 4-fluoro-1-methylpiperidin-4-yl, 4-methylpiperazin-1-yl, tetrahydrofuran-3-yl, 1,1-dioxidotetrahydrothiophen-3-yl, and cyclobutyl.

44. The compound of claim 1, or a pharmaceutically acceptable salt thereof, wherein $R^{10}$ is methyl.

45. The compound of claim 1, or a pharmaceutically acceptable salt thereof, wherein each $R^{11}$ is independently selected from $C_{1-6}$ alkyl, 4-6 membered heterocycloalkyl, and $OR^{a3}$; wherein said $C_{1-6}$ alkyl and 4-6 membered heterocycloalkyl are each optionally substituted with 1 or 2 substituents independently selected from $R^{12}$.

46. The compound of claim 1, or a pharmaceutically acceptable salt thereof, wherein each $R^{11}$ is independently selected from $C_{1-6}$ alkyl, CN, 4-7 membered heterocycloalkyl, $C(O)NR^{c3}R^{d3}$, halo, 5-10 membered heteroaryl, and $OR^{a3}$; wherein said $C_{1-6}$ alkyl and 4-7 membered heterocycloalkyl are each optionally substituted with 1 or 2 substituents independently selected from $R^{12}$.

47. The compound of claim 1, or a pharmaceutically acceptable salt thereof, wherein each $R^{11}$ is independently selected from $C_{1-6}$ alkyl, 4-6 membered heterocycloalkyl, and $OR^{a3}$.

48. The compound of claim 1, or a pharmaceutically acceptable salt thereof, wherein each $R^{11}$ is independently selected from $C_{1-6}$ alkyl, CN, 4-7 membered heterocycloalkyl, $C(O)NR^{c3}R^{d3}$, halo, and $OR^{a3}$.

49. The compound of claim 1, or a pharmaceutically acceptable salt thereof, wherein each $R^{11}$ is independently selected from methyl, OH, and morpholino.

50. The compound of claim 1, or a pharmaceutically acceptable salt thereof, wherein each $R^{11}$ is independently selected from methyl, OH, methoxy, CN, $C(O)N(CH_3)_2$, isopropyl, pyridinyl, tetrahydropyranyl, fluoro, 2-oxa-5-azabicyclo[2.2.1]heptanyl, and morpholino.

51. The compound of claim 1, each $R^{20}$ is independently selected from D.

52. The compound of claim 1, having Formula IIa:

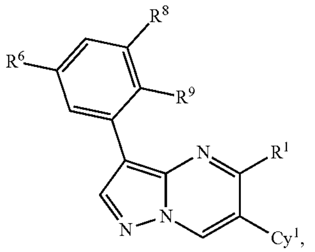

IIa or a pharmaceutically acceptable salt thereof.

53. The compound of claim 1, having Formula IIb:

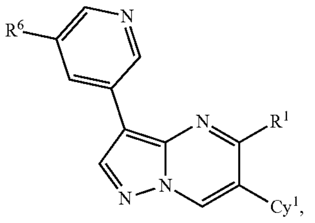

IIb or a pharmaceutically acceptable salt thereof.

54. The compound of claim 1, having Formula IIIa:

IIIa

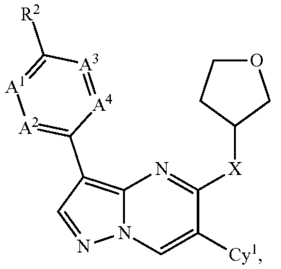

or a pharmaceutically acceptable salt thereof, wherein X is O or NH.

55. The compound of claim 1, having Formula IIIb:

IIb

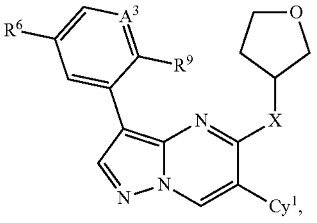

or a pharmaceutically acceptable salt thereof, wherein X is O or NH.

56. The compound of claim 1, having Formula IVc:

IVc

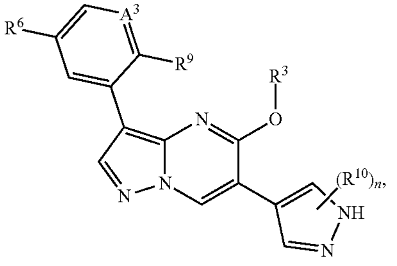

or a pharmaceutically acceptable salt thereof, wherein n is 0, 1, or 2.

57. The compound of claim 1, or a pharmaceutically acceptable salt thereof, wherein:

$Cy^1$ is selected from $C_{6-10}$ aryl and 5-10 membered heteroaryl; wherein each 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

$R^1$ is $OR^3$ or $NR^4R^5$;

$R^2$ is selected from H, D, and halo;

$A^1$ is selected from N and $CR^6$;

$A^2$ is selected from N and $CR^7$;

$A^3$ is selected from N and $CR^8$;

$A^4$ is selected from N and $CR^9$;

$R^3$ is selected from $C_{1-6}$ alkyl, $C_{1-6}$ haloalkyl, $C_{3-10}$ cycloalkyl, 4-14 membered heterocycloalkyl, wherein said $C_{3-10}$ cycloalkyl, and 4-14 membered heterocycloalkyl, are each optionally substituted with 1, 2, 3, or 4 substituents independently selected from $R^{30}$;

$R^4$ is selected from $C_{1-6}$ alkyl, $C_{1-6}$ haloalkyl, $C_{3-10}$ cycloalkyl, and 4-14 membered heterocycloalkyl; wherein said $C_{1-6}$ alkyl, $C_{3-10}$ cycloalkyl, and 4-14 membered heterocycloalkyl, are each optionally substituted with 1, 2, 3, or 4 substituents independently selected from $R^{40}$;

$R^5$ is H;

$R^6$, $R^7$, $R^8$, and $R^9$ is each independently selected from H, D, $C_{1-6}$ alkyl, $C_{1-6}$ haloalkyl, 5-10 membered heteroaryl, halo, CN, $OR^{a2}$, $C(O)R^{b2}$, $C(O)NR^{c2}R^{d2}$, $C(O)OR^{a2}$, $NR^{c2}R^{d2}$, $S(O)_2R^{b2}$, and $S(O)_2NR^{c2}R^{d2}$; wherein said $C_{1-6}$ alkyl and 5-10 membered heteroaryl are each optionally substituted with 1, 2, 3, or 4 substituents independently selected from $R^{20}$;

each $R^{10}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a1}$, $C(O)R^{b1}$, $C(O)NR^{c1}R^{d1}$, $C(O)R^{a1}$, $NR^{c1}R^{d1}$, $NR^{c1}$ $C(O)R^{b1}$, and $S(O)_2R^{b1}$; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$;

each $R^{11}$ is independently selected from $C_{1-6}$ alkyl, $C_{1-6}$ haloalkyl, $C_{3-10}$ cycloalkyl, 4-10 membered heterocycloalkyl, 5-10 membered heteroaryl, halo, D, CN, $OR^{a3}$, $C(O)R^{b3}$, $C(O)NR^{c3}R^{d3}$, $C(O)OR^{a3}$, $NR^{c3}R^{d3}$, and $S(O)_2R^{b3}$; wherein said $C_{1-6}$ alkyl, $C_{3-10}$ cycloalkyl, 4-10 membered heterocycloalkyl, and 5-10 membered heteroaryl are each optionally substituted with 1, 2, 3, or 4 substituents independently selected from $R^{12}$;

each $R^{12}$ is independently selected from $C_{1-6}$ alkyl, $C_{1-6}$ haloalkyl, halo, D, CN, $OR^{a5}$, and $NR^{c5}R^{d5}$;

each $R^{20}$ is independently selected from $C_{1-6}$ alkyl, $C_{1-6}$ haloalkyl, halo, D, CN, $OR^{a4}$, and $NR^{c4}R^{d4}$;

each $R^{30}$ is independently selected from $C_{1-6}$ alkyl, $C_{1-6}$ haloalkyl halo, D, CN, $OR^{a6}$, and $NR^{c6}R^{d6}$;

each $R^{40}$ is independently selected from $C_{1-6}$ alkyl, $C_{1-6}$ haloalkyl, halo, D, CN, $OR^{a7}$, and $NR^{c7}R^{d7}$;

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl;

or any $R^{c1}$ and $R^{d1}$ attached to the same N atom, together with the N atom to which they are attached, form a 4-, 5-, or 6- membered heterocycloalkyl group optionally substituted with 1, 2, 3, or 4 substituents independently selected from $R^{11}$;

each $R^{b1}$ is independently selected from $C_{1-6}$ alkyl, $C_{1-6}$ haloalkyl, $C_{3-10}$ cycloalkyl, and 4-10 membered heterocycloalkyl;

each $R^{a2}$, $R^{c2}$, and $R^{d2}$ is independently selected from H, $C_{1-6}$ alkyl, and $C_{1-6}$ haloalkyl; wherein said $C_{1-6}$ alkyl, is optionally substituted with 1, 2, 3, or 4 substituents independently selected from $R^{20}$;

each $R^{b2}$ is independently selected from $C_{1-6}$ alkyl, and $C_{1-6}$ haloalkyl;

each $R^{a3}$, $R^{c3}$ and $R^{d3}$, is independently selected from H, $C_{1-6}$ alkyl, and $C_{1-6}$ haloalkyl;

each $R^{b3}$ is independently selected from $C_{1-6}$ alkyl and $C_{1-6}$ haloalkyl;

each $R^{a4}$, $R^{c4}$ and $R^{d4}$, is independently selected from H, $C_{1-6}$ alkyl, and $C_{1-6}$ haloalkyl;

each $R^{a5}$, $R^{c5}$ and $R^{d5}$, is independently selected from H, $C_{1-6}$ alkyl, and $C_{1-6}$ haloalkyl;

each $R^{a6}$, $R^{c6}$ and $R^{d6}$, is independently selected from H, $C_{1-6}$ alkyl, and $C_{1-6}$ haloalkyl; and each $R^{a7}$, $R^{c7}$ and $R^{d7}$, is independently selected from H, $C_{1-6}$ alkyl, and $C_{1-6}$ haloalkyl.

58. The compound of claim 1, or a pharmaceutically acceptable salt thereof, wherein:

$Cy^1$ is selected from $C_{6-10}$ aryl and 5-10 membered heteroaryl; wherein each 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$, $R^1$ is $OR^3$ or $NR^4R^5$;

$R^2$ is H;

$A^1$ is selected from N and $CR^6$;

$A^2$ is selected from N and $CR^7$;

$A^3$ is selected from N and $CR^8$;

$A^4$ is selected from N and $CR^9$;

$R^3$ is 4-14 membered heterocycloalkyl;

$R^4$ is 4-14 membered heterocycloalkyl;

$R^5$ is H;

$R^6$, $R^7$, $R^8$, and $R^9$ is each independently selected from H, $C_{1-6}$ alkyl, $C_{1-6}$ haloalkyl, 5-10 membered heteroaryl, halo, CN, $OR^{a2}$, $C(O)NR^{c2}R^{d2}$, and $S(O)_2R^{b2}$; wherein said $C_{1-6}$ alkyl and 5-10 membered heteroaryl are each optionally substituted with 1, 2, 3, or 4 substituents independently selected from $R^{20}$;

each $R^{10}$ is independently selected from $C_{1-6}$ alkyl, $C_{3-10}$ cycloalkyl, 4-10 membered heterocycloalkyl, and $NR^{c1}R^{d1}$; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$;

each $R^{11}$ is independently selected from $C_{1-6}$ alkyl, 4-10 membered heterocycloalkyl, 5-10 membered heteroaryl, halo, CN, $OR^{a3}$, and $C(O)NR^{c3}R^{d3}$;

$R^{20}$is D;

each $R^{c1}$ and $R^{d1}$ is independently selected from H and $C_{1-6}$ alkyl;

each $R^{a2}$, $R^{c2}$,and $R^{d2}$ is independently selected from H and $C_{1-6}$ alkyl; wherein said $C_{1-6}$ alkyl, is optionally substituted with 1, 2, 3, or 4 substituents independently selected from $R^{20}$;

$R^{b2}$ is $C_{1-6}$ alkyl; and each $R^{a3}$, $R^{c3}$ and $R^{d3}$, is independently selected from H and $C_{1-6}$ alkyl.

59. The compound of claim 1, or a pharmaceutically acceptable salt thereof, wherein:

$Cy^1$ is selected from phenyl and 5-10 membered heteroaryl; wherein each 5-10 membered heteroaryl has at least one ring-forming carbon atom and 1, 2, 3, or 4 ring-forming heteroatoms independently selected from N, O, and S; and wherein the phenyl and 5-10 membered heteroaryl are each optionally substituted with 1, 2 or 3 substituents independently selected from $R^{10}$;

$R^1$ is $OR^3$ or $NR^4R^5$;

$R^2$ is H;

$A^1$ is selected from N and $CR^6$;

$A^2$ is selected from N and $CR^7$;

$A^3$ is selected from N and $CR^8$;

$A^4$ is selected from N and $CR^9$;

$R^3$ is 4-6 membered heterocycloalkyl;

$R^4$ is 4-6 membered heterocycloalkyl;

$R^5$ is H;

$R^6$, $R^7$, $R^8$, and $R^9$ is each independently selected from H, D, $C_{1-6}$ alkyl, $C_{1-6}$ haloalkyl, 5-6 membered heteroaryl, halo, CN, $OR^{a2}$, $C(O)NR^{c2}R^{d2}$, $NR^{c2}R^{d2}$, $S(O)_2R^{b2}$, and $S(O)_2NR^{c2}R^{d2}$;

each $R^{10}$ is independently selected from $C_{1-6}$ alkyl, $C_{1-6}$ haloalkyl, $C_{3-6}$ cycloalkyl, 4-7 membered heterocycloalkyl, halo, D, CN, $OR^{a1}$, and $NR^{c1}R^{d1}$, ; wherein said $C_{1-6}$ alkyl and $C_{3-10}$ cycloalkyl, and 4-10 membered heterocycloalkyl, are each optionally substituted with 1 or 2 substituents independently selected from $R^{11}$;

each $R^{11}$ is independently selected from $C_{1-6}$ alkyl, $C_{1-6}$ haloalkyl, $C_{3-10}$ cycloalkyl, 4-7 membered heterocycloalkyl, 5-6 membered heteroaryl, halo, D, CN, $OR^{a3}$, $C(O)NR^{c3}R^{d3}$, and $NR^{c3}R^{d3}$;

each $R^{20}$ is independently selected from D;

each $R^{a1}$, $R^{c1}$ and $R^{d1}$ is independently selected from H, $C_{1-6}$ alkyl, and $C_{1-6}$ haloalkyl;

each $R^{a2}$, $R^{c2}$, and $R^{d2}$ is independently selected from H, $C_{1-6}$ alkyl, and $C_{1-6}$ haloalkyl; wherein said $C_{1-6}$ alkyl, is optionally substituted with 1, 2, or 3 substituents independently selected from $R^{20}$;

each $R^{b2}$ is independently selected from $C_{1-6}$ alkyl, and $C_{1-6}$ haloalkyl; and each $R^{a3}$, $R^{c3}$ and $R^{d3}$, is independently selected from H, $C_{1-6}$ alkyl, and $C_{1-6}$ haloalkyl.

60. The compound of claim 1, wherein the compound is selected from:

N-methyl-3-(6-(1-methyl-1H-pyrazol-4-yl)-5-((tetrahydrofuran-3-yl)oxy)pyrazolo[1,5-a]pyrimidin-3-yl)benzamide;

4-fluoro-N-methyl-3-(6-(1-methyl-1H-pyrazol-4-yl)-5-((tetrahydrofuran-3-yl)oxy)pyrazolo[1,5-a]pyrimidin-3-yl)benzamide;

N-methyl-5-(6-(1-methyl-1H-pyrazol-4-yl)-5-((tetrahydrofuran-3-yl)oxy)pyrazolo[1,5-a]pyrimidin-3-yl) nicotinamide;

4-fluoro-N,3-dimethyl-5-(6-(1-methyl-1H-pyrazol-4-yl)-5-((tetrahydrofuran-3-yl)oxy)pyrazolo[1,5-a]pyrimidin-3-yl)benzamide;

(S)-4-fluoro-N,3-dimethyl-5-(6-(1-methyl-1H-pyrazol-4-yl)-5-((tetrahydrofuran-3-yl)oxy)pyrazolo[1,5-a]pyrimidin-3-yl)benzamide;

(S)-3-cyano-N-methyl-5-(6-(1-methyl-1H-pyrazol-4-yl)-5-((tetrahydrofuran-3-yl)oxy)pyrazolo[1,5-a]pyrimidin-3-yl)benzamide;

(S)-N-methyl-5-(6-(1-methyl-1H-pyrazol-4-yl)-5-((tetrahydrofuran-3-yl)amino)pyrazolo[1,5-a]pyrimidin-3-yl) nicotinamide;

(S)-3-cyano-N-methyl-5-(6-(1-methyl-1H-pyrazol-4-yl)-5-((tetrahydrofuran-3-yl)amino)pyrazolo[1,5-a]pyrimidin-3-yl)benzamide;

(S)-5-(6-(1-isopropyl-1H-pyrazol-4-yl-5-((tetrahydrofuran-3-yl)oxy)pyrazolo[1,5-a]pyrimidin-3-yl)-N-methylnicotinamide;

(S)-5-(6-(1-isopropyl-1H-pyrazol-4-yl)-5-((tetrahydrofuran-3-yl)amino)pyrazolo[1,5-a]pyrimidin-3-yl)-N-methylnicotinamide;

(S)-3,4-difluoro-N-methyl-5-(6-(1-(1-methylpiperidin-4-yl)-1H-pyrazol-4-yl)-5-((tetrahydrofuran-3-yl)oxy) pyrazolo[1,5-a]pyrimidin-3-yl)benzamide;

(S)-3,4-difluoro-N-methyl-5-(6-(4-(4-methylpiperazin-1-yl)phenyl)-5-((tetrahydrofuran-3-yl)oxy)pyrazolo[1,5-a]pyrimidin-3-yl)benzamide;

(S)-3,4-difluoro-N-methyl-5-(6-(6-(4-methylpiperazin-1-yl)pyridin-3-yl)-5-((tetrahydrofuran-3-yl)oxy)pyrazolo[1,5-a]pyrimidin-3-yl)benzamide;

(S)-3,4-difluoro-N-methyl-5-(6-(1-(2-morpholinoethyl)-1H-pyrazol-4-yl)-5-((tetrahydrofuran-3-yl)oxy)pyrazolo[1,5-a]pyrimidin-3-yl)benzamide;

(S)-3,4-difluoro-N-methyl-5-(6-(6-methylpyridin-3-yl)-5-((tetrahydrofuran-3-yl)oxy)pyrazolo[1,5-a]pyrimidin-3-yl)benzamide;

(S)-4-fluoro-N,3-dimethyl-5-(6-(1-methyl-1H-pyrazol-4-yl)-5-((tetrahydrofuran-3-yl)amino)pyrazolo[1,5-a]pyrimidin-3-yl)benzamide;

(S)-3,4-difluoro-N-methyl-5-(6-(1-(1-methylazetidin-3-yl)-1H-pyrazol-4-yl)-5-((tetrahydrofuran-3-yl)oxy)pyrazolo[1,5-a]pyrimidin-3-yl)benzamide;

(S)-N-methyl-5-(6-(4-(4-methylpiperazin-1-yl)phenyl)-5-((tetrahydrofuran-3-yl)oxy)pyrazolo[1,5-a]pyrimidin-3-yl)nicotinamide;

(S)-N-methyl-5-(6-(6-(4-methylpiperazin-1-yl)pyridin-3-yl)-5-((tetrahydrofuran-3-yl)oxy)pyrazolo[1,5-a]pyrimidin-3-yl)nicotinamide;

(S)-N-methyl-5-(6-(6-morpholinopyridin-3-yl)-5-((tetrahydrofuran-3-yl)oxy)pyrazolo[1,5-a]pyrimidin-3-yl)nicotinamide;

(S)-5-(6-(1-cyclopropyl-1H-pyrazol-4-yl)-5-((tetrahydrofuran-3-yl)oxy)pyrazolo[1,5-a]pyrimidin-3-yl)-N-methylnicotinamide;

(S)-5-(6-(1-cyclobutyl-1H-pyrazol-4-yl)-5-((tetrahydrofuran-3-yl)oxy)pyrazolo[1,5-a]pyrimidin-3-yl)-N-methylnicotinamide;

(S)-3-(difluoromethyl)-4-fluoro-N-methyl-5-(6-(pyridin-3-yl)-5-((tetrahydrofuran-3-yl)oxy)pyrazolo[1,5-a]pyrimidin-3-yl)benzamide;

(S)-3-(difluoromethyl)-4-fluoro-N-methyl-5-(6-(5-methyl-6-(methylamino)pyridin-3-yl)-5-((tetrahydrofuran-3-yl)oxy)pyrazolo[1,5-a]pyrimidin-3-yl)benzamide;

(S)-3-(difluoromethyl)-4-fluoro-5-(6-(6-(2-hydroxypropan-2-yl)pyridin-3-yl)-5-((tetrahydrofuran-3-yl)oxy)pyrazolo[1,5-a]pyrimidin-3-yl)-N-methylbenzamide;

(S)-3-(difluoromethyl)-4-fluoro-N-methyl-5-(6-(1-(1-methylazetidin-3-yl)-1H-pyrazol-4-yl)-5-((tetrahydrofuran-3-yl)oxy)pyrazolo[1,5-a]pyrimidin-3-yl)benzamide;

(S)-3-cyano-N-methyl-5-(6-(pyridin-3-yl)-5-((tetrahydrofuran-3-yl)oxy)pyrazolo[1,5-a]pyrimidin-3-yl)benzamide;

(S)-3-cyano-N-methyl-5-(6-(6-methylpyridin-3-yl)-5-((tetrahydrofuran-3-yl)oxy)pyrazolo[1,5-a]pyrimidin-3-yl)benzamide;

(S)-3-cyano-N-methyl-5-(6-(5-methylpyridin-3-yl)-5-((tetrahydrofuran-3-yl)oxy)pyrazolo[1,5-a]pyrimidin-3-yl)benzamide;

(S)-3-cyano-N-methyl-5-(6-(pyridin-4-yl)-5-((tetrahydrofuran-3-yl)oxy)pyrazolo[1,5-a]pyrimidin-3-yl)benzamide;

(S)-4-fluoro-3-hydroxy-N-methyl-5-(6-(1-methyl-1H-pyrazol-4-yl)-5-((tetrahydrofuran-3-yl)oxy)pyrazolo[1,5-a]pyrimidin-3-yl)benzamide; and (S)-3-(6-(1-cyclobutyl-1H-pyrazol-4-yl)-5-((tetrahydrofuran-3-yl)oxy)pyrazolo[1,5-a]pyrimidin-3-yl)-N-methyl-5-(methylsulfonyl)benzamide;

or a pharmaceutically acceptable salt of any of the aforementioned.

61. The compound of claim 1, wherein the compound is selected from:

(S)-3-(1H-Indazol-4-yl)-6-(1-methyl-1H-pyrazol-4-yl)-5-((tetrahydrofuran-3-yl)oxy)pyrazolo[1,5-a]pyrimidine;

(S)-4-Fluoro-N,3-dimethyl-5-(6-(1-(1-methylpiperidin-4-yl)-1H-pyrazol-4-yl)-5-((tetrahydrofuran-3-yl)amino)pyrazolo[1,5-a]pyrimidin-3-yl)benzamide;

(S)-4-Fluoro-N,3-dimethyl-5-(6-(1-(1-methylazetidin-3-yl)-1H-pyrazol-4-yl)-5-((tetrahydrofuran-3-yl)amino)pyrazolo[1,5-a]pyrimidin-3-yl)benzamide;

(S)-4-Fluoro-3-(6-(1-(2-hydroxyethyl)-1H-pyrazol-4-yl)-5-((tetrahydrofuran-3-y1)amino)pyrazolo[1,5-a]pyrimidin-3-yl)-N,5-dimethylbenzamide;

(S)-3-(6-(1-(2-Cyanoethyl)-1H-pyrazol-4-yl)-5-((tetrahydrofuran-3-y1)amino)pyrazolo[1,5-a]pyrimidin-3-yl)-4-fluoro-N,5-dimethylbenzamide;

3-(6-(1-(1, 1-Dioxidotetrahydrothiophen-3-yl)-1H-pyrazol-4-yl)-5-(((S)-tetrahydrofuran-3-yl)amino)pyrazolo [1, 5-a]pyrimidin-3-yl)-4-fluoro-N, 5-dimethylbenzamide;

(S)-3-(6-(1-(2-(Dimethylamino)-2-oxoethyl)- 1H-pyrazol-4-yl)-5-((tetrahydrofuran-3-yl)amino)pyrazolo [1, 5-a]pyrimidin-3-yl)-4-fluoro-N, 5-dimethylbenzamide;

(S)-4-Fluoro-3-(6-(1-(2-hydroxy-2-methylpropyl)-1H-pyrazol-4-yl)-5-((tetrahydrofuran-3-yl)amino)pyrazolo [1, 5-a]pyrimidin-3-yl)-N,5-dimethylbenzamide;

4-Fluoro-N,3-dimethyl-5-(6-(1-(tetrahydrofuran-3-yl)-1H-pyrazol-4-yl)-5 4((S)-tetrahydrofuran-3-yl)amino) pyrazolo [1, 5-a]pyrimidin-3-yl)benzamide;

(S)-4-Fluoro-N,3-dimethyl-5-(6-(2-methyloxazol-5-yl)-5-((tetrahydrofuran-3-yl)amino)pyrazolo [1, 5-a]pyrimidin-3-yl)benzamide;

(S)-3-(6-(1-Ethyl-1H-pyrazol-3-yl)-5-((tetrahydrofuran-3-yl)amino)pyrazolo [1, 5-a]pyrimidin-3-yl)-4-fluoro-N, 5-dimethylbenzamide;

(S)-4-Fluoro-N,3-dimethyl-5-(6-(pyridazin-4-yl)-5-((tetrahydrofuran-3-yl)amino)pyrazolo [1, 5-a]pyrimidin-3-yl)benzamide;

(S)-3-(5-(Ethylsulfonyl)-2, 3-difluorophenyl)-6-(1-methyl-1H-pyrazol-4-yl)-N-(tetrahydrofuran-3-yl) pyrazolo [1, 5-a] pyrimidin-5-amine;

(S)-3-(5-(Ethylsulfonyl)-2, 3-difluorophenyl)-6-(1-methyl-1H-pyrazol-4-yl)-5-((tetrahydrofuran-3-yl) oxy)pyrazolo [1, 5-a]pyrimidine;

(S)-3-(Difluoromethyl)-4-fluoro-N-methyl-5-(6-(1-methyl-1H-pyrazol-4-yl)-5-((tetrahydrofuran-3-yl) amino)pyrazolo [1, 5-a]pyrimidin-3-yl)benzamide;

(S)-3-(Difluoromethyl)-5-(6-(1-ethyl-1H-pyrazol-4-yl)-5-((tetrahydrofuran-3-yl)amino)pyrazolo [1, 5-a]pyrimidin-3-yl)-4-fluoro-N-methylbenzamide;

3-(Difluoromethyl)-4-fluoro-N-methyl-5-(6-(1-(tetrahydrofuran-3-yl)-1H-pyrazol-4-yl)-5-(((S)-tetrahydrofuran-3-yl)amino)pyrazolo[1, 5-a]pyrimidin-3-yl)benzamide;

(S)-3-(Difluoromethyl)-4-fluoro-5-(6-(1-(2-methoxyethyl)-1H-pyrazol-4-yl)-5-((tetrahydrofuran-3-yl) amino)pyrazolo [1, 5-a]pyrimidin-3-yl)-N-methylbenzamide;

(S)-3-(3-(1H-Pyrazol-3-yl)phenyl)-6-(1-methyl-1H-pyrazol-4-yl)-5-((tetrahydrofuran-3-yl)oxy)pyrazolo [1, 5-a]pyrimidine;

(S)-3,4-Difluoro-N-methyl-5-(6-(1-(pyridin-3-ylmethyl)-1H-pyrazol-4-yl)-5-((tetrahydrofuran-3-yl)amino) pyrazolo [1, 5-a]pyrimidin-3-yl)benzamide;

(S)-3-(6-(1-Ethyl-1H-pyrazol-4-yl)-5-((tetrahydrofuran-3-yl)amino)pyrazolo[1,5-a]pyrimidin-3-yl)-4,5-difluoro-N-methylbenzamide;

(S)-3,4-Difluoro-N-methyl-5-(6-(1-((tetrahydro-2H-pyran-4-yl)methyl)-1H-pyrazol-4-yl)-5-((tetrahydrofuran-3-yl)amino)pyrazolo[1,5-a]pyrimidin-3-yl)benzamide;

(S)-3,4-Difluoro-N-methyl-5-(6-(1-(2-morpholinoethyl)-1H-pyrazol-4-yl)-5-((tetrahydrofuran-3-yl)amino)pyrazolo[1,5-a]pyrimidin-3-yl)benzamide;

(S)-3,4-Difluoro-5-(6-(1-isopropyl-2-oxo-1,2-dihydropyridin-4-yl)-5-((tetrahydrofuran-3-yl)amino)pyrazolo[1,5-a]pyrimidin-3-yl)-N-methylbenzamide;

(S)-3,4-Difluoro-5-(6-(6-(2-hydroxypropan-2-yl)pyridin-3-yl)-5-((tetrahydrofuran-3-yl)amino)pyrazolo[1,5-a]pyrimidin-3-yl)-N-methylbenzamide;

(S)-3,4-Difluoro-N-methyl-5-(6-(2-methyloxazol-5-yl)-5-((tetrahydrofuran-3-yl)amino)pyrazolo[1,5-a]pyrimidin-3-yl)benzamide;

(S)-N-Methyl-5-(6-(1-methyl-1H-pyrazol-3-yl)-5-((tetrahydrofuran-3-yl)amino)pyrazolo[1,5-a]pyrimidin-3-yl)nicotinamide;

(S)-N-Methyl-5-(6-(2-methyl-2H-1,2,3-triazol-4-yl)-5-((tetrahydrofuran-3-yl)amino)pyrazolo[1,5-a]pyrimidin-3-yl)nicotinamide;

(S)-N-Ethyl-5-(6-(1-methyl-1H-pyrazol-3-yl)-5-((tetrahydrofuran-3-yl)amino)pyrazolo[1,5-a]pyrimidin-3-yl)nicotinamide;

(S)-N-Isopropyl-5-(6-(1-methyl-1H-pyrazol-3-yl)-5-((tetrahydrofuran-3-yl)amino)pyrazolo[1,5-a]pyrimidin-3-yl)nicotinamide;

(S)-5-(6-(1-Isopropyl-1H-pyrazol-4-yl)-5-((tetrahydrofuran-3-yl)oxy)pyrazolo[1,5-a]pyrimidin-3-yl)-N-(methyl-$d_3$)nicotinamide;

4-Fluoro-3-(6-(1-((3R,4R)-3-fluoro-1-methylpiperidin-4-yl)-1H-pyrazol-4-yl)-5-(((5)-tetrahydrofuran-3-yl)oxy)pyrazolo[1,5-a] pyrimidin-3-yl)-5-methyl-N-(methyl-$d_3$)benzamide;

4-Fluoro-3-(6-(1-((3R,4R)-3-fluoro-1-methylpiperidin-4-yl)-1H-pyrazol-4-yl)-5-(((5)-tetrahydrofuran-3-yl)amino)pyrazolo[1,5-a]pyrimidin-3-yl)-N,5-dimethylbenzamide;

3-(6-(6-(((1R,4R)-2-Oxa-5-azabicyclo[2,2,1]heptan-5-yl)methyl)pyridin-3-yl)-5-(((5)-tetrahydrofuran-3-yl)oxy)pyrazolo[1,5-a] pyrimidin-3-yl)-5-(difluoromethyl)-4-fluoro-N-(methyl-d3)benzamide;

(S)-4-Fluoro-3-(6-(2-(1-isopropylpiperidin-4-yl)-2H-1,2,3-triazol-4-yl)-5-((tetrahydrofuran-3-yl)amino)pyrazolo[1,5-a]pyrimidin-3-yl)-5-methyl-N-(methyl-$d_3$)benzamide;

(S)-4-Fluoro-3-(6-(2-(1-isopropylpiperidin-4-yl)oxazol-5-yl)-5-((tetrahydrofuran-3-yl)amino)pyrazolo[1,5-a]pyrimidin-3-yl)-5-methyl-N-(methyl-$d_3$)benzamide;

(S)-4-Fluoro-3-(6-(2-(4-fluoro-1-methylpiperidin-4-yl)oxazol-5-yl)-5-((tetrahydrofuran-3-yl)amino)pyrazolo[1,5-a]pyrimidin-3-yl)-N,5-dimethylbenzamide; and (S)-4-Fluoro-N,3-dimethyl-5-(6-(2-(4-methylpiperazin-1-yl)oxazol-5-yl)-5-((tetrahydrofuran-3-yl)amino)pyrazolo[1,5-a]pyrimidin-3-yl)benzamide;

or a pharmaceutically acceptable salt of any of the aforementioned.

62. A pharmaceutical composition comprising a compound of claim 1 or a pharmaceutically acceptable salt thereof, and a pharmaceutically acceptable carrier or excipient.

63. A method of inhibiting an FGFR3 enzyme comprising contacting said enzyme with a compound of claim 1 or a pharmaceutically acceptable salt thereof.

64. A method of treating cancer in a patient comprising administering to said patient a therapeutically effective amount of a compound of claim 1 or a pharmaceutically acceptable salt thereof, wherein the cancer is associated with abnormal activity or expression of an FGFR enzyme.

65. A method of treating cancer in a patient comprising administering to said patient a therapeutically effective amount of a compound of claim 1 or a pharmaceutically acceptable salt thereof in combination with another therapy or therapeutic agent, wherein the cancer is associated with abnormal activity or expression of an FGFR enzyme.

66. The method of claim 64, wherein said cancer is selected from hepatocellular cancer, bladder cancer, breast cancer, cervical cancer, colorectal cancer, endometrial cancer, gastric cancer, head and neck cancer, kidney cancer, liver cancer, cholangiocarcinoma, lung cancer, ovarian cancer, prostate cancer, esophageal cancer, gall bladder cancer, pancreatic cancer, thyroid cancer, skin cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, hairy cell lymphoma, Burkett's lymphoma, glioblastoma, melanoma, and rhabdosarcoma.

67. The method of claim 64, wherein said cancer is selected from bladder cancer, breast cancer, colorectal cancer, endometrial cancer, gastric cancer, head and neck cancer, kidney cancer, liver cancer, cholangiocarcinoma, lung cancer, ovarian cancer, pancreatic cancer, glioblastoma, melanoma, and rhabdosarcoma.

68. A method for treating a skeletal or chondrocyte disorder in a patient comprising administering to said patient a therapeutically effective amount of a compound of claim 1 or a pharmaceutically acceptable salt thereof, wherein the skeletal or chondrocyte disorder is associated with abnormal activity or expression of an FGFR enzyme.

69. The method of claim 68 wherein said skeletal or chondrocyte disorder is selected from achrondroplasia, hypochondroplasia, dwarfism, thanatophoric dysplasia (TD), Apert syndrome, Crouzon syndrome, Jackson-Weiss syndrome, Beare-Stevenson cutis gyrate syndrome, Pfeiffer syndrome, and craniosynostosis syndrome.

* * * * *

SEQUENCE LISTING

<160> NUMBER OF SEQ ID NOS: 1

<210> SEQ ID NO 1
<211> LENGTH: 15
<212> TYPE: PRT
<213> ORGANISM: Artificial
<220> FEATURE:
<223> OTHER INFORMATION: synthetic peptide

<400> SEQUENCE: 1

Glu Gln Glu Asp Glu Pro Glu Gly Asp Tyr Phe Glu Trp Leu Glu
1 5 10 15